United States Patent
Keller et al.

(10) Patent No.: US 9,745,630 B2
(45) Date of Patent: Aug. 29, 2017

(54) MIRNA FINGERPRINT IN THE DIAGNOSIS OF PROSTATE CANCER

(71) Applicant: Comprehensive Biomarker Center GmbH, Heidelberg (DE)

(72) Inventors: Andreas Keller, Puettlingen (DE); Eckart Meese, Huetschenhausen (DE); Anne Borries, Heidelberg (DE); Markus Beier, Weinheim (DE)

(73) Assignee: Hummingbird Diagnostics GmbH, Heidelberg (DE)

( * ) Notice: Subject to any disclaimer, the term of this patent is extended or adjusted under 35 U.S.C. 154(b) by 0 days.

(21) Appl. No.: 14/823,545

(22) Filed: Aug. 11, 2015

(65) Prior Publication Data

US 2015/0337393 A1 Nov. 26, 2015

Related U.S. Application Data

(62) Division of application No. 13/520,014, filed as application No. PCT/EP2010/070924 on Dec. 30, 2010, now abandoned.

(60) Provisional application No. 61/291,074, filed on Dec. 30, 2009.

(30) Foreign Application Priority Data

Dec. 30, 2009 (EP) .................................. 09181024

(51) Int. Cl.
  *C12Q 1/68* (2006.01)
  *A61N 5/10* (2006.01)
(52) U.S. Cl.
  CPC .............. *C12Q 1/6883* (2013.01); *A61N 5/10* (2013.01); *C12Q 1/6886* (2013.01); *C12Q 2600/112* (2013.01); *C12Q 2600/158* (2013.01); *C12Q 2600/178* (2013.01)
(58) Field of Classification Search
  None
  See application file for complete search history.

(56) References Cited

U.S. PATENT DOCUMENTS

| | | | |
|---|---|---|---|
| 2007/0161004 A1* | 7/2007 | Brown | C12N 15/111 435/6.14 |
| 2007/0259352 A1 | 11/2007 | Bentwich et al. | |
| 2007/0292878 A1 | 12/2007 | Raymond | |
| 2010/0297652 A1 | 11/2010 | Shelton et al. | |
| 2011/0251098 A1 | 10/2011 | Showe et al. | |

FOREIGN PATENT DOCUMENTS

| | | |
|---|---|---|
| WO | 2005111211 A2 | 11/2005 |
| WO | 2005/118806 A2 | 12/2005 |
| WO | 2007259352 A1 | 11/2007 |
| WO | 2008116267 A1 | 10/2008 |
| WO | 2009015357 A1 | 1/2009 |
| WO | 2009108860 A2 | 9/2009 |
| WO | 2009143379 A2 | 11/2009 |
| WO | 2010135692 A2 | 11/2010 |

OTHER PUBLICATIONS

Office Action issued on Dec. 4, 2015, in corresponding European Application No. 10 801 172.7, 5 pages.
Shi Xu-Bao et al: "microRNAs and prostate cancer", Journal of Cellular and Molecular Medicine, vol. 12, No. 5A, Sep. 2008 (Sep. 2008), pp. 1456-1465.
Tong A W et al: "MicroRNA profile analysis of human prostate cancers", Cancer Gene Therapy, vol. 16, No. 3, Mar. 2009 (Mar. 2009), pp. 206-216.
Sun Ruping et al: "Global gene expression analysis reveals reduced abundance of putative microRNA targets in human prostate tumours", BMC Genomics, vol. 10, Feb. 2009.
Porkka Kati P et al: "MicroRNA expression profiling in prostate cancer", Cancer Research, vol. 67, No. 13, Jul. 2007 (Jul. 2007), pp. 6130-6135.
Lodes Michael J et al: "Detection of Cancer with Serum miRNAs on an Oligonucleotide Microarray", PLOS One, vol. 4, No. 7, Jul. 2009.
Keller et al., "miRNAs in lung cancer—Studying complex fingerprints in patient's blood cells by microarray experiments"(BMC Cancer, Biomed Central, London, GB ) Oct. 6, 2009; vol. 9, No. 1, entire document, IDS reference).
Hoyt Dissertation entitled The Role of MicroRNA-155 and MicroRNA-146A as PUtative Oncomirs in the Tumor Progressin of Prostate Cancer (Virginia Commonwealth University, Richmond, Virginia, Aug. 2008).

* cited by examiner

*Primary Examiner* — Catherine S Hibbert
(74) *Attorney, Agent, or Firm* — Kilpatrick Townsend & Stockton LLP

(57) ABSTRACT

MicroRNAs (miRNA) are a recently discovered class of small non-coding RNAs (17-14 nucleotides). Due to their function as regulators of gene expression they play a critical role both in physiological and in pathological processes, such as cancer. The present invention provides novel methods for diagnosing prostate cancer based on the determination of specific miRNAs that have altered expression levels in different conditions, e.g. disease states compared to healthy controls.

12 Claims, 63 Drawing Sheets

Figure 1

Figure 3:
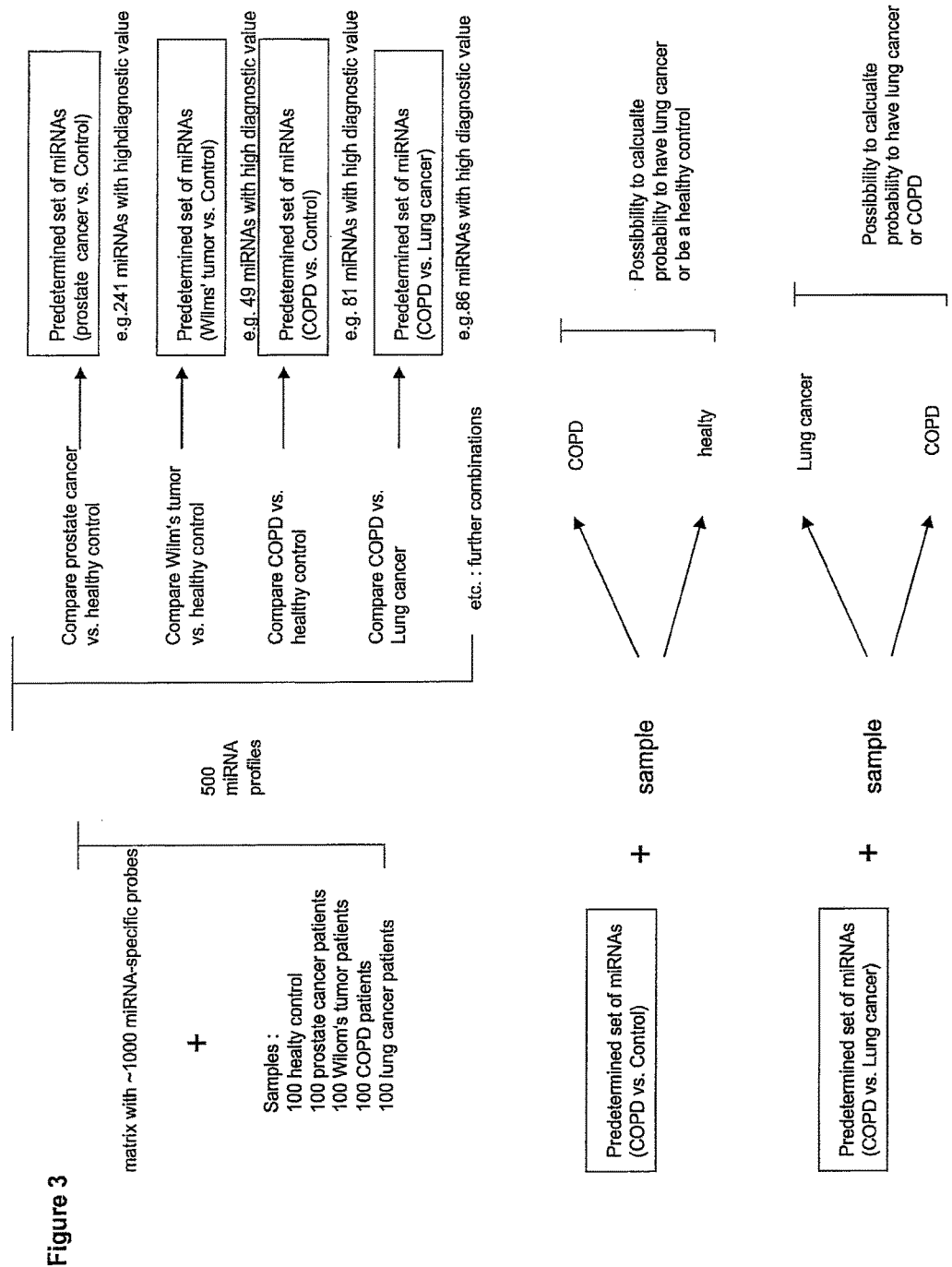

| SEQ ID NO: | Name (miRNA, miRNA*) | SEQUENCE |
|---|---|---|
| 1 | hsa-miR-99b* | caagcucgugucuguggguccg |
| 2 | hsa-miR-99b | cacccguagaaccgaccuugcg |
| 3 | hsa-miR-99a* | caagcucgcuucuaugggucug |
| 4 | hsa-miR-99a | aacccguagauccgaucuugug |
| 5 | hsa-miR-98 | ugagguaguaaguuguauuguu |
| 6 | hsa-miR-96* | aaucaugugcagugccaauaug |
| 7 | hsa-miR-96 | uuuggcacuagcacauuuuugcu |
| 8 | hsa-miR-95 | uucaacggguauuuauugagca |
| 9 | hsa-miR-944 | aaauuauuguacaucggaugag |
| 10 | hsa-miR-943 | cugacguugccguccuccag |
| 11 | hsa-miR-942 | ucuucucuguuuuggccaugug |
| 12 | hsa-miR-941 | cacccggcugugugcacaugugc |
| 13 | hsa-miR-940 | aaggcagggccccgcuccc |
| 14 | hsa-miR-939 | uggggagcugaggcucuggggug |
| 15 | hsa-miR-938 | ugcccuuaaaggugaacccagu |
| 16 | hsa-miR-937 | auccgcgcucugacucucugcc |
| 17 | hsa-miR-936 | acaguagagggaggaaucgcag |
| 18 | hsa-miR-935 | ccaguuaccgcuuccgcuaccgc |
| 19 | hsa-miR-934 | ugucuacuacuggagacacugg |
| 20 | hsa-miR-933 | ugugcgcagggagaccucuccc |
| 21 | hsa-miR-93* | acugcugagcuagcacuuccccg |
| 22 | hsa-miR-93 | caaagugcuguucgugcagguag |
| 23 | hsa-miR-92b* | agggacgggacgcggugcagug |
| 24 | hsa-miR-92b | uauugcacucgucccggccucc |
| 25 | hsa-miR-92a-2* | gggguggggauuuguugcauuac |
| 26 | hsa-miR-92a-1* | agguugggaucgguugcaaugcu |
| 27 | hsa-miR-92a | uauugcacuugucccggccugu |
| 28 | hsa-miR-924 | agagucuugugaugucuugc |
| 29 | hsa-miR-922 | gcagcagagaauaggacuacguc |
| 30 | hsa-miR-921 | cuagugagggacagaaccaggauuc |
| 31 | hsa-miR-920 | ggggagcuguggaagcagua |
| 32 | hsa-miR-9* | auaaagcuagauaaccgaaagu |
| 33 | hsa-miR-9 | ucuuugguuaucagcuguauga |
| 34 | hsa-miR-892b | cacuggcuccuuucuggguaga |
| 35 | hsa-miR-892a | cacuguguccuuucugcguag |
| 36 | hsa-miR-891b | ugcaacuuaccugagucauuga |
| 37 | hsa-miR-891a | ugcaacgaaccugagccacuga |
| 38 | hsa-miR-890 | uacuuggaaaggcaucaguug |
| 39 | hsa-miR-889 | uuaauaucggacaaccauugu |
| 40 | hsa-miR-888* | gacugacaccucuuugggugaa |
| 41 | hsa-miR-888 | uacucaaaaagcugucaguca |
| 42 | hsa-miR-887 | gugaacgggcgccaucccgagg |
| 43 | hsa-miR-886-5p | cggcucggaguuagcucaagcgg |
| 44 | hsa-miR-886-3p | cgcgggugcuuacugacccuu |
| 45 | hsa-miR-885-5p | uccauuacacuacccugccucu |
| 46 | hsa-miR-885-3p | aggcagcggggguguaguggaua |
| 47 | hsa-miR-877* | uccucuucucccuccucccag |
| 48 | hsa-miR-877 | guagaggagauggcgcaggg |
| 49 | hsa-miR-876-5p | uggauuucuuugugaaucacca |
| 50 | hsa-miR-876-3p | uggugguuuacaaaguaauuca |

FIG. 1 (Continued)

| 51 | hsa-miR-875-5p | uauaccucaguuuaucaggug |
|---|---|---|
| 52 | hsa-miR-875-3p | ccuggaaacacugagguugug |
| 53 | hsa-miR-874 | cugcccuggcccgagggaccga |
| 54 | hsa-miR-873 | gcaggaacuugugagucuccu |
| 55 | hsa-miR-802 | caguaacaaagauucauccuugu |
| 56 | hsa-miR-770-5p | uccaguaccacgugucagggcca |
| 57 | hsa-miR-769-5p | ugagaccucuggguucugagcu |
| 58 | hsa-miR-769-3p | cugggaucuccggggucuugguu |
| 59 | hsa-miR-767-5p | ugcaccaugguugucugagcaug |
| 60 | hsa-miR-767-3p | ucugcucauaccccaugguuucu |
| 61 | hsa-miR-766 | acuccagccccacagccucagc |
| 62 | hsa-miR-765 | uggaggagaaggaaggugaug |
| 63 | hsa-miR-764 | gcaggugcucacuuguccuccu |
| 64 | hsa-miR-762 | ggggcuggggcggggccgagc |
| 65 | hsa-miR-761 | gcagcagggugaaacugacaca |
| 66 | hsa-miR-760 | cggcucuggggucuguggga |
| 67 | hsa-miR-759 | gcagagugcaaacaauuuugac |
| 68 | hsa-miR-758 | uuugugaccugguccacuaacc |
| 69 | hsa-miR-744* | cuguugccacuaaccucaaccu |
| 70 | hsa-miR-744 | ugcggggcuagggcuaacagca |
| 71 | hsa-miR-720 | ucucgcuggggccucca |
| 72 | hsa-miR-7-2* | caacaaaucccagucuaccuaa |
| 73 | hsa-miR-718 | cuuccgccccgccgggcgucg |
| 74 | hsa-miR-711 | gggacccagggagagacguaag |
| 75 | hsa-miR-7-1* | caacaaaucacagucugccaua |
| 76 | hsa-miR-708* | caacuagacugugagcuucag |
| 77 | hsa-miR-708 | aaggagcuuacaaucuagcuggg |
| 78 | hsa-miR-7 | uggaagacuagugauuuuguugu |
| 79 | hsa-miR-675* | cuguaugcccucaccgcuca |
| 80 | hsa-miR-675 | uggugcggagagggcccacagug |
| 81 | hsa-miR-671-5p | aggaagcccuggaggggcuggag |
| 82 | hsa-miR-671-3p | uccgguucucagggcuccacc |
| 83 | hsa-miR-670 | gucccugaguguauguggug |
| 84 | hsa-miR-668 | ugucacucggcucggcccacuac |
| 85 | hsa-miR-665 | accaggaggcugaggccccu |
| 86 | hsa-miR-664* | acuggcuagggaaaaugauuggau |
| 87 | hsa-miR-664 | uauucauuuaucccagccuaca |
| 88 | hsa-miR-663b | ggugcccggccgugccugagg |
| 89 | hsa-miR-663 | aggcggggcgccgcgggaccgc |
| 90 | hsa-miR-662 | ucccacguuguggccagcag |
| 91 | hsa-miR-661 | ugccuggucucuggccugcgcgu |
| 92 | hsa-miR-660 | uacccauugcauaucggaguug |
| 93 | hsa-miR-659 | cuugguucagggaggguccca |
| 94 | hsa-miR-658 | ggcggagggaaguagguccguuggu |
| 95 | hsa-miR-657 | ggcagguucucacccucucuagg |
| 96 | hsa-miR-656 | aauauuauacagucaaccucu |
| 97 | hsa-miR-655 | auaauacaugguuaaccucuuu |
| 98 | hsa-miR-654-5p | uggugggccgcagaacaugugc |
| 99 | hsa-miR-654-3p | uaugucugcugaccaucaccuu |
| 100 | hsa-miR-653 | guguugaaacaaucucuacug |
| 101 | hsa-miR-652 | aauggcgccacuagggguugug |
| 102 | hsa-miR-651 | uuuaggauaagcuugacuuug |
| 103 | hsa-miR-650 | aggaggcagcgcucucaggac |

FIG. 1 (Continued)

| 104 | hsa-miR-649 | aaaccuguguuguucaagaguc |
|---|---|---|
| 105 | hsa-miR-648 | aagugugcagggcacuggu |
| 106 | hsa-miR-647 | guggcugcacucacuuccuuc |
| 107 | hsa-miR-646 | aagcagcugccucugaggc |
| 108 | hsa-miR-645 | ucuaggcugguacugcuga |
| 109 | hsa-miR-644 | aguguggcuuucuuagagc |
| 110 | hsa-miR-643 | acuuguaugcuagcucagguag |
| 111 | hsa-miR-642 | gucccucuccaaauguguucuug |
| 112 | hsa-miR-641 | aaagacauaggauagagucaccuc |
| 113 | hsa-miR-640 | augauccaggaaccugccucu |
| 114 | hsa-miR-639 | aucgcugcgguugcgagcgcugu |
| 115 | hsa-miR-638 | agggaucgcgggcgggguggcggccu |
| 116 | hsa-miR-637 | acugggggcuuucgggcucugcgu |
| 117 | hsa-miR-636 | ugugcuugcucguccegeccgca |
| 118 | hsa-miR-635 | acuugggcacugaaacaaugucc |
| 119 | hsa-miR-634 | aaccagcaccccaacuuuggac |
| 120 | hsa-miR-633 | cuaauaguaucuaccacaauaaa |
| 121 | hsa-miR-632 | gugucugcuuccuguggga |
| 122 | hsa-miR-631 | agaccuggcccagaccucagc |
| 123 | hsa-miR-630 | aguauucuguaccagggaaggu |
| 124 | hsa-miR-629* | guucucccaacguaagcccagc |
| 125 | hsa-miR-629 | uggguuuacguugggagaacu |
| 126 | hsa-miR-628-5p | augcugacauauuuacuagagg |
| 127 | hsa-miR-628-3p | ucuaguaagaguggcagucga |
| 128 | hsa-miR-627 | gugagucucuaagaaaagagga |
| 129 | hsa-miR-626 | agcugucugaaaaugucuu |
| 130 | hsa-miR-625* | gacauagaacuuuccccuca |
| 131 | hsa-miR-625 | aggggaaaguucuauagucc |
| 132 | hsa-miR-624* | uaguaccaguaccuuguguuca |
| 133 | hsa-miR-624 | cacaagguauugguauuaccu |
| 134 | hsa-miR-623 | aucccuugcagggcuguugggu |
| 135 | hsa-miR-622 | acagucugcugagguuggagc |
| 136 | hsa-miR-621 | ggcuagcaacagcgcuuaccu |
| 137 | hsa-miR-620 | auggagauagauauagaaau |
| 138 | hsa-miR-619 | gaccuggacauguuugugcccagu |
| 139 | hsa-miR-618 | aaacucuacuuguccuucugagu |
| 140 | hsa-miR-617 | agacuucccauuugaaggugg |
| 141 | hsa-miR-616* | acucaaaaccuucagugacuu |
| 142 | hsa-miR-616 | agucauuggaggguuugagcag |
| 143 | hsa-miR-615-5p | gggggucccggugucuggauc |
| 144 | hsa-miR-615-3p | uccgagccugggucucccucuu |
| 145 | hsa-miR-614 | gaacgccuguucuugccaggugg |
| 146 | hsa-miR-613 | aggaauguuccuucuuugcc |
| 147 | hsa-miR-612 | gcugggcagggcuucugagcuccuu |
| 148 | hsa-miR-611 | gcgaggacccucggggucugac |
| 149 | hsa-miR-610 | ugagcuaaaugugugcuggga |
| 150 | hsa-miR-609 | aggguguuucucucaucucu |
| 151 | hsa-miR-608 | aggggguggugguugggacagcuccgu |
| 152 | hsa-miR-607 | guucaaauccagaucuauaac |
| 153 | hsa-miR-606 | aaacuacugaaaaucaaagau |
| 154 | hsa-miR-605 | uaaauccauggugccuucuccu |
| 155 | hsa-miR-604 | aggcugcggaauucaggac |
| 156 | hsa-miR-603 | cacacacugcaauuacuuuugc |

FIG. 1 (Continued)

| | | |
|---|---|---|
| 157 | hsa-miR-602 | gacacgggcgacagcugcggccc |
| 158 | hsa-miR-601 | uggucuaggauuguuggaggag |
| 159 | hsa-miR-600 | acuuacagacaagagccuugcuc |
| 160 | hsa-miR-599 | guugugucaguuuaucaaac |
| 161 | hsa-miR-598 | uacgucaucguugucaucguca |
| 162 | hsa-miR-597 | ugugucacucgaugaccacugu |
| 163 | hsa-miR-596 | aagccugcccggcuccucggg |
| 164 | hsa-miR-595 | gaagugugccguggugugucu |
| 165 | hsa-miR-593* | aggcaccagccaggcauugcucagc |
| 166 | hsa-miR-593 | ugucucugcuggggguuucu |
| 167 | hsa-miR-592 | uugugucaauaugcgaugaugu |
| 168 | hsa-miR-591 | agaccaugggguucucauugu |
| 169 | hsa-miR-590-5p | gagcuuauucauaaaagugcag |
| 170 | hsa-miR-590-3p | uaauuuuauguauaagcuagu |
| 171 | hsa-miR-589* | ucagaacaaaugccgguucccaga |
| 172 | hsa-miR-589 | ugagaaccacgucugcucugag |
| 173 | hsa-miR-588 | uuggccacaauggguuagaac |
| 174 | hsa-miR-587 | uuuccauaggugaugagucac |
| 175 | hsa-miR-586 | uaugcauuguauuuuuaggucc |
| 176 | hsa-miR-585 | ugggcguaucuguaugcua |
| 177 | hsa-miR-584 | uuaugguuugccugggacugag |
| 178 | hsa-miR-583 | caaagaggaaggucccauuac |
| 179 | hsa-miR-582-5p | uuacaguuguucaaccaguuacu |
| 180 | hsa-miR-582-3p | uaacugguugaacaacugaacc |
| 181 | hsa-miR-581 | ucuuguguucucuagaucagu |
| 182 | hsa-miR-580 | uugagaaugaugaaucauuagg |
| 183 | hsa-miR-579 | uucauuugguauaaaccgcgauu |
| 184 | hsa-miR-578 | cuucuugugcucuaggauugu |
| 185 | hsa-miR-577 | uagauaaaauauugguaccug |
| 186 | hsa-miR-576-5p | auucuaauuucuccacgucuuu |
| 187 | hsa-miR-576-3p | aagaugggaaaaauuggaauc |
| 188 | hsa-miR-575 | gagccaguuggacaggagc |
| 189 | hsa-miR-574-5p | ugagugugugugugagugugu |
| 190 | hsa-miR-574-3p | cacgcucaugcacacacccaca |
| 191 | hsa-miR-573 | cugaagugauguguaacgaucag |
| 192 | hsa-miR-572 | guccgcucggcggguggccca |
| 193 | hsa-miR-571 | ugaguuggccaucugagugag |
| 194 | hsa-miR-570 | cgaaaacagcaauuaccuugc |
| 195 | hsa-miR-569 | aguuaaugaauccuggaaagu |
| 196 | hsa-miR-568 | auguauaaauguauacacac |
| 197 | hsa-miR-567 | aguauguucuuccaggacagaac |
| 198 | hsa-miR-566 | gggcgccugugaucccaac |
| 199 | hsa-miR-564 | aggcacgugucagcaggc |
| 200 | hsa-miR-563 | agguugacauacguuuccc |
| 201 | hsa-miR-562 | aaaguagcuguaccauuugc |
| 202 | hsa-miR-561 | caaaguuuaagauccuugaagu |
| 203 | hsa-miR-559 | uaaaguaaauaugcaccaaaa |
| 204 | hsa-miR-558 | ugagcugcuguaccaaaau |
| 205 | hsa-miR-557 | guuugcacgggugggccuugcu |
| 206 | hsa-miR-556-5p | gaugagcucauuguaauaugag |
| 207 | hsa-miR-556-3p | auauuaccauuagcucaucuuu |
| 208 | hsa-miR-555 | aggguaagcugaaccucugau |
| 209 | hsa-miR-554 | gcuaguccugacucagccagu |

FIG. 1 (Continued)

| | | |
|---|---|---|
| 210 | hsa-miR-553 | aaaacggugagauuuuguuuu |
| 211 | hsa-miR-552 | aacaggugacugguuagacaa |
| 212 | hsa-miR-551b* | gaaaucaagcgugggugagacc |
| 213 | hsa-miR-551b | gcgacccauacuugguuucag |
| 214 | hsa-miR-551a | gcgacccacucuugguuucca |
| 215 | hsa-miR-550* | ugucuuacucccucaggcacau |
| 216 | hsa-miR-550 | agugccugagggaguaagagccc |
| 217 | hsa-miR-549 | ugacaacuauggaugagcucu |
| 218 | hsa-miR-548q | gcuggugcaaaaguaauggcgg |
| 219 | hsa-miR-548p | uagcaaaaacugcaguuacuuu |
| 220 | hsa-miR-548o | ccaaaacugcaguuacuuugc |
| 221 | hsa-miR-548n | caaaaguaauugugggauuuugu |
| 222 | hsa-miR-548m | caaagguauugugguuuuug |
| 223 | hsa-miR-548l | aaaaguauuugcgggguuuuguc |
| 224 | hsa-miR-548k | aaaaguacuugcgggauuuugcu |
| 225 | hsa-miR-548j | aaaaguaauugcggucuuuggu |
| 226 | hsa-miR-548i | aaaaguaauugcggauuuugcc |
| 227 | hsa-miR-548h | aaaaguaaucgcgguuuuuguc |
| 228 | hsa-miR-548g | aaaacuguaauuacuuuuguac |
| 229 | hsa-miR-548f | aaaaacuguaauuacuuuu |
| 230 | hsa-miR-548e | aaaaacugagacuacuuuugca |
| 231 | hsa-miR-548d-5p | aaaaguaauugugguuuuugcc |
| 232 | hsa-miR-548d-3p | caaaaaccacaguuucuuuugc |
| 233 | hsa-miR-548c-5p | aaaaguaauugcgguuuuugcc |
| 234 | hsa-miR-548c-3p | caaaaaucucaauuacuuuugc |
| 235 | hsa-miR-548b-5p | aaaaguaauugugguuuuggcc |
| 236 | hsa-miR-548b-3p | caagaaccucaguugcuuuugu |
| 237 | hsa-miR-548a-5p | aaaaguaauugcgaguuuuacc |
| 238 | hsa-miR-548a-3p | caaaacuggcaauuacuuuugc |
| 239 | hsa-miR-545* | ucaguaaaauguuuauuagauga |
| 240 | hsa-miR-545 | ucagcaaacauuuauugugugc |
| 241 | hsa-miR-544 | auucugcauuuuuagcaaguuc |
| 242 | hsa-miR-543 | aaacauucgcggugcacuucuu |
| 243 | hsa-miR-542-5p | ucggggaucaucaugucacgaga |
| 244 | hsa-miR-542-3p | ugugacagaugauaaacugaaa |
| 245 | hsa-miR-541* | aaaggauucugcugucggucccacu |
| 246 | hsa-miR-541 | uggugggcacagaaucuggacu |
| 247 | hsa-miR-539 | ggagaaauuauccuuggugugu |
| 248 | hsa-miR-532-5p | caugccuugaguguaggaccgu |
| 249 | hsa-miR-532-3p | ccucccacacccaaggcuugca |
| 250 | hsa-miR-527 | cugcaaagggaagcccuuuc |
| 251 | hsa-miR-526b* | gaaagugcuuccuuuuagaggc |
| 252 | hsa-miR-526b | cucuugagggaagcacuuucugu |
| 253 | hsa-miR-526a | cucuagagggaagcacuuucug |
| 254 | hsa-miR-525-5p | cuccagagggaugcacuuucu |
| 255 | hsa-miR-525-3p | gaaggcgcuucccuuuagagcg |
| 256 | hsa-miR-524-5p | cuacaaagggaagcacuuucuc |
| 257 | hsa-miR-524-3p | gaaggcgcuucccuuuggagu |
| 258 | hsa-miR-523* | cucuagagggaagcgcuuucug |
| 259 | hsa-miR-523 | gaacgcgcuucccuauagagggu |
| 260 | hsa-miR-522* | cucuagagggaagcgcuuucug |
| 261 | hsa-miR-522 | aaaaugguucccuuuagagugu |
| 262 | hsa-miR-521 | aacgcacuucccuuuagagugu |

FIG. 1 (Continued)

| 263 | hsa-miR-520h | acaaagugcuucccuuuagagu |
|---|---|---|
| 264 | hsa-miR-520g | acaaagugcuucccuuuagagugu |
| 265 | hsa-miR-520f | aagugcuuccuuuuagagggu |
| 266 | hsa-miR-520e | aaagugcuuccuuuugaggg |
| 267 | hsa-miR-520d-5p | cuacaaagggaagcccuuuc |
| 268 | hsa-miR-520d-3p | aaagugcuucucuuuggugggu |
| 269 | hsa-miR-520c-5p | cucuagagggaagcacuuucug |
| 270 | hsa-miR-520c-3p | aaagugcuuccuuuuagagggu |
| 271 | hsa-miR-520b | aaagugcuuccuuuuagaggg |
| 272 | hsa-miR-520a-5p | cuccagagggaaguacuuucu |
| 273 | hsa-miR-520a-3p | aaagugcuucccuuuggacugu |
| 274 | hsa-miR-519e* | uucuccaaaagggagcacuuuc |
| 275 | hsa-miR-519e | aagugccuccuuuuagaguguu |
| 276 | hsa-miR-519d | caaagugccucccuuuagagug |
| 277 | hsa-miR-519c-5p | cucuagagggaagcgcuuucug |
| 278 | hsa-miR-519c-3p | aaagugcaucuuuuagaggau |
| 279 | hsa-miR-519b-5p | cucuagagggaagcgcuuucug |
| 280 | hsa-miR-519b-3p | aaagugcauccuuuuagagguu |
| 281 | hsa-miR-519a* | cucuagagggaagcgcuuucug |
| 282 | hsa-miR-519a | aaagugcaucuuuuagagugu |
| 283 | hsa-miR-518f* | cucuagagggaagcacuuucuc |
| 284 | hsa-miR-518f | gaaagcgcuucucuuuagagg |
| 285 | hsa-miR-518e* | cucuagagggaagcgcuuucug |
| 286 | hsa-miR-518e | aaagcgcuucccuucagagug |
| 287 | hsa-miR-518d-5p | cucuagagggaagcacuuucug |
| 288 | hsa-miR-518d-3p | caaagcgcuucccuuuggagc |
| 289 | hsa-miR-518c* | ucucuggagggaagcacuuucug |
| 290 | hsa-miR-518c | caaagcgcuucucuuuagagugu |
| 291 | hsa-miR-518b | caaagcgcucccuuuagaggu |
| 292 | hsa-miR-518a-5p | cugcaaagggaagcccuuuc |
| 293 | hsa-miR-518a-3p | gaaagcgcuuccuuugcugga |
| 294 | hsa-miR-517c | aucgugcauccuuuuagagugu |
| 295 | hsa-miR-517b | ucgugcaucccuuuagaguguu |
| 296 | hsa-miR-517a | aucgugcaucccuuuagagugu |
| 297 | hsa-miR-517* | ccucuagauggaagcacugucu |
| 298 | hsa-miR-516b* | ugcuuccuuucagagggu |
| 299 | hsa-miR-516b | aucggagguaagaagcacuuu |
| 300 | hsa-miR-516a-5p | uucucgaggaaagaagcacuuuc |
| 301 | hsa-miR-516a-3p | ugcuuccuuucagagggu |
| 302 | hsa-miR-515-5p | uucuccaaaagaaagcacuuucug |
| 303 | hsa-miR-515-3p | gagugccuucuuuuggagcguu |
| 304 | hsa-miR-514 | auugacacuucugugaguaga |
| 305 | hsa-miR-513c | uucucaaggaggugucguuuau |
| 306 | hsa-miR-513b | uucacaaggaggugucauuuau |
| 307 | hsa-miR-513a-5p | uucacagggaggugucau |
| 308 | hsa-miR-513a-3p | uaaauuucaccuuucugagaagg |
| 309 | hsa-miR-512-5p | cacucagccuugagggcacuuuc |
| 310 | hsa-miR-512-3p | aagugcugucauagcugagguc |
| 311 | hsa-miR-511 | gugucuuuugcucugcaguca |
| 312 | hsa-miR-510 | uacucaggagaguggcaaucac |
| 313 | hsa-miR-509-5p | uacugcagacaguggcaauca |
| 314 | hsa-miR-509-3p | ugauugguacgucugugggua |
| 315 | hsa-miR-509-3-5p | uacugcagacguggcaaucaug |

FIG. 1 (Continued)

| 316 | hsa-miR-508-5p | uacuccagagggcgucacucaug |
|---|---|---|
| 317 | hsa-miR-508-3p | ugauuguagccuuuuggaguaga |
| 318 | hsa-miR-507 | uuuugcaccuuuuggagugaa |
| 319 | hsa-miR-506 | uaaggcacccuucugaguaga |
| 320 | hsa-miR-505* | gggagccaggaaguauugaugu |
| 321 | hsa-miR-505 | cgucaacacuugcugguuuccu |
| 322 | hsa-miR-504 | agacccuggucugcacucuauc |
| 323 | hsa-miR-503 | uagcagcgggaacaguucugcag |
| 324 | hsa-miR-502-5p | auccuugcuaucugggugcua |
| 325 | hsa-miR-502-3p | aaugcaccugggcaaggauuca |
| 326 | hsa-miR-501-5p | aauccuuugcccugggugaga |
| 327 | hsa-miR-501-3p | aaugcaccgggcaaggauucu |
| 328 | hsa-miR-500* | augcaccugggcaaggauucug |
| 329 | hsa-miR-500 | uaauccuugcuaccugggugaga |
| 330 | hsa-miR-499-5p | uuaagacuugcagugauguuu |
| 331 | hsa-miR-499-3p | aacaucacagcaagucugugcu |
| 332 | hsa-miR-498 | uuucaagccaggggggcguuuuuc |
| 333 | hsa-miR-497* | caaaccacacuguggguguuaga |
| 334 | hsa-miR-497 | cagcagcacacuguggguugu |
| 335 | hsa-miR-496 | ugaguauuacauggccaaucuc |
| 336 | hsa-miR-495 | aaacaaacauggugcacuucuu |
| 337 | hsa-miR-494 | ugaaacauacacgggaaaccuc |
| 338 | hsa-miR-493* | uuguacaugguaggcuuucauu |
| 339 | hsa-miR-493 | ugaaggucuacugugugccagg |
| 340 | hsa-miR-492 | aggaccugcgggacaagauucuu |
| 341 | hsa-miR-491-5p | aguggggaacccuuccaugagg |
| 342 | hsa-miR-491-3p | cuuaugcaagauucccuucuac |
| 343 | hsa-miR-490-5p | ccauggaucuccaggugggu |
| 344 | hsa-miR-490-3p | caaccuggaggacuccaugcug |
| 345 | hsa-miR-489 | gugacaucacauauacggcagc |
| 346 | hsa-miR-488* | cccagauaauggcacucucaa |
| 347 | hsa-miR-488 | uugaaaggcuauuucuugguc |
| 348 | hsa-miR-487b | aaucguacagggucauccacuu |
| 349 | hsa-miR-487a | aaucauacagggacauccaguu |
| 350 | hsa-miR-486-5p | uccuguacugagcugccccgag |
| 351 | hsa-miR-486-3p | cggggcagcucacaguacaggau |
| 352 | hsa-miR-485-5p | agaggcuggccgugaugaauuc |
| 353 | hsa-miR-485-3p | gucauacacggcucuccucucu |
| 354 | hsa-miR-484 | ucaggcucagucccccucccgau |
| 355 | hsa-miR-483-5p | aagacgggaggaaagaagggag |
| 356 | hsa-miR-483-3p | ucacuccucuccuccogucuu |
| 357 | hsa-miR-455-5p | uaugugccuuuggacuacaucg |
| 358 | hsa-miR-455-3p | gcaguccaugggcauauacac |
| 359 | hsa-miR-454* | acccuaucaauauugucucugc |
| 360 | hsa-miR-454 | uagugcaauauugcuuauagggu |
| 361 | hsa-miR-453 | agguuguccguggugaguucgca |
| 362 | hsa-miR-452* | cucaucugcaaagaaguaagug |
| 363 | hsa-miR-452 | aacuguuugcagaggaaacuga |
| 364 | hsa-miR-451 | aaaccguuaccauuacugaguu |
| 365 | hsa-miR-450b-5p | uuuugcaauauguuccugaaua |
| 366 | hsa-miR-450b-3p | uugggaucauuuugcauccaua |
| 367 | hsa-miR-450a | uuuugcgauguguuccuaauau |
| 368 | hsa-miR-449c* | uugcuaguugcacuccucucugu |

FIG. 1 (Continued)

| 369 | hsa-miR-449c | uaggcaguguauugcuagcggcugu |
| --- | --- | --- |
| 370 | hsa-miR-449b* | cagccacaacuacccugccacu |
| 371 | hsa-miR-449b | aggcaguguauuguuagcuggc |
| 372 | hsa-miR-449a | uggcaguguauuguuagcuggu |
| 373 | hsa-miR-448 | uugcauauguaggaugucccau |
| 374 | hsa-miR-433 | aucaugaugggcuccucggugu |
| 375 | hsa-miR-432* | cuggauggcuccuccaugucu |
| 376 | hsa-miR-432 | ucuuggaguaggucauugggugg |
| 377 | hsa-miR-431* | caggucgucuugcagggcuucu |
| 378 | hsa-miR-431 | ugucuugcaggccgucaugca |
| 379 | hsa-miR-429 | uaauacugucugguaaaaccgu |
| 380 | hsa-miR-425* | aucgggaaugucguguccgccc |
| 381 | hsa-miR-425 | aaugacacgaucacucccguuga |
| 382 | hsa-miR-424* | caaaacgugaggcgcugcuau |
| 383 | hsa-miR-424 | cagcagcaauucauguuuugaa |
| 384 | hsa-miR-423-5p | ugaggggcagagagcgagacuuu |
| 385 | hsa-miR-423-3p | agcucggucugaggccccucagu |
| 386 | hsa-miR-422a | acuggacuuagggucagaaggc |
| 387 | hsa-miR-421 | aucaacagacauuaauugggcgc |
| 388 | hsa-miR-412 | acuucaccugguccacuagcgu |
| 389 | hsa-miR-411* | uauguaacacgguccacuaacc |
| 390 | hsa-miR-411 | uaguagaccguauagcguacg |
| 391 | hsa-miR-410 | aauauaacacagauggccugu |
| 392 | hsa-miR-409-5p | agguuacccgagcaacuuugcau |
| 393 | hsa-miR-409-3p | gaauguugcucggugaaccccu |
| 394 | hsa-miR-384 | auuccuagaaauuguucaua |
| 395 | hsa-miR-383 | agaucagaaggugauuguggcu |
| 396 | hsa-miR-382 | gaaguuguucguggugauucg |
| 397 | hsa-miR-381 | uauacaagggcaagcucucugu |
| 398 | hsa-miR-380* | ugguugaccauagaacaugcgc |
| 399 | hsa-miR-380 | uauguaauaugguccacaucuu |
| 400 | hsa-miR-379* | uauguaacaugguccacuaacu |
| 401 | hsa-miR-379 | ugguagacuauggaacguagg |
| 402 | hsa-miR-378* | cuccugacuccagguccugugu |
| 403 | hsa-miR-378 | acuggacuuggagucagaagg |
| 404 | hsa-miR-377* | agagguugcccuuggugaauuc |
| 405 | hsa-miR-377 | aucacacaaaggcaacuuuugu |
| 406 | hsa-miR-376c | aacauagaggaaauuccacgu |
| 407 | hsa-miR-376b | aucauagaggaaaauccauguu |
| 408 | hsa-miR-376a* | guagauucuccuucuaugagua |
| 409 | hsa-miR-376a | aucauagaggaaaauccacgu |
| 410 | hsa-miR-375 | uuuguucguucggcucgcguga |
| 411 | hsa-miR-374b* | cuuagcagguuguauuaucauu |
| 412 | hsa-miR-374b | auauaauacaaccugcuaagug |
| 413 | hsa-miR-374a* | cuuaucagauuguauuguaauu |
| 414 | hsa-miR-374a | uuauaauacaaccugauaagug |
| 415 | hsa-miR-373* | acucaaaauggggcgcuuucc |
| 416 | hsa-miR-373 | gaagugcuucgauuuuggggugu |
| 417 | hsa-miR-372 | aaagugcugcgacauuugagcgu |
| 418 | hsa-miR-371-5p | acucaaacugugggggcacu |
| 419 | hsa-miR-371-3p | aagugccgccaucuuugagugu |
| 420 | hsa-miR-370 | gccugcuggggugaaccuggu |
| 421 | hsa-miR-369-5p | agaucgaccguguuauauucgc |

FIG. 1 (Continued)

| 422 | hsa-miR-369-3p | aauaauacaugguugaucuuu |
|---|---|---|
| 423 | hsa-miR-367* | acuguugcuaauaugcaacucu |
| 424 | hsa-miR-367 | aauugcacuuuagcaauggguga |
| 425 | hsa-miR-365* | agggacuuucaggggcagcugu |
| 426 | hsa-miR-365 | uaaugcccuaaaaauccuuau |
| 427 | hsa-miR-363* | cggguggaucacgaugcaauuu |
| 428 | hsa-miR-363 | aauugcacgguauccaucugua |
| 429 | hsa-miR-362-5p | aauccuuggaaccuaggugugagu |
| 430 | hsa-miR-362-3p | aacacaccuauucaaggauuca |
| 431 | hsa-miR-361-5p | uuaucagaaucuccaggguac |
| 432 | hsa-miR-361-3p | uccccaggugugauucugauuu |
| 433 | hsa-miR-34c-5p | aggcaguguaguuagcugauugc |
| 434 | hsa-miR-34c-3p | aaucacuaaccacacggccagg |
| 435 | hsa-miR-34b* | uaggcagugucauuagcugauug |
| 436 | hsa-miR-34b | caaucacuaacuccacugccau |
| 437 | hsa-miR-34a* | caaucagcaaguauacugcccu |
| 438 | hsa-miR-34a | uggcagugucuuagcugguugu |
| 439 | hsa-miR-346 | ugucugcccgcaugccugcucu |
| 440 | hsa-miR-345 | gcugacuccuagucagggcuc |
| 441 | hsa-miR-342-5p | aggggugcuaucugugauuga |
| 442 | hsa-miR-342-3p | ucucacacagaaaucgcacccgu |
| 443 | hsa-miR-340* | uccgucucaguuacuuuauagc |
| 444 | hsa-miR-340 | uuauaaagcaaugagacugauu |
| 445 | hsa-miR-33b* | cagugccucggcagugcagccc |
| 446 | hsa-miR-33b | gugcauugcuguugcauugc |
| 447 | hsa-miR-33a* | caauguuuccacagugcaucac |
| 448 | hsa-miR-33a | gugcauuguaguugcauugca |
| 449 | hsa-miR-339-5p | ucccuguccuccaggagcucacg |
| 450 | hsa-miR-339-3p | ugagcgccucgacgacagagccg |
| 451 | hsa-miR-338-5p | aacaauauccuggugcugagug |
| 452 | hsa-miR-338-3p | uccagcaucagugauuuuguug |
| 453 | hsa-miR-337-5p | gaacggcuucauacaggaguu |
| 454 | hsa-miR-337-3p | cuccuauaugaugccuuucuuc |
| 455 | hsa-miR-335* | uuuuucauuauugcuccugacc |
| 456 | hsa-miR-335 | ucaagagcaauaacgaaaaaugu |
| 457 | hsa-miR-331-5p | cuagguauggucccagggaucc |
| 458 | hsa-miR-331-3p | gccccugggccuauccuagaa |
| 459 | hsa-miR-330-5p | ucucugggccugugucuuaggc |
| 460 | hsa-miR-330-3p | gcaaagcacacggccugcagaga |
| 461 | hsa-miR-329 | aacacaccugguuaaccucuuu |
| 462 | hsa-miR-328 | cuggcccucucugcccuuccgu |
| 463 | hsa-miR-326 | ccucugggcccuuccuccag |
| 464 | hsa-miR-325 | ccuaguaggguguccaguaagugu |
| 465 | hsa-miR-324-5p | cgcauccccagggcauuggugu |
| 466 | hsa-miR-324-3p | acugcccaggugcugcugg |
| 467 | hsa-miR-323-5p | aggugguccguggcgcguucgc |
| 468 | hsa-miR-323-3p | cacauuacacggucgaccucu |
| 469 | hsa-miR-320d | aaaagcuggguugagagga |
| 470 | hsa-miR-320c | aaaagcuggguugagagggu |
| 471 | hsa-miR-320b | aaaagcuggguugagagggcaa |
| 472 | hsa-miR-320a | aaaagcuggguugagagggcga |
| 473 | hsa-miR-32* | caauuuagugugugugauauuu |
| 474 | hsa-miR-32 | uauugcacauuacaaguugca |

FIG. 1 (Continued)

| | | |
|---|---|---|
| 475 | hsa-miR-31* | ugcuaugccaacauauugccau |
| 476 | hsa-miR-31 | aggcaagaugcuggcauagcu |
| 477 | hsa-miR-30e* | cuuucagucggauguuuacagc |
| 478 | hsa-miR-30e | uguaaacauccuugacuggaag |
| 479 | hsa-miR-30d* | cuuucagucagauguuugcugc |
| 480 | hsa-miR-30d | uguaaacauccccgacuggaag |
| 481 | hsa-miR-30c-2* | cugggagaaggcuguuuacucu |
| 482 | hsa-miR-30c-1* | cugggagagguuguuuacucc |
| 483 | hsa-miR-30c | uguaaacauccuacacucucagc |
| 484 | hsa-miR-30b* | cugggaggugggauguuuacuuc |
| 485 | hsa-miR-30b | uguaaacauccuacacucagcu |
| 486 | hsa-miR-30a* | cuuucagucggauguuugcagc |
| 487 | hsa-miR-30a | uguaaacauccucgacuggaag |
| 488 | hsa-miR-302f | uaauugcuuccauguuu |
| 489 | hsa-miR-302e | uaagugcuuccaugcuu |
| 490 | hsa-miR-302d* | acuuuaacauggaggcacuugc |
| 491 | hsa-miR-302d | uaagugcuuccauguuugagugu |
| 492 | hsa-miR-302c* | uuuaacauggggguaccugcug |
| 493 | hsa-miR-302c | uaagugcuuccauguuucagugg |
| 494 | hsa-miR-302b* | acuuuaacauggaagugcuuuc |
| 495 | hsa-miR-302b | uaagugcuuccauguuuuaguag |
| 496 | hsa-miR-302a* | acuuaaacguggauguacuugcu |
| 497 | hsa-miR-302a | uaagugcuuccauguuuugguga |
| 498 | hsa-miR-301b | cagugcaaugauauugucaaagc |
| 499 | hsa-miR-301a | cagugcaauaguauugucaaagc |
| 500 | hsa-miR-300 | uauacaagggcagacucucucu |
| 501 | hsa-miR-29c* | ugaccgauuucuccgguguuc |
| 502 | hsa-miR-29c | uagcaccauuugaaaucgguua |
| 503 | hsa-miR-29b-2* | cugguuucacaugguggcuuag |
| 504 | hsa-miR-29b-1* | gcugguuucauaugguggguuuaga |
| 505 | hsa-miR-29b | uagcaccauuugaaaucaguguu |
| 506 | hsa-miR-29a* | acugauuucuuuugguguucag |
| 507 | hsa-miR-29a | uagcaccaucugaaaucgguua |
| 508 | hsa-miR-299-5p | ugguuuaccgucccacauacau |
| 509 | hsa-miR-299-3p | uaugugggaugguaaaccgcuu |
| 510 | hsa-miR-298 | agcagaagcagggagguucuccca |
| 511 | hsa-miR-297 | auguaugugugcaugugcaug |
| 512 | hsa-miR-296-5p | agggcccccccucaauccugu |
| 513 | hsa-miR-296-3p | gaggguuggguggaggcucucc |
| 514 | hsa-miR-28-5p | aaggagcucacagucuauugag |
| 515 | hsa-miR-28-3p | cacuagauugugagcuccugga |
| 516 | hsa-miR-27b* | agagcuuagcugauuggugaac |
| 517 | hsa-miR-27b | uucacaguggcuaaguucugc |
| 518 | hsa-miR-27a* | agggcuuagcugcuugugagca |
| 519 | hsa-miR-27a | uucacaguggcuaaguuccgc |
| 520 | hsa-miR-26b* | ccuguucuccauuacuuggcuc |
| 521 | hsa-miR-26b | uucaaguaauucaggauaggu |
| 522 | hsa-miR-26a-2* | ccuauucuugauuacuuguuuc |
| 523 | hsa-miR-26a-1* | ccuauucuugguuacuugcacg |
| 524 | hsa-miR-26a | uucaaguaauccaggauaggcu |
| 525 | hsa-miR-25* | aggcggagacuugggcaauug |
| 526 | hsa-miR-25 | cauugcacuugucucggucuga |
| 527 | hsa-miR-24-2* | ugccuacugagcugaaacacag |

FIG. 1 (Continued)

| 528 | hsa-miR-24-1* | ugccuacugagcugauaucagu |
|---|---|---|
| 529 | hsa-miR-24 | uggcucaguucagcaggaacag |
| 530 | hsa-miR-23b* | ugggguuccuggcaugcugauuu |
| 531 | hsa-miR-23b | aucacauugccagggauuacc |
| 532 | hsa-miR-23a* | gggguuccuggggaugggauuu |
| 533 | hsa-miR-23a | aucacauugccagggauuucc |
| 534 | hsa-miR-2278 | gagagcagugugaguugccugg |
| 535 | hsa-miR-2277 | ugacagcgcccugccuggcuc |
| 536 | hsa-miR-2276 | ucugcaagugucagaggcgagg |
| 537 | hsa-miR-224* | aaaauggugcccuagugacuaca |
| 538 | hsa-miR-224 | caagucacuagugguuccguu |
| 539 | hsa-miR-223* | cguguauuugacaagcugaguu |
| 540 | hsa-miR-223 | ugucaguuugucaaauacccca |
| 541 | hsa-miR-222* | cucaguagccaguguagauccu |
| 542 | hsa-miR-222 | agcuacaucuggcuacugggu |
| 543 | hsa-miR-221* | accuggcauacaauguagauuu |
| 544 | hsa-miR-221 | agcuacauugucugcuggguuuc |
| 545 | hsa-miR-220c | acacagggcuguugugaagacu |
| 546 | hsa-miR-220b | ccaccaccgugucugacacuu |
| 547 | hsa-miR-220a | ccacaccguaucugacacuuu |
| 548 | hsa-miR-22* | aguucuucaguggcaagcuuua |
| 549 | hsa-miR-22 | aagcugccaguugaagaacugu |
| 550 | hsa-miR-219-5p | ugauuguccaaacgcaauucu |
| 551 | hsa-miR-219-2-3p | agaauugugcuggacaucugu |
| 552 | hsa-miR-219-1-3p | agaguugagucuggacgucccg |
| 553 | hsa-miR-218-2* | caugguucugucaagcaccgcg |
| 554 | hsa-miR-218-1* | augguuccgucaagcaccaugg |
| 555 | hsa-miR-218 | uugugcuugaucuaaccaugu |
| 556 | hsa-miR-217 | uacugcaucaggaacugauugga |
| 557 | hsa-miR-216b | aaaucucugcaggcaaauguga |
| 558 | hsa-miR-216a | uaaucucagcuggcaacuguga |
| 559 | hsa-miR-215 | augaccuaugaauugacagac |
| 560 | hsa-miR-214* | ugccugucuacacuugcugugc |
| 561 | hsa-miR-214 | acagcaggcacagacaggcagu |
| 562 | hsa-miR-212 | uaacagucuccagucacggcc |
| 563 | hsa-miR-2117 | uguucucuuugccaaggacag |
| 564 | hsa-miR-2116* | ccucccaugccaagaacuccc |
| 565 | hsa-miR-2116 | gguucuuagcauaggaggucu |
| 566 | hsa-miR-2115* | caucagaauucauggaggcuag |
| 567 | hsa-miR-2115 | agcuuccaugacuccugaugga |
| 568 | hsa-miR-2114* | cgagccucaagcaagggacuu |
| 569 | hsa-miR-2114 | uaguccuuccuugaagcgguc |
| 570 | hsa-miR-2113 | auuugugcuuggcucugucac |
| 571 | hsa-miR-2110 | uuggggaaacggccgcugagug |
| 572 | hsa-miR-211 | uucccuuugucauccuucgccu |
| 573 | hsa-miR-210 | cugugcgugugacagcggcuga |
| 574 | hsa-miR-21* | caacaccagucgaugggcugu |
| 575 | hsa-miR-21 | uagcuuaucagacugauguuga |
| 576 | hsa-miR-20b* | acuguaguaugggcacuuccag |
| 577 | hsa-miR-20b | caaagugcucauagugcagguag |
| 578 | hsa-miR-20a* | acugcauuaugagcacuuaaag |
| 579 | hsa-miR-20a | uaaagugcuuauagugcagguag |
| 580 | hsa-miR-208b | auaagacgaacaaaagguuugu |

FIG. 1 (Continued)

| 581 | hsa-miR-208a | auaagacgagcaaaaagcuugu |
|---|---|---|
| 582 | hsa-miR-206 | uggaauguaaggaagugugugg |
| 583 | hsa-miR-2054 | cuguaauauaaauuuaauuuauu |
| 584 | hsa-miR-2053 | guguuaauuaaaccucuauuuac |
| 585 | hsa-miR-2052 | uguuuugauaacaguaaugu |
| 586 | hsa-miR-205* | gauuucaguggagugaaguuc |
| 587 | hsa-miR-205 | uccuucauuccaccggagucug |
| 588 | hsa-miR-204 | uucccuuugucauccuaugccu |
| 589 | hsa-miR-203 | gugaaauguuuaggaccacuag |
| 590 | hsa-miR-202* | uuccuaugcauauacuucuuug |
| 591 | hsa-miR-202 | agagguauagggcaugggaa |
| 592 | hsa-miR-200c* | cgucuuaccagcaguguuugg |
| 593 | hsa-miR-200c | uaauacugccggguaaugaugga |
| 594 | hsa-miR-200b* | caucuuacugggcagcauugga |
| 595 | hsa-miR-200b | uaauacugccugguaaugauga |
| 596 | hsa-miR-200a* | caucuuaccggacagugcugga |
| 597 | hsa-miR-200a | uaacacugucugguaacgaugu |
| 598 | hsa-miR-19b-2* | aguuuugcagguuugcauuuca |
| 599 | hsa-miR-19b-1* | aguuuugcagguuugcauccagc |
| 600 | hsa-miR-19b | ugugcaaauccaugcaaaacuga |
| 601 | hsa-miR-19a* | aguuuugcauaguugcacuaca |
| 602 | hsa-miR-19a | ugugcaaaucuaugcaaaacuga |
| 603 | hsa-miR-199b-5p | cccaguguuuagacuaucuguuc |
| 604 | hsa-miR-199b-3p | acaguagucugcacauugguua |
| 605 | hsa-miR-199a-5p | cccaguguucagacuaccuguuc |
| 606 | hsa-miR-199a-3p | acaguagucugcacauugguua |
| 607 | hsa-miR-198 | gguccagaggggagauagguuc |
| 608 | hsa-miR-1979 | cucccacugcuucacuugacua |
| 609 | hsa-miR-1978 | gguuugguccuagccuuucua |
| 610 | hsa-miR-1977 | gauuagggugcuuagcuguuaa |
| 611 | hsa-miR-1976 | ccuccugcccuccuugcugu |
| 612 | hsa-miR-1975 | cccccacaaccgcgcuugacuagcu |
| 613 | hsa-miR-1974 | ugguuguaguccgugcgagaaua |
| 614 | hsa-miR-1973 | accgugcaaagguagcaua |
| 615 | hsa-miR-1972 | ucaggccaggcacaguggcuca |
| 616 | hsa-miR-197 | uucaccaccuucuccacccagc |
| 617 | hsa-miR-196b* | ucgacagcacgacacugccuuc |
| 618 | hsa-miR-196b | uagguaguuuccuguuguuggg |
| 619 | hsa-miR-196a* | cggcaacaagaaacugccugag |
| 620 | hsa-miR-196a | uagguaguuucauguuguuggg |
| 621 | hsa-miR-195* | ccaauauuggcugugcugcucc |
| 622 | hsa-miR-195 | uagcagcacagaaauauuggc |
| 623 | hsa-miR-194* | ccaguggggcugcuguuaucug |
| 624 | hsa-miR-194 | uguaacagcaacuccaugugga |
| 625 | hsa-miR-193b* | cggggguuugagggcgagauga |
| 626 | hsa-miR-193b | aacuggcccucaaaguccgcu |
| 627 | hsa-miR-193a-5p | ugggucuuugcgggcgagauga |
| 628 | hsa-miR-193a-3p | aacuggccuacaaaguccagu |
| 629 | hsa-miR-192* | cugccaauuccauaggucacag |
| 630 | hsa-miR-192 | cugaccuaugaauugacagcc |
| 631 | hsa-miR-1915* | accuugccuugcugcccgggcc |
| 632 | hsa-miR-1915 | ccccagggcgacgcggcggg |
| 633 | hsa-miR-1914* | ggaggggucccgcacugggagg |

FIG. 1 (Continued)

| 634 | hsa-miR-1914 | cccugugcccggcccacuucug |
|---|---|---|
| 635 | hsa-miR-1913 | ucugcccccuccgcugcugcca |
| 636 | hsa-miR-1912 | uaccagagcaugcagugugaa |
| 637 | hsa-miR-1911* | caccaggcauguggucucc |
| 638 | hsa-miR-1911 | ugaguaccgccaugucuguugg |
| 639 | hsa-miR-1910 | ccaguccugugccugccgccu |
| 640 | hsa-miR-191* | gcugcgcuuggauuucgucccc |
| 641 | hsa-miR-191 | caacggaaucccaaaagcagcug |
| 642 | hsa-miR-190b | ugauauguuugauauuggguu |
| 643 | hsa-miR-1909* | ugagugccggugccugcccug |
| 644 | hsa-miR-1909 | cgcaggggccggguqcucaccg |
| 645 | hsa-miR-1908 | cggcggggacggcgauugguc |
| 646 | hsa-miR-190 | ugauauguuugauauauuaggu |
| 647 | hsa-miR-18b* | ugcccuaaaugcccccuucuggc |
| 648 | hsa-miR-18b | uaaggugcaucuagugcaguuag |
| 649 | hsa-miR-18a* | acugcccuaagugcuccuucugg |
| 650 | hsa-miR-18a | uaaggugcaucuagugcagauag |
| 651 | hsa-miR-188-5p | caucccuugcaugguggaggg |
| 652 | hsa-miR-188-3p | cucccacaugcagggu uugca |
| 653 | hsa-miR-187* | ggcuacaacacaggacccgggc |
| 654 | hsa-miR-187 | ucgugucuuguguugcagccgg |
| 655 | hsa-miR-186* | gcccaaaggugaauuuuuuggg |
| 656 | hsa-miR-186 | caaagaauucuccuuuugggcu |
| 657 | hsa-miR-185* | aggggcuggcuuuccucugguc |
| 658 | hsa-miR-185 | uggagagaaaggcaguuccuga |
| 659 | hsa-miR-184 | uggacggagaacugauaagggu |
| 660 | hsa-miR-183* | gugaauuaccgaagggccauaa |
| 661 | hsa-miR-183 | uauggcacugguagaauucacu |
| 662 | hsa-miR-1827 | ugaggcaguagauugaau |
| 663 | hsa-miR-1826 | auugaucaucgacacuucgaacgcaau |
| 664 | hsa-miR-1825 | uccagugcccuccucucc |
| 665 | hsa-miR-182* | ugguucuagacuugccaacua |
| 666 | hsa-miR-182 | uuuggcaaugguagaacucacacu |
| 667 | hsa-miR-181d | aacauucauuguugucgguggu |
| 668 | hsa-miR-181c* | aaccaucgaccguugaguggac |
| 669 | hsa-miR-181c | aacauucaaccugucggugagu |
| 670 | hsa-miR-181b | aacauucauugcugucgguggu |
| 671 | hsa-miR-181a-2* | accacugaccguugacuguacc |
| 672 | hsa-miR-181a* | accaucgaccguugauuguacc |
| 673 | hsa-miR-181a | aacauucaacgcugucggugagu |
| 674 | hsa-miR-17* | acugcagugaaggcacuuguag |
| 675 | hsa-miR-17 | caaagugcuuacagugcagguag |
| 676 | hsa-miR-16-2* | ccauauuacugugcugcuuua |
| 677 | hsa-miR-16-1* | ccaguauuaacugugcugcuga |
| 678 | hsa-miR-16 | uagcagcacguaaauauuggcg |
| 679 | hsa-miR-15b* | cgaaucauuauugcugcucua |
| 680 | hsa-miR-15b | uagcagcacaucaugguuuaca |
| 681 | hsa-miR-15a* | caggccauauugugcugccuca |
| 682 | hsa-miR-15a | uagcagcacauaaugguuugug |
| 683 | hsa-miR-155* | cuccuacauauuagcauuaaca |
| 684 | hsa-miR-155 | uuaaugcuaaucugauaggggu |
| 685 | hsa-miR-154* | aaucauacacgguugaccuauu |
| 686 | hsa-miR-154 | uagguuauccguguugccuucg |

FIG. 1 (Continued)

| 687 | hsa-miR-1539 | uccugcgcgucccagaugccc |
|---|---|---|
| 688 | hsa-miR-1538 | cggcccgggcugcugcuguuccu |
| 689 | hsa-miR-1537 | aaaaccgucuaguuacaguugu |
| 690 | hsa-miR-153 | uugcauagucacaaaagugauc |
| 691 | hsa-miR-152 | ucagugcaugacagaacuugg |
| 692 | hsa-miR-151-5p | ucgaggagcucacagucuagu |
| 693 | hsa-miR-151-3p | cuagacugaagcuccuugagg |
| 694 | hsa-miR-150* | cugguacaggccuggggacag |
| 695 | hsa-miR-150 | ucucccaacccuuguaccagug |
| 696 | hsa-miR-149* | agggagggacggggcugugc |
| 697 | hsa-miR-149 | ucuggcuccgugucuucacuccc |
| 698 | hsa-miR-148b* | aaguucuguuauacacucaggc |
| 699 | hsa-miR-148b | ucagugcaucacagaacuuugu |
| 700 | hsa-miR-148a* | aaaguucugagacacuccgacu |
| 701 | hsa-miR-148a | ucagugcacuacagaacuuugu |
| 702 | hsa-miR-147b | gugugcggaaaugcuucugcua |
| 703 | hsa-miR-1471 | gcccgcguguggagccaggugu |
| 704 | hsa-miR-1470 | gcccuccgcccgugcaccccg |
| 705 | hsa-miR-147 | gugugugaaaugcuucugc |
| 706 | hsa-miR-146b-5p | ugagaacugaauuccauaggcu |
| 707 | hsa-miR-146b-3p | ugcccuguggacucaguucugg |
| 708 | hsa-miR-146a* | ccucugaaauucaguucuucag |
| 709 | hsa-miR-146a | ugagaacugaauuccauggguu |
| 710 | hsa-miR-1469 | cucggcgcggggcgcgggcucc |
| 711 | hsa-miR-1468 | cuccguuugccuguuucgcug |
| 712 | hsa-miR-145* | ggauuccuggaaauacuguucu |
| 713 | hsa-miR-145 | guccaguuuucccaggaaucccu |
| 714 | hsa-miR-144* | ggauaucaucauauacuguaag |
| 715 | hsa-miR-144 | uacaguauagaugauguacu |
| 716 | hsa-miR-143* | ggugcagugcugcaucucuggu |
| 717 | hsa-miR-143 | ugagaugaagcacuguagcuc |
| 718 | hsa-miR-142-5p | cauaaaguagaaagcacuacu |
| 719 | hsa-miR-142-3p | uguaguguuuccuacuuuaugga |
| 720 | hsa-miR-141* | caucuuccaguacaguguugga |
| 721 | hsa-miR-141 | uaacacugucugguaaagaugg |
| 722 | hsa-miR-140-5p | caguguuuuacccuaugguag |
| 723 | hsa-miR-140-3p | uaccacaggguagaaccacgg |
| 724 | hsa-miR-139-5p | ucuacagugcacgugucuccag |
| 725 | hsa-miR-139-3p | gggacgcggcccuguuggagu |
| 726 | hsa-miR-138-2* | gcuauuucacgacaccagggu |
| 727 | hsa-miR-138-1* | gcuacuucacaacaccagggcc |
| 728 | hsa-miR-138 | agcugguguugugaaucaggccg |
| 729 | hsa-miR-137 | uuauugcuuaagaauacgcguag |
| 730 | hsa-miR-136* | caucaucgucucaaaugagucu |
| 731 | hsa-miR-136 | acuccauuuguuugaugaugga |
| 732 | hsa-miR-135b* | auagggcuaaaagccauggg |
| 733 | hsa-miR-135b | uauggcuuuucauuccuauguga |
| 734 | hsa-miR-135a* | uauagggauuggagccguggcg |
| 735 | hsa-miR-135a | uauggcuuuuuauuccuauguga |
| 736 | hsa-miR-134 | ugugacugguugaccagagggg |
| 737 | hsa-miR-133b | uuuggucccuucaaccagcua |
| 738 | hsa-miR-133a | uuuggucccuucaaccagcug |
| 739 | hsa-miR-1324 | ccagacagaauucuaugcacuuuc |

FIG. 1 (Continued)

| | | |
|---|---|---|
| 740 | hsa-miR-1323 | ucaaaacugaggggcauuuucu |
| 741 | hsa-miR-1322 | gaugaugcugcugaugcug |
| 742 | hsa-miR-1321 | cagggaggugaaugugau |
| 743 | hsa-miR-132* | accguggcuuucgauuguuacu |
| 744 | hsa-miR-132 | uaacagucuacagccauggucg |
| 745 | hsa-miR-130b* | acucuuucccuguugcacuac |
| 746 | hsa-miR-130b | cagugcaaugaugaaagggcau |
| 747 | hsa-miR-130a* | uucacauugugcuacugucugc |
| 748 | hsa-miR-130a | cagugcaauguuaaaagggcau |
| 749 | hsa-miR-1308 | gcaugggugguucagugg |
| 750 | hsa-miR-1307 | acucggcguggcgucggucgug |
| 751 | hsa-miR-1306 | acguuggcucgguggug |
| 752 | hsa-miR-1305 | uuuucaacucuaaugggagaga |
| 753 | hsa-miR-1304 | uuugaggcuacagugagaugug |
| 754 | hsa-miR-1303 | uuuagagacggggucuugcucu |
| 755 | hsa-miR-1302 | uugggacauacuuaugcuaaa |
| 756 | hsa-miR-1301 | uugcagcugccugggagugacuuc |
| 757 | hsa-miR-1299 | uucuggaauucugugugaggga |
| 758 | hsa-miR-1298 | uucauucggcguccagaugua |
| 759 | hsa-miR-1297 | uucaaguaauucaggug |
| 760 | hsa-miR-1296 | uuagggcccuggcuccaucucc |
| 761 | hsa-miR-129-5p | cuuuuugcggucugggcuugc |
| 762 | hsa-miR-1295 | uuaggccgcagaucuggguga |
| 763 | hsa-miR-1294 | ugugagguuggcauuguugucu |
| 764 | hsa-miR-129-3p | aagcccuuaccccaaaaagcau |
| 765 | hsa-miR-1293 | uggguggucuggagauuugugc |
| 766 | hsa-miR-1292 | ugggaacggguuccggcagacgcug |
| 767 | hsa-miR-1291 | uggcccugacugaagaccagcagu |
| 768 | hsa-miR-1290 | uggauuuuuggaucaggga |
| 769 | hsa-miR-129* | aagcccuuaccccaaaaaguau |
| 770 | hsa-miR-1289 | uggaguccaggaaucugcauuuu |
| 771 | hsa-miR-1288 | uggacugcccugaucuggaga |
| 772 | hsa-miR-1287 | ugcuggaucagugguucgaguc |
| 773 | hsa-miR-1286 | ugcaggaccaagaugagcccu |
| 774 | hsa-miR-1285 | ucugggcaacaaagugagaccu |
| 775 | hsa-miR-1284 | ucuauacagacccuggcuuuuc |
| 776 | hsa-miR-1283 | ucuacaaaggaaagcgcuuucu |
| 777 | hsa-miR-1282 | ucguuugccuuuuucugcuu |
| 778 | hsa-miR-1281 | ucgccuccuccucuccc |
| 779 | hsa-miR-1280 | ucccaccgcugccaccc |
| 780 | hsa-miR-128 | ucacagugaaccggucucuuu |
| 781 | hsa-miR-1279 | ucauauugcuucuuucu |
| 782 | hsa-miR-1278 | uaguacugugcauaucaucuau |
| 783 | hsa-miR-1277 | uacguagauauauauguauuuu |
| 784 | hsa-miR-1276 | uaaagagcccguggagaca |
| 785 | hsa-miR-127-5p | cugaagcucagagggcucugau |
| 786 | hsa-miR-1275 | gugggggagaggcuguc |
| 787 | hsa-miR-1274b | ucccuguucgggcgcca |
| 788 | hsa-miR-1274a | gucccuguucaggcgcca |
| 789 | hsa-miR-127-3p | ucggauccgucugagcuuggcu |
| 790 | hsa-miR-1273 | gggcgacaaagcaagacucuuucuu |
| 791 | hsa-miR-1272 | gaugaugauggcagcaaauucugaaa |
| 792 | hsa-miR-1271 | cuuggcaccuagcaagcacuca |

FIG. 1 (Continued)

| 793 | hsa-miR-1270 | cuggagauauggaagagcugugu |
|---|---|---|
| 794 | hsa-miR-1269 | cuggacugagccgugcuacugg |
| 795 | hsa-miR-1268 | cgggcgugguggugggg |
| 796 | hsa-miR-1267 | ccuguugaaguguaaucccca |
| 797 | hsa-miR-1266 | ccucagggcuguagaacagggcu |
| 798 | hsa-miR-1265 | caggaugguggucaaguguuguu |
| 799 | hsa-miR-1264 | caagucuuauuugagcaccuguu |
| 800 | hsa-miR-1263 | augguacccuggcauacugagu |
| 801 | hsa-miR-1262 | augggugaauuuguagaaggau |
| 802 | hsa-miR-1261 | auggauaaggcuuuggcuu |
| 803 | hsa-miR-1260 | aucccaccucugccacca |
| 804 | hsa-miR-126* | cauuauuacuuuugguacgcg |
| 805 | hsa-miR-126 | ucguaccgugaguaauaaugcg |
| 806 | hsa-miR-125b-2* | ucacaagucaggcucuugggac |
| 807 | hsa-miR-125b-1* | acggguuaggcucuugggagcu |
| 808 | hsa-miR-125b | ucccugagacccuaacuuguga |
| 809 | hsa-miR-125a-5p | ucccugagacccuuuaaccuguga |
| 810 | hsa-miR-125a-3p | acaggugagguucuugggagcc |
| 811 | hsa-miR-1259 | auauaugaugacuuagcuuuu |
| 812 | hsa-miR-1258 | aguuaggauuaggucguggaa |
| 813 | hsa-miR-1257 | agugaaugauggguucugacc |
| 814 | hsa-miR-1256 | aggcauugacuucucacuagcu |
| 815 | hsa-miR-1255b | cggaugagcaaagaaagugguu |
| 816 | hsa-miR-1255a | aggaugagcaaagaaaguagauu |
| 817 | hsa-miR-1254 | agccuggaagcuggagccugcagu |
| 818 | hsa-miR-1253 | agagaagaagaucagccugca |
| 819 | hsa-miR-1252 | agaaggaaauugaauucauuua |
| 820 | hsa-miR-1251 | acucuagcugccaaaggcgcu |
| 821 | hsa-miR-1250 | acggugcuggaugugguccuuu |
| 822 | hsa-miR-1249 | acgcccuucccccccuucuuca |
| 823 | hsa-miR-1248 | accuucuuguauaagcacugugcuaaa |
| 824 | hsa-miR-1247 | accgucccguucguccccgga |
| 825 | hsa-miR-1246 | aauggauuuuuggagcagg |
| 826 | hsa-miR-1245 | aagugaucuaaaggccuacau |
| 827 | hsa-miR-1244 | aaguaguugguuuguaugagaugguu |
| 828 | hsa-miR-1243 | aacuggaucaauuauaggagug |
| 829 | hsa-miR-124* | cguguucacagcggaccuugau |
| 830 | hsa-miR-124 | uaaggcacgcggugaaugcc |
| 831 | hsa-miR-1238 | cuuccucgucugucugcccc |
| 832 | hsa-miR-1237 | uccuucugcuccguccccag |
| 833 | hsa-miR-1236 | ccucuuccccuugucucuccag |
| 834 | hsa-miR-1234 | ucggccugaccacccacccac |
| 835 | hsa-miR-1233 | ugagcccuguccucccgcag |
| 836 | hsa-miR-1231 | gugucugggcggacagcugc |
| 837 | hsa-miR-1229 | cucucaccacugcccucccacag |
| 838 | hsa-miR-1228* | gugggcggggcaggugugug |
| 839 | hsa-miR-1228 | ucacaccugccucgcccccc |
| 840 | hsa-miR-1227 | cgugccacccuuuucccag |
| 841 | hsa-miR-1226* | gugagggcaugcaggccuggaugggg |
| 842 | hsa-miR-1226 | ucaccagcccuguguucccuag |
| 843 | hsa-miR-1225-5p | guggguacgcccaguggggg |
| 844 | hsa-miR-1225-3p | ugagcccugugccgccccag |
| 845 | hsa-miR-1224-5p | gugaggacucgggaggugg |

FIG. 1 (Continued)

| | | |
|---|---|---|
| 846 | hsa-miR-1224-3p | ccccaccuccucucuccucag |
| 847 | hsa-miR-122* | aacgccauuaucacacuaaaua |
| 848 | hsa-miR-122 | uggagugugacaauggguguuug |
| 849 | hsa-miR-1208 | ucacuguucagacaggcgga |
| 850 | hsa-miR-1207-5p | uggcagggaggcugggagggg |
| 851 | hsa-miR-1207-3p | ucagcuggcccucauuuc |
| 852 | hsa-miR-1206 | uguucauguagauguuuaagc |
| 853 | hsa-miR-1205 | ucugcaggguuugcuuugag |
| 854 | hsa-miR-1204 | ucguggccuggucuccauuau |
| 855 | hsa-miR-1203 | cccggagccaggaugcagcuc |
| 856 | hsa-miR-1202 | gugccagcugcaguggggag |
| 857 | hsa-miR-1201 | agccugauuaaacacaugcucuga |
| 858 | hsa-miR-1200 | cuccugagccauucugagccuc |
| 859 | hsa-miR-1197 | uaggacacauggucuacuucu |
| 860 | hsa-miR-1185 | agaggauacccuuuguauguu |
| 861 | hsa-miR-1184 | ccugcagcgacuugauggcuucc |
| 862 | hsa-miR-1183 | cacguaggugauggugagaguggca |
| 863 | hsa-miR-1182 | gagggucuugggagggaugugac |
| 864 | hsa-miR-1181 | ccgucgccgccacccgagccg |
| 865 | hsa-miR-1180 | uuuccggcucgcgugggugugu |
| 866 | hsa-miR-1179 | aagcauucuuucauugguugg |
| 867 | hsa-miR-1178 | uugcucacuguucuucccuag |
| 868 | hsa-miR-10b* | acagauucgauucuaggggaau |
| 869 | hsa-miR-10b | uacccguagaaccgaauuugug |
| 870 | hsa-miR-10a* | caaauucguaucuaggggaaua |
| 871 | hsa-miR-10a | uacccguagauccgaauuugug |
| 872 | hsa-miR-107 | agcagcauuguacagggcuauca |
| 873 | hsa-miR-106b* | ccgcacugugggacuugcugc |
| 874 | hsa-miR-106b | uaaagugcugacagugcagau |
| 875 | hsa-miR-106a* | cugcaauguaagcacuucuuac |
| 876 | hsa-miR-106a | aaaagugcuuacagugcagguag |
| 877 | hsa-miR-105* | acggauguuugagcaugugcua |
| 878 | hsa-miR-105 | ucaaaugcucagacuccuggu |
| 879 | hsa-miR-103-as | ucauagcccuguacaaugcugcu |
| 880 | hsa-miR-103-2* | agcuucuuuacagugcugccuug |
| 881 | hsa-miR-103 | agcagcauuguacagggcuauga |
| 882 | hsa-miR-101* | caguuaucacagugcugaugcu |
| 883 | hsa-miR-101 | uacaguacugugauaacugaa |
| 884 | hsa-miR-100* | caagcuuguaucuauagguaug |
| 885 | hsa-miR-100 | aacccguagauccgaacuugug |
| 886 | hsa-miR-1 | uggaauguaaagaaguauguau |
| 887 | hsa-let-7i* | cugcgcaagcuacugccuugcu |
| 888 | hsa-let-7i | ugagguaguaguuugugcuguu |
| 889 | hsa-let-7g* | cuguacaggccacugccuugc |
| 890 | hsa-let-7g | ugagguaguaguuuguacaguu |
| 891 | hsa-let-7f-2* | cuauacagucuacugucuuucc |
| 892 | hsa-let-7f-1* | cuauacaaucuauugccuuccc |
| 893 | hsa-let-7f | ugagguaguagauuguauaguu |
| 894 | hsa-let-7e* | cuauacggccuccuagcuuucc |
| 895 | hsa-let-7e | ugagguaggagguuguauaguu |
| 896 | hsa-let-7d* | cuauacgaccugcugccuuucu |
| 897 | hsa-let-7d | agagguaguagguugcauaguu |
| 898 | hsa-let-7c* | uagaguuacacccugggaguua |

FIG. 1 (Continued)

| 899 | hsa-let-7c | ugagguaguagguuguauggu |
|---|---|---|
| 900 | hsa-let-7b* | cuauacaaccuacugccuuccc |
| 901 | hsa-let-7b | ugagguaguagguugugugguu |
| 902 | hsa-let-7a-2* | cuguacagccuccuagcuuucc |
| 903 | hsa-let-7a* | cuauacaaucuacugucuuuc |
| 904 | hsa-let-7a | ugagguaguagguuguauaguu |
| 905 | hsa-life-1 | uaauacugccugguaaugauga |
| 906 | hsa-life-2 | cucuccucuccuaaccucgcu |
| 907 | hsa-life-2-AS | agucgagagugggagaagagcgg |
| 908 | hsa-life-3 | aaaaccgucuaguuacagu |
| 909 | hsa-life-4 | cucagugaugaaaacuuugucca |
| 910 | hsa-life-6-5p | guugccuuuuguucccaugc |
| 911 | hsa-life-6-3p | uaggcaccaaaaagcaacaac |
| 912 | hsa-life-7-AS | gcugcaccggagacuggguaa |
| 913 | hsa-life-7 | uacccagucuccggugcagcc |
| 914 | hsa-life-9 | uuccucugaugacuuccuguuagu |
| 915 | hsa-life-9-AS | uggaacugaggaucugaggaa |
| 916 | hsa-life-11 | aguggcaaagucuuuccauau |
| 917 | hsa-life-12-5p | uuagcucagcgguuacuucgac |
| 918 | hsa-life-12-3p | caagcaaccugucugggluugu |
| 919 | hsa-life-13-3p | uaacgcauaauauggacau |
| 920 | hsa-life-13-5p | auguccauauuauggguuagu |
| 921 | hsa-life-14-3p | caguugcuaguugcacuccuc |
| 922 | hsa-life-14-5p | aggcaguguauugcuagcggc |
| 923 | hsa-life-17 | aguucuugccugguuucucua |
| 924 | hsa-life-21 | ucugcauugccagggauu |
| 925 | hsa-life-22 | uagcuuuagagacugagag |
| 926 | hsa-life-26-3p | ugagacaggcuuaugcugcuauc |
| 927 | hsa-life-26-5p | agcagcaugaaccugucucac |
| 928 | hsa-life-27 | ccggcggcaggggluggcaccg |
| 929 | hsa-life-31-5p | gccuuaggagaaaguuucug |
| 930 | hsa-life-31-3p | uccuaaggcagucccugga |
| 931 | hsa-life-33-AS | aaggucgcccucaaggugacc |
| 932 | hsa-life-33 | augccugggaguugcgaucug |
| 933 | hsa-life-36-3p | uggaguuaaagacuuuucuc |
| 934 | hsa-life-36-5p | cagagaauaguuuaaauuagaauc |
| 935 | hsa-life-37-3p | ugcaacuuacugagggcuuugaa |
| 936 | hsa-life-37-5p | uggggguuuugcaguccuuagc |
| 937 | hsa-life-5-5p | agacacauacgagucauaua |
| 938 | hsa-life-5-3p | auaggacucauauagugccag |
| 939 | hsa-life-8 | auccccagauacaauggacaau |
| 940 | hsa-life-10 | uucaccuguuagccuguccagag |
| 941 | hsa-life-15-3p | ugacagcgcccugccuggcucgg |
| 942 | hsa-life-15-5p | agcgcgggcugagcgcugccagu |
| 943 | hsa-life-16-5p | uauacuacauauaauauaugua |
| 944 | hsa-life-16-3p | uauacuacauauaauauaugua |
| 945 | hsa-life-18 | uagcaccaucugaaaucgguuau |
| 946 | hsa-life-19-5p | gugcaaaagucaucacgguuu |
| 947 | hsa-life-19-3p | accgcgaugacuuuugcauca |
| 948 | hsa-life-20-3p | ucaccgcggucuuuuccucccac |
| 949 | hsa-life-20-5p | uugggggaaacgccgcugagu |
| 950 | hsa-life-23-3p | uccucccaugccaagaacucc |
| 951 | hsa-life-23-5p | gguucuuagcauaggaggucu |

FIG. 1 (Continued)

| 952 | hsa-life-24 | cugcguguccuaggugagggg |
| 953 | hsa-life-25 | ggcacagggcgaguggaaagaa |
| 954 | hsa-life-28-3p | ucacuaccugacaauacaguau |
| 955 | hsa-life-28-5p | ugcuguauugucagguagugau |
| 956 | hsa-life-29 | uggaggugaugaacugucugagcc |
| 957 | hsa-life-30 | ugcgugucccgccuguucccu |
| 958 | hsa-life-32-AS | ugugcugauugucacguucugauu |
| 959 | hsa-life-32 | acagaugaugaacuuauugacggg |
| 960 | hsa-life-34-3p | accuuccucuccaugggucuuuc |
| 961 | hsa-life-34-5p | agacccauugaggagaagguuc |
| 962 | hsa-life-35 | uucucaagagggaggcaauca |

Figure 2

| SEQ ID NO | miRNA | median ctrl | median 22Rv1 | mean ctrl | mean 22Rv1 | log2 median | hsa_t.avg | test_sd.up | mean t.avg | mean_sd.up |
|---|---|---|---|---|---|---|---|---|---|---|
| 714 | hsa-miR-144* | 6,543E+02 | 2,204E+02 | 2,968E+00 | 1,088E+00 | 2,392E-10 | 2,064E-07 | 9,182E-05 | 1,554E-03 |
| 701 | hsa-miR-148a | 9,557E+02 | 4,595E+02 | 2,080E+00 | 7,323E-01 | 1,666E-08 | 7,201E-06 | 5,627E-04 | 5,781E-03 |
| 279 | hsa-miR-519b-5p | 1,280E+02 | 1,450E+01 | 8,630E+00 | 2,178E+00 | 2,217E-07 | 5,002E-07 | 4,682E-11 | 4,041E-08 |
| 739 | hsa-miR-1324 | 1,254E+02 | 7,160E+00 | 1,751E+00 | 5,604E-01 | 2,898E-07 | 5,002E-05 | 5,818E-05 | 1,168E-03 |
| 729 | hsa-miR-137 | 7,689E+01 | 3,000E+00 | 2,563E+00 | 9,412E-01 | 2,350E-07 | 5,002E-05 | 3,320E-07 | 2,866E-05 |
| 206 | hsa-miR-556-5p | 1,181E+02 | 3,274E+01 | 3,607E+00 | 1,283E+00 | 5,268E-07 | 7,577E-05 | 1,615E-08 | 2,323E-06 |
| 460 | hsa-miR-330-3p | 3,784E+02 | 2,144E+02 | 1,765E+00 | 5,680E-01 | 6,383E-07 | 7,869E-05 | 3,094E-04 | 3,901E-03 |
| 431 | hsa-miR-361-5p | 4,159E+02 | 7,305E+02 | 5,693E-01 | -5,634E-01 | 9,470E-07 | 1,022E-04 | 1,030E-05 | 3,766E-04 |
| 36 | hsa-miR-891b | 9,652E+01 | 4,299E+01 | 2,245E+00 | 8,088E-01 | 1,423E-06 | 1,365E-04 | 1,348E-05 | 4,153E-04 |
| 59 | hsa-miR-767-5p | 1,590E+02 | 8,687E+01 | 1,831E+00 | 6,047E-01 | 1,762E-06 | 1,521E-04 | 3,865E-05 | 9,529E-04 |
| 69 | hsa-miR-744* | 3,994E+01 | 1,120E+02 | 3,565E-01 | -1,032E+00 | 2,507E-06 | 1,967E-04 | 1,869E-04 | 2,658E-03 |
| 580 | hsa-miR-208b | 6,046E+01 | 1,235E+01 | 4,895E+00 | 1,588E+00 | 4,567E-06 | 2,463E-04 | 6,462E-06 | 6,971E-06 |
| 219 | hsa-miR-548p | 1,145E+02 | 5,577E+01 | 2,054E+00 | 7,196E-01 | 4,060E-06 | 2,463E-04 | 9,703E-04 | 8,290E-03 |
| 578 | hsa-miR-20a* | 1,407E+02 | 6,398E+01 | 2,199E+00 | 7,881E-01 | 4,301E-06 | 2,463E-04 | 7,960E-07 | 5,284E-05 |
| 622 | hsa-miR-195 | 6,222E+02 | 3,662E+02 | 1,699E+00 | 5,301E-01 | 4,321E-06 | 2,463E-04 | 1,197E-02 | 4,917E-02 |
| 446 | hsa-miR-33b | 1,728E+02 | 1,021E+02 | 1,691E+00 | 5,256E-01 | 3,682E-06 | 3,682E-06 | 5,899E-03 | 3,030E-02 |
| 776 | hsa-miR-1283 | 1,098E+02 | 1,650E+02 | 6,653E-01 | 1,895E+00 | 5,792E-06 | 2,940E-04 | 4,335E-10 | 9,352E-08 |
| 277 | hsa-miR-519c-5p | 1,283E+02 | 4,546E+02 | 2,822E+00 | 1,038E+00 | 7,702E-06 | 3,693E-04 | 7,675E-06 | 3,154E-04 |
| 334 | hsa-miR-497 | 1,672E+02 | 1,033E+02 | 1,618E+00 | 4,814E-01 | 8,686E-06 | 3,945E-04 | 5,079E-05 | 1,154E-03 |
| 32 | hsa-miR-9* | 8,586E+01 | 3,515E+01 | 2,442E+00 | 8,930E-01 | 1,052E-05 | 4,532E-04 | 6,118E-04 | 6,212E-03 |
| 597 | hsa-miR-200a | 9,031E+01 | 5,220E+01 | 1,737E+00 | 5,520E-01 | 1,103E-05 | 4,532E-04 | 1,692E-02 | 6,189E-02 |
| 452 | hsa-miR-338-3p | 1,273E+02 | 4,967E+02 | 2,562E+00 | 9,409E-01 | 1,166E-05 | 4,573E-04 | 9,388E-04 | 8,183E-03 |
| 302 | hsa-miR-515-5p | 1,609E+02 | 8,279E+02 | 1,944E+00 | 6,645E-01 | 1,339E-05 | 5,025E-04 | 6,235E-05 | 1,199E-03 |
| 475 | hsa-miR-31* | 1,722E+02 | 7,661E+02 | 2,247E+00 | 8,098E-01 | 1,591E-05 | 5,642E-04 | 3,065E-06 | 1,470E-04 |
| 212 | hsa-miR-551b* | 3,800E+01 | 1,218E+02 | 3,120E-01 | -1,165E+00 | 1,716E-05 | 5,642E-04 | 5,623E-05 | 1,168E-03 |
| 285 | hsa-miR-518e* | 1,407E+02 | 5,015E+01 | 2,806E+00 | 1,032E+00 | 1,653E-05 | 5,642E-04 | 4,902E-04 | 5,417E-03 |
| 785 | hsa-miR-127-5p | 1,264E+02 | 4,639E+01 | 2,725E+00 | 1,002E+00 | 1,766E-05 | 5,642E-04 | 1,994E-03 | 1,471E-02 |
| 574 | hsa-miR-21* | 1,016E+02 | 4,060E+02 | 2,502E+00 | 9,170E-01 | 2,131E-05 | 6,569E-04 | 1,879E-04 | 2,658E-03 |
| 556 | hsa-miR-216a | 1,420E+02 | 6,926E+02 | 2,051E+00 | 7,182E-01 | 2,308E-05 | 6,869E-04 | 1,428E-02 | 5,577E-02 |
| 362 | hsa-miR-452* | 2,947E+02 | 1,748E+02 | 1,686E+00 | 5,221E-01 | 2,484E-05 | 7,146E-04 | 7,489E-05 | 1,405E-02 |
| 660 | hsa-miR-183* | 8,383E+01 | 2,078E+02 | 4,035E-01 | -9,076E-01 | 2,649E-05 | 7,373E-04 | 5,521E-03 | 2,923E-02 |
| 329 | hsa-miR-500 | 2,119E+02 | 4,993E+02 | 4,244E-01 | -8,571E-01 | 2,932E-05 | 7,909E-04 | 1,980E-04 | 2,712E-03 |
| 663 | hsa-miR-1826 | 1,952E+02 | 1,273E+02 | 1,534E+00 | 4,277E-01 | 3,483E-05 | 8,840E-04 | 2,772E-03 | 1,785E-02 |
| 130 | hsa-miR-625* | 2,318E+02 | 1,653E+02 | 1,402E+00 | 3,382E-01 | 3,464E-05 | 8,840E-04 | 1,574E-02 | 5,880E-02 |
| 306 | hsa-miR-513b | 4,708E+02 | 7,680E+02 | 6,129E+00 | 1,813E+00 | 3,595E-05 | 8,863E-04 | 1,999E-05 | 5,750E-04 |
| 253 | hsa-miR-526a | 1,385E+02 | 1,694E+02 | 8,179E+00 | 2,102E+00 | 3,769E-05 | 8,896E-04 | 2,601E-10 | 7,845E-08 |
| 448 | hsa-miR-33a | 1,027E+02 | 4,639E+01 | 2,213E+00 | 7,945E-01 | 3,814E-05 | 8,896E-04 | 4,958E-05 | 5,417E-03 |
| 828 | hsa-miR-1243 | 5,046E+01 | 1,000E+00 | 5,046E+01 | 3,921E+00 | 4,064E-05 | 9,229E-04 | 1,208E-07 | 1,159E-05 |
| 297 | hsa-miR-517* | 1,661E+02 | 9,633E+01 | 1,724E+00 | 5,447E-01 | 4,625E-05 | 1,024E-03 | 1,036E-03 | 8,682E-03 |
| 246 | hsa-miR-541 | 1,051E+02 | 4,865E+01 | 2,159E+00 | 7,699E-01 | 5,320E-05 | 1,080E-03 | 8,615E-03 | 3,935E-02 |

FIG. 2 (Continued)

| | | | | | | | | |
|---|---|---|---|---|---|---|---|---|
| 556 | hsa-miR-217 | 1,417E+02 | 8,352E+01 | 1,697E+00 | 5,289E-01 | 5,469E-05 | 1,080E-03 | 8,157E-04 | 7,410E-03 |
| 136 | hsa-miR-621 | 3,404E+02 | 1,509E+02 | 2,255E+00 | 8,133E-01 | 5,368E-05 | 1,080E-03 | 1,494E-03 | 1,183E-02 |
| 287 | hsa-miR-518d-5p | 1,569E+02 | 5,280E+01 | 2,971E+00 | 1,089E+00 | 5,191E-05 | 1,080E-03 | 1,229E-05 | 4,078E-04 |
| 54 | hsa-miR-873 | 6,387E+01 | 3,178E+01 | 2,011E+00 | 6,986E-01 | 5,509E-05 | 1,080E-03 | 5,304E-04 | 5,582E-03 |
| 879 | hsa-miR-103-as | 1,264E+02 | 9,266E+01 | 1,364E+00 | 3,105E-01 | 6,083E-05 | 1,167E-03 | 5,973E-03 | 3,050E-02 |
| 365 | hsa-miR-450b-5p | 6,084E+01 | 3,010E+01 | 2,021E+00 | 7,037E-01 | 6,913E-05 | 1,297E-03 | 2,733E-06 | 1,387E-04 |
| 240 | hsa-miR-545 | 1,152E+02 | 6,612E+01 | 1,742E+00 | 5,549E-01 | 7,623E-05 | 1,400E-03 | 2,883E-03 | 1,843E-02 |
| 820 | hsa-miR-1251 | 1,300E+02 | 7,016E+01 | 1,853E+00 | 6,168E-01 | 8,301E-05 | 1,471E-03 | 5,766E-05 | 1,168E-03 |
| 45 | hsa-miR-885-5p | 2,515E+02 | 7,170E+01 | 3,508E+00 | -1,048E+00 | 8,453E-05 | 1,471E-03 | 2,885E-05 | 7,546E-04 |
| 29 | hsa-miR-922 | 1,266E+02 | 4,981E+01 | 2,542E+00 | 9,331E-01 | 8,520E-05 | 1,471E-03 | 2,677E-04 | 3,500E-03 |
| 126 | hsa-miR-628-5p | 7,874E+01 | 3,515E+01 | 2,240E+00 | 8,063E-01 | 9,331E-05 | 1,579E-03 | 4,802E-07 | 3,767E-05 |
| 229 | hsa-miR-548f | 4,835E+01 | 1,000E+00 | 4,835E+01 | 3,878E+00 | 9,567E-05 | 1,588E-03 | 1,058E-05 | 3,766E-04 |
| 55 | hsa-miR-802 | 5,975E+01 | 3,048E+01 | 1,960E+00 | 6,731E-01 | 1,012E-04 | 1,647E-03 | 4,241E-04 | 4,816E-03 |
| 526 | hsa-miR-25 | 6,228E+03 | 5,129E+03 | 1,214E+00 | 1,940E-01 | 1,036E-04 | 1,659E-03 | 1,166E-02 | 4,893E-02 |
| 385 | hsa-miR-423-3p | 1,096E+03 | 1,830E+03 | 5,990E-01 | -5,124E-01 | 1,063E-04 | 1,668E-03 | 5,273E-05 | 1,162E-03 |
| 260 | hsa-miR-522* | 1,325E+02 | 4,546E+01 | 2,915E+00 | 1,070E+00 | 1,082E-04 | 1,682E-03 | 3,591E-08 | 4,427E-06 |
| 281 | hsa-miR-519a* | 1,458E+02 | 4,908E+01 | 2,971E+00 | 1,089E+00 | 1,191E-04 | 1,804E-03 | 2,032E-02 | 7,015E-02 |
| 358 | hsa-miR-455-3p | 1,706E+02 | 1,060E+02 | 1,610E+00 | 4,763E-01 | 1,298E-04 | 1,853E-03 | 1,505E-02 | 5,773E-02 |
| 427 | hsa-miR-363* | 6,193E+01 | 3,692E+01 | 1,678E+00 | 5,173E-01 | 1,271E-04 | 1,853E-03 | 1,065E-04 | 1,702E-03 |
| 826 | hsa-miR-1245 | 4,459E+01 | 9,114E+00 | 4,893E+00 | 1,588E+00 | 1,292E-04 | 1,853E-03 | 5,384E-05 | 1,162E-03 |
| 429 | hsa-miR-362-5p | 1,259E+02 | 2,272E+02 | 5,543E-01 | -5,900E-01 | 1,310E-04 | 1,853E-03 | 3,397E-05 | 8,621E-04 |
| 861 | hsa-miR-1184 | 1,769E+02 | 9,633E+01 | 1,836E+00 | 6,078E-01 | 1,361E-04 | 1,868E-03 | 1,607E-04 | 2,390E-03 |
| 641 | hsa-miR-191 | 1,198E+04 | 1,763E+04 | 6,792E-01 | -3,868E-01 | 1,364E-04 | 1,868E-03 | 8,436E-04 | 7,506E-03 |
| 349 | hsa-miR-487a | 6,487E+01 | 3,902E+01 | 1,662E+00 | 5,082E-01 | 1,446E-04 | 1,950E-03 | 4,039E-04 | 4,647E-03 |
| 557 | hsa-miR-216b | 1,184E+02 | 8,432E+01 | 1,404E+00 | 4,898E-01 | 1,474E-04 | 1,957E-03 | 3,526E-03 | 2,128E-02 |
| 254 | hsa-miR-525-5p | 8,126E+01 | 3,326E+01 | 2,444E+00 | 8,935E-01 | 1,650E-04 | 2,158E-03 | 6,178E-03 | 3,100E-02 |
| 315 | hsa-miR-509-3-5p | 2,136E+02 | 1,356E+02 | 1,575E+00 | 4,543E-01 | 1,766E-04 | 2,178E-03 | 1,660E-03 | 1,279E-02 |
| 518 | hsa-miR-27a* | 3,406E+01 | 7,037E+01 | 4,839E-01 | -7,258E-01 | 1,707E-04 | 2,178E-03 | 3,403E-03 | 2,068E-02 |
| 346 | hsa-miR-488* | 7,382E+01 | 4,546E+01 | 1,624E+00 | 4,848E-01 | 1,742E-04 | 2,178E-03 | 3,711E-04 | 4,448E-03 |
| 842 | hsa-miR-1226 | 4,944E+01 | 1,060E+02 | 4,665E-01 | -7,624E-01 | 1,738E-04 | 2,178E-03 | 6,876E-04 | 6,682E-03 |
| 107 | hsa-miR-646 | 2,063E+02 | 1,309E+02 | 1,577E+00 | 4,553E-01 | 1,823E-04 | 2,216E-03 | 6,810E-03 | 3,309E-02 |
| 250 | hsa-miR-527 | 1,562E+02 | 8,912E+01 | 1,752E+00 | 5,610E-01 | 1,913E-04 | 2,293E-03 | 9,170E-02 | 2,037E-01 |
| 118 | hsa-miR-635 | 1,008E+02 | 5,540E+01 | 1,819E+00 | 5,981E-01 | 1,991E-04 | 2,354E-03 | 1,530E-03 | 2,316E-02 |
| 664 | hsa-miR-1825 | 4,629E+01 | 1,358E+02 | 3,408E-01 | -1,076E+00 | 2,188E-04 | 2,533E-03 | 4,029E-04 | 4,647E-03 |
| 887 | hsa-let-7i* | 2,293E+02 | 1,168E+02 | 1,964E+00 | 6,751E-01 | 2,201E-04 | 2,533E-03 | 5,222E-04 | 5,564E-03 |
| 98 | hsa-miR-654-5p | 1,820E+02 | 1,402E+02 | 1,298E+00 | 2,608E-01 | 2,287E-04 | 2,597E-03 | 2,013E-02 | 6,984E-02 |
| 715 | hsa-miR-144 | 1,687E+03 | 1,203E+03 | 1,402E+00 | 3,376E-01 | 2,347E-04 | 2,630E-03 | 1,579E-01 | 2,969E-01 |
| 272 | hsa-miR-520a-5p | 1,003E+02 | 4,981E+01 | 2,014E+00 | 1,594E+00 | 2,419E-04 | 2,676E-03 | 2,154E-05 | 5,998E-04 |
| 313 | hsa-miR-509-5p | 2,165E+02 | 1,358E+02 | 1,594E+00 | 4,660E-01 | 2,461E-04 | 2,688E-03 | 4,149E-02 | 1,163E-01 |
| 465 | hsa-miR-324-5p | 3,304E+02 | 4,953E+02 | 6,670E-01 | -4,049E-01 | 2,496E-04 | 2,693E-03 | 7,572E-04 | 6,952E-03 |
| 356 | hsa-miR-483-3p | 1,898E+01 | 8,472E+01 | 2,240E-01 | -1,496E+00 | 2,563E-04 | 2,711E-03 | 2,586E-04 | 3,434E-03 |
| 875 | hsa-miR-106a* | 1,318E+02 | 7,057E+01 | 1,867E+00 | 6,246E-01 | 3,000E-04 | 3,119E-03 | 1,014E-07 | 8,576E-05 |
| 316 | hsa-miR-508-5p | 1,139E+02 | 6,829E+01 | 1,668E+00 | 5,116E-01 | 3,000E-04 | 3,119E-03 | 5,687E-07 | 4,090E-05 |
| 474 | hsa-miR-32 | 1,417E+02 | 1,114E+02 | 1,273E+00 | 2,410E-01 | 3,058E-04 | 3,142E-03 | 1,686E-02 | 6,189E-02 |

FIG. 2 (Continued)

| | | | | | | | | |
|---|---|---|---|---|---|---|---|---|
| 462 | hsa-miR-328 | 5.447E-01 | 1.620E+02 | 3.363E-01 | -1.090E+00 | 3.127E-04 | 3.175E-03 | 3.286E-04 | 4.051E-03 |
| 168 | hsa-miR-591 | 5.361E-01 | 2.056E+01 | 2.607E+00 | 9.583E-01 | 3.168E-04 | 3.179E-03 | 8.461E-05 | 1.477E-03 |
| 577 | hsa-miR-20b | 2.877E-03 | 1.687E-01 | 1.706E+00 | 5.341E-01 | 3.591E-04 | 3.562E-03 | 2.264E-01 | 3.794E-01 |
| 47 | hsa-miR-877* | 7.382E-01 | 1.827E+02 | 4.041E-01 | -9.061E-01 | 3.791E-04 | 3.717E-03 | 2.153E-03 | 1.534E-02 |
| 42 | hsa-miR-887 | 1.027E-02 | 6.999E+01 | 1.467E+00 | 3.831E-01 | 3.935E-04 | 3.816E-03 | 9.677E-02 | 2.120E-01 |
| 713 | hsa-miR-145 | 1.264E-02 | 3.254E+02 | 3.884E-01 | -9.458E-01 | 4.127E-04 | 3.957E-03 | 1.103E-04 | 1.731E-03 |
| 841 | hsa-miR-1226* | 1.900E-02 | 1.300E+02 | 1.461E+00 | 3.793E-01 | 4.203E-04 | 3.986E-03 | 5.739E-02 | 1.470E-01 |
| 216 | hsa-miR-550 | 1.137E-02 | 2.014E+02 | 5.646E-01 | -5.716E-01 | 4.430E-04 | 4.166E-03 | 8.723E-02 | 1.976E-01 |
| 737 | hsa-miR-133b | 1.880E-01 | 5.577E+01 | 3.012E-01 | -1.200E+00 | 4.733E-04 | 4.329E-03 | 1.437E-05 | 4.276E-04 |
| 344 | hsa-miR-490-3p | 8.739E-01 | 5.397E+01 | 1.619E+00 | 4.820E-01 | 4.665E-04 | 4.329E-03 | 6.252E-05 | 1.199E-03 |
| 619 | hsa-miR-196a* | 1.400E+02 | 7.244E+01 | 1.932E+00 | 6.586E-01 | 4.765E-04 | 4.329E-03 | 4.085E-05 | 9.792E-04 |
| 114 | hsa-miR-639 | 6.105E-01 | 3.515E-01 | 1.737E+00 | 5.519E-01 | 4.940E-04 | 4.441E-03 | 9.486E-04 | 8.186E-03 |
| 579 | hsa-miR-20a | 3.623E-03 | 2.630E+03 | 1.377E+00 | 3.202E-01 | 5.007E-04 | 4.455E-03 | 5.663E-01 | 7.012E-01 |
| 424 | hsa-miR-367 | 8.557E-01 | 3.692E+01 | 2.318E+00 | 8.406E-01 | 5.069E-04 | 4.464E-03 | 1.145E-08 | 1.977E-06 |
| 778 | hsa-miR-1281 | 6.814E-01 | 2.086E+02 | 3.267E-01 | -1.119E+00 | 5.169E-04 | 4.506E-03 | 1.349E-03 | 1.098E-02 |
| 455 | hsa-miR-335* | 1.000E+00 | 4.299E-01 | 2.326E-02 | -3.761E+00 | 5.254E-04 | 4.514E-03 | 1.091E-05 | 3.766E-04 |
| 652 | hsa-miR-186-3p | 1.312E-02 | 7.294E+01 | 1.798E+00 | 5.869E-01 | 5.263E-04 | 4.514E-03 | 2.300E-03 | 1.581E-02 |
| 762 | hsa-miR-1295 | 1.110E-02 | 6.853E+01 | 1.619E+00 | 4.819E-01 | 5.419E-04 | 4.585E-03 | 8.731E-03 | 3.966E-02 |
| 152 | hsa-miR-607 | 8.159E-01 | 6.105E+01 | 1.336E+00 | 2.900E-01 | 5.587E-04 | 4.682E-03 | 5.120E-02 | 1.343E-01 |
| 398 | hsa-miR-380* | 7.294E-02 | 4.639E+01 | 1.572E+00 | 4.527E-01 | 5.897E-04 | 4.847E-03 | 5.726E-02 | 1.470E-01 |
| 699 | hsa-miR-148b | 5.277E+02 | 3.961E+02 | 1.332E+00 | 2.869E-01 | 5.847E-04 | 4.847E-03 | 6.003E-02 | 1.510E-01 |
| 16 | hsa-miR-937 | 3.940E+01 | 9.283E+01 | 4.244E-01 | -8.570E-01 | 6.135E-04 | 4.994E-03 | 3.243E-03 | 2.028E-02 |
| 124 | hsa-miR-629* | 9.088E-01 | 2.214E+02 | 4.105E-01 | -8.903E-01 | 6.266E-04 | 5.054E-03 | 4.272E-02 | 1.199E-01 |
| 516 | hsa-miR-27b* | 6.105E-01 | 3.692E+01 | 1.654E+00 | 5.029E-01 | 6.744E-04 | 5.389E-03 | 5.581E-06 | 2.408E-04 |
| 407 | hsa-miR-376b | 6.046E-01 | 2.397E+01 | 2.522E+00 | 9.252E-01 | 7.222E-04 | 5.718E-03 | 1.975E-02 | 6.942E-02 |
| 165 | hsa-miR-593* | 2.965E-02 | 1.931E+02 | 1.536E+00 | 4.292E-01 | 7.311E-04 | 5.736E-03 | 7.318E-03 | 3.509E-02 |
| 773 | hsa-miR-1286 | 1.200E-02 | 8.761E+01 | 1.370E+00 | 3.149E-01 | 7.500E-04 | 5.831E-03 | 1.065E-01 | 2.284E-01 |
| 872 | hsa-miR-107 | 1.326E+03 | 1.065E+03 | 1.246E+00 | 2.197E-01 | 7.731E-04 | 5.940E-03 | 1.484E-01 | 2.845E-01 |
| 712 | hsa-miR-145* | 6.006E-01 | 3.753E+01 | 1.600E+00 | 4.702E-01 | 7.777E-04 | 5.940E-03 | 1.410E-01 | 2.759E-01 |
| 292 | hsa-miR-518a-5p | 1.649E+02 | 9.452E+01 | 1.744E+00 | 5.564E-01 | 8.129E-04 | 6.108E-03 | 5.099E-04 | 5.501E-03 |
| 283 | hsa-miR-518* | 1.220E+02 | 7.294E+02 | 1.673E+00 | 5.146E-01 | 8.139E-04 | 6.108E-03 | 7.111E-04 | 6.744E-03 |
| 786 | hsa-miR-1275 | 6.006E-01 | 1.513E+02 | 3.970E-01 | -9.239E-01 | 9.644E-04 | 7.175E-03 | 2.230E-02 | 7.517E-02 |
| 46 | hsa-miR-877 | 5.900E-01 | 1.297E+02 | 4.547E-01 | -7.881E-01 | 9.944E-04 | 7.335E-03 | 1.979E-02 | 6.942E-02 |
| 627 | hsa-miR-193a-5p | 5.447E-01 | 1.220E+02 | 4.464E-01 | -8.066E-01 | 1.019E-03 | 7.450E-03 | 1.651E-02 | 5.872E-02 |
| 543 | hsa-miR-221* | 1.034E-02 | 9.597E+01 | 1.078E+00 | 2.378E+00 | 1.033E-03 | 7.489E-03 | 2.727E-10 | 7.845E-08 |
| 732 | hsa-miR-135b* | 5.332E-01 | 3.087E+01 | 1.727E+00 | 5.464E-01 | 1.048E-03 | 7.533E-03 | 9.164E-05 | 4.098E-03 |
| 666 | hsa-miR-182 | 4.196E-03 | 6.572E+03 | 6.384E-01 | -4.489E-01 | 1.066E-03 | 7.601E-03 | 6.986E-03 | 3.358E-02 |
| 527 | hsa-miR-24-2* | 1.506E-02 | 1.309E+02 | 1.151E+00 | 1.402E-01 | 1.135E-03 | 7.971E-03 | 2.374E-02 | 7.831E-02 |
| 625 | hsa-miR-193b* | 3.479E-01 | 9.633E+01 | 3.612E-01 | -1.018E+00 | 1.136E-03 | 7.971E-03 | 2.107E-03 | 1.515E-02 |
| 84 | hsa-miR-668 | 3.705E-01 | 8.219E+01 | 4.508E-01 | -7.967E-01 | 1.163E-03 | 8.094E-03 | 1.285E-03 | 5.182E-02 |
| 153 | hsa-miR-606 | 6.273E-01 | 3.902E+01 | 1.607E+00 | 4.746E-01 | 1.187E-03 | 8.197E-03 | 2.138E-01 | 3.654E-01 |
| 82 | hsa-miR-671-3p | 3.637E+01 | 7.192E+01 | 5.057E+00 | -6.818E-01 | 1.277E-03 | 8.748E-03 | 2.543E-03 | 1.662E-02 |
| 680 | hsa-miR-15b | 1.415E-04 | 1.041E+04 | 1.359E+00 | 3.069E-01 | 1.354E-03 | 9.201E-03 | 8.267E-02 | 1.892E-01 |
| 665 | hsa-miR-182* | 4.708E-01 | 9.439E+00 | 4.987E+00 | 1.607E+00 | 1.395E-03 | 9.408E-03 | 1.563E-06 | 9.759E-05 |

FIG. 2 (Continued)

| | | | | | | | | |
|---|---|---|---|---|---|---|---|---|
| 636 | hsa-miR-1912 | 1.539E+02 | 1.333E+02 | 1.154E+00 | 1.433E-01 | 1.474E-03 | 9.863E-03 | 4.623E-04 | 5.181E-03 |
| 635 | hsa-miR-1913 | 3.543E+02 | 2.555E+02 | 1.387E+00 | 3.271E-01 | 1.507E-03 | 1.000E-02 | 6.980E-02 | 1.678E-01 |
| 853 | hsa-miR-1205 | 7.070E+01 | 4.088E+01 | 1.729E+00 | 5.477E-01 | 1.573E-03 | 1.036E-02 | 4.310E-03 | 2.415E-02 |
| 159 | hsa-miR-600 | 7.396E+01 | 4.060E+01 | 1.822E+00 | 5.998E-01 | 1.603E-03 | 1.048E-02 | 1.899E-03 | 1.437E-02 |
| 348 | hsa-miR-487b | 5.424E+01 | 2.452E+01 | 2.213E+00 | 7.941E-01 | 1.657E-03 | 1.075E-02 | 2.420E-06 | 1.305E-04 |
| 473 | hsa-miR-32* | 2.821E+01 | 1.060E+02 | 2.662E-01 | -1.323E+00 | 1.829E-03 | 1.178E-02 | 2.473E-02 | 7.934E-02 |
| 681 | hsa-miR-15a* | 1.107E+02 | 7.275E+01 | 1.521E+00 | 4.196E-01 | 1.854E-03 | 1.185E-02 | 8.171E-03 | 1.885E-01 |
| 35 | hsa-miR-892a | 2.646E+00 | 3.280E+01 | 8.046E-02 | -2.520E+00 | 1.917E-03 | 1.217E-02 | 2.103E-03 | 1.515E-02 |
| 169 | hsa-miR-590-5p | 1.539E+02 | 6.926E+01 | 2.222E+00 | 7.983E-01 | 1.966E-03 | 1.251E-02 | 2.742E-05 | 7.395E-04 |
| 68 | hsa-miR-760 | 4.181E+01 | 1.322E+02 | 3.161E-01 | -1.152E+00 | 2.000E-03 | 1.256E-02 | 3.952E-03 | 2.259E-02 |
| 386 | hsa-miR-422a | 1.366E+02 | 2.660E+02 | 5.209E-01 | -6.522E-01 | 2.084E-03 | 1.294E-02 | 3.447E-04 | 4.190E-03 |
| 10 | hsa-miR-943 | 3.902E+01 | 6.563E+01 | 5.946E-01 | -5.198E-01 | 2.187E-03 | 1.348E-02 | 9.029E-03 | 4.058E-02 |
| 697 | hsa-miR-149 | 2.100E+01 | 8.586E+01 | 2.446E-01 | -1.408E+00 | 2.261E-03 | 1.384E-02 | 6.610E-04 | 6.603E-03 |
| 840 | hsa-miR-1227 | 6.327E+01 | 1.244E+02 | 5.086E-01 | -6.761E-01 | 2.318E-03 | 1.399E-02 | 7.926E-03 | 3.717E-02 |
| 797 | hsa-miR-1266 | 1.129E+02 | 9.140E+01 | 1.235E+00 | 2.109E-01 | 2.303E-03 | 1.399E-02 | 3.010E-02 | 3.010E-02 |
| 809 | hsa-miR-125a-5p | 1.506E+02 | 3.352E+02 | 4.492E-01 | -8.003E-01 | 2.349E-03 | 1.408E-02 | 3.963E-04 | 4.647E-03 |
| 62 | hsa-miR-765 | 4.861E+01 | 1.367E+02 | 3.570E-01 | -1.030E+00 | 2.427E-03 | 1.444E-02 | 1.216E-02 | 4.956E-02 |
| 20 | hsa-miR-933 | 1.763E+02 | 1.278E+02 | 1.380E+00 | 3.222E-01 | 2.427E-03 | 1.444E-02 | 5.904E-02 | 1.490E-01 |
| 843 | hsa-miR-1225-5p | 5.975E+01 | 1.356E+02 | 4.407E-01 | -8.194E-01 | 2.486E-03 | 1.455E-02 | 8.417E-04 | 7.506E-03 |
| 323 | hsa-miR-603 | 2.595E+02 | 2.240E+02 | 1.159E+00 | 1.474E-01 | 2.495E-03 | 1.455E-02 | 2.493E-01 | 4.087E-01 |
| 310 | hsa-miR-512-3p | 3.587E+02 | 3.671E+00 | 9.769E+01 | 2.779E+00 | 2.539E-03 | 1.471E-02 | 8.060E-03 | 3.740E-02 |
| 374 | hsa-miR-433 | 6.273E+01 | 3.902E+01 | 1.607E+00 | -4.746E-01 | 2.576E-03 | 1.482E-02 | 1.331E-02 | 5.322E-02 |
| 405 | hsa-miR-377 | 1.135E+02 | 8.761E+01 | 1.295E+00 | 2.587E-01 | 2.825E-03 | 1.614E-02 | 1.116E-02 | 4.793E-02 |
| 412 | hsa-miR-374b | 4.953E+02 | 3.352E+02 | 1.478E+00 | 3.904E-01 | 2.865E-03 | 1.623E-02 | 3.458E-02 | 1.021E-01 |
| 342 | hsa-miR-491-3p | 7.766E+01 | 4.299E+01 | 1.811E+00 | 5.940E-01 | 2.877E-03 | 1.623E-02 | 3.468E-02 | 1.021E-01 |
| 213 | hsa-miR-551b | 7.370E+01 | 5.200E+01 | 1.417E+00 | 3.488E-01 | 3.119E-03 | 1.748E-02 | 2.302E-02 | 3.830E-01 |
| 300 | hsa-miR-516a-5p | 1.900E+02 | 1.021E+02 | 1.860E+00 | 6.205E-01 | 3.161E-03 | 1.760E-02 | 2.057E-03 | 1.504E-02 |
| 383 | hsa-miR-424 | 2.194E+02 | 1.758E+02 | 1.248E+00 | 2.216E-01 | 3.277E-03 | 1.813E-02 | 5.166E-02 | 1.344E-01 |
| 707 | hsa-miR-146b-3p | 5.447E+01 | 2.808E+01 | 1.940E+00 | 6.624E-01 | 3.382E-03 | 1.859E-02 | 1.923E-02 | 6.852E-02 |
| 414 | hsa-miR-374a | 2.496E+02 | 1.972E+02 | 1.266E+00 | 2.356E-01 | 3.456E-03 | 1.888E-02 | 3.449E-02 | 5.051E-01 |
| 324 | hsa-miR-502-5p | 1.015E+02 | 5.447E+01 | 1.862E+00 | -1.661E+00 | 3.602E-03 | 1.943E-02 | 3.119E-02 | 3.901E-01 |
| 196 | hsa-miR-568 | 7.147E+01 | 3.515E+01 | 2.033E+00 | 7.095E-01 | 3.596E-03 | 1.943E-02 | 1.431E-03 | 1.144E-02 |
| 855 | hsa-miR-1203 | 2.001E+02 | 1.340E+02 | 1.494E+00 | 4.014E-01 | 3.646E-03 | 1.954E-02 | 5.556E-03 | 2.924E-02 |
| 629 | hsa-miR-192* | 1.141E+02 | 7.661E+01 | 1.490E+00 | 3.985E-01 | 3.703E-03 | 1.973E-02 | 1.044E-03 | 1.700E-03 |
| 769 | hsa-miR-129* | 4.433E+02 | 6.926E+01 | 6.401E+00 | 2.266E+00 | 3.743E-03 | 1.982E-02 | 1.449E-02 | 5.634E-02 |
| 298 | hsa-miR-516b* | 2.024E+02 | 5.629E+01 | 3.596E+00 | 1.023E+00 | 3.873E-03 | 2.038E-02 | 2.265E-03 | 1.576E-02 |
| 503 | hsa-miR-29b-2* | 3.526E+02 | 7.606E+01 | 4.636E+00 | -7.686E-01 | 3.998E-03 | 2.078E-02 | 5.009E-02 | 1.318E-01 |
| 691 | hsa-miR-152 | 2.154E+02 | 1.718E+02 | 1.254E+00 | 2.266E-01 | 3.997E-03 | 2.078E-02 | 8.255E-02 | 1.892E-01 |
| 498 | hsa-miR-301b | 1.857E+02 | 1.322E+02 | 1.404E+00 | 3.394E-01 | 4.146E-03 | 2.143E-02 | 3.952E-03 | 2.259E-02 |
| 510 | hsa-miR-298 | 1.192E+02 | 1.002E+02 | 1.190E+00 | 1.739E-01 | 4.334E-03 | 2.210E-02 | 1.049E-01 | 2.264E-01 |
| 500 | hsa-miR-300 | 4.865E+01 | 2.013E+01 | 2.417E+00 | 8.825E-01 | 4.353E-03 | 2.210E-02 | 1.395E-02 | 5.499E-02 |
| 76 | hsa-miR-708* | 5.144E+01 | 1.723E+01 | 2.986E+00 | 1.094E+00 | 4.334E-03 | 2.210E-02 | 1.947E-03 | 1.458E-02 |
| 11 | hsa-miR-942 | 1.576E+01 | 6.170E+01 | 2.553E-01 | -1.365E+00 | 4.437E-03 | 2.239E-02 | 1.512E-04 | 2.316E-03 |
| 133 | hsa-miR-624 | 5.144E+01 | 1.773E+01 | 2.902E+00 | 1.065E+00 | 4.641E-03 | 2.329E-02 | 1.228E-02 | 4.976E-02 |

FIG. 2 (Continued)

| | | | | | | | | | |
|---|---|---|---|---|---|---|---|---|---|
| 761 | hsa-miR-129-5p | 3,315E-01 | 8,023E-01 | 4,132E-01 | -8,837E-01 | 4,820E-03 | 2,404E-02 | 5,403E-03 | 2,878E-02 |
| 403 | hsa-miR-378 | 2,555E-02 | 3,515E-02 | 7,268E-01 | -3,191E-01 | 4,979E-03 | 2,461E-02 | 1,004E-02 | 4,466E-02 |
| 848 | hsa-miR-122 | 2,066E-01 | 7,160E-01 | 2,886E-01 | -1,243E+00 | 4,990E-03 | 2,461E-02 | 1,183E-02 | 4,908E-02 |
| 541 | hsa-miR-222* | 6,170E-01 | 3,274E-01 | 1,884E+00 | 6,336E-01 | 5,197E-03 | 2,528E-02 | 1,339E-05 | 4,153E-04 |
| 858 | hsa-miR-1200 | 7,370E-01 | 4,546E-01 | 1,621E+00 | 4,832E-01 | 5,213E-03 | 2,528E-02 | 1,813E-04 | 2,651E-03 |
| 814 | hsa-miR-1256 | 6,665E-01 | 4,088E-01 | 1,630E+00 | 4,887E-01 | 5,214E-03 | 2,528E-02 | 2,385E-03 | 1,585E-02 |
| 171 | hsa-miR-589* | 8,323E-01 | 1,137E+02 | 7,321E-03 | -3,118E-01 | 5,310E-03 | 2,560E-02 | 1,406E-02 | 2,758E-02 |
| 499 | hsa-miR-301a | 2,694E-02 | 1,986E+02 | 1,356E+00 | -3,046E-01 | 5,470E-03 | 2,622E-02 | 2,383E-03 | 1,585E-02 |
| 23 | hsa-miR-92b* | 1,283E-02 | 2,086E+02 | 6,150E-01 | -4,861E-01 | 5,541E-03 | 2,642E-02 | 5,855E-02 | 1,482E-01 |
| 131 | hsa-miR-625 | 5,728E-01 | 1,520E-02 | 3,768E-01 | -9,761E-01 | 5,826E-03 | 2,763E-02 | 1,085E-02 | 4,704E-02 |
| 435 | hsa-miR-34a* | 4,482E-02 | 2,452E-01 | 1,828E+00 | 6,034E-01 | 5,966E-03 | 2,809E-02 | 3,937E-02 | 1,125E-01 |
| 837 | hsa-miR-1229 | 1,841E-02 | 4,342E-02 | 4,240E-01 | -8,579E-01 | 5,990E-03 | 2,809E-02 | 1,069E-01 | 2,284E-01 |
| 105 | hsa-miR-648 | 4,708E-01 | 2,013E-01 | 2,339E+00 | 8,496E-01 | 6,474E-03 | 3,020E-02 | 7,106E-04 | 6,744E-03 |
| 267 | hsa-miR-520d-5p | 5,975E-01 | 3,705E-01 | 1,613E+00 | 4,779E-01 | 6,571E-03 | 3,025E-02 | 1,279E-03 | 1,051E-02 |
| 164 | hsa-miR-595 | 1,025E-02 | 1,701E+02 | 6,027E-01 | -5,064E-01 | 6,536E-03 | 3,025E-02 | 1,415E-02 | 5,550E-02 |
| 177 | hsa-miR-584 | 8,363E-01 | 2,204E-01 | 3,794E-01 | -9,692E-01 | 6,590E-03 | 3,025E-02 | 4,265E-03 | 2,406E-02 |
| 791 | hsa-miR-1272 | 1,312E-02 | 9,882E-01 | 1,330E+00 | 2,852E-01 | 6,777E-03 | 3,094E-02 | 6,080E-03 | 3,068E-02 |
| 353 | hsa-miR-485-3p | 5,144E-01 | 8,586E-01 | 5,991E-01 | -5,123E-01 | 7,002E-03 | 3,180E-02 | 8,618E-03 | 3,935E-02 |
| 436 | hsa-miR-34b | 4,111E-01 | 7,133E-01 | 5,763E-01 | -5,511E-01 | 7,044E-03 | 3,183E-02 | 1,332E-02 | 5,322E-02 |
| 865 | hsa-miR-1180 | 6,116E-01 | 1,645E+02 | 3,718E-01 | -9,894E-01 | 7,110E-03 | 3,196E-02 | 1,887E-02 | 6,814E-02 |
| 741 | hsa-miR-1322 | 7,419E-01 | 4,398E-01 | 1,687E+00 | 5,229E-01 | 7,313E-03 | 3,256E-02 | 4,975E-02 | 1,313E-01 |
| 343 | hsa-miR-490-5p | 1,306E-02 | 1,017E+02 | 1,284E+00 | 2,500E-01 | 7,320E-03 | 3,256E-02 | 1,455E-01 | 2,816E-01 |
| 756 | hsa-miR-1301 | 2,019E-02 | 1,444E+02 | 1,398E+00 | 3,352E-01 | 7,383E-03 | 3,267E-02 | 7,174E-02 | 1,709E-01 |
| 753 | hsa-miR-1304 | 4,944E-01 | 8,219E-01 | 6,015E-01 | -5,083E-01 | 7,747E-03 | 3,411E-02 | 2,672E-01 | 4,278E-01 |
| 94 | hsa-miR-658 | 4,881E-01 | 9,633E-01 | 5,067E-01 | -6,798E-01 | 7,909E-03 | 3,466E-02 | 7,423E-02 | 1,750E-01 |
| 217 | hsa-miR-549 | 5,144E-01 | 3,692E-01 | 1,393E+00 | 3,317E-01 | 8,051E-03 | 3,509E-02 | 3,823E-02 | 1,103E-01 |
| 734 | hsa-miR-135a* | 1,000E+00 | 6,864E-01 | 1,457E-02 | -4,229E+00 | 8,357E-03 | 3,624E-02 | 9,857E-06 | 3,766E-04 |
| 326 | hsa-miR-501-5p | 3,808E-01 | 8,887E-01 | 4,383E-01 | -8,248E-01 | 8,568E-03 | 3,697E-02 | 7,460E-03 | 3,538E-02 |
| 14 | hsa-miR-939 | 4,938E-01 | 1,186E-02 | 4,162E-01 | -8,766E-01 | 8,833E-03 | 3,774E-02 | 3,317E-02 | 9,939E-02 |
| 639 | hsa-miR-1910 | 3,902E-01 | 7,160E-01 | 5,450E-01 | -6,070E-01 | 8,795E-03 | 3,774E-02 | 4,530E-02 | 1,225E-01 |
| 384 | hsa-miR-423-5p | 2,877E-02 | 4,401E-03 | 8,724E+00 | 2,166E+00 | 8,900E-03 | 3,784E-02 | 2,466E-03 | 1,625E-02 |
| 49 | hsa-miR-876-5p | 3,674E-02 | 3,070E-02 | 7,660E-01 | -2,666E-01 | 8,948E-03 | 3,785E-02 | 2,569E-02 | 4,168E-02 |
| 784 | hsa-miR-1276 | 3,985E-01 | 6,482E-01 | 7,494E-01 | -2,885E-01 | 9,092E-03 | 3,828E-02 | 6,653E-03 | 3,262E-02 |
| 382 | hsa-miR-424* | 1,110E-02 | 1,809E-02 | 6,134E-01 | -4,887E-01 | 9,270E-03 | 3,866E-02 | 1,535E-02 | 2,915E-02 |
| 189 | hsa-miR-574-5p | 8,284E-01 | 1,376E-03 | 6,022E-01 | -5,071E-01 | 9,250E-03 | 3,866E-02 | 2,226E-02 | 1,562E-01 |
| 674 | hsa-miR-17* | 5,591E-01 | 5,591E-02 | 1,000E+00 | 0,000E+00 | 9,633E-03 | 3,983E-02 | 7,448E-01 | 8,294E-01 |
| 173 | hsa-miR-588 | 1,197E-02 | 1,045E-02 | 1,146E+00 | 1,363E-01 | 9,647E-03 | 3,983E-02 | 1,449E-01 | 2,816E-01 |
| 731 | hsa-miR-136 | 2,904E-01 | 3,329E+00 | 8,724E+00 | 2,166E+00 | 9,799E-03 | 4,027E-02 | 1,209E-03 | 1,003E-02 |
| 437 | hsa-miR-34a* | 9,061E-01 | 7,244E+03 | 1,251E+00 | 2,238E-01 | 1,001E-02 | 4,092E-02 | 1,544E-02 | 2,923E-01 |
| 605 | hsa-miR-199a-5p | 2,352E-02 | 3,070E+02 | 7,660E-01 | -2,666E-01 | 1,006E-02 | 4,095E-02 | 1,508E-03 | 1,183E-02 |
| 182 | hsa-miR-680 | 4,327E-01 | 6,482E+00 | 6,676E+00 | 1,898E+00 | 1,022E-02 | 4,141E-02 | 8,560E-05 | 1,477E-03 |
| 337 | hsa-miR-494 | 5,553E-01 | 9,322E-01 | 5,957E-01 | -5,180E-01 | 1,043E-02 | 4,204E-02 | 2,151E-02 | 7,305E-02 |
| 125 | hsa-miR-629 | 5,447E-01 | 1,322E-01 | 4,119E-01 | -8,870E-01 | 1,055E-02 | 4,236E-02 | 3,738E-03 | 2,179E-02 |
| 106 | hsa-miR-647 | 6,864E-01 | 5,566E-01 | 1,237E+00 | 2,126E-01 | 1,070E-02 | 4,275E-02 | 2,695E-03 | 1,749E-02 |

FIG. 2 (Continued)

| | | | | | | | | |
|---|---|---|---|---|---|---|---|---|
| 881 | hsa-miR-103 | 6.927E+03 | 4.861E+03 | 1.425E+00 | 3.543E-01 | 1.080E-02 | 4.277E-02 | 1.095E-01 | 2.303E-01 |
| 884 | hsa-miR-100* | 6.193E+01 | 1.235E+01 | 5.014E+00 | 1.612E+00 | 1.082E-02 | 4.277E-02 | 2.314E-06 | 1.305E-04 |
| 804 | hsa-miR-126* | 2.133E+00 | 2.653E+01 | 8.040E-02 | -2.521E+00 | 1.085E-02 | 4.277E-02 | 6.350E-03 | 3.150E-02 |
| 134 | hsa-miR-623 | 5.068E+01 | 7.037E+01 | 7.201E-01 | -3.284E-01 | 1.091E-02 | 4.280E-02 | 3.309E-02 | 9.939E-02 |
| 93 | hsa-miR-659 | 6.387E+01 | 1.107E+02 | 5.771E-01 | -5.498E-01 | 1.102E-02 | 4.303E-02 | 5.359E-03 | 2.873E-02 |
| 869 | hsa-miR-10b | 5.068E+01 | 3.037E+01 | 1.669E+00 | 5.119E-01 | 1.109E-02 | 4.311E-02 | 4.412E-02 | 2.441E-02 |
| 60 | hsa-miR-767-3p | 4.433E-01 | 2.013E-01 | 2.202E+00 | 7.896E-01 | 1.131E-02 | 4.362E-02 | 2.016E-02 | 6.984E-02 |
| 782 | hsa-miR-1278 | 5.447E+01 | 2.704E+01 | 2.014E+00 | 7.003E-01 | 1.132E-02 | 4.362E-02 | 7.995E-05 | 1.450E-03 |
| 155 | hsa-miR-604 | 8.976E+01 | 7.160E+01 | 1.254E+00 | 2.260E-01 | 1.160E-02 | 4.413E-02 | 2.602E-02 | 8.257E-02 |
| 299 | hsa-miR-516b | 3.581E+01 | 1.235E+01 | 2.899E+00 | 1.064E+00 | 1.160E-02 | 4.413E-02 | 2.387E-02 | 7.831E-02 |
| 441 | hsa-miR-342-5p | 8.373E+01 | 1.583E+02 | 5.291E-01 | -6.366E-01 | 1.166E-02 | 4.413E-02 | 1.808E-01 | 3.245E-01 |
| 485 | hsa-miR-30b | 7.310E+03 | 4.861E+03 | 1.504E+00 | 4.081E-01 | 1.166E-02 | 4.413E-02 | 4.431E-02 | 1.218E-01 |
| 156 | hsa-miR-603 | 1.152E+02 | 1.005E+02 | 1.146E+00 | 1.364E-01 | 1.192E-02 | 4.472E-02 | 1.031E-01 | 2.232E-01 |
| 322 | hsa-miR-504 | 3.406E+01 | 1.795E+01 | 1.897E+00 | 6.401E-01 | 1.191E-02 | 4.472E-02 | 2.959E-01 | 4.564E-01 |
| 749 | hsa-miR-1308 | 4.419E+01 | 7.294E+01 | 6.059E-01 | -5.010E-01 | 1.255E-02 | 4.688E-02 | 3.763E-02 | 1.090E-01 |
| 771 | hsa-miR-1288 | 5.447E+01 | 9.452E+01 | 5.763E-01 | -5.512E-01 | 1.270E-02 | 4.724E-02 | 1.377E-02 | 5.452E-02 |
| 845 | hsa-miR-1224-5p | 2.888E+02 | 8.472E+01 | 3.408E+00 | -1.076E+00 | 1.290E-02 | 4.778E-02 | 2.568E-02 | 8.177E-02 |
| 458 | hsa-miR-331-3p | 9.557E+02 | 1.326E+03 | 7.206E-01 | -3.277E-01 | 1.309E-02 | 4.828E-02 | 4.405E-03 | 2.441E-02 |
| 439 | hsa-miR-346 | 5.397E+01 | 7.786E+01 | 6.931E-01 | -3.666E-01 | 1.349E-02 | 4.919E-02 | 2.452E-02 | 7.927E-02 |
| 1 | hsa-miR-99b* | 4.995E+01 | 7.160E+01 | 6.976E-01 | -3.601E-01 | 1.350E-02 | 4.919E-02 | 1.530E-02 | 5.842E-02 |
| 752 | hsa-miR-1305 | 9.061E+01 | 7.275E+01 | 1.245E+00 | 2.195E-01 | 1.351E-02 | 4.919E-02 | 4.141E-01 | 5.727E-01 |
| 269 | hsa-miR-520c-5p | 1.212E+02 | 8.836E+01 | 1.372E+00 | 3.159E-01 | 1.371E-02 | 4.973E-02 | 2.255E-02 | 7.544E-02 |
| 514 | hsa-miR-28-5p | 3.635E+02 | 3.753E+02 | 9.685E-01 | -3.198E-02 | 1.385E-02 | 4.981E-02 | 3.542E-02 | 1.033E-01 |
| 291 | hsa-miR-518b | 9.590E+01 | 6.563E+01 | 1.461E+00 | 3.794E-01 | 1.380E-02 | 4.981E-02 | 4.704E-01 | 6.217E-01 |
| 478 | hsa-miR-30e | 2.331E+02 | 3.840E+02 | 6.069E-01 | -4.993E-01 | 1.391E-02 | 4.981E-02 | 1.149E-02 | 4.884E-02 |
| 738 | hsa-miR-133a | 4.958E+01 | 8.472E+01 | 5.852E-01 | -5.357E-01 | 1.411E-02 | 5.032E-02 | 8.409E-02 | 1.915E-01 |
| 720 | hsa-miR-141* | 8.857E+01 | 6.612E+01 | 1.340E+00 | 2.923E-01 | 1.433E-02 | 5.089E-02 | 3.706E-09 | 2.177E-02 |
| 832 | hsa-miR-1237 | 7.937E+01 | 1.535E+02 | 5.171E-01 | -6.594E-01 | 1.445E-02 | 5.110E-02 | 1.284E-01 | 2.576E-01 |
| 391 | hsa-miR-410 | 7.244E+01 | 6.612E+01 | 1.096E+00 | 9.124E-02 | 1.525E-02 | 5.373E-02 | 6.882E-01 | 7.888E-01 |
| 690 | hsa-miR-153 | 1.027E+02 | 9.452E+01 | 1.086E+00 | 8.266E-02 | 1.538E-02 | 5.386E-02 | 1.537E-02 | 2.915E-02 |
| 688 | hsa-miR-1538 | 7.057E+01 | 3.692E+01 | 1.911E+00 | 6.478E-01 | 1.549E-02 | 5.410E-02 | 4.691E-02 | 1.256E-01 |
| 846 | hsa-miR-1224-3p | 9.372E+01 | 2.240E+02 | 4.184E-01 | -8.712E-01 | 1.579E-02 | 5.493E-02 | 4.043E-02 | 1.148E-01 |
| 232 | hsa-miR-548d-3p | 4.508E+01 | 1.450E+01 | 3.110E+00 | 1.135E+00 | 1.622E-02 | 5.621E-02 | 5.090E-03 | 2.745E-02 |
| 288 | hsa-miR-518d-3p | 7.874E+01 | 5.629E+01 | 1.399E+00 | 3.356E-01 | 1.684E-02 | 5.790E-02 | 4.528E-02 | 1.225E-01 |
| 428 | hsa-miR-363 | 3.450E+03 | 2.877E+03 | 1.199E+00 | 1.814E-01 | 1.678E-02 | 5.790E-02 | 7.806E-02 | 8.603E-01 |
| 770 | hsa-miR-1289 | 9.249E+01 | 7.244E+01 | 1.277E+00 | 2.444E-01 | 1.709E-02 | 5.852E-02 | 3.124E-01 | 4.723E-01 |
| 388 | hsa-miR-412 | 5.144E+01 | 4.546E+01 | 1.132E+00 | 1.237E-01 | 1.745E-02 | 5.953E-02 | 2.386E-02 | 7.831E-02 |
| 623 | hsa-miR-194* | 4.339E+01 | 7.160E+01 | 6.060E-01 | -5.009E-01 | 1.766E-02 | 6.000E-02 | 1.807E-02 | 6.581E-02 |
| 451 | hsa-miR-338-5p | 3.200E+01 | 5.035E+01 | 6.355E-01 | -4.534E-01 | 1.783E-02 | 6.033E-02 | 5.490E-02 | 1.418E-01 |
| 191 | hsa-miR-573 | 5.144E+01 | 2.319E+01 | 2.218E+00 | 7.967E-01 | 1.819E-02 | 6.131E-02 | 1.638E-03 | 1.273E-02 |
| 194 | hsa-miR-570 | 7.701E+01 | 3.326E+01 | 2.316E+00 | 8.399E-01 | 1.834E-02 | 6.159E-02 | 6.891E-04 | 6.682E-03 |
| 432 | hsa-miR-361-3p | 1.886E+02 | 1.628E+02 | 1.159E+00 | 1.473E-01 | 1.850E-02 | 6.166E-02 | 1.267E-01 | 2.549E-01 |
| 158 | hsa-miR-601 | 1.000E+00 | 7.016E+01 | 1.425E-02 | -4.251E+00 | 1.856E-02 | 6.166E-02 | 4.220E-05 | 9.843E-04 |
| 561 | hsa-miR-214 | 3.006E+02 | 2.027E+02 | 1.483E+00 | 3.942E-01 | 1.856E-02 | 6.166E-02 | 4.945E-02 | 1.312E-01 |

FIG. 2 (Continued)

| | | | | | | | | | |
|---|---|---|---|---|---|---|---|---|---|
| 631 | hsa-miR-1915* | 2,765E+01 | 4,981E-01 | 5,552E-01 | -5,884E-01 | 1,865E-02 | 6,168E-02 | 2,316E-03 | 1,581E-02 |
| 833 | hsa-miR-1236 | 2,177E+01 | 6,563E+01 | 3,318E-01 | -1,103E+00 | 1,898E-02 | 6,250E-02 | 1,387E-01 | 2,752E-01 |
| 694 | hsa-miR-150* | 7,626E+01 | 1,177E+02 | 6,480E-01 | -4,338E-01 | 1,990E-02 | 6,531E-02 | 6,070E-01 | 1,518E-01 |
| 595 | hsa-miR-200b | 4,865E+01 | 3,010E+01 | 1,616E+00 | 4,802E-01 | 2,044E-02 | 6,681E-02 | 3,398E-03 | 2,068E-02 |
| 572 | hsa-miR-211 | 1,000E+00 | 4,908E-01 | 2,037E-02 | -3,893E+00 | 2,061E-02 | 6,713E-02 | 5,427E-06 | 2,408E-04 |
| 345 | hsa-miR-489 | 1,562E-02 | 1,598E-02 | 9,774E-01 | -2,287E-02 | 2,092E-02 | 6,763E-02 | 4,127E-01 | 5,727E-01 |
| 193 | hsa-miR-571 | 4,419E-01 | 5,991E-01 | 7,377E-01 | -3,042E-01 | 2,092E-02 | 6,763E-02 | 8,902E-02 | 2,003E-01 |
| 393 | hsa-miR-409-3p | 3,526E+01 | 7,786E+01 | 4,529E-01 | -7,921E-01 | 2,104E-02 | 6,774E-02 | 6,228E-03 | 3,107E-02 |
| 670 | hsa-miR-181b | 4,708E+00 | 9,310E+00 | 5,057E-01 | -6,819E-01 | 2,167E-02 | 6,953E-02 | 1,649E-01 | 3,061E-01 |
| 68 | hsa-miR-758 | 9,746E+00 | 5,200E+00 | 1,874E+00 | -1,674E+00 | 2,183E-02 | 7,010E-02 | 3,627E-03 | 2,174E-02 |
| 483 | hsa-miR-30c | 2,158E+03 | 1,873E+03 | 1,152E+00 | 1,413E-01 | 2,206E-02 | 7,025E-02 | 5,423E-01 | 6,882E-01 |
| 683 | hsa-miR-155* | 5,900E+01 | 4,737E+01 | 1,246E+00 | 2,194E-01 | 2,224E-02 | 7,056E-02 | 1,645E-01 | 3,060E-01 |
| 378 | hsa-miR-431 | 1,758E-02 | 1,393E-02 | 1,262E+00 | 2,330E-01 | 2,262E-02 | 7,151E-02 | 2,295E-01 | 3,830E-01 |
| 708 | hsa-miR-146a* | 6,841E+01 | 6,612E+01 | 1,035E+00 | 3,403E-02 | 2,290E-02 | 7,212E-02 | 3,265E-01 | 4,875E-01 |
| 508 | hsa-miR-299-5p | 2,066E+01 | 7,016E+01 | 2,945E-01 | -1,222E+00 | 2,323E-02 | 7,248E-02 | 2,432E-02 | 7,890E-02 |
| 157 | hsa-miR-602 | 1,072E-02 | 8,238E-01 | 1,302E+00 | 2,636E-01 | 2,319E-02 | 7,248E-02 | 8,019E-03 | 3,740E-02 |
| 590 | hsa-miR-202* | 5,447E+01 | 4,639E+01 | 1,174E+00 | 1,607E-01 | 2,327E-02 | 7,248E-02 | 1,135E-01 | 2,360E-01 |
| 434 | hsa-miR-34c-3p | 8,188E-01 | 1,632E-02 | 5,017E+01 | -6,897E-01 | 2,459E-02 | 7,616E-02 | 2,496E-02 | 7,979E-02 |
| 538 | hsa-miR-224 | 4,774E+01 | 1,000E+00 | 4,774E+01 | 3,866E+00 | 2,471E-02 | 7,616E-02 | 3,681E-03 | 2,176E-02 |
| 539 | hsa-miR-223* | 2,888E+01 | 5,015E+01 | 5,758E-01 | -5,521E-01 | 2,466E-02 | 7,616E-02 | 2,473E-02 | 7,934E-02 |
| 41 | hsa-miR-888 | 4,958E+01 | 7,329E+01 | 6,765E-01 | -3,909E-01 | 2,550E-02 | 7,807E-02 | 1,841E-02 | 6,676E-02 |
| 341 | hsa-miR-491-5p | 8,739E+01 | 1,393E-02 | 6,275E-01 | -4,661E-01 | 2,551E-02 | 7,807E-02 | 1,053E-01 | 2,265E-01 |
| 190 | hsa-miR-574-3p | 2,110E+03 | 3,450E+03 | 6,116E-01 | -4,917E-01 | 2,583E-02 | 7,877E-02 | 2,677E-02 | 8,431E-02 |
| 760 | hsa-miR-1296 | 4,723E+01 | 6,999E+01 | 6,747E-01 | -3,935E-01 | 2,595E-02 | 7,885E-02 | 2,961E-02 | 9,192E-02 |
| 111 | hsa-miR-642 | 2,704E+01 | 5,577E+01 | 4,849E-01 | -7,239E-01 | 2,640E-02 | 7,995E-02 | 1,044E-02 | 4,572E-02 |
| 655 | hsa-miR-186* | 1,016E-02 | 5,280E-01 | 1,924E+00 | 6,542E-01 | 2,788E-02 | 8,413E-02 | 1,329E-01 | 2,643E-01 |
| 728 | hsa-miR-138 | 3,376E+01 | 7,244E+01 | 4,660E-01 | -7,635E-01 | 2,823E-02 | 8,468E-02 | 4,332E-02 | 1,198E-01 |
| 836 | hsa-miR-1231 | 8,373E+01 | 7,192E+01 | 1,164E+00 | 1,520E-01 | 2,813E-02 | 8,458E-02 | 1,787E-01 | 3,220E-01 |
| 531 | hsa-miR-23b | 3,143E+03 | 3,450E+03 | 9,112E-01 | -9,295E-02 | 2,924E-02 | 8,873E-02 | 5,311E-02 | 1,381E-01 |
| 290 | hsa-miR-518o | 6,298E+01 | 7,910E+01 | 7,961E-01 | -2,280E-01 | 2,920E-02 | 8,873E-02 | 4,543E-02 | 1,225E-01 |
| 525 | hsa-miR-25* | 5,802E+01 | 7,275E+01 | 7,976E-01 | -2,262E-01 | 2,919E-02 | 8,673E-02 | 4,505E-02 | 1,225E-01 |
| 80 | hsa-miR-675 | 1,354E-02 | 2,144E-02 | 6,312E-01 | -4,601E-01 | 2,964E-02 | 8,759E-02 | 1,068E-01 | 2,284E-01 |
| 616 | hsa-miR-197 | 6,478E-02 | 1,028E-03 | 6,299E-01 | -4,622E-01 | 2,978E-02 | 8,770E-02 | 3,346E-03 | 2,068E-02 |
| 238 | hsa-miR-548a-3p | 7,070E+01 | 4,648E+01 | 1,521E+00 | 4,194E-01 | 3,077E-02 | 9,033E-02 | 1,094E-01 | 2,303E-01 |
| 444 | hsa-miR-340 | 1,411E-02 | 9,266E-01 | 1,523E+00 | 4,204E-01 | 3,094E-02 | 9,051E-02 | 9,044E-01 | 2,022E-01 |
| 43 | hsa-miR-886-5p | 7,170E+01 | 1,124E-02 | 6,378E-01 | -4,497E-01 | 3,139E-02 | 9,148E-02 | 2,428E-01 | 4,006E-01 |
| 501 | hsa-miR-29c* | 1,359E+00 | 3,037E-01 | 4,476E-02 | -3,107E+00 | 3,159E-02 | 9,148E-02 | 8,912E-02 | 2,003E-01 |
| 409 | hsa-miR-376a | 8,836E-01 | 5,959E-01 | 1,463E+00 | 3,939E-01 | 3,153E-02 | 9,148E-02 | 8,753E-04 | 7,708E-03 |
| 37 | hsa-miR-891a | 1,082E-02 | 1,033E-02 | 1,047E+00 | 4,567E-02 | 3,236E-02 | 9,339E-02 | 1,132E-02 | 4,838E-02 |
| 750 | hsa-miR-1307 | 5,601E-01 | 8,472E-01 | 6,611E-01 | -4,139E-01 | 3,279E-02 | 9,433E-02 | 1,825E-01 | 3,261E-01 |
| 12 | hsa-miR-941 | 1,027E-02 | 1,393E-02 | 7,371E-01 | -3,050E-01 | 3,302E-02 | 9,468E-02 | 3,835E-01 | 5,399E-01 |
| 400 | hsa-miR-379* | 5,397E+01 | 3,692E-02 | 1,462E+00 | 3,796E-01 | 3,319E-02 | 9,484E-02 | 1,083E-02 | 4,704E-02 |
| 649 | hsa-miR-18a* | 1,900E-02 | 3,160E-02 | 6,012E-01 | -5,088E-01 | 3,355E-02 | 9,554E-02 | 1,569E-02 | 5,880E-02 |
| 325 | hsa-miR-502-3p | 6,676E-02 | 8,391E-02 | 7,957E-01 | -2,285E-01 | 3,372E-02 | 9,573E-02 | 5,853E-02 | 1,462E-01 |

FIG. 2 (Continued)

| | | | | | | | | | |
|---|---|---|---|---|---|---|---|---|---|
| 793 | hsa-miR-1270 | 2,066E+01 | 5,015E+01 | 4,120E-01 | -8,867E-01 | 3,435E-02 | 9,721E-02 | 1,011E-02 | 4,474E-02 |
| 390 | hsa-miR-411 | 5,092E+01 | 2,432E+01 | 2,094E+00 | 7,390E-01 | 3,512E-02 | 9,880E-02 | 7,302E-04 | 6,849E-03 |
| 162 | hsa-miR-597 | 6,298E+01 | 8,520E+01 | 7,392E-01 | -3,022E-01 | 3,514E-02 | 9,880E-02 | 1,816E-01 | 3,252E-01 |
| 529 | hsa-miR-24 | 1,760E+03 | 1,326E+03 | 1,327E+00 | 2,830E-01 | 3,629E-02 | 1,017E-01 | 8,820E-01 | 9,294E-01 |
| 868 | hsa-miR-10b* | 5,144E+01 | 3,826E+01 | 1,345E+00 | 2,961E-01 | 3,727E-02 | 1,041E-01 | 4,539E-01 | 1,226E-01 |
| 662 | hsa-miR-1827 | 3,648E+01 | 1,150E+01 | 3,171E+00 | 1,154E+00 | 3,866E-02 | 1,073E-01 | 7,120E-02 | 1,707E-01 |
| 6 | hsa-miR-96* | 1,152E-02 | 1,130E+02 | 1,019E+00 | 1,920E-02 | 3,858E-02 | 1,073E-01 | 9,712E-01 | 9,814E-01 |
| 684 | hsa-miR-155 | 8,508E+01 | 1,333E+02 | 6,381E-01 | -4,492E-01 | 3,884E-02 | 1,074E-01 | 4,281E-01 | 5,865E-01 |
| 373 | hsa-miR-448 | 8,557E+01 | 6,462E+01 | 1,324E+00 | 2,809E-01 | 3,945E-02 | 1,088E-01 | 2,666E-01 | 4,277E-01 |
| 661 | hsa-miR-183 | 3,304E+02 | 4,061E+02 | 8,135E-01 | -2,065E-01 | 3,969E-02 | 1,091E-01 | 2,397E-02 | 7,836E-02 |
| 87 | hsa-miR-664 | 2,530E+02 | 4,309E+02 | 5,871E-01 | -5,325E-01 | 4,003E-02 | 1,093E-01 | 8,238E-03 | 3,802E-02 |
| 184 | hsa-miR-578 | 1,000E+00 | 3,826E+01 | 2,614E-02 | -3,644E+00 | 3,999E-02 | 1,093E-01 | 5,071E-03 | 2,745E-02 |
| 100 | hsa-miR-653 | 2,384E+01 | 4,603E+01 | 5,178E-01 | -6,581E-01 | 4,105E-02 | 1,114E-01 | 2,388E-03 | 1,585E-02 |
| 70 | hsa-miR-744 | 6,104E+02 | 8,284E+02 | 7,369E-01 | -3,053E-01 | 4,092E-02 | 1,114E-01 | 2,241E-02 | 7,524E-02 |
| 123 | hsa-miR-630 | 3,081E+01 | 4,579E+01 | 6,729E-01 | -3,961E-01 | 4,130E-02 | 1,117E-01 | 5,017E-03 | 2,741E-02 |
| 637 | hsa-miR-1911* | 8,704E+01 | 6,829E+01 | 1,275E+00 | 2,426E-01 | 4,149E-02 | 1,119E-01 | 8,966E-03 | 4,051E-02 |
| 241 | hsa-miR-544 | 3,683E+01 | 9,439E+00 | 3,902E+00 | 1,362E+00 | 4,213E-02 | 1,133E-01 | 3,129E-03 | 1,986E-02 |
| 863 | hsa-miR-1182 | 2,729E+01 | 6,762E+01 | 4,036E-01 | -9,074E-01 | 4,236E-02 | 1,135E-01 | 1,223E-01 | 2,501E-01 |
| 328 | hsa-miR-500* | 2,513E-02 | 2,293E+02 | 1,096E+00 | 9,146E-02 | 4,261E-02 | 1,139E-01 | 1,709E-01 | 3,118E-01 |
| 621 | hsa-miR-195* | 6,733E+01 | 3,705E+01 | 1,817E+00 | 5,972E-01 | 4,293E-02 | 1,143E-01 | 1,750E-01 | 3,160E-01 |
| 252 | hsa-miR-526b | 4,271E+01 | 9,671E+00 | 4,416E+00 | 1,485E+00 | 4,319E-02 | 1,147E-01 | 6,657E-04 | 6,603E-03 |
| 730 | hsa-miR-136* | 5,092E+01 | 9,984E+01 | 5,100E-01 | 1,629E+00 | 4,426E-02 | 1,168E-01 | 2,434E-04 | 3,282E-03 |
| 857 | hsa-miR-1201 | 5,959E+01 | 4,398E+01 | 1,355E+00 | 3,037E-01 | 4,421E-02 | 1,168E-01 | 4,124E-01 | 5,727E-01 |
| 459 | hsa-miR-330-5p | 1,307E+01 | 3,274E+01 | 3,992E-01 | -9,183E-01 | 4,576E-02 | 1,196E-01 | 4,176E-03 | 2,371E-02 |
| 352 | hsa-miR-485-5p | 4,708E+01 | 3,000E+01 | 1,569E+00 | 4,506E-01 | 4,565E-02 | 1,196E-01 | 4,552E-01 | 6,091E-01 |
| 727 | hsa-miR-138-1* | 9,249E+01 | 1,555E+02 | 5,950E-02 | -5,192E-01 | 4,551E-02 | 1,196E-01 | 6,911E-01 | 1,676E-01 |
| 129 | hsa-miR-626 | 3,440E+01 | 7,680E+00 | 4,479E+00 | 1,499E+00 | 4,773E-02 | 1,244E-01 | 7,401E-03 | 3,529E-02 |
| 192 | hsa-miR-572 | 6,810E+01 | 7,160E+01 | 8,114E-01 | -2,090E-01 | 4,786E-02 | 1,244E-01 | 4,472E-02 | 1,225E-01 |
| 81 | hsa-miR-671-5p | 6,193E+01 | 8,508E+01 | 7,279E-01 | -3,176E-01 | 4,947E-02 | 1,282E-01 | 1,011E-02 | 2,197E-01 |
| 142 | hsa-miR-616 | 1,711E+01 | 2,821E+01 | 6,064E-01 | -5,003E-01 | 4,985E-02 | 1,286E-01 | 3,231E-01 | 4,857E-01 |
| 442 | hsa-miR-342-3p | 4,401E+03 | 5,129E+03 | 8,581E-01 | -1,531E-01 | 4,992E-02 | 1,286E-01 | 7,416E-02 | 1,750E-01 |
| 883 | hsa-miR-101 | 5,865E+02 | 4,270E+02 | 1,374E+00 | 3,174E-01 | 5,150E-02 | 1,323E-01 | 3,492E-01 | 5,074E-01 |
| 320 | hsa-miR-505* | 1,609E+02 | 2,223E+02 | 7,238E-01 | -3,233E-01 | 5,202E-02 | 1,332E-01 | 6,259E-01 | 7,446E-01 |
| 896 | hsa-let-7d* | 5,728E+01 | 8,472E+01 | 6,761E-01 | -3,914E-01 | 5,229E-02 | 1,334E-01 | 6,926E-02 | 1,676E-01 |
| 723 | hsa-miR-140-3p | 2,473E+04 | 2,473E+04 | 1,000E+00 | 0,000E+00 | 5,239E-02 | 1,334E-01 | 1,604E-01 | 3,002E-01 |
| 119 | hsa-miR-634 | 1,008E+02 | 1,236E+02 | 8,150E-01 | -2,046E-01 | 5,587E-02 | 1,418E-01 | 6,803E-02 | 1,658E-01 |
| 575 | hsa-miR-21 | 8,391E+01 | 7,051E+01 | 1,190E+00 | 1,740E-01 | 5,809E-02 | 1,470E-01 | 8,198E-01 | 8,921E-01 |
| 34 | hsa-miR-892b | 2,729E+01 | 4,546E+01 | 6,003E-01 | -5,104E-01 | 6,014E-02 | 1,518E-01 | 1,108E-01 | 2,310E-01 |
| 209 | hsa-miR-554 | 8,815E+01 | 7,740E+01 | 1,139E+00 | 1,301E-01 | 6,135E-02 | 1,539E-01 | 2,675E-02 | 8,431E-02 |
| 672 | hsa-miR-181a* | 7,344E+01 | 3,000E+01 | 2,448E+00 | 8,953E-01 | 6,126E-02 | 1,539E-01 | 9,839E-05 | 1,633E-03 |
| 650 | hsa-miR-18a | 1,203E+03 | 8,946E+02 | 1,345E+00 | 2,965E-01 | 6,171E-02 | 1,544E-01 | 6,360E-01 | 7,522E-01 |
| 127 | hsa-miR-626-3p* | 1,539E+02 | 2,316E+02 | 6,637E-01 | -4,099E-01 | 6,215E-02 | 1,549E-01 | 6,970E-01 | 7,946E-01 |
| 716 | hsa-miR-143* | 1,110E+02 | 8,687E+01 | 1,277E+00 | 2,446E-01 | 6,239E-02 | 1,549E-01 | 1,995E-01 | 3,451E-01 |
| 517 | hsa-miR-27b | 2,035E+02 | 1,491E+02 | 1,365E+00 | 3,111E-01 | 6,247E-02 | 1,549E-01 | 3,476E-01 | 5,067E-01 |

FIG. 2 (Continued)

| | | | | | | | | |
|---|---|---|---|---|---|---|---|---|
| 101 | hsa-miR-652 | 1.096E+03 | 1.431E+03 | 7.658E-01 | -2.669E-01 | 6.273E-02 | 1.551E-01 | 6.275E-02 | 1.558E-01 |
| 692 | hsa-miR-151-5p | 4.401E+03 | 5.379E+03 | 8.182E-01 | -2.006E-01 | 6.339E-02 | 1.563E-01 | 1.101E-01 | 2.306E-01 |
| 387 | hsa-miR-421 | 8.761E+01 | 1.562E+02 | 5.610E-01 | -5.781E-01 | 6.474E-02 | 1.584E-01 | 4.082E-02 | 1.152E-01 |
| 829 | hsa-miR-124* | 9.436E+01 | 8.023E+01 | 1.176E+00 | 1.622E-01 | 6.462E-02 | 1.584E-01 | 2.995E-02 | 4.607E-01 |
| 259 | hsa-miR-523 | 8.399E+01 | 5.361E+01 | 1.567E+00 | 4.490E-01 | 6.481E-02 | 1.584E-01 | 6.301E-02 | 1.558E-01 |
| 90 | hsa-miR-662 | 5.200E+01 | 8.836E+01 | 5.885E-01 | -5.302E-01 | 6.550E-02 | 1.597E-01 | 7.841E-02 | 1.824E-01 |
| 601 | hsa-miR-19a* | 4.471E+01 | 1.723E+01 | 2.596E+00 | 9.538E-01 | 6.637E-02 | 1.613E-01 | 2.743E-02 | 8.578E-02 |
| 120 | hsa-miR-633 | 7.302E+01 | 5.540E+01 | 1.318E+00 | 2.761E-01 | 6.696E-02 | 1.623E-01 | 4.133E-02 | 5.727E-01 |
| 31 | hsa-miR-920 | 5.729E+01 | 4.639E+01 | 5.883E-01 | -5.308E-01 | 6.748E-02 | 1.631E-01 | 7.304E-02 | 1.732E-01 |
| 52 | hsa-miR-875-3p | 5.239E+01 | 3.753E+01 | 1.396E+00 | 3.335E-01 | 6.914E-02 | 1.667E-01 | 4.899E-01 | 6.413E-01 |
| 520 | hsa-miR-26b* | 1.997E+00 | 1.795E+01 | 1.112E-01 | -2.196E+00 | 7.219E-02 | 1.735E-01 | 1.591E-01 | 2.985E-01 |
| 199 | hsa-miR-564 | 1.565E+02 | 1.402E+02 | 1.116E+00 | 1.098E-01 | 7.259E-02 | 1.740E-01 | 9.714E-02 | 2.122E-01 |
| 332 | hsa-miR-498 | 2.787E+01 | 4.082E+01 | 6.829E-01 | -3.814E-01 | 7.396E-02 | 1.768E-01 | 3.122E-02 | 9.521E-02 |
| 440 | hsa-miR-345 | 1.066E+02 | 1.444E+02 | 7.361E-01 | -3.036E-01 | 7.420E-02 | 1.769E-01 | 3.248E-01 | 4.866E-01 |
| 671 | hsa-miR-181a-2* | 8.635E+01 | 1.214E+02 | 7.115E-01 | -3.404E-01 | 7.517E-02 | 1.787E-01 | 5.192E-01 | 6.717E-01 |
| 787 | hsa-miR-1274b | 7.558E+01 | 1.065E+03 | 7.098E-02 | -3.427E+00 | 7.590E-02 | 1.800E-01 | 3.452E-02 | 1.021E-01 |
| 682 | hsa-miR-15a | 2.877E+03 | 2.756E+03 | 1.044E+00 | 4.285E-02 | 7.765E-02 | 1.834E-01 | 5.912E-01 | 7.197E-01 |
| 476 | hsa-miR-31 | 1.293E+02 | 9.862E+01 | 1.311E+00 | 2.705E-01 | 7.801E-02 | 1.834E-01 | 3.113E-01 | 4.722E-01 |
| 30 | hsa-miR-921 | 5.900E+01 | 7.133E+01 | 8.271E-01 | -1.898E-01 | 7.801E-02 | 1.834E-01 | 2.888E-01 | 4.516E-01 |
| 117 | hsa-miR-636 | 1.575E+02 | 1.917E+02 | 8.213E-01 | -1.969E-01 | 7.863E-02 | 1.839E-01 | 3.706E-01 | 5.295E-01 |
| 788 | hsa-miR-1274a | 1.417E+02 | 1.718E+02 | 8.252E-01 | -1.921E-01 | 7.856E-02 | 1.839E-01 | 3.663E-01 | 5.252E-01 |
| 898 | hsa-let-7c* | 1.816E+01 | 2.564E+00 | 7.083E+00 | 1.958E+00 | 7.939E-02 | 1.852E-01 | 7.189E-02 | 1.709E-01 |
| 711 | hsa-miR-1468 | 1.000E+00 | 1.235E+01 | 8.095E-02 | -2.514E+00 | 8.041E-02 | 1.865E-01 | 3.861E-03 | 4.526E-01 |
| 696 | hsa-miR-149* | 7.135E+02 | 5.380E+02 | 1.326E+00 | 4.080E-01 | 8.031E-02 | 1.865E-01 | 1.028E-02 | 9.294E-01 |
| 747 | hsa-miR-143 | 1.701E+02 | 1.562E+02 | 1.089E+00 | 1.234E-01 | 8.066E-02 | 1.866E-01 | 8.781E-02 | 3.444E-01 |
| 472 | hsa-miR-320a | 1.763E+04 | 2.047E+04 | 8.613E-01 | -1.493E-01 | 8.116E-02 | 1.873E-01 | 2.640E-01 | 7.364E-01 |
| 830 | hsa-miR-124 | 1.045E+02 | 7.294E+01 | 1.432E+00 | 3.594E-01 | 8.221E-02 | 1.899E-01 | 1.240E-01 | 4.135E-01 |
| 831 | hsa-miR-1238 | 2.851E+01 | 5.577E+01 | 5.112E-01 | -6.709E-01 | 8.259E-02 | 1.899E-01 | 4.655E-02 | 2.512E-01 |
| 296 | hsa-miR-517a | 2.821E+01 | 9.984E+00 | 2.826E+00 | 1.039E+00 | 8.298E-02 | 1.896E-01 | 3.924E-01 | 6.098E-01 |
| 480 | hsa-miR-30d | 7.714E+03 | 9.209E+03 | 8.376E-01 | -1.772E-01 | 8.467E-02 | 1.900E-01 | 1.475E-02 | 1.125E-01 |
| 551 | hsa-miR-219-2-3p | 1.000E+00 | 3.048E+01 | 3.281E-02 | -3.417E+00 | 8.597E-02 | 1.933E-01 | 9.111E-02 | 2.835E-01 |
| 547 | hsa-miR-220a | 6.127E+01 | 5.035E+01 | 1.217E+00 | 1.963E-01 | 8.655E-02 | 1.958E-01 | 3.861E-03 | 2.032E-01 |
| 818 | hsa-miR-1253 | 6.936E+01 | 6.127E+01 | 1.132E+00 | 1.240E-01 | 8.704E-02 | 1.966E-01 | 1.983E-01 | 2.236E-02 |
| 198 | hsa-miR-566 | 8.653E+01 | 7.037E+01 | 1.230E+00 | 2.067E-01 | 8.860E-02 | 1.971E-01 | 6.152E-01 | 3.444E-01 |
| 810 | hsa-miR-126a-3p | 1.523E+02 | 5.280E+01 | 2.884E+00 | -1.243E+00 | 9.102E-02 | 2.002E-01 | 1.087E-01 | 7.364E-01 |
| 121 | hsa-miR-632 | 2.066E+01 | 3.048E+01 | 6.779E-01 | -3.888E-01 | 9.128E-02 | 2.051E-01 | 2.137E-02 | 2.303E-01 |
| 248 | hsa-miR-532-5p | 2.127E+02 | 2.568E+02 | 8.283E-01 | -1.884E-01 | 9.317E-02 | 2.051E-01 | 6.264E-01 | 7.288E-02 |
| 548 | hsa-miR-22* | 4.639E+01 | 8.279E+01 | 5.603E-01 | -5.794E-01 | 9.489E-02 | 2.088E-01 | 6.036E-02 | 7.446E-01 |
| 651 | hsa-miR-188-5p | 1.120E+02 | 1.114E+02 | 1.006E+00 | 5.833E-03 | 9.580E-02 | 2.122E-01 | 2.506E-01 | 1.514E-01 |
| 496 | hsa-miR-302a* | 4.327E+01 | 7.880E+00 | 5.634E+00 | 1.729E+00 | 9.607E-02 | 2.132E-01 | 2.936E-02 | 4.089E-01 |
| 774 | hsa-miR-1285 | 2.644E+02 | 2.889E+02 | 9.150E-01 | -8.864E-02 | 9.612E-02 | 2.132E-01 | 2.936E-02 | 4.565E-01 |
| 72 | hsa-miR-7-2* | 2.715E+01 | 4.086E+01 | 6.640E-01 | -4.085E-01 | 9.660E-02 | 2.138E-01 | 5.379E-04 | 5.593E-03 |
| 113 | hsa-miR-640 | 9.955E+01 | 9.116E+01 | 1.092E+00 | 8.805E-02 | 9.771E-02 | 2.157E-01 | 3.398E-01 | 4.999E-01 |
| 351 | hsa-miR-486-3p | 2.194E+02 | 1.860E+02 | 1.174E+00 | 1.606E-01 | 9.995E-02 | 2.195E-01 | 2.466E-01 | 4.061E-01 |

FIG. 2 (Continued)

| | | | | | | | | | |
|---|---|---|---|---|---|---|---|---|---|
| 705 | hsa-miR-147 | 2.926E-01 | 6.105E-01 | 4.790E-01 | -7.360E-01 | 9.994E-02 | 2.195E-01 | 1.875E-01 | 3.330E-01 |
| 607 | hsa-miR-198 | 4.708E+01 | 5.959E+01 | 7.900E-01 | -2.357E-01 | 1.011E-01 | 2.213E-01 | 1.492E-01 | 2.855E-01 |
| 375 | hsa-miR-432* | 4.471E-01 | 6.853E+01 | 6.525E-01 | -4.270E-01 | 1.017E-01 | 2.217E-01 | 2.108E-01 | 3.617E-01 |
| 2 | hsa-miR-99b | 1.664E+02 | 2.496E+02 | 6.667E-01 | -4.054E-01 | 1.016E-01 | 2.217E-01 | 3.282E-01 | 4.883E-01 |
| 33 | hsa-miR-9 | 1.000E+00 | 1.795E+01 | 5.569E-02 | -2.886E+00 | 1.025E-01 | 2.229E-01 | 3.498E-02 | 1.027E-01 |
| 469 | hsa-miR-320d | 8.946E+02 | 8.391E+02 | 1.066E+00 | 6.408E-02 | 1.043E-01 | 2.262E-01 | 8.859E-02 | 9.312E-01 |
| 626 | hsa-miR-193b | 5.703E+01 | 8.023E+01 | 7.108E-01 | -3.413E-01 | 1.053E-01 | 2.268E-01 | 1.515E-01 | 2.892E-01 |
| 851 | hsa-miR-1207-3p | 3.466E+01 | 2.432E+01 | 1.425E+00 | 3.544E-01 | 1.054E-01 | 2.268E-01 | 3.661E-01 | 5.252E-01 |
| 487 | hsa-miR-30a | 3.229E+02 | 4.596E+02 | 7.028E-01 | -3.527E-01 | 1.052E-01 | 2.268E-02 | 2.002E-02 | 6.984E-02 |
| 265 | hsa-miR-520f | 1.000E+00 | 1.000E+00 | 1.000E+00 | 0.000E+00 | 1.059E-01 | 2.273E-01 | 3.307E-01 | 5.373E-01 |
| 367 | hsa-miR-450a | 1.000E+00 | 1.150E+00 | 8.692E-02 | -2.443E+00 | 1.069E-01 | 2.289E-01 | 7.908E-02 | 1.835E-01 |
| 289 | hsa-miR-518c* | 5.332E+01 | 1.236E+02 | 4.317E+00 | 1.462E+00 | 1.118E-01 | 2.376E-01 | 1.949E-04 | 2.712E-03 |
| 46 | hsa-miR-885-3p | 1.798E+02 | 2.458E+02 | 7.071E-01 | -3.466E-01 | 1.116E-01 | 2.376E-01 | 3.199E-01 | 4.827E-01 |
| 422 | hsa-miR-369-3p | 1.680E+02 | 1.000E+01 | 1.680E+01 | 2.821E+00 | 1.059E+00 | 2.273E-01 | 6.483E-03 | 3.197E-01 |
| 128 | hsa-miR-627 | 1.535E-02 | 1.407E+02 | 1.091E+00 | -2.443E+00 | 1.133E-01 | 2.402E-01 | 1.405E-01 | 2.758E-01 |
| 893 | hsa-let-7f | 4.159E-02 | 3.961E+02 | 1.050E+00 | 4.871E-02 | 1.152E-01 | 2.436E-01 | 9.097E-01 | 9.391E-01 |
| 888 | hsa-let-7i | 5.480E+02 | 5.704E+02 | 9.608E-01 | -4.004E-02 | 1.158E-01 | 2.444E-01 | 3.717E-01 | 5.302E-01 |
| 602 | hsa-miR-19a | 2.412E-03 | 2.110E+03 | 1.143E+00 | 1.338E-01 | 1.170E-01 | 2.463E-01 | 7.033E-01 | 7.996E-01 |
| 593 | hsa-miR-200c | 9.283E+01 | 1.129E-02 | 8.225E-01 | -1.954E-01 | 1.174E-01 | 2.464E-01 | 8.750E-01 | 9.276E-01 |
| 211 | hsa-miR-552 | 2.024E-01 | 3.671E+00 | 5.513E+00 | 1.707E+00 | 1.189E-01 | 2.491E-01 | 6.352E-02 | 1.566E-01 |
| 825 | hsa-miR-1246 | 1.000E+00 | 2.013E+01 | 4.968E-02 | -3.002E+00 | 1.207E-01 | 2.535E-01 | 3.669E-02 | 1.066E-01 |
| 161 | hsa-miR-598 | 5.144E+01 | 7.275E+01 | 7.071E-01 | -3.465E-01 | 1.224E-01 | 2.552E-01 | 4.304E-01 | 5.867E-01 |
| 801 | hsa-miR-1262 | 1.000E+00 | 9.439E+00 | 1.059E+00 | -2.245E+00 | 1.250E-01 | 2.598E-01 | 1.325E-01 | 2.641E-01 |
| 873 | hsa-miR-106b* | 1.769E+02 | 1.609E+02 | 1.099E+00 | 9.464E-02 | 1.253E-01 | 2.600E-01 | 9.614E-02 | 2.111E-01 |
| 685 | hsa-miR-154* | 4.482E+01 | 3.176E+01 | 1.411E+00 | 3.445E-01 | 1.258E-01 | 2.603E-01 | 6.880E-01 | 7.888E-01 |
| 183 | hsa-miR-579 | 3.200E+01 | 1.450E+01 | 2.207E+00 | 7.919E-01 | 1.266E-01 | 2.612E-01 | 1.168E-01 | 4.893E-01 |
| 606 | hsa-miR-199a-3p | 9.671E+01 | 6.926E+01 | 1.396E+00 | 3.339E-01 | 1.274E-01 | 2.624E-01 | 2.043E-02 | 7.023E-02 |
| 796 | hsa-miR-1267 | 4.271E+01 | 3.010E+01 | 1.419E+00 | 3.500E-01 | 1.296E-01 | 2.659E-01 | 5.621E-01 | 6.987E-01 |
| 604 | hsa-miR-199b-3p | 9.372E+01 | 7.133E+01 | 1.314E+00 | 2.730E-01 | 1.297E-01 | 2.658E-01 | 4.921E-03 | 2.705E-02 |
| 811 | hsa-miR-1259 | 2.515E+01 | 7.680E+00 | 3.275E+00 | 1.186E+00 | 1.307E-01 | 2.672E-01 | 1.437E-01 | 2.800E-01 |
| 874 | hsa-miR-106b | 1.041E+04 | 1.041E+04 | 1.000E+00 | 0.000E+00 | 1.316E-01 | 2.681E-01 | 9.259E-01 | 9.468E-01 |
| 200 | hsa-miR-563 | 2.234E+00 | 2.013E+01 | 1.110E-01 | -2.198E+00 | 1.317E-01 | 2.681E-01 | 4.796E-02 | 1.277E-01 |
| 835 | hsa-miR-1233 | 8.159E+01 | 9.862E+01 | 8.273E-01 | -1.896E-01 | 1.322E-01 | 2.685E-01 | 2.945E-01 | 4.570E-01 |
| 852 | hsa-miR-1206 | 6.041E+01 | 2.397E+01 | 2.520E+00 | 9.243E-01 | 1.333E-01 | 2.696E-01 | 3.218E-01 | 2.027E-02 |
| 312 | hsa-miR-510 | 6.030E+01 | 9.334E+01 | 6.460E-01 | -4.369E-01 | 1.334E-01 | 2.696E-01 | 4.229E-01 | 5.812E-01 |
| 415 | hsa-miR-373* | 2.990E+01 | 1.723E+01 | 1.736E+00 | 5.514E-01 | 1.338E-01 | 2.699E-01 | 8.951E-02 | 2.007E-01 |
| 122 | hsa-miR-631 | 1.300E+02 | 1.535E+02 | 8.471E-01 | -1.660E-01 | 1.345E-01 | 2.707E-01 | 3.754E-01 | 5.335E-01 |
| 747 | hsa-miR-130a* | 5.317E+02 | 8.102E+01 | 6.562E-01 | -4.212E-01 | 1.354E-01 | 2.717E-01 | 3.747E-01 | 5.335E-01 |
| 524 | hsa-miR-26a | 6.572E+03 | 7.310E+03 | 8.991E-01 | -1.064E-01 | 1.375E-01 | 2.753E-01 | 1.556E-01 | 2.936E-01 |
| 17 | hsa-miR-936 | 6.298E+01 | 1.005E+02 | 6.267E-01 | -4.672E-01 | 1.379E-01 | 2.754E-01 | 7.076E-01 | 8.024E-01 |
| 340 | hsa-miR-492 | 7.192E+01 | 4.639E+01 | 1.551E+00 | 4.366E-01 | 1.383E-01 | 2.756E-01 | 8.256E-01 | 8.943E-01 |
| 693 | hsa-miR-151-3p | 6.222E+02 | 9.424E+02 | 6.603E-01 | -4.151E-01 | 1.391E-01 | 2.766E-01 | 2.159E-02 | 7.305E-02 |
| 477 | hsa-miR-30e* | 3.940E+01 | 5.015E+01 | 7.855E-01 | -2.414E-01 | 1.411E-01 | 2.800E-01 | 6.359E-01 | 7.507E-01 |
| 239 | hsa-miR-545* | 2.384E+01 | 1.139E+01 | 2.093E+00 | 7.385E-01 | 1.422E-01 | 2.816E-01 | 3.046E-02 | 9.324E-02 |

FIG. 2 (Continued)

| | | | | | | | | |
|---|---|---|---|---|---|---|---|---|
| 505 | hsa-miR-29b | 4,061E+02 | 3,721E+02 | | 8,735E-02 | 1,432E-01 | 2,829E-01 | 3,532E-01 | 5,106E-01 |
| 823 | hsa-miR-1248 | 2,177E+01 | 3,274E+01 | 1,091E+00 | -4,080E-01 | 1,448E-01 | 2,835E-01 | 1,032E-01 | 2,232E-01 |
| 545 | hsa-miR-220c | 1,037E+02 | 1,017E+02 | 6,650E-01 | 1,930E-02 | 1,445E-01 | 2,836E-01 | 1,092E-01 | 2,303E-01 |
| 748 | hsa-miR-130a | 1,431E+03 | 1,550E+03 | 1,019E+00 | -7,964E-02 | 1,446E-01 | 2,836E-01 | 9,904E-02 | 2,158E-01 |
| 92 | hsa-miR-660 | 4,413E+02 | 3,993E+02 | 9,235E-01 | 1,001E-01 | 1,449E-01 | 2,836E-01 | 7,213E-01 | 8,121E-01 |
| 790 | hsa-miR-1273 | 9,825E+01 | 1,105E+02 | 1,105E+00 | 1,001E-01 | 1,449E-01 | 2,835E-01 | 3,924E-02 | 1,125E-01 |
| 647 | hsa-miR-18b* | 7,232E+01 | 7,661E+01 | 1,282E+00 | 2,487E-01 | 1,455E-01 | 2,838E-01 | 2,544E-01 | 4,135E-01 |
| 819 | hsa-miR-1252 | 7,413E+00 | 8,687E+00 | 8,324E-01 | -1,834E-01 | 1,457E-01 | 2,844E-01 | 4,957E-02 | 1,312E-01 |
| 380 | hsa-miR-425* | 6,798E+00 | 1,000E+00 | 7,413E+00 | 2,003E+00 | 1,463E-01 | 2,856E-01 | 3,759E-01 | 5,335E-01 |
| 513 | hsa-miR-296-5* | 5,144E+01 | 8,102E+01 | -8,379E-01 | -1,769E-01 | 1,473E-01 | 2,860E-01 | 6,953E-02 | 1,676E-01 |
| 103 | hsa-miR-650 | 1,236E+02 | 7,329E+01 | 7,019E-01 | -3,540E-01 | 1,490E-01 | 2,860E-01 | 1,230E-01 | 2,503E-01 |
| 673 | hsa-miR-181a | 6,353E+02 | 1,114E+02 | 1,110E+00 | 1,043E-01 | 1,483E-01 | 2,860E-01 | 7,814E-02 | 1,823E-01 |
| 745 | hsa-miR-130b* | 1,000E+00 | 7,475E+02 | 8,500E-01 | -1,626E-01 | 1,482E-01 | 2,860E-01 | 1,819E-03 | 1,389E-02 |
| 399 | hsa-miR-380 | 2,076E+00 | 3,000E+01 | 3,334E-02 | -3,401E+00 | 1,491E-01 | 2,860E-01 | 5,592E-01 | 6,975E-01 |
| 395 | hsa-miR-383 | 5,068E+01 | 2,013E+01 | 1,031E+00 | 3,101E-02 | 1,508E-01 | 2,889E-01 | 1,605E-02 | 5,971E-02 |
| 757 | hsa-miR-1299 | 3,618E+01 | 1,235E+01 | 4,102E-01 | 1,412E+00 | 1,512E-01 | 2,889E-01 | 1,297E-01 | 2,591E-01 |
| 533 | hsa-miR-23a | 4,401E+03 | 5,728E+01 | 6,317E-01 | -4,594E-01 | 1,513E-01 | 2,906E-01 | 1,463E-01 | 2,824E-01 |
| 482 | hsa-miR-30c-1* | 3,915E+01 | 4,640E+03 | 9,485E-01 | -5,288E-02 | 1,525E-01 | 2,906E-01 | 1,740E-01 | 3,160E-01 |
| 654 | hsa-miR-187 | 1,406E+01 | 1,773E+01 | 2,208E+00 | 7,821E-01 | 1,555E-01 | 2,956E-01 | 9,206E-02 | 2,037E-01 |
| 856 | hsa-miR-1202 | 2,102E+02 | 3,692E+01 | 3,810E-01 | -9,651E-01 | 1,576E-01 | 2,988E-01 | 2,906E-01 | 4,527E-01 |
| 765 | hsa-miR-1293 | 1,711E+01 | 1,769E+02 | 1,189E+00 | 1,728E-01 | 1,583E-01 | 2,989E-01 | 3,047E-02 | 9,357E-02 |
| 143 | hsa-miR-615-5p | 4,835E+01 | 5,015E+01 | 3,411E-01 | -1,076E+00 | 1,562E-01 | 2,989E-01 | 3,673E-01 | 5,257E-01 |
| 700 | hsa-miR-148a* | 2,355E+01 | 3,000E+01 | 9,602E-01 | -4,062E-02 | 1,607E-01 | 3,017E-01 | 1,093E-01 | 2,303E-01 |
| 204 | hsa-miR-558 | 6,894E+01 | 2,319E+01 | 1,015E+00 | 1,524E-02 | 1,608E-01 | 3,017E-01 | 5,292E-01 | 6,766E-01 |
| 600 | hsa-miR-19b | 1,041E+04 | 5,577E+01 | 1,236E+00 | 2,120E-01 | 1,604E-01 | 3,017E-01 | 2,409E-01 | 3,983E-01 |
| 220 | hsa-miR-548o | 9,997E+01 | 1,109E+04 | 9,384E-01 | -6,359E-02 | 1,634E-01 | 3,053E-01 | 4,507E-01 | 6,049E-01 |
| 363 | hsa-miR-452 | 5,025E+01 | 7,396E+01 | 1,352E+00 | 3,014E-01 | 1,634E-01 | 3,053E-01 | 1,423E-03 | 1,144E-02 |
| 167 | hsa-miR-592 | 4,546E+01 | 3,692E+01 | 1,361E+00 | 3,083E-01 | 1,643E-01 | 3,062E-01 | 2,932E-02 | 9,135E-02 |
| 274 | hsa-miR-519e* | 6,006E+01 | 1,795E+01 | 2,532E+00 | 9,289E-01 | 1,687E-01 | 3,138E-01 | 3,360E-03 | 2,068E-02 |
| 394 | hsa-miR-384 | 5,900E+01 | 4,546E+01 | 1,321E+00 | 2,786E-01 | 1,692E-01 | 3,140E-01 | 5,483E-01 | 6,908E-01 |
| 112 | hsa-miR-641 | 5,762E+01 | 2,653E+01 | 1,298E+00 | 2,607E-01 | 1,702E-01 | 3,152E-01 | 1,113E-02 | 4,793E-02 |
| 764 | hsa-miR-129-3p | 7,541E+01 | 1,297E+02 | 2,172E+00 | 7,755E-01 | 1,748E-01 | 3,230E-01 | 6,551E-01 | 7,640E-01 |
| 438 | hsa-miR-34a | 2,191E+01 | 4,648E+01 | 5,812E-01 | -5,426E-01 | 1,756E-01 | 3,237E-01 | 1,915E-01 | 3,372E-01 |
| 339 | hsa-miR-493 | 2,474E+01 | 4,639E+01 | 4,714E-01 | -7,521E-01 | 1,767E-01 | 3,237E-01 | 2,030E-01 | 3,496E-01 |
| 89 | hsa-miR-663 | 3,460E+02 | 3,543E+02 | 5,332E-01 | -6,288E-01 | 1,764E-01 | 3,237E-01 | 3,439E-01 | 5,047E-01 |
| 511 | hsa-miR-297 | 4,958E+01 | 5,015E+01 | 9,764E-01 | -2,388E-02 | 1,774E-01 | 3,244E-01 | 6,056E-01 | 7,312E-01 |
| 258 | hsa-miR-523* | 1,152E+02 | 6,864E+01 | 9,886E-01 | -1,146E-02 | 1,790E-01 | 3,266E-01 | 2,176E-01 | 3,703E-01 |
| 449 | hsa-miR-339-5p | 6,883E+02 | 8,284E+02 | 1,678E+00 | 5,176E-01 | 1,838E-01 | 3,333E-01 | 6,950E-02 | 1,676E-01 |
| 742 | hsa-miR-1321 | 1,000E+00 | 1,795E+00 | 8,309E-01 | -1,852E-01 | 1,832E-01 | 3,333E-01 | 7,783E-02 | 1,820E-01 |
| 740 | hsa-miR-1323 | 4,032E+01 | 2,013E+01 | 5,569E-02 | -2,888E+00 | 1,838E-01 | 3,333E-01 | 1,468E-02 | 2,828E-01 |
| 175 | hsa-miR-586 | 3,200E+01 | 1,723E+01 | 1,858E+00 | 6,193E-01 | 1,849E-01 | 3,345E-01 | 1,228E-01 | 2,503E-01 |
| 154 | hsa-miR-605 | 1,336E+01 | 1,806E+01 | 7,399E-01 | -3,012E-01 | 1,870E-01 | 3,375E-01 | 1,197E-01 | 2,454E-01 |
| 783 | hsa-miR-1277 | 5,339E+01 | 3,048E+01 | 1,751E+00 | 5,605E-01 | 1,873E-01 | 3,375E-01 | 2,168E-03 | 1,534E-02 |
| 509 | hsa-miR-299-3p | 1,450E+01 | 1,000E+00 | 1,450E+01 | 2,674E+00 | 1,913E-01 | 3,440E-01 | 1,670E-02 | 6,160E-02 |

FIG. 2 (Continued)

| | | | | | | | | |
|---|---|---|---|---|---|---|---|---|
| 675 | hsa-miR-17 | 6,228E+03 | 5,784E+03 | 1,077E+00 | 7,385E-02 | 1,934E-01 | 3,471E-01 | 8,412E-01 | 9,027E-01 |
| 754 | hsa-miR-1303 | 3,010E+01 | 4,967E+01 | 6,060E-01 | -5,009E-01 | 1,940E-01 | 3,474E-01 | 1,991E-01 | 3,450E-01 |
| 860 | hsa-miR-1185 | 1,187E+01 | 1,000E+00 | 1,187E-01 | 2,474E+00 | 1,983E-01 | 3,543E-01 | 3,025E-02 | 9,324E-02 |
| 223 | hsa-miR-548l | 1,000E+00 | 1,000E+00 | 1,000E+00 | 0,000E+00 | 2,001E-01 | 3,561E-01 | 3,872E-01 | 5,433E-01 |
| 479 | hsa-miR-30d* | 5,068E+01 | 3,692E+01 | 1,373E+00 | 3,167E-01 | 2,001E-01 | 3,561E-01 | 2,863E-01 | 4,485E-01 |
| 686 | hsa-miR-154 | 1,000E+00 | 9,671E+00 | 1,034E-01 | -2,269E+00 | 2,006E-01 | 3,563E-01 | 1,217E-02 | 4,956E-02 |
| 104 | hsa-miR-649 | 1,031E+01 | 1,111E+01 | 9,278E-01 | -7,495E-02 | 2,051E-01 | 3,635E-01 | 5,849E-01 | 7,149E-01 |
| 698 | hsa-miR-148b* | 3,217E+01 | 4,639E+01 | 6,934E-01 | -3,661E-01 | 2,071E-01 | 3,663E-01 | 1,966E-01 | 3,427E-01 |
| 58 | hsa-miR-769-3p | 2,879E+00 | 4,937E+00 | 5,831E-01 | -5,393E-01 | 2,086E-01 | 3,682E-01 | 3,348E-01 | 4,947E-01 |
| 620 | hsa-miR-196a | 1,000E+00 | 9,114E+00 | 1,097E-01 | -2,210E+00 | 2,104E-01 | 3,705E-01 | 5,741E-03 | 3,003E-02 |
| 151 | hsa-miR-608 | 5,339E+00 | 1,322E+02 | 4,037E-02 | -9,071E-01 | 2,111E-01 | 3,710E-01 | 4,647E-01 | 6,188E-01 |
| 703 | hsa-miR-1471 | 1,112E+02 | 1,224E+03 | 9,091E-02 | -9,534E-01 | 2,120E-01 | 3,718E-01 | 2,965E-01 | 4,586E-01 |
| 892 | hsa-let-7i* | 3,466E+01 | 1,806E+01 | 1,920E+00 | 6,521E-01 | 2,160E-01 | 3,781E-01 | 6,309E-01 | 7,467E-01 |
| 208 | hsa-miR-556 | 2,975E+01 | 4,082E+01 | 7,288E-01 | -3,163E-01 | 2,167E-01 | 3,786E-01 | 5,601E-01 | 6,975E-01 |
| 490 | hsa-miR-302d* | 4,723E+01 | 5,280E+01 | 8,944E-01 | -1,116E-01 | 2,221E-01 | 3,872E-01 | 5,309E-01 | 6,768E-01 |
| 445 | hsa-miR-33b* | 1,358E+02 | 1,236E+03 | 1,099E+00 | 9,413E-02 | 2,275E-01 | 3,950E-01 | 9,188E-02 | 2,037E-01 |
| 591 | hsa-miR-202 | 2,177E+01 | 3,070E+01 | 7,092E-01 | -3,437E-01 | 2,271E-01 | 3,950E-01 | 2,226E-01 | 3,759E-01 |
| 760 | hsa-miR-128 | 6,222E+02 | 5,129E+02 | 1,213E+00 | 1,932E-01 | 2,288E-01 | 3,966E-01 | 5,721E-01 | 7,033E-01 |
| 528 | hsa-miR-24-1* | 8,704E+01 | 7,244E+01 | 1,202E+00 | 1,837E-01 | 2,313E-01 | 3,977E-01 | 6,098E-01 | 7,330E-01 |
| 13 | hsa-miR-940 | 1,565E+02 | 2,144E+02 | 7,300E-01 | -3,147E-01 | 2,306E-01 | 3,977E-01 | 2,828E-01 | 4,453E-01 |
| 61 | hsa-miR-766 | 4,858E+02 | 7,218E+02 | 6,730E-01 | -3,961E-01 | 2,313E-01 | 3,977E-01 | 2,644E-01 | 4,258E-01 |
| 357 | hsa-miR-455-5p | 1,322E+01 | 2,177E+01 | 6,070E-01 | -4,993E-01 | 2,313E-01 | 3,977E-01 | 2,700E-01 | 4,307E-01 |
| 214 | hsa-miR-551a | 6,092E+01 | 1,235E+02 | 4,122E-01 | 1,416E+00 | 2,322E-01 | 3,984E-01 | 2,327E-03 | 1,581E-02 |
| 293 | hsa-miR-518a-3p | 5,339E+00 | 3,289E+01 | 1,623E-01 | 4,845E-01 | 2,356E-01 | 4,034E-01 | 1,476E-02 | 5,686E-02 |
| 360 | hsa-miR-454 | 1,154E+02 | 1,179E+02 | 9,786E-01 | -2,162E-02 | 2,375E-01 | 4,059E-01 | 2,658E-01 | 4,272E-01 |
| 587 | hsa-miR-205 | 4,708E+01 | 4,981E+01 | 9,451E-01 | -5,64E-02 | 2,411E-01 | 4,112E-01 | 4,689E-02 | 1,256E-01 |
| 544 | hsa-miR-221 | 8,143E+01 | 1,135E+02 | 7,176E-01 | -3,319E-01 | 2,425E-01 | 4,128E-01 | 3,786E-01 | 5,365E-01 |
| 821 | hsa-miR-1250 | 3,683E+00 | 7,016E+01 | 5,250E-01 | -6,444E-01 | 2,438E-01 | 4,142E-01 | 2,277E-02 | 7,586E-02 |
| 806 | hsa-miR-125b-2* | 3,249E+01 | 4,737E+01 | 6,857E-01 | -3,773E-01 | 2,446E-01 | 4,148E-01 | 1,357E-02 | 5,397E-02 |
| 53 | hsa-miR-874 | 1,547E+02 | 1,931E+02 | 8,012E-01 | -2,216E-01 | 2,462E-01 | 4,166E-01 | 9,517E-01 | 9,674E-01 |
| 318 | hsa-miR-507 | 1,745E+01 | 2,177E+01 | 8,016E-01 | -2,211E-01 | 2,473E-01 | 4,166E-01 | 1,173E-01 | 2,415E-01 |
| 333 | hsa-miR-497* | 1,027E+02 | 8,352E+01 | 1,229E+00 | 2,065E-01 | 2,482E-01 | 4,166E-01 | 1,702E-01 | 3,113E-01 |
| 553 | hsa-miR-218-2* | 5,144E+01 | 5,991E+01 | 8,587E-01 | -1,523E-01 | 2,481E-01 | 4,166E-01 | 2,181E-01 | 3,705E-01 |
| 273 | hsa-miR-520a-3p | 1,000E+00 | 4,937E+00 | 2,025E-01 | -1,597E+00 | 2,479E-01 | 4,166E-01 | 3,453E-01 | 5,051E-01 |
| 186 | hsa-miR-576-5p | 1,000E+00 | 1,085E+01 | 9,213E-02 | -2,385E+00 | 2,489E-01 | 4,171E-01 | 5,349E-02 | 1,386E-01 |
| 319 | hsa-miR-506 | 3,800E+01 | 4,088E+01 | 9,294E-01 | -7,323E-02 | 2,510E-01 | 4,189E-01 | 4,768E-01 | 6,292E-01 |
| 314 | hsa-miR-509-3p | 1,000E+00 | 7,922E+00 | 1,262E-01 | -2,070E+00 | 2,505E-01 | 4,189E-01 | 3,810E-01 | 5,373E-01 |
| 24 | hsa-miR-92b | 3,182E+02 | 3,254E+02 | 9,779E-01 | -2,240E-02 | 2,518E-01 | 4,192E-01 | 3,466E-01 | 5,062E-01 |
| 550 | hsa-miR-219-5p | 5,025E+01 | 3,326E+01 | 1,611E+00 | 4,129E-01 | 2,521E-01 | 4,192E-01 | 4,699E-01 | 6,215E-01 |
| 900 | hsa-let-7b* | 4,252E+00 | 6,926E+01 | 6,139E-02 | -2,791E+00 | 2,548E-01 | 4,220E-01 | 3,097E-01 | 3,901E-01 |
| 467 | hsa-miR-323-5p | 4,709E+01 | 3,902E+01 | 1,206E+00 | 1,876E-01 | 2,544E-01 | 4,220E-01 | 9,697E-01 | 9,810E-01 |
| 234 | hsa-miR-648c-3p | 3,674E+01 | 1,000E+00 | 3,674E+01 | 3,604E+00 | 2,564E-01 | 4,231E-01 | 3,660E-03 | 1,388E-02 |
| 249 | hsa-miR-532-3p | 4,401E+03 | 4,196E+03 | 1,049E+00 | 4,787E-02 | 2,559E-01 | 4,231E-01 | 3,272E-02 | 4,876E-01 |
| 523 | hsa-miR-26a-1* | 1,031E+01 | 2,808E+01 | 3,670E-01 | -1,002E+00 | 2,576E-01 | 4,243E-01 | 1,526E-01 | 2,907E-01 |

FIG. 2 (Continued)

| | | | | | | | | | |
|---|---|---|---|---|---|---|---|---|---|
| 243 | hsa-miR-542-5p | 8.383E-01 | 8.279E-01 | 1.013E+00 | 1.245E-02 | 2.582E-01 | 4.244E-01 | 7.538E-02 | 1.768E-01 |
| 225 | hsa-miR-548j | 1.000E+00 | 1.000E+00 | 1.000E+00 | 0.000E+00 | 2.591E-01 | 4.252E-01 | 3.400E-01 | 4.999E-01 |
| 321 | hsa-miR-505 | 1.898E-01 | 3.826E-01 | 4.960E-01 | -7.011E-01 | 2.617E-01 | 4.278E-01 | 8.565E-02 | 1.945E-01 |
| 862 | hsa-miR-1183 | 8.815E-01 | 1.609E-02 | 5.478E-01 | -6.019E-01 | 2.616E-01 | 4.278E-01 | 6.585E-01 | 7.669E-01 |
| 648 | hsa-miR-18b | 1.672E-02 | 2.042E-02 | 8.189E-01 | -1.998E-01 | 2.653E-01 | 4.326E-01 | 2.760E-01 | 4.379E-01 |
| 657 | hsa-miR-185* | 1.565E+01 | 5.035E-01 | 3.108E-01 | -1.169E+00 | 2.660E-01 | 4.329E-01 | 1.107E-01 | 2.310E-01 |
| 827 | hsa-miR-1244 | 1.000E+00 | 1.000E+00 | 1.000E+00 | 0.000E+00 | 2.664E-01 | 4.329E-01 | 5.772E-01 | 7.085E-01 |
| 721 | hsa-miR-141 | 3.902E+01 | 2.056E+01 | 1.898E+00 | 6.407E-01 | 2.673E-01 | 4.337E-01 | 2.410E-02 | 7.849E-02 |
| 822 | hsa-miR-1249 | 6.645E+01 | 1.565E+02 | 4.246E-01 | -8.567E-01 | 2.680E-01 | 4.399E-01 | 1.940E-01 | 3.397E-01 |
| 808 | hsa-miR-125b | 5.429E+02 | 1.096E+03 | 4.953E-01 | -7.026E-01 | 2.721E-01 | 4.389E-01 | 6.294E-02 | 1.558E-01 |
| 815 | hsa-miR-1265b | 7.515E-01 | 8.508E-01 | 8.833E-01 | -1.241E-01 | 2.718E-01 | 4.389E-01 | 2.504E-01 | 4.089E-01 |
| 751 | hsa-miR-1306 | 2.496E-01 | 3.000E-01 | 8.320E-01 | -1.839E-01 | 2.735E-01 | 4.403E-01 | 5.697E-01 | 7.033E-01 |
| 237 | hsa-miR-548a-5p | 1.000E+00 | 1.000E+00 | 1.000E+00 | 0.000E+00 | 2.758E-01 | 4.424E-01 | 7.384E-01 | 8.243E-01 |
| 599 | hsa-miR-19b-1* | 4.944E+01 | 5.447E+01 | 9.076E-01 | -9.697E-02 | 2.753E-01 | 4.424E-01 | 4.469E-01 | 6.016E-01 |
| 789 | hsa-miR-127-3p | 5.339E+01 | 4.546E+01 | 1.174E+00 | 1.608E-01 | 2.781E-01 | 4.453E-01 | 4.908E-01 | 6.417E-01 |
| 404 | hsa-miR-377* | 1.000E+00 | 1.000E+00 | 1.000E+00 | 0.000E+00 | 2.813E-01 | 4.478E-01 | 8.527E-01 | 9.114E-01 |
| 515 | hsa-miR-28-3p | 1.809E+02 | 2.014E+02 | 8.982E-01 | -1.073E-01 | 2.807E-01 | 4.478E-01 | 1.398E-01 | 2.758E-01 |
| 904 | hsa-let-7a | 9.830E+02 | 1.080E+03 | 9.099E-01 | -9.447E-02 | 2.809E-01 | 4.478E-01 | 4.303E-01 | 5.867E-01 |
| 885 | hsa-miR-100 | 1.224E+02 | 2.694E+02 | 4.542E-01 | -7.891E-01 | 2.826E-01 | 4.489E-01 | 8.992E-01 | 9.371E-01 |
| 139 | hsa-miR-618 | 1.534E+01 | 1.000E+00 | 1.534E+01 | 2.730E+00 | 2.833E-01 | 4.495E-01 | 2.471E-01 | 4.062E-01 |
| 276 | hsa-miR-519d | 5.762E+01 | 5.317E+01 | 1.084E+00 | 8.035E-02 | 2.840E-01 | 4.496E-01 | 1.729E-01 | 3.149E-01 |
| 71 | hsa-miR-720 | 4.196E+03 | 6.572E+03 | 6.384E-01 | -4.489E-01 | 2.871E-01 | 4.530E-01 | 7.635E-02 | 1.768E-01 |
| 396 | hsa-miR-382 | 1.439E+01 | 3.692E+00 | 3.899E+00 | -9.419E-01 | 2.871E-01 | 4.530E-02 | 4.380E-01 | 1.208E-01 |
| 109 | hsa-miR-644 | 2.530E+01 | 3.288E+00 | 7.694E+00 | -2.622E-01 | 2.887E-01 | 4.546E-01 | 6.537E-01 | 7.634E-01 |
| 347 | hsa-miR-488 | 1.000E+00 | 1.000E+00 | 1.000E+00 | 0.000E+00 | 2.935E-01 | 4.613E-01 | 6.118E-01 | 7.333E-01 |
| 201 | hsa-miR-562 | 2.904E+01 | 3.671E+00 | 7.911E+00 | 2.068E+00 | 2.942E-01 | 4.617E-01 | 2.742E-02 | 8.578E-02 |
| 205 | hsa-miR-557 | 2.715E+01 | 4.546E+01 | 5.972E-01 | -5.156E-01 | 2.948E-01 | 4.617E-01 | 2.200E-01 | 3.723E-01 |
| 470 | hsa-miR-320c | 7.734E+02 | 8.946E+02 | 8.646E-01 | -1.455E-01 | 2.964E-01 | 4.634E-01 | 7.280E-01 | 8.159E-01 |
| 163 | hsa-miR-596 | 7.255E+01 | 8.991E+01 | 8.070E-01 | -2.144E-01 | 2.989E-01 | 4.664E-01 | 4.016E-01 | 5.626E-01 |
| 798 | hsa-miR-34c-5p | 1.359E+00 | 3.048E-01 | 4.460E-02 | -9.577E-02 | 3.010E-01 | 4.672E-01 | 7.142E-02 | 1.707E-01 |
| 303 | hsa-miR-515-3p | 1.000E+00 | 4.155E+00 | 2.407E-01 | -1.424E+00 | 3.053E-01 | 4.713E-01 | 7.142E-02 | 1.707E-01 |
| 222 | hsa-miR-548m | 1.000E+00 | 1.000E+00 | 1.000E+00 | 0.000E+00 | 3.005E-01 | 4.672E-01 | 3.636E-01 | 5.239E-01 |
| 56 | hsa-miR-770-5p | 5.447E+01 | 6.762E+01 | 8.056E-01 | -2.162E-01 | 3.066E-01 | 4.725E-01 | 2.388E-01 | 3.956E-01 |
| 689 | hsa-miR-1537 | 2.729E+01 | 3.515E+01 | 7.762E-01 | -1.191E+00 | 3.022E-01 | 4.672E-01 | 6.939E-01 | 7.942E-01 |
| 4 | hsa-miR-99a | 1.021E+02 | 1.402E+02 | 7.283E-01 | -3.170E-01 | 3.022E-01 | 4.682E-01 | 6.939E-01 | 7.942E-01 |
| 433 | hsa-miR-34c-5p | 5.068E+00 | 5.577E+00 | 9.087E-01 | -9.577E-02 | 3.051E-01 | 4.713E-01 | 5.473E-01 | 6.908E-01 |
| 303 | hsa-miR-515-3p | 1.000E+00 | 4.155E+00 | 2.407E-01 | -1.424E+00 | 3.053E-01 | 4.713E-01 | 3.636E-01 | 5.239E-01 |
| 56 | hsa-miR-770-5p | 5.447E+01 | 6.762E+01 | 8.056E-01 | -2.162E-01 | 3.066E-01 | 4.725E-01 | 1.455E-01 | 2.816E-01 |
| 589 | hsa-miR-203 | 8.436E+00 | 2.564E+00 | 3.291E+00 | 1.191E+00 | 3.081E-01 | 4.740E-01 | 6.316E-01 | 7.467E-01 |
| 854 | hsa-miR-1204 | 1.935E+01 | 7.680E+00 | 2.519E+00 | 9.238E-01 | 3.087E-01 | 4.740E-01 | 3.020E-01 | 4.629E-01 |
| 95 | hsa-miR-657 | 5.943E+01 | 4.981E+01 | 1.193E+00 | 1.765E-01 | 3.098E-01 | 4.749E-01 | 1.798E-01 | 3.233E-01 |
| 376 | hsa-miR-432 | 1.000E+00 | 9.439E+00 | 1.059E-01 | -2.245E+00 | 3.163E-01 | 4.815E-01 | 1.156E-01 | 2.393E-01 |
| 372 | hsa-miR-449a | 1.000E+00 | 1.000E+00 | 1.000E+00 | 0.000E+00 | 3.152E-01 | 4.815E-01 | 1.657E-01 | 3.065E-01 |
| 40 | hsa-miR-888* | 4.708E+00 | 3.826E+00 | 1.230E+00 | 2.074E-01 | 3.164E-01 | 4.815E-01 | 9.027E-01 | 9.372E-01 |
| 746 | hsa-miR-130b | 1.492E+03 | 1.431E+03 | 1.042E+00 | 4.140E-02 | 3.163E-01 | 4.815E-01 | 7.218E-01 | 8.121E-01 |
| 849 | hsa-miR-1208 | 9.372E+01 | 9.436E+01 | 9.932E-01 | -6.836E-03 | 3.171E-01 | 4.818E-01 | 1.154E-01 | 2.393E-01 |

FIG. 2 (Continued)

| | | | | | | | | | |
|---|---|---|---|---|---|---|---|---|---|
| 638 | hsa-miR-1911 | 2.319E-01 | 3.176E-01 | 7.302E-01 | -3.145E-01 | 3.178E-01 | 4.821E-01 | 5.799E-02 | 1.476E-01 |
| 554 | hsa-miR-218-1* | 6.666E+00 | 7.276E+01 | 9.190E-01 | -8.445E-02 | 3.187E-01 | 4.826E-01 | 1.891E-01 | 3.351E-01 |
| 282 | hsa-miR-519a | 3.200E+01 | 1.235E+01 | 2.590E+00 | 9.518E-01 | 3.207E-01 | 4.847E-01 | 5.769E-02 | 1.473E-01 |
| 215 | hsa-miR-550* | 6.883E-02 | 8.099E+02 | 8.499E-01 | -1.627E-01 | 3.233E-01 | 4.870E-01 | 4.700E-02 | 1.256E-01 |
| 146 | hsa-miR-613 | 2.449E+00 | 1.000E+00 | 2.449E+00 | 8.959E-01 | 3.234E-01 | 4.870E-01 | 3.238E-01 | 4.860E-01 |
| 767 | hsa-miR-1291 | 9.487E-01 | 1.129E-02 | 8.407E-01 | -1.736E-01 | 3.278E-01 | 4.928E-01 | 3.081E-01 | 4.682E-01 |
| 366 | hsa-miR-450b-3p | 3.376E+00 | 1.694E+01 | 1.993E+00 | 6.895E-01 | 3.289E-01 | 4.936E-01 | 3.118E-02 | 9.521E-02 |
| 463 | hsa-miR-326 | 8.606E+01 | 9.420E+01 | 9.136E-01 | -9.037E-02 | 3.323E-01 | 4.979E-01 | 5.626E-01 | 6.987E-01 |
| 799 | hsa-miR-1264 | 2.013E-01 | 7.680E+00 | 2.621E+00 | 9.635E-01 | 3.337E-01 | 4.991E-01 | 1.961E-02 | 6.936E-02 |
| 552 | hsa-miR-219-1-3p | 1.586E+00 | 2.304E+01 | 6.882E-01 | -3.737E-01 | 3.419E-01 | 5.065E-01 | 6.503E-01 | 7.614E-01 |
| 901 | hsa-let-7b | 9.066E+02 | 1.127E+03 | 8.042E-01 | -2.179E-01 | 3.419E-01 | 5.065E-01 | 3.152E-01 | 9.579E-01 |
| 137 | hsa-miR-620 | 1.354E-01 | 2.564E+00 | 5.280E+00 | 1.664E+00 | 3.417E-01 | 5.065E-01 | 6.689E-01 | 1.620E-01 |
| 491 | hsa-miR-302d | 1.000E+00 | 1.000E+00 | 1.000E+00 | 0.000E+00 | 3.422E-01 | 5.065E-01 | 1.456E-02 | 5.641E-02 |
| 419 | hsa-miR-371-3p | 3.466E+00 | 3.010E+01 | 1.152E+00 | 1.411E-01 | 3.422E-01 | 5.065E-01 | 9.394E-02 | 2.073E-01 |
| 179 | hsa-miR-582-5p | 1.898E+01 | 3.010E+01 | 6.305E-01 | -4.613E-01 | 3.401E-01 | 5.065E-01 | 6.659E-02 | 1.633E-01 |
| 759 | hsa-miR-1297 | 4.433E-01 | 4.944E-01 | 8.968E-01 | -1.089E-01 | 3.437E-01 | 5.079E-01 | 5.286E-01 | 6.753E-01 |
| 75 | hsa-miR-7-1* | 2.947E+02 | 3.328E+02 | 8.855E-01 | -1.216E-01 | 3.446E-01 | 5.084E-01 | 8.577E-01 | 9.127E-01 |
| 19 | hsa-miR-934 | 8.572E+01 | 8.912E-01 | 9.619E-01 | -3.887E-02 | 3.505E-01 | 5.162E-01 | 8.092E-01 | 8.830E-01 |
| 864 | hsa-miR-1181 | 1.710E+02 | 2.331E+02 | 7.336E-01 | -3.096E-01 | 3.520E-01 | 5.175E-01 | 5.839E-01 | 7.148E-01 |
| 839 | hsa-miR-1228 | 2.272E+02 | 4.452E+02 | 5.103E-01 | -6.727E-01 | 3.533E-01 | 5.185E-01 | 3.483E-01 | 5.069E-01 |
| 859 | hsa-miR-1197 | 3.710E+01 | 1.395E+01 | 2.660E+00 | 9.783E-01 | 3.579E-01 | 5.244E-01 | 7.766E-03 | 3.662E-02 |
| 202 | hsa-miR-661 | 3.994E+01 | 1.000E+00 | 3.994E+01 | 1.687E+00 | 3.591E-01 | 5.249E-01 | 8.073E-05 | 1.451E-03 |
| 85 | hsa-miR-665 | 9.565E+01 | 7.294E+01 | 1.311E+01 | 2.710E+00 | 3.595E-01 | 5.249E-01 | 5.848E-01 | 7.004E-01 |
| 582 | hsa-miR-206 | 1.000E+00 | 4.639E+00 | 2.156E-02 | -3.837E+00 | 3.602E-01 | 5.251E-01 | 2.323E-02 | 7.712E-02 |
| 481 | hsa-miR-30c-2* | 2.222E+01 | 1.395E+01 | 1.593E+00 | 4.659E-01 | 3.609E-01 | 5.253E-01 | 8.416E-01 | 9.027E-01 |
| 317 | hsa-miR-508-3p | 1.000E+00 | 1.000E+00 | 1.000E+00 | 0.000E+00 | 3.621E-01 | 5.257E-01 | 5.447E-01 | 6.893E-01 |
| 195 | hsa-miR-569 | 1.139E+00 | 1.000E+00 | 1.139E+00 | 2.433E-01 | 3.624E-01 | 5.257E-01 | 9.453E-01 | 2.081E-01 |
| 377 | hsa-miR-431* | 2.728E+01 | 3.000E+01 | 9.096E-01 | -9.472E-02 | 3.641E-01 | 5.263E-01 | 6.962E-01 | 7.946E-01 |
| 889 | hsa-let-7g* | 1.107E+02 | 1.137E+02 | 9.735E-01 | -2.690E-02 | 3.636E-01 | 5.263E-01 | 3.795E-01 | 5.368E-01 |
| 489 | hsa-miR-302e | 2.335E+00 | 1.000E+00 | 2.335E+00 | 8.481E-01 | 3.676E-01 | 5.305E-01 | 5.804E-03 | 7.114E-01 |
| 735 | hsa-miR-135a | 1.000E+00 | 1.000E+00 | 1.000E+00 | 0.000E+00 | 3.683E-01 | 5.306E-01 | 1.537E-02 | 5.845E-02 |
| 494 | hsa-miR-302b* | 6.685E+00 | 1.723E+01 | 3.881E-01 | -9.466E-01 | 3.723E-01 | 5.355E-01 | 6.043E-01 | 7.312E-01 |
| 406 | hsa-miR-376c | 6.788E+00 | 6.105E+01 | 1.112E+00 | 1.061E-01 | 3.781E-01 | 5.429E-01 | 3.262E-01 | 4.875E-01 |
| 642 | hsa-miR-190b | 1.000E+00 | 1.000E+00 | 1.000E+00 | 0.000E+00 | 3.801E-01 | 5.449E-01 | 2.015E-01 | 3.478E-01 |
| 542 | hsa-miR-222 | 4.489E+02 | 4.452E+02 | 1.008E+00 | 8.310E-03 | 3.817E-01 | 5.463E-01 | 2.308E-01 | 3.830E-01 |
| 336 | hsa-miR-495 | 6.746E+00 | 5.280E+01 | 1.278E+00 | 2.451E-01 | 3.852E-01 | 5.503E-01 | 7.509E-01 | 8.341E-01 |
| 25 | hsa-miR-92a-2* | 1.000E+00 | 1.331E+02 | 1.000E+00 | -2.739E+00 | 3.868E-01 | 5.518E-01 | 8.332E-02 | 1.902E-01 |
| 644 | hsa-miR-1909 | 1.012E+02 | 1.331E+02 | 7.604E-01 | -7.138E-01 | 3.892E-01 | 5.543E-01 | 3.864E-01 | 5.430E-01 |
| 181 | hsa-miR-581 | 8.436E+00 | 1.723E+01 | 4.898E-01 | -4.840E-02 | 3.903E-01 | 5.549E-01 | 2.754E-01 | 4.377E-01 |
| 484 | hsa-miR-306* | 1.711E+01 | 1.795E+01 | 9.528E-01 | -4.840E-02 | 3.930E-01 | 5.573E-01 | 4.507E-01 | 6.049E-01 |
| 777 | hsa-miR-1282 | 1.000E+00 | 2.704E+00 | 3.698E-02 | -3.297E+00 | 3.932E-01 | 5.573E-01 | 7.488E-04 | 6.949E-03 |
| 226 | hsa-miR-548i | 4.779E+00 | 2.646E+00 | 1.806E+00 | 5.911E-01 | 3.948E-01 | 5.578E-01 | 9.047E-01 | 9.372E-01 |
| 231 | hsa-miR-548d-5p | 1.000E+00 | 1.000E+00 | 1.000E+00 | 0.000E+00 | 3.949E-01 | 5.578E-01 | 4.397E-01 | 5.947E-01 |
| 262 | hsa-miR-521 | 4.708E+01 | 5.016E+01 | 9.386E-01 | -6.331E-02 | 3.969E-01 | 5.597E-01 | 7.167E-01 | 8.091E-01 |

FIG. 2 (Continued)

| | | | | | | | | |
|---|---|---|---|---|---|---|---|---|
| 502 | hsa-miR-29c | 5,591E+02 | 5,224E+02 | 1,070E+00 | 6,791E-02 | 3,993E-01 | 5,621E-01 | 6,058E-01 | 7,312E-01 |
| 546 | hsa-miR-220b | 4,639E-01 | 5,397E+01 | 8,595E-01 | -1,514E-01 | 4,001E-01 | 5,624E-01 | 8,253E-02 | 1,892E-01 |
| 800 | hsa-miR-1263 | 5,339E+01 | 5,397E+01 | 9,892E-01 | -1,081E-02 | 4,027E-01 | 5,650E-01 | 3,950E-02 | 1,125E-01 |
| 102 | hsa-miR-651 | 1,359E+00 | 2,004E+01 | 6,783E-02 | -2,691E+00 | 4,063E-01 | 5,693E-01 | 1,403E-01 | 2,758E-01 |
| 371 | hsa-miR-449b | 3,406E+00 | 4,060E+00 | 8,389E-01 | -1,757E-01 | 4,108E-01 | 5,746E-01 | 2,197E-01 | 3,723E-01 |
| 813 | hsa-miR-1257 | 3,777E+00 | 8,370E+00 | 4,512E-01 | -7,958E-01 | 4,131E-01 | 5,769E-01 | 9,628E-01 | 9,764E-01 |
| 307 | hsa-miR-513a-5p | 4,797E+01 | 6,762E+01 | 7,094E-01 | -3,433E-01 | 4,147E-01 | 5,782E-01 | 1,296E-01 | 2,591E-01 |
| 278 | hsa-miR-519c-3p | 3,879E+01 | 7,413E+01 | 5,232E+00 | 1,655E+00 | 4,169E-01 | 5,822E-01 | 5,801E-03 | 3,010E-02 |
| 493 | hsa-miR-302c | 7,413E+02 | 1,795E+01 | 4,129E-01 | -8,846E-01 | 4,183E-01 | 5,822E-01 | 1,246E-01 | 2,513E-01 |
| 817 | hsa-miR-1254 | 1,129E+02 | 1,110E+02 | 1,017E+00 | 1,698E-02 | 4,216E-01 | 5,841E-01 | 7,592E-01 | 8,410E-01 |
| 413 | hsa-miR-374a* | 3,249E+01 | 2,056E+01 | 1,580E+00 | 4,574E-01 | 4,212E-01 | 5,841E-01 | 2,702E-01 | 4,307E-01 |
| 468 | hsa-miR-323-3p | 3,376E+01 | 3,249E+01 | 1,039E+00 | 3,836E-02 | 4,239E-01 | 5,863E-01 | 4,363E-01 | 5,920E-01 |
| 744 | hsa-miR-132 | 1,105E+02 | 9,014E+01 | 1,226E+00 | 2,034E-01 | 4,270E-01 | 5,886E-01 | 1,776E-01 | 2,416E-01 |
| 677 | hsa-miR-16-1* | 7,396E+01 | 6,127E+01 | 1,207E+00 | 1,881E-01 | 4,269E-01 | 5,886E-01 | 4,332E-02 | 1,198E-01 |
| 560 | hsa-miR-214* | 5,794E+01 | 6,193E+01 | 9,356E-01 | -6,661E-02 | 4,385E-01 | 5,988E-01 | 2,853E-01 | 4,483E-01 |
| 305 | hsa-miR-513c | 2,133E+00 | 9,439E+00 | 2,260E-01 | -1,487E+00 | 4,278E-01 | 5,888E-01 | 4,971E-01 | 3,100E-01 |
| 891 | hsa-let-7f-2* | 4,779E+00 | 1,000E+00 | 4,779E+00 | 1,564E+00 | 4,347E-01 | 5,974E-01 | 1,690E-01 | 3,372E-01 |
| 530 | hsa-miR-23b* | 2,851E+01 | 1,694E+01 | 1,683E+00 | 5,206E-01 | 4,358E-01 | 5,960E-01 | 1,163E-02 | 4,893E-02 |
| 743 | hsa-miR-132* | 1,000E+00 | 1,000E+00 | 1,000E+00 | 0,000E+00 | 4,381E-01 | 5,988E-01 | 8,378E-01 | 9,027E-01 |
| 560 | hsa-miR-214* | 5,794E+01 | 6,193E+01 | 9,356E-01 | -6,661E-02 | 4,385E-01 | 5,988E-01 | 4,332E-02 | 7,614E-01 |
| 7 | hsa-miR-96 | 1,569E+02 | 1,340E+02 | 1,171E+00 | 1,579E-01 | 4,385E-01 | 5,988E-01 | 1,750E-01 | 3,160E-01 |
| 207 | hsa-miR-556-3p | 1,000E+00 | 1,000E+00 | 1,000E+00 | 0,000E+00 | 4,402E-01 | 6,001E-01 | 5,921E-01 | 7,197E-01 |
| 457 | hsa-miR-331-5p | 3,260E+01 | 1,694E+01 | 1,056E+00 | 5,431E-02 | 4,440E-01 | 6,033E-01 | 5,308E-01 | 6,766E-01 |
| 379 | hsa-miR-429 | 3,037E+01 | 3,753E+01 | 8,093E-01 | -2,116E-01 | 4,438E-01 | 6,033E-01 | 6,497E-01 | 7,614E-01 |
| 180 | hsa-miR-582-3p | 6,018E+01 | 6,398E+01 | 9,406E-01 | -6,119E-02 | 4,453E-01 | 6,033E-01 | 5,921E-01 | 7,197E-01 |
| 669 | hsa-miR-181c | 1,269E+02 | 1,402E+02 | 8,979E-01 | -1,077E-01 | 4,449E-01 | 6,033E-01 | 6,112E-01 | 7,333E-01 |
| 630 | hsa-miR-192 | 5,646E+03 | 6,228E+03 | 9,067E-01 | -9,800E-02 | 4,487E-01 | 6,069E-01 | 4,033E-01 | 5,642E-01 |
| 588 | hsa-miR-204 | 1,000E+00 | 1,000E+00 | 1,000E+00 | 0,000E+00 | 4,532E-01 | 6,121E-01 | 6,837E-01 | 7,856E-01 |
| 903 | hsa-let-7a* | 1,000E+00 | 3,671E+00 | 2,724E-01 | -1,301E+00 | 4,619E-01 | 6,219E-01 | 8,310E-01 | 8,986E-01 |
| 426 | hsa-miR-365 | 6,366E+01 | 9,014E+01 | 7,063E-01 | -3,478E-01 | 4,613E-01 | 6,219E-01 | 9,251E-01 | 9,466E-01 |
| 816 | hsa-miR-1255a | 4,835E+01 | 4,981E+01 | 9,707E-01 | -2,974E-02 | 4,692E-01 | 6,298E-01 | 7,331E-01 | 8,206E-01 |
| 327 | hsa-miR-501-3p | 3,753E+02 | 3,961E+02 | 9,475E-01 | -5,398E-02 | 4,690E-01 | 6,298E-01 | 9,180E-01 | 9,454E-01 |
| 221 | hsa-miR-548n | 2,896E+01 | 2,821E+01 | 1,026E+00 | 2,614E-02 | 4,785E-01 | 6,392E-01 | 9,070E-01 | 9,375E-01 |
| 878 | hsa-miR-105 | 4,881E+01 | 4,967E+01 | 9,827E-01 | -1,750E-02 | 4,783E-01 | 6,392E-01 | 6,636E-01 | 7,702E-01 |
| 301 | hsa-miR-516a-3p | 6,768E+00 | 8,370E+00 | 8,086E-01 | -2,125E-01 | 4,773E-01 | 6,392E-01 | 7,967E-01 | 8,714E-01 |
| 331 | hsa-miR-499-3p | 5,601E+00 | 6,462E+00 | 8,667E-01 | -1,430E-01 | 4,844E-01 | 6,461E-01 | 6,721E-01 | 7,785E-01 |
| 230 | hsa-miR-548e | 3,789E+01 | 1,723E+01 | 2,199E+00 | 7,882E-01 | 4,869E-01 | 6,484E-01 | 1,179E-02 | 4,908E-02 |
| 724 | hsa-miR-139-5p | 1,249E+02 | 1,420E+02 | 8,793E-01 | -1,286E-01 | 4,918E-01 | 6,540E-01 | 1,980E-01 | 3,444E-01 |
| 411 | hsa-miR-374b* | 2,384E+01 | 3,048E+01 | 7,820E-01 | -2,459E-01 | 4,965E-01 | 6,571E-01 | 4,178E-01 | 5,760E-01 |
| 203 | hsa-miR-559 | 4,850E+01 | 5,180E+01 | 9,364E-01 | -6,574E-02 | 4,952E-01 | 6,571E-01 | 7,465E-01 | 8,302E-01 |
| 361 | hsa-miR-453 | 2,056E+02 | 3,692E+02 | 5,569E-01 | -5,853E-01 | 4,965E-01 | 6,571E-01 | 2,495E-01 | 4,087E-01 |
| 676 | hsa-miR-16-2* | 8,373E+01 | 4,981E+01 | 1,681E+00 | 5,194E-01 | 4,972E-01 | 6,571E-01 | 3,190E-02 | 9,660E-02 |
| 581 | hsa-miR-208a | 5,959E+01 | 5,566E+01 | 1,071E+00 | 6,830E-02 | 4,985E-01 | 6,578E-01 | 4,129E-01 | 5,727E-01 |
| 188 | hsa-miR-575 | 1,273E+02 | 1,234E+02 | 1,031E+00 | 3,054E-02 | 4,995E-01 | 6,581E-01 | 5,483E-01 | 6,908E-01 |
| 270 | hsa-miR-520c-3p | 1,000E+00 | 1,000E+00 | 1,000E+00 | 0,000E+00 | 5,014E-01 | 6,597E-01 | 3,304E-01 | 4,908E-01 |

FIG. 2 (Continued)

| | | | | | | | | |
|---|---|---|---|---|---|---|---|---|
| 634 | hsa-miR-1914 | 5,144E-01 | 5,280E-01 | 9,743E-01 | -2,602E-02 | 5,046E-01 | 6,626E-01 | 4,919E-01 | 6,422E-01 |
| 618 | hsa-miR-196b | 1,000E+00 | 1,000E+00 | 1,000E+00 | 0,000E+00 | 5,073E-01 | 6,653E-01 | 1,394E-01 | 2,758E-01 |
| 38 | hsa-miR-890 | 3,674E+01 | 3,000E+01 | 1,225E+00 | 2,028E-01 | 5,126E-01 | 6,713E-01 | 9,045E-01 | 9,372E-01 |
| 710 | hsa-miR-1469 | 1,609E+02 | 2,293E+02 | 7,017E-01 | -3,543E-01 | 5,136E-01 | 6,713E-01 | 8,259E-01 | 8,943E-01 |
| 172 | hsa-miR-589 | 7,844E+01 | 6,105E+01 | 1,285E+00 | 2,506E-01 | 5,147E-01 | 6,713E-01 | 1,431E-01 | 2,795E-01 |
| 779 | hsa-miR-1280 | 4,196E+03 | 5,646E+03 | 7,431E-01 | -2,970E-01 | 5,149E-01 | 6,713E-01 | 1,689E-01 | 3,100E-01 |
| 408 | hsa-miR-376a* | 1,000E+00 | 3,329E+00 | 3,004E-01 | -1,203E+00 | 5,202E-01 | 6,751E-01 | 9,227E-01 | 9,466E-01 |
| 176 | hsa-miR-585 | 1,336E+01 | 7,680E+00 | 1,740E+00 | 5,536E-01 | 5,189E-01 | 6,751E-01 | 6,640E-01 | 7,702E-01 |
| 522 | hsa-miR-26a-2* | 1,000E+00 | 1,000E+00 | 1,000E+00 | 0,000E+00 | 5,196E-01 | 6,751E-01 | 5,325E-01 | 6,778E-01 |
| 725 | hsa-miR-139-3p | 7,874E-01 | 9,975E-01 | 7,893E-01 | -2,366E-01 | 5,212E-01 | 6,753E-01 | 9,406E-01 | 9,606E-01 |
| 882 | hsa-miR-101* | 6,894E+01 | 7,419E+01 | 9,292E-01 | -7,346E-02 | 5,236E-01 | 6,775E-01 | 4,973E-01 | 6,473E-01 |
| 812 | hsa-miR-1268 | 1,000E+00 | 1,235E+01 | 8,095E-02 | -2,514E+00 | 5,288E-01 | 6,811E-01 | 1,087E-01 | 2,303E-01 |
| 402 | hsa-miR-378* | 5,106E+01 | 3,835E+01 | 1,331E+00 | 2,860E-01 | 5,278E-01 | 6,811E-01 | 7,873E-01 | 8,633E-01 |
| 256 | hsa-miR-524-5p | 4,865E+00 | 4,358E+00 | 1,117E+00 | 1,102E-01 | 5,280E-01 | 6,811E-01 | 1,558E-01 | 2,936E-01 |
| 687 | hsa-miR-1539 | 8,086E+01 | 9,140E+01 | 8,847E-01 | -1,225E-01 | 5,332E-01 | 6,857E-01 | 3,125E-01 | 4,723E-01 |
| 187 | hsa-miR-576-3p | 1,000E+00 | 1,111E+01 | 9,002E-02 | -2,408E+00 | 5,373E-01 | 6,901E-01 | 6,194E-02 | 1,545E-01 |
| 170 | hsa-miR-590-3p | 4,779E+00 | 1,000E+00 | 4,779E+00 | 1,564E+00 | 5,398E-01 | 6,919E-01 | 3,225E-01 | 4,857E-01 |
| 28 | hsa-miR-924 | 1,816E+02 | 2,397E+01 | 7,575E+00 | 2,778E-01 | 5,404E-01 | 6,919E-01 | 7,254E-01 | 8,141E-01 |
| 850 | hsa-miR-1207-5p | 4,673E+02 | 6,104E+02 | 7,655E-01 | -2,672E-01 | 5,473E-01 | 6,991E-01 | 1,246E-01 | 2,513E-01 |
| 294 | hsa-miR-517c | 8,713E+00 | 7,680E+00 | 1,134E+00 | 1,262E-01 | 5,476E-01 | 6,991E-01 | 8,344E-01 | 9,013E-01 |
| 871 | hsa-miR-10a | 4,697E+01 | 1,085E+01 | 4,328E+00 | 1,465E+00 | 5,536E-01 | 7,057E-01 | 3,467E-02 | 1,021E-01 |
| 255 | hsa-miR-525-3p | 5,802E+01 | 5,035E+01 | 1,152E+00 | 1,417E-01 | 5,564E-01 | 7,082E-01 | 1,621E-01 | 3,022E-01 |
| 488 | hsa-miR-302f | 1,000E+00 | 1,997E+00 | 5,008E-01 | -6,915E-01 | 5,580E-01 | 7,092E-01 | 7,739E-01 | 8,543E-01 |
| 803 | hsa-miR-1260 | 2,412E+03 | 2,877E+03 | 8,383E-01 | -1,764E-01 | 5,595E-01 | 7,101E-01 | 5,128E-01 | 6,664E-01 |
| 890 | hsa-let-7g | 2,694E+02 | 3,515E+02 | 7,664E-01 | -2,661E-01 | 5,639E-01 | 7,146E-01 | 2,857E-01 | 4,483E-01 |
| 132 | hsa-miR-624* | 2,076E+01 | 5,397E+01 | 3,847E-01 | -9,552E-01 | 5,654E-01 | 7,154E-01 | 2,285E-01 | 3,822E-01 |
| 870 | hsa-miR-10a* | 3,879E+00 | 3,000E+01 | 1,293E+00 | 2,569E-01 | 5,688E-01 | 7,187E-01 | 2,905E-01 | 4,527E-01 |
| 464 | hsa-miR-325 | 5,144E+01 | 4,082E+01 | 1,260E+00 | 2,314E-01 | 5,709E-01 | 7,203E-01 | 1,832E-01 | 3,267E-01 |
| 381 | hsa-miR-425 | 1,198E+04 | 1,298E+04 | 9,225E-01 | -8,063E-02 | 5,751E-01 | 7,238E-01 | 3,354E-01 | 4,948E-01 |
| 824 | hsa-miR-1247 | 5,339E+01 | 7,160E+01 | 7,456E-01 | -2,936E-01 | 5,754E-01 | 7,238E-01 | 8,471E-01 | 9,070E-01 |
| 242 | hsa-miR-543 | 3,800E+01 | 1,235E+01 | 3,076E+00 | 1,124E+00 | 5,785E-01 | 7,280E-01 | 1,960E-03 | 1,458E-02 |
| 116 | hsa-miR-637 | 9,439E+00 | 5,959E+00 | 1,584E+00 | -1,843E+00 | 5,809E-01 | 7,287E-01 | 6,035E-03 | 3,064E-02 |
| 264 | hsa-miR-520g | 4,835E+01 | 2,004E+01 | 2,413E+00 | 8,807E-01 | 5,863E-01 | 7,291E-01 | 6,825E-03 | 3,309E-02 |
| 397 | hsa-miR-381 | 8,739E+01 | 6,926E+01 | 1,262E+00 | 2,326E-01 | 5,856E-01 | 7,291E-01 | 3,245E-02 | 9,793E-02 |
| 781 | hsa-miR-1279 | 1,000E+00 | 1,000E+00 | 1,000E+00 | 0,000E+00 | 5,831E-01 | 7,291E-01 | 4,420E-01 | 5,969E-01 |
| 271 | hsa-miR-520b | 1,450E+02 | 9,984E+01 | 1,452E+00 | 3,729E-01 | 5,847E-01 | 7,291E-01 | 6,261E-01 | 7,446E-01 |
| 844 | hsa-miR-1225-3p | 1,371E+02 | 1,609E+02 | 8,518E-01 | -1,604E-01 | 5,824E-01 | 7,291E-01 | 5,563E-01 | 6,967E-01 |
| 304 | hsa-miR-514 | 3,902E+01 | 3,021E+01 | 1,292E+00 | 2,559E-01 | 5,845E-01 | 7,291E-01 | 7,166E-01 | 8,091E-01 |
| 876 | hsa-miR-106a | 5,922E+03 | 6,226E+03 | 9,510E-01 | -5,028E-02 | 5,894E-01 | 7,310E-01 | 5,137E-01 | 6,664E-01 |
| 755 | hsa-miR-1302 | 3,119E+01 | 1,723E+01 | 1,810E+00 | 5,936E-01 | 5,904E-01 | 7,310E-01 | 8,549E-01 | 9,120E-01 |
| 866 | hsa-miR-1179 | 2,715E+01 | 2,013E+01 | 1,349E+00 | 2,990E-01 | 5,900E-01 | 7,310E-01 | 3,340E-01 | 4,944E-01 |
| 21 | hsa-miR-93* | 1,326E+03 | 1,521E+03 | 8,720E-01 | -1,369E-01 | 5,968E-01 | 7,368E-01 | 2,147E-01 | 3,662E-01 |
| 646 | hsa-miR-190 | 1,000E+00 | 1,000E+00 | 1,000E+00 | 0,000E+00 | 5,963E-01 | 7,368E-01 | 4,279E-01 | 5,865E-01 |
| 8 | hsa-miR-95 | 1,635E+01 | 9,439E+00 | 1,732E+00 | 5,493E-01 | 5,981E-01 | 7,374E-01 | 4,372E-01 | 5,923E-01 |

FIG. 2 (Continued)

FIG. 2 (Continued)

| | | | | | | | | | |
|---|---|---|---|---|---|---|---|---|---|
| 456 | hsa-miR-335 | 4.413E+02 | 4.231E+02 | 1.043E+00 | 4.214E-02 | 6.862E-01 | 7.956E-01 | 6.614E-01 | 7.692E-01 |
| 235 | hsa-miR-548b-5p | 1.000E+00 | 1.000E+00 | 1.000E+00 | 0.000E+00 | 6.879E-01 | 7.957E-01 | 8.398E-01 | 9.027E-01 |
| 110 | hsa-miR-643 | 4.016E+01 | 3.176E+01 | 1.264E+00 | 2.346E-01 | 6.904E-01 | 7.976E-01 | 8.800E-01 | 9.294E-01 |
| 834 | hsa-miR-1234 | 6.745E+02 | 8.497E+02 | 7.938E-01 | -2.309E-01 | 6.948E-01 | 8.009E-01 | 1.685E-01 | 3.100E-01 |
| 559 | hsa-miR-215 | 3.753E+02 | 3.902E+02 | 9.617E-01 | -3.901E-02 | 6.951E-01 | 8.009E-01 | 3.323E-01 | 4.928E-01 |
| 97 | hsa-miR-655 | 2.765E+01 | 1.723E+01 | 1.605E+00 | 4.734E-01 | 6.983E-01 | 8.026E-01 | 3.511E-01 | 5.093E-01 |
| 144 | hsa-miR-615-3p | 2.896E+01 | 3.000E+01 | 9.654E-01 | -3.523E-02 | 6.984E-01 | 8.026E-01 | 8.913E-01 | 9.332E-01 |
| 420 | hsa-miR-370 | 4.835E+01 | 6.563E+01 | 7.368E-01 | -3.055E-01 | 7.006E-01 | 8.040E-01 | 5.896E-01 | 7.187E-01 |
| 659 | hsa-miR-184 | 1.322E+01 | 1.395E+01 | 9.476E-01 | -5.382E-02 | 7.051E-01 | 8.081E-01 | 1.941E-01 | 3.397E-01 |
| 77 | hsa-miR-708 | 3.648E+01 | 3.515E+01 | 1.038E+00 | 3.700E-02 | 7.061E-01 | 8.081E-01 | 7.436E-01 | 8.291E-01 |
| 364 | hsa-miR-451 | 1.585E+03 | 1.585E+03 | 1.000E+00 | 0.000E+00 | 7.114E-01 | 8.132E-01 | 2.643E-01 | 4.258E-01 |
| 506 | hsa-miR-29a* | 1.000E+00 | 1.395E+01 | 7.170E-02 | -2.635E+00 | 7.179E-01 | 8.195E-01 | 4.085E-02 | 1.152E-01 |
| 775 | hsa-miR-1284 | 1.784E+01 | 2.704E+01 | 6.598E-01 | -4.158E-01 | 7.229E-01 | 8.242E-01 | 1.929E-02 | 6.852E-02 |
| 266 | hsa-miR-520e | 1.000E+00 | 3.443E+00 | 2.905E-01 | -1.236E+00 | 7.244E-01 | 8.244E-01 | 4.537E-01 | 6.080E-01 |
| 418 | hsa-miR-371-5p | 4.348E+01 | 5.317E+01 | 8.179E-01 | -2.011E-01 | 7.257E-01 | 8.244E-01 | 4.317E-01 | 5.867E-01 |
| 592 | hsa-miR-200c* | 4.835E+01 | 3.753E+01 | 1.288E+00 | 2.534E-01 | 7.260E-01 | 8.244E-01 | 9.983E-01 | 9.983E-01 |
| 280 | hsa-miR-519b-3p | 2.666E+00 | 7.680E+00 | 3.472E-01 | 1.245E+00 | 7.288E-01 | 8.259E-01 | 8.753E-02 | 1.977E-01 |
| 22 | hsa-miR-93 | 3.450E+02 | 3.623E+02 | 9.521E-01 | -4.909E-02 | 7.293E-01 | 8.326E-01 | 7.831E-01 | 8.620E-01 |
| 247 | hsa-miR-539 | 1.000E+00 | 1.235E+01 | 8.095E-02 | -2.514E+00 | 7.324E-01 | 8.284E-01 | 3.426E-02 | 1.021E-01 |
| 5 | hsa-miR-98 | 4.937E+00 | 1.450E+01 | 3.406E-01 | -1.077E+00 | 7.390E-01 | 8.326E-01 | 2.305E-01 | 3.830E-01 |
| 594 | hsa-miR-200b* | 6.788E+01 | 7.133E+01 | 9.517E-01 | -4.950E-02 | 7.386E-01 | 8.326E-01 | 5.512E-01 | 6.924E-01 |
| 733 | hsa-miR-135b | 1.000E+00 | 9.057E+00 | 1.104E-01 | -2.204E+00 | 7.383E-01 | 8.326E-01 | 2.059E-01 | 3.539E-01 |
| 178 | hsa-miR-583 | 4.708E+01 | 4.579E+01 | 1.028E+00 | 2.774E-02 | 7.408E-01 | 8.335E-01 | 4.904E-01 | 6.417E-01 |
| 210 | hsa-miR-553 | 3.329E+00 | 1.000E+00 | 3.329E+00 | 1.203E+00 | 7.435E-01 | 8.354E-01 | 4.877E-01 | 6.410E-01 |
| 99 | hsa-miR-654-3p | 3.087E+01 | 3.070E+01 | 1.006E+00 | 5.568E-03 | 7.448E-01 | 8.359E-01 | 5.432E-01 | 6.884E-01 |
| 576 | hsa-miR-20b* | 6.151E+01 | 6.999E+01 | 8.787E-01 | -1.293E-01 | 7.469E-01 | 8.371E-01 | 9.744E-01 | 9.835E-01 |
| 573 | hsa-miR-210 | 7.902E+02 | 8.284E+02 | 9.539E-01 | -4.714E-02 | 7.507E-01 | 8.393E-01 | 1.613E-01 | 3.013E-01 |
| 894 | hsa-let-7e* | 1.139E+01 | 3.671E+00 | 3.102E+00 | 1.132E+00 | 7.514E-01 | 8.393E-01 | 6.955E-01 | 7.946E-01 |
| 359 | hsa-miR-454* | 1.252E+01 | 9.597E+00 | 1.304E+00 | 2.655E-01 | 7.517E-01 | 8.383E-01 | 8.809E-01 | 9.294E-01 |
| 795 | hsa-miR-1268 | 3.635E+02 | 5.591E+02 | 6.501E-01 | -4.306E-01 | 7.537E-01 | 8.404E-01 | 1.573E-02 | 5.880E-02 |
| 624 | hsa-miR-194 | 6.572E+03 | 6.572E+03 | 1.000E+00 | 0.000E+00 | 7.553E-01 | 8.411E-01 | 5.497E-01 | 6.915E-01 |
| 135 | hsa-miR-622 | 6.387E+01 | 7.740E+01 | 8.252E-01 | -1.921E-01 | 7.577E-01 | 8.427E-01 | 7.240E-01 | 8.136E-01 |
| 263 | hsa-miR-520h | 3.648E+01 | 1.155E+01 | 3.171E+00 | 1.154E+00 | 7.587E-01 | 8.427E-01 | 5.561E-02 | 1.433E-01 |
| 847 | hsa-miR-122* | 4.881E+01 | 6.105E+01 | 7.995E-01 | -2.238E-01 | 7.609E-01 | 8.440E-01 | 3.082E-01 | 4.682E-01 |
| 286 | hsa-miR-518e | 5.959E+01 | 6.864E+01 | 8.682E-01 | -1.413E-01 | 7.632E-01 | 8.455E-01 | 7.856E-01 | 8.626E-01 |
| 507 | hsa-miR-29a | 6.967E+02 | 7.305E+02 | 9.537E-01 | -4.742E-02 | 7.703E-01 | 8.512E-01 | 4.311E-01 | 5.867E-01 |
| 718 | hsa-miR-142-5p | 7.475E+02 | 7.475E+02 | 1.000E+00 | 0.000E+00 | 7.703E-01 | 8.512E-01 | 3.523E-01 | 5.102E-01 |
| 679 | hsa-miR-15b* | 6.281E+01 | 5.975E+01 | 1.051E+00 | 4.997E-02 | 7.714E-01 | 8.513E-01 | 8.365E-01 | 9.024E-01 |
| 532 | hsa-miR-23a* | 4.779E+00 | 3.515E+01 | 1.359E-01 | -1.996E+00 | 7.788E-01 | 8.579E-01 | 1.903E-02 | 6.815E-02 |
| 612 | hsa-miR-296-5p | 2.352E+02 | 3.433E+02 | 6.851E-01 | -3.762E-01 | 7.794E-01 | 8.579E-01 | 7.545E-01 | 8.370E-01 |
| 261 | hsa-miR-522 | 1.000E+00 | 1.000E+00 | 1.000E+00 | 0.000E+00 | 7.850E-01 | 8.625E-01 | 8.692E-01 | 9.238E-01 |
| 772 | hsa-miR-1287 | 5.424E+01 | 6.762E+01 | 8.022E-01 | -2.204E-01 | 7.865E-01 | 8.625E-01 | 5.597E-01 | 6.975E-01 |
| 658 | hsa-miR-185 | 2.473E+04 | 2.473E+04 | 1.000E+00 | 0.000E+00 | 7.862E-01 | 8.625E-01 | 6.811E-01 | 7.848E-01 |
| 150 | hsa-miR-609 | 1.000E+00 | 1.000E+00 | 1.000E+00 | 0.000E+00 | 7.902E-01 | 8.654E-01 | 7.346E-01 | 8.212E-01 |

FIG. 2 (Continued)

| | | | | | | | | |
|---|---|---|---|---|---|---|---|---|
| 521 | hsa-miR-26b | 3,229E+02 | 4,270E+02 | 7,564E-01 | -2,792E-01 | 7,945E-01 | 8,690E-01 | 6,436E-01 | 7,578E-01 |
| 311 | hsa-miR-511 | 2,821E+01 | 3,000E+01 | 9,405E-01 | -6,137E-02 | 7,987E-01 | 8,725E-01 | 5,371E-01 | 6,827E-01 |
| 656 | hsa-miR-186 | 3,227E+01 | 4,908E+01 | 6,575E-01 | -4,193E-01 | 8,024E-01 | 8,754E-01 | 5,237E-01 | 6,740E-01 |
| 802 | hsa-miR-1261 | 1,000E+00 | 1,000E+00 | 1,000E+00 | 0,000E+00 | 8,050E-01 | 8,772E-01 | 8,904E-01 | 9,332E-01 |
| 147 | hsa-miR-612 | 6,841E-01 | 8,399E+01 | 8,145E-01 | -2,052E-01 | 8,100E-01 | 8,815E-01 | 4,311E-01 | 5,867E-01 |
| 236 | hsa-miR-548b-3p | 4,708E+01 | 5,280E+01 | 8,916E-01 | -1,147E-01 | 8,121E-01 | 8,827E-01 | 2,819E-01 | 4,447E-01 |
| 555 | hsa-miR-218 | 3,305E+01 | 2,056E+01 | 1,608E+00 | 4,747E-01 | 8,144E-01 | 8,840E-01 | 2,811E-01 | 4,443E-01 |
| 805 | hsa-miR-126 | 1,620E+03 | 1,586E+03 | 1,022E+00 | 2,173E-02 | 8,186E-01 | 8,847E-01 | 8,093E-01 | 8,830E-01 |
| 160 | hsa-miR-569 | 3,010E+01 | 1,795E+01 | 1,676E+00 | 5,166E-01 | 8,176E-01 | 8,847E-01 | 7,850E-01 | 8,626E-01 |
| 709 | hsa-miR-146a | 1,886E+02 | 2,281E+02 | 8,272E-01 | -1,898E-01 | 8,191E-01 | 8,847E-01 | 3,027E-01 | 4,632E-01 |
| 166 | hsa-miR-593 | 1,071E+01 | 1,795E+01 | 5,967E-01 | -5,164E-01 | 8,176E-01 | 8,847E-01 | 1,659E-01 | 3,066E-01 |
| 149 | hsa-miR-610 | 4,835E+01 | 7,294E+01 | 6,629E-01 | -4,112E-01 | 8,230E-01 | 8,878E-01 | 2,630E-01 | 4,250E-01 |
| 519 | hsa-miR-27a | 2,728E+02 | 3,029E+02 | 9,008E-01 | -1,046E-01 | 8,255E-01 | 8,894E-01 | 8,791E-01 | 9,294E-01 |
| 309 | hsa-miR-512-5p | 5,361E+01 | 6,999E+01 | 7,659E-01 | -2,667E-01 | 8,267E-01 | 8,896E-01 | 4,669E-01 | 6,209E-01 |
| 355 | hsa-miR-483-5p | 1,792E+02 | 2,786E+02 | 6,436E-01 | -4,407E-01 | 8,343E-01 | 8,933E-01 | 1,196E-02 | 4,917E-02 |
| 886 | hsa-miR-1 | 1,322E+01 | 1,000E+00 | 1,322E+01 | 2,581E+00 | 8,318E-01 | 8,933E-01 | 1,945E-01 | 3,397E-01 |
| 244 | hsa-miR-542-3p | 7,419E+01 | 7,924E+01 | 9,363E-01 | -6,577E-02 | 8,331E-01 | 8,933E-01 | 3,069E-01 | 4,678E-01 |
| 416 | hsa-miR-373 | 1,000E+00 | 1,450E+01 | 6,899E-02 | -2,674E+00 | 8,334E-01 | 8,933E-01 | 8,084E-02 | 1,870E-01 |
| 645 | hsa-miR-1908 | 1,028E+03 | 7,734E+02 | 1,330E+00 | 2,850E-01 | 8,390E-01 | 8,972E-01 | 6,075E-01 | 7,322E-01 |
| 454 | hsa-miR-337-3p | 8,436E+00 | 2,397E+01 | 3,519E-01 | -1,044E+00 | 8,401E-01 | 8,972E-01 | 1,840E-01 | 3,274E-01 |
| 695 | hsa-miR-150 | 1,620E+03 | 2,008E+03 | 8,068E-01 | -2,147E-01 | 8,415E-01 | 8,976E-01 | 3,050E-01 | 4,659E-01 |
| 598 | hsa-miR-19b-2* | 1,000E+00 | 1,000E+00 | 1,000E+00 | 0,000E+00 | 8,455E-01 | 9,008E-01 | 2,231E-01 | 3,760E-01 |
| 450 | hsa-miR-339-3p | 2,728E+02 | 2,836E+02 | 9,619E-01 | -3,884E-02 | 8,471E-01 | 9,014E-01 | 7,095E-01 | 8,036E-01 |
| 640 | hsa-miR-191* | 4,967E+01 | 5,180E+01 | 9,889E-01 | -4,192E-02 | 8,516E-01 | 9,029E-01 | 2,783E-01 | 4,407E-01 |
| 807 | hsa-miR-125b-1* | 7,413E+00 | 9,439E+00 | 7,854E-01 | -2,416E-01 | 8,516E-01 | 9,029E-01 | 5,970E-01 | 7,246E-01 |
| 719 | hsa-miR-142-3p | 1,784E+01 | 1,457E+01 | 1,224E+00 | 2,025E-01 | 8,502E-01 | 9,029E-01 | 3,554E-01 | 5,129E-01 |
| 392 | hsa-miR-409-5p | 7,844E+01 | 7,294E+01 | 1,075E+00 | 7,263E-02 | 8,562E-01 | 9,033E-01 | 9,967E-01 | 9,983E-01 |
| 138 | hsa-miR-619 | 5,397E+01 | 5,280E+01 | 1,022E+00 | 2,190E-02 | 8,555E-01 | 9,033E-01 | 9,442E-01 | 9,632E-01 |
| 141 | hsa-miR-616* | 5,447E+01 | 6,926E+01 | 7,865E-01 | -2,402E-01 | 8,573E-01 | 9,033E-01 | 4,585E-01 | 6,115E-01 |
| 794 | hsa-miR-1269 | 4,656E+01 | 3,176E+01 | 1,466E+00 | 3,825E-01 | 8,563E-01 | 9,033E-01 | 2,119E-01 | 3,629E-01 |
| 540 | hsa-miR-223 | 2,206E+03 | 2,206E+03 | 1,000E+00 | 0,000E+00 | 8,530E-01 | 9,033E-01 | 5,288E-01 | 6,766E-01 |
| 668 | hsa-miR-181c* | 6,030E+01 | 8,023E+01 | 7,515E-01 | -2,856E-01 | 8,576E-01 | 9,033E-01 | 4,224E-01 | 5,812E-01 |
| 86 | hsa-miR-664* | 5,424E+01 | 5,447E+01 | 9,958E-01 | -4,225E-03 | 8,605E-01 | 9,046E-01 | 8,912E-01 | 9,332E-01 |
| 763 | hsa-miR-1294 | 9,057E+00 | 1,723E+01 | 5,258E-01 | -6,428E-01 | 8,621E-01 | 9,051E-01 | 6,233E-01 | 7,440E-01 |
| 148 | hsa-miR-611 | 9,955E+00 | 9,140E+00 | 1,089E+00 | 8,550E-02 | 8,636E-01 | 9,056E-01 | 9,889E-01 | 9,929E-01 |
| 603 | hsa-miR-199b-5p | 3,443E+00 | 3,443E+00 | 1,000E+00 | 0,000E+00 | 8,659E-01 | 9,069E-01 | 9,238E-01 | 9,466E-01 |
| 768 | hsa-miR-1290 | 1,000E+00 | 1,000E+00 | 1,000E+00 | 0,000E+00 | 8,718E-01 | 9,119E-01 | 9,144E-01 | 9,429E-01 |
| 335 | hsa-miR-496 | 6,894E+01 | 6,462E+01 | 1,067E+00 | 6,474E-02 | 8,746E-01 | 9,138E-01 | 4,682E-01 | 6,215E-01 |
| 504 | hsa-miR-29b-1* | 1,000E+00 | 1,650E+01 | 6,059E-02 | -2,804E+00 | 8,788E-01 | 9,171E-01 | 5,153E-02 | 1,344E-01 |
| 471 | hsa-miR-320b | 2,998E+03 | 2,998E+03 | 1,000E+00 | 0,000E+00 | 8,983E-01 | 9,351E-01 | 8,238E-01 | 8,943E-01 |
| 447 | hsa-miR-33a* | 6,151E+01 | 6,999E+01 | 8,787E-01 | -1,293E-01 | 8,961E-01 | 9,351E-01 | 8,921E-01 | 9,332E-01 |
| 227 | hsa-miR-548h | 1,000E+00 | 1,000E+00 | 1,000E+00 | 0,000E+00 | 9,002E-01 | 9,360E-01 | 8,992E-01 | 9,371E-01 |
| 275 | hsa-miR-519e | 1,000E+00 | 1,000E+00 | 1,000E+00 | 0,000E+00 | 9,033E-01 | 9,360E-01 | 8,197E-01 | 8,921E-01 |
| 228 | hsa-miR-548g | 2,615E+01 | 2,013E+01 | 1,299E+00 | 2,617E-01 | 9,120E-01 | 9,460E-01 | 6,785E-01 | 7,828E-01 |

FIG. 2 (Continued)

| | | | | | | | | |
|---|---|---|---|---|---|---|---|---|
| 653 | hsa-miR-187* | 1,251E+02 | 1,678E+02 | 7,455E-01 | -2,936E-01 | 9,199E-01 | 9,488E-01 | 4,695E-01 | 6,215E-01 |
| 706 | hsa-miR-146b-5p | 1,016E+02 | 1,114E+02 | 9,118E-01 | -9,228E-02 | 9,188E-01 | 9,488E-01 | 6,743E-01 | 7,790E-01 |
| 295 | hsa-miR-517b | 1,680E+01 | 9,984E+00 | 1,683E+00 | 5,204E-01 | 9,181E-01 | 9,488E-01 | 7,172E-01 | 8,091E-01 |
| 268 | hsa-miR-520d-3p | 1,000E+00 | 2,004E+01 | 4,990E-02 | -2,998E+00 | 9,186E-01 | 9,488E-01 | 2,114E-02 | 7,240E-02 |
| 91 | hsa-miR-661 | 4,419E+01 | 4,299E+01 | 1,028E+00 | 2,769E-02 | 9,202E-01 | 9,488E-01 | 6,511E-01 | 7,614E-01 |
| 51 | hsa-miR-875-5p | 2,660E+01 | 2,808E+01 | 9,470E-01 | -5,443E-02 | 9,217E-01 | 9,492E-01 | 9,516E-01 | 9,674E-01 |
| 667 | hsa-miR-181d | 3,010E+01 | 3,000E+01 | 1,003E+00 | 3,365E-03 | 9,242E-01 | 9,506E-01 | 8,846E-01 | 9,310E-01 |
| 233 | hsa-miR-548c-5p | 5,192E+00 | 1,235E+01 | 4,203E-01 | -8,667E-01 | 9,260E-01 | 9,514E-01 | 5,711E-01 | 7,033E-01 |
| 461 | hsa-miR-329 | 5,447E+01 | 5,035E+01 | 1,082E+00 | 7,856E-02 | 9,339E-01 | 9,584E-01 | 7,741E-01 | 8,543E-01 |
| 596 | hsa-miR-200a* | 6,273E+01 | 7,057E+01 | 8,889E-01 | -1,178E-01 | 9,387E-01 | 9,618E-01 | 6,729E-01 | 7,785E-01 |
| 44 | hsa-miR-886-3p | 1,000E+00 | 2,056E+01 | 4,863E-02 | -3,023E+00 | 9,398E-01 | 9,618E-01 | 6,728E-02 | 1,645E-01 |
| 389 | hsa-miR-411* | 5,046E+01 | 4,737E+01 | 1,065E+00 | 6,319E-02 | 9,406E-01 | 9,618E-01 | 4,173E-01 | 5,760E-01 |
| 895 | hsa-let-7e | 1,385E+02 | 2,050E+02 | 6,760E-01 | -3,916E-01 | 9,420E-01 | 9,620E-01 | 1,239E-01 | 2,512E-01 |
| 330 | hsa-miR-499-5p | 2,056E+01 | 1,235E+01 | 1,665E+00 | 5,095E-01 | 9,506E-01 | 9,697E-01 | 5,255E-01 | 6,748E-01 |
| 18 | hsa-miR-935 | 2,904E+01 | 3,326E+01 | 8,733E-01 | -1,355E-01 | 9,589E-01 | 9,770E-01 | 7,912E-01 | 8,665E-01 |
| 308 | hsa-miR-513a-3p | 3,315E+01 | 3,753E+01 | 8,835E-01 | -1,239E-01 | 9,604E-01 | 9,774E-01 | 3,661E-01 | 5,252E-01 |
| 197 | hsa-miR-567 | 5,339E+01 | 6,127E+01 | 8,713E-01 | -1,378E-01 | 9,635E-01 | 9,785E-01 | 2,591E-01 | 4,195E-01 |
| 224 | hsa-miR-548k | 1,139E+01 | 1,997E+00 | 5,704E+00 | 1,741E+00 | 9,638E-01 | 9,785E-01 | 6,227E-01 | 7,440E-01 |
| 633 | hsa-miR-1914* | 1,374E+02 | 1,710E+02 | 8,037E-01 | -2,185E-01 | 9,667E-01 | 9,803E-01 | 5,895E-01 | 7,187E-01 |
| 350 | hsa-miR-486-5p | 4,147E+04 | 4,147E+04 | 1,000E+00 | 0,000E+00 | 9,698E-01 | 9,824E-01 | 9,492E-01 | 9,671E-01 |
| 562 | hsa-miR-212 | 5,653E+01 | 7,740E+01 | 7,304E-01 | -3,142E-01 | 9,764E-01 | 9,878E-01 | 7,667E-01 | 8,483E-01 |
| 704 | hsa-miR-1470 | 1,590E+02 | 1,966E+02 | 8,090E-01 | -2,120E-01 | 9,780E-01 | 9,883E-01 | 5,714E-01 | 7,033E-01 |
| 632 | hsa-miR-1915 | 6,883E+02 | 6,222E+02 | 1,106E+00 | 1,009E-01 | 9,808E-01 | 9,900E-01 | 9,202E-01 | 9,465E-01 |
| 410 | hsa-miR-375 | 8,713E+00 | 2,564E+00 | 3,399E+00 | 1,223E+00 | 9,863E-01 | 9,921E-01 | 5,143E-01 | 6,664E-01 |
| 96 | hsa-miR-656 | 2,821E+01 | 2,177E+01 | 1,296E+00 | 2,591E-01 | 9,853E-01 | 9,921E-01 | 4,140E-01 | 5,727E-01 |
| 430 | hsa-miR-362-3p | 2,019E+02 | 2,386E+02 | 8,463E-01 | -1,669E-01 | 9,852E-01 | 9,921E-01 | 9,002E-01 | 9,371E-01 |
| 257 | hsa-miR-524-3p | 2,066E+01 | 1,795E+01 | 1,151E+00 | 1,405E-01 | 9,881E-01 | 9,927E-01 | 7,044E-01 | 7,999E-01 |
| 792 | hsa-miR-1271 | 1,509E+02 | 2,086E+02 | 7,237E-01 | -3,234E-01 | 9,895E-01 | 9,930E-01 | 6,478E-01 | 7,606E-01 |
| 443 | hsa-miR-340* | 1,586E+01 | 9,439E+00 | 1,680E+00 | 5,187E-01 | 9,922E-01 | 9,945E-01 | 5,683E-01 | 7,026E-01 |
| 497 | hsa-miR-302a | 1,000E+00 | 1,000E+00 | 1,000E+00 | 0,000E+00 | 9,955E-01 | 9,966E-01 | 9,895E-01 | 9,929E-01 |
| 3 | hsa-miR-99a* | 3,526E+01 | 4,546E+01 | 7,758E-01 | -2,539E-01 | 9,985E-01 | 9,985E-01 | 3,015E-01 | 4,629E-01 |

Figure 5

| SEQ ID NO | miRNA | median g1 | median g2 | qmedian | logqmedian | ttest_rawp | ttest_adjp | AUC | limma_rawp | limma_adjp |
|---|---|---|---|---|---|---|---|---|---|---|
| 714 | hsa-miR-144* | 797 | 218 | 3,65 | 1,30 | 7,76E-17 | 6,69E-14 | 0,92 | 9,63E-19 | 8,30E-16 |
| 701 | hsa-miR-148a | 1165 | 485 | 2,40 | 0,88 | 1,22E-15 | 5,24E-13 | 0,91 | 1,74E-16 | 5,01E-14 |
| 577 | hsa-miR-20b | 3376 | 1377 | 2,45 | 0,90 | 6,84E-14 | 1,96E-11 | 0,87 | 6,50E-13 | 1,40E-10 |
| 36 | hsa-miR-891b | 96 | 35 | 2,74 | 1,01 | 8,43E-13 | 1,82E-10 | 0,85 | 9,94E-09 | 5,66E-07 |
| 715 | hsa-miR-144 | 2445 | 860 | 2,84 | 1,04 | 4,71E-12 | 8,13E-10 | 0,84 | 1,04E-11 | 1,49E-09 |
| 699 | hsa-miR-148b | 596 | 344 | 1,73 | 0,55 | 2,11E-11 | 3,04E-09 | 0,83 | 1,01E-10 | 1,25E-08 |
| 499 | hsa-miR-301a | 327 | 177 | 1,85 | 0,61 | 4,63E-10 | 5,70E-08 | 0,80 | 1,95E-07 | 6,11E-06 |
| 448 | hsa-miR-33a | 111 | 51 | 2,20 | 0,79 | 7,31E-10 | 7,88E-08 | 0,81 | 4,68E-06 | 7,61E-05 |
| 579 | hsa-miR-20a | 3708 | 1640 | 2,26 | 0,82 | 8,95E-10 | 8,57E-08 | 0,81 | 9,53E-10 | 1,03E-07 |
| 384 | hsa-miR-423-5p | 2555 | 7334 | 0,35 | -1,05 | 1,22E-09 | 1,02E-07 | 0,09 | 4,67E-17 | 2,01E-14 |
| 206 | hsa-miR-556-5p | 122 | 36 | 3,42 | 1,23 | 1,30E-09 | 1,02E-07 | 0,81 | 3,01E-06 | 5,89E-05 |
| 412 | hsa-miR-374b | 562 | 265 | 2,12 | 0,75 | 1,60E-09 | 1,15E-07 | 0,82 | 3,95E-09 | 2,84E-07 |
| 883 | hsa-miR-101 | 674 | 363 | 1,86 | 0,62 | 3,51E-09 | 2,33E-07 | 0,80 | 3,50E-09 | 2,74E-07 |
| 358 | hsa-miR-455-3p | 178 | 114 | 1,57 | 0,45 | 4,02E-09 | 2,48E-07 | 0,81 | 1,98E-07 | 6,11E-06 |
| 826 | hsa-miR-1245 | 45 | 1 | 44,64 | 3,80 | 4,54E-09 | 2,61E-07 | 0,81 | 8,46E-12 | 1,46E-09 |
| 414 | hsa-miR-374a | 306 | 150 | 2,04 | 0,71 | 5,49E-09 | 2,96E-07 | 0,82 | 2,21E-08 | 1,04E-06 |
| 776 | hsa-miR-1283 | 108 | 38 | 2,83 | 1,04 | 7,19E-09 | 3,65E-07 | 0,79 | 7,80E-09 | 5,17E-07 |
| 446 | hsa-miR-33b | 162 | 101 | 1,61 | 0,47 | 8,48E-09 | 3,87E-07 | 0,80 | 2,89E-06 | 5,80E-05 |
| 680 | hsa-miR-15b | 15690 | 11382 | 1,38 | 0,32 | 8,54E-09 | 3,87E-07 | 0,78 | 3,74E-07 | 1,01E-05 |
| 428 | hsa-miR-363 | 4304 | 2500 | 1,72 | 0,54 | 9,24E-09 | 3,98E-07 | 0,80 | 1,61E-07 | 5,35E-06 |
| 472 | hsa-miR-320a | 14174 | 23985 | 0,59 | -0,53 | 1,39E-08 | 5,69E-07 | 0,21 | 2,48E-08 | 1,07E-06 |
| 842 | hsa-miR-1226 | 58 | 109 | 0,53 | -0,64 | 1,79E-08 | 6,99E-07 | 0,21 | 6,51E-06 | 9,85E-05 |
| 574 | hsa-miR-21* | 97 | 41 | 2,39 | 0,87 | 3,07E-08 | 1,15E-06 | 0,78 | 6,52E-05 | 5,91E-04 |
| 190 | hsa-miR-574-3p | 1781 | 3462 | 0,51 | -0,66 | 3,65E-08 | 1,31E-06 | 0,20 | 1,05E-08 | 5,66E-07 |
| 575 | hsa-miR-21 | 1101 | 474 | 2,32 | 0,84 | 6,19E-08 | 2,14E-06 | 0,78 | 1,27E-08 | 6,45E-07 |
| 641 | hsa-miR-191 | 10920 | 15690 | 0,70 | -0,36 | 7,03E-08 | 2,33E-06 | 0,21 | 3,13E-07 | 8,99E-06 |
| 398 | hsa-miR-380* | 78 | 50 | 1,56 | 0,44 | 1,04E-07 | 3,31E-06 | 0,77 | 6,42E-05 | 5,88E-04 |
| 297 | hsa-miR-517* | 171 | 101 | 1,70 | 0,53 | 1,55E-07 | 4,77E-06 | 0,77 | 1,89E-04 | 1,38E-03 |
| 219 | hsa-miR-548p | 117 | 54 | 2,14 | 0,76 | 4,57E-07 | 1,31E-05 | 0,76 | 3,00E-03 | 1,18E-02 |
| 729 | hsa-miR-137 | 75 | 34 | 2,23 | 0,80 | 4,57E-07 | 1,31E-05 | 0,74 | 1,57E-04 | 1,20E-03 |
| 773 | hsa-miR-1286 | 128 | 90 | 1,42 | 0,35 | 4,83E-07 | 1,34E-05 | 0,75 | 7,24E-05 | 6,37E-04 |
| 900 | hsa-let-7b* | 12 | 78 | 0,15 | -1,90 | 5,06E-07 | 1,36E-05 | 0,20 | 2,29E-08 | 1,04E-06 |
| 580 | hsa-miR-208b | 65 | 24 | 2,69 | 0,99 | 5,41E-07 | 1,41E-05 | 0,75 | 2,10E-06 | 4,53E-05 |
| 142 | hsa-miR-616 | 13 | 68 | 0,19 | -1,68 | 6,30E-07 | 1,60E-05 | 0,26 | 1,38E-04 | 1,10E-03 |
| 217 | hsa-miR-549 | 56 | 26 | 2,17 | 0,77 | 1,06E-06 | 2,61E-05 | 0,75 | 2,60E-07 | 7,74E-06 |
| 650 | hsa-miR-18a | 1234 | 694 | 1,78 | 0,58 | 1,19E-06 | 2,83E-05 | 0,77 | 4,13E-07 | 1,08E-05 |
| 681 | hsa-miR-15a* | 118 | 75 | 1,57 | 0,45 | 1,21E-06 | 2,83E-05 | 0,77 | 5,86E-05 | 5,61E-04 |
| 865 | hsa-miR-1180 | 67 | 152 | 0,44 | -0,81 | 1,33E-06 | 3,02E-05 | 0,22 | 3,07E-06 | 5,89E-05 |
| 471 | hsa-miR-320b | 2185 | 4529 | 0,48 | -0,73 | 1,49E-06 | 3,29E-05 | 0,22 | 3,44E-08 | 1,41E-06 |
| 691 | hsa-miR-152 | 225 | 170 | 1,32 | 0,28 | 1,74E-06 | 3,74E-05 | 0,74 | 1,08E-05 | 1,43E-04 |
| 782 | hsa-miR-1278 | 61 | 30 | 2,05 | 0,72 | 1,85E-06 | 3,90E-05 | 0,74 | 3,60E-06 | 6,76E-05 |
| 171 | hsa-miR-589* | 86 | 115 | 0,74 | -0,30 | 2,30E-06 | 4,73E-05 | 0,26 | 4,34E-05 | 4,35E-04 |
| 424 | hsa-miR-367 | 88 | 42 | 2,08 | 0,73 | 2,51E-06 | 5,03E-05 | 0,76 | 1,05E-08 | 5,66E-07 |
| 343 | hsa-miR-490-5p | 130 | 71 | 1,84 | 0,61 | 2,77E-06 | 5,42E-05 | 0,75 | 1,64E-04 | 1,24E-03 |
| 597 | hsa-miR-200a | 88 | 47 | 1,89 | 0,63 | 2,91E-06 | 5,57E-05 | 0,75 | 1,19E-03 | 5,59E-03 |
| 71 | hsa-miR-720 | 3376 | 6944 | 0,49 | -0,72 | 3,62E-06 | 6,79E-05 | 0,21 | 4,09E-08 | 1,53E-06 |
| 712 | hsa-miR-145* | 74 | 38 | 1,93 | 0,66 | 3,77E-06 | 6,92E-05 | 0,74 | 5,58E-03 | 1,86E-02 |
| 770 | hsa-miR-1289 | 103 | 74 | 1,38 | 0,32 | 3,97E-06 | 7,14E-05 | 0,75 | 1,09E-05 | 1,43E-04 |
| 843 | hsa-miR-1225-5p | 65 | 109 | 0,59 | -0,52 | 4,25E-06 | 7,47E-05 | 0,25 | 3,39E-05 | 3,48E-04 |
| 14 | hsa-miR-939 | 43 | 116 | 0,37 | -0,99 | 4,35E-06 | 7,50E-05 | 0,25 | 1,11E-04 | 9,06E-04 |
| 887 | hsa-let-7i* | 249 | 130 | 1,91 | 0,65 | 4,64E-06 | 7,85E-05 | 0,81 | 1,48E-07 | 5,09E-06 |
| 629 | hsa-miR-192* | 114 | 72 | 1,59 | 0,47 | 5,69E-06 | 9,44E-05 | 0,74 | 1,08E-04 | 8,91E-04 |
| 169 | hsa-miR-590-5p | 171 | 99 | 1,72 | 0,54 | 6,26E-06 | 1,02E-04 | 0,74 | 1,55E-06 | 3,43E-05 |
| 469 | hsa-miR-320d | 627 | 1138 | 0,55 | -0,60 | 6,73E-06 | 1,08E-04 | 0,24 | 9,01E-08 | 3,24E-06 |
| 360 | hsa-miR-454 | 143 | 75 | 1,90 | 0,64 | 7,23E-06 | 1,13E-04 | 0,73 | 7,31E-07 | 1,71E-05 |
| 543 | hsa-miR-221* | 109 | 57 | 1,90 | 0,64 | 8,04E-06 | 1,24E-04 | 0,74 | 1,45E-06 | 3,29E-05 |
| 470 | hsa-miR-320c | 579 | 1110 | 0,52 | -0,65 | 8,23E-06 | 1,24E-04 | 0,19 | 2,22E-09 | 1,92E-07 |
| 62 | hsa-miR-765 | 50 | 95 | 0,53 | -0,63 | 8,89E-06 | 1,32E-04 | 0,25 | 9,78E-06 | 1,35E-04 |
| 474 | hsa-miR-32 | 144 | 94 | 1,54 | 0,43 | 9,72E-06 | 1,42E-04 | 0,76 | 7,72E-06 | 1,11E-04 |
| 214 | hsa-miR-551a | 63 | 24 | 2,58 | 0,95 | 1,05E-05 | 1,50E-04 | 0,73 | 4,17E-06 | 7,38E-05 |
| 602 | hsa-miR-19a | 2445 | 1822 | 1,34 | 0,29 | 1,11E-05 | 1,57E-04 | 0,76 | 9,84E-06 | 1,35E-04 |
| 627 | hsa-miR-193a-5p | 78 | 130 | 0,60 | -0,51 | 1,21E-05 | 1,69E-04 | 0,25 | 8,29E-04 | 4,28E-03 |
| 875 | hsa-miR-106a* | 139 | 83 | 1,68 | 0,52 | 1,25E-05 | 1,71E-04 | 0,75 | 2,47E-04 | 1,69E-03 |
| 828 | hsa-miR-1243 | 58 | 25 | 2,35 | 0,85 | 1,30E-05 | 1,75E-04 | 0,72 | 1,84E-05 | 2,24E-04 |
| 876 | hsa-miR-106a | 6586 | 4529 | 1,45 | 0,37 | 1,35E-05 | 1,79E-04 | 0,72 | 1,49E-05 | 1,89E-04 |
| 734 | hsa-miR-135a* | 1 | 35 | 0,03 | -3,56 | 1,40E-05 | 1,82E-04 | 0,27 | 5,15E-06 | 8,07E-05 |
| 616 | hsa-miR-197 | 512 | 1214 | 0,42 | -0,86 | 1,57E-05 | 2,02E-04 | 0,20 | 4,70E-07 | 1,19E-05 |
| 810 | hsa-miR-125a-3p | 17 | 50 | 0,34 | -1,09 | 1,60E-05 | 2,02E-04 | 0,29 | 3,54E-03 | 1,33E-02 |
| 675 | hsa-miR-17 | 7534 | 5003 | 1,51 | 0,41 | 1,80E-05 | 2,24E-04 | 0,73 | 6,25E-05 | 5,86E-04 |
| 785 | hsa-miR-127-5p | 129 | 71 | 1,83 | 0,60 | 1,85E-05 | 2,25E-04 | 0,75 | 7,57E-04 | 4,05E-03 |
| 476 | hsa-miR-31 | 134 | 92 | 1,46 | 0,38 | 1,85E-05 | 2,25E-04 | 0,71 | 1,50E-03 | 6,67E-03 |
| 198 | hsa-miR-566 | 93 | 63 | 1,47 | 0,39 | 2,03E-05 | 2,43E-04 | 0,72 | 6,77E-06 | 1,01E-04 |
| 216 | hsa-miR-550 | 120 | 162 | 0,74 | -0,31 | 2,09E-05 | 2,47E-04 | 0,26 | 9,11E-04 | 4,59E-03 |
| 462 | hsa-miR-328 | 62 | 135 | 0,46 | -0,78 | 2,16E-05 | 2,52E-04 | 0,26 | 5,44E-05 | 5,33E-04 |
| 279 | hsa-miR-519b-5p | 131 | 35 | 3,72 | 1,31 | 2,38E-05 | 2,73E-04 | 0,81 | 4,06E-08 | 1,53E-06 |
| 786 | hsa-miR-1275 | 59 | 109 | 0,54 | -0,62 | 2,41E-05 | 2,73E-04 | 0,28 | 2,20E-03 | 9,33E-03 |

FIG. 5 (Continued)

| | | | | | | | | | |
|---|---|---|---|---|---|---|---|---|---|
| 590 | hsa-miR-202* | 71 | 46 | 1,52 | 0,42 | 2,49E-05 | 2,78E-04 | 0,71 | 3,66E-04 | 2,27E-03 |
| 690 | hsa-miR-153 | 114 | 77 | 1,48 | 0,39 | 2,58E-05 | 2,85E-04 | 0,70 | 5,29E-04 | 3,02E-03 |
| 805 | hsa-miR-126 | 2044 | 1138 | 1,80 | 0,59 | 2,63E-05 | 2,87E-04 | 0,74 | 6,15E-07 | 1,51E-05 |
| 335 | hsa-miR-496 | 72 | 33 | 2,17 | 0,78 | 2,66E-05 | 2,87E-04 | 0,74 | 1,52E-09 | 1,45E-07 |
| 11 | hsa-miR-942 | 11 | 56 | 0,19 | -1,66 | 3,07E-05 | 3,23E-04 | 0,26 | 1,02E-05 | 1,37E-04 |
| 797 | hsa-miR-1266 | 111 | 72 | 1,55 | 0,44 | 3,07E-05 | 3,23E-04 | 0,71 | 7,10E-04 | 3,85E-03 |
| 281 | hsa-miR-519a* | 138 | 76 | 1,80 | 0,59 | 3,22E-05 | 3,35E-04 | 0,71 | 3,83E-02 | 8,84E-02 |
| 329 | hsa-miR-500 | 223 | 379 | 0,59 | -0,53 | 4,06E-05 | 4,17E-04 | 0,28 | 9,44E-04 | 4,68E-03 |
| 356 | hsa-miR-483-3p | 12 | 65 | 0,18 | -1,71 | 4,18E-05 | 4,24E-04 | 0,27 | 2,72E-05 | 3,01E-04 |
| 289 | hsa-miR-518c* | 49 | 18 | 2,67 | 0,98 | 4,31E-05 | 4,32E-04 | 0,72 | 6,36E-05 | 5,88E-04 |
| 32 | hsa-miR-9* | 100 | 52 | 1,91 | 0,65 | 4,81E-05 | 4,75E-04 | 0,71 | 4,41E-03 | 1,58E-02 |
| 717 | hsa-miR-143 | 214 | 154 | 1,39 | 0,33 | 4,85E-05 | 4,75E-04 | 0,70 | 2,12E-04 | 1,50E-03 |
| 24 | hsa-miR-92b | 290 | 426 | 0,68 | -0,38 | 4,92E-05 | 4,77E-04 | 0,27 | 8,19E-06 | 1,16E-04 |
| 16 | hsa-miR-937 | 47 | 90 | 0,52 | -0,65 | 5,37E-05 | 5,12E-04 | 0,29 | 4,59E-04 | 2,69E-03 |
| 92 | hsa-miR-660 | 487 | 342 | 1,43 | 0,35 | 5,40E-05 | 5,12E-04 | 0,69 | 4,34E-04 | 2,60E-03 |
| 545 | hsa-miR-220c | 108 | 71 | 1,52 | 0,42 | 5,83E-05 | 5,47E-04 | 0,70 | 3,62E-03 | 1,35E-02 |
| 397 | hsa-miR-381 | 90 | 60 | 1,49 | 0,40 | 5,98E-05 | 5,48E-04 | 0,72 | 3,41E-04 | 2,19E-03 |
| 270 | hsa-miR-520c-3p | 1 | 15 | 0,07 | -2,71 | 5,96E-05 | 5,48E-04 | 0,29 | 4,76E-06 | 7,61E-05 |
| 518 | hsa-miR-27a* | 30 | 60 | 0,51 | -0,67 | 6,38E-05 | 5,79E-04 | 0,29 | 3,19E-04 | 2,10E-03 |
| 517 | hsa-miR-27b | 227 | 163 | 1,39 | 0,33 | 6,78E-05 | 6,09E-04 | 0,69 | 1,55E-04 | 1,20E-03 |
| 45 | hsa-miR-885-5p | 11 | 36 | 0,31 | -1,17 | 7,40E-05 | 6,58E-04 | 0,29 | 5,77E-05 | 5,58E-04 |
| 893 | hsa-let-7f | 512 | 335 | 1,53 | 0,43 | 7,62E-05 | 6,70E-04 | 0,69 | 3,33E-05 | 3,46E-04 |
| 455 | hsa-miR-335* | 1 | 32 | 0,03 | -3,46 | 7,72E-05 | 6,72E-04 | 0,28 | 4,03E-06 | 7,38E-05 |
| 293 | hsa-miR-518a-3p | 58 | 31 | 1,86 | 0,62 | 7,83E-05 | 6,75E-04 | 0,70 | 2,30E-03 | 9,56E-03 |
| 126 | hsa-miR-628-5p | 81 | 44 | 1,83 | 0,61 | 9,17E-05 | 7,83E-04 | 0,70 | 8,88E-05 | 7,58E-04 |
| 840 | hsa-miR-1227 | 65 | 111 | 0,58 | -0,54 | 9,66E-05 | 8,16E-04 | 0,29 | 6,99E-02 | 1,39E-01 |
| 61 | hsa-miR-766 | 381 | 694 | 0,55 | -0,60 | 1,03E-04 | 8,42E-04 | 0,23 | 3,47E-07 | 9,66E-06 |
| 131 | hsa-miR-625 | 79 | 155 | 0,51 | -0,68 | 1,03E-04 | 8,42E-04 | 0,29 | 1,69E-04 | 1,26E-03 |
| 224 | hsa-miR-548k | 11 | 36 | 0,32 | -1,14 | 1,01E-04 | 8,42E-04 | 0,31 | 2,16E-03 | 9,23E-03 |
| 881 | hsa-miR-103 | 7956 | 4750 | 1,68 | 0,52 | 1,18E-04 | 9,49E-04 | 0,74 | 4,37E-06 | 7,53E-05 |
| 713 | hsa-miR-145 | 153 | 263 | 0,58 | -0,54 | 1,18E-04 | 9,49E-04 | 0,30 | 6,05E-03 | 1,98E-02 |
| 889 | hsa-let-7g* | 123 | 107 | 1,15 | 0,14 | 1,21E-04 | 9,69E-04 | 0,67 | 3,34E-04 | 2,16E-03 |
| 117 | hsa-miR-636 | 159 | 206 | 0,77 | -0,26 | 1,25E-04 | 9,91E-04 | 0,26 | 1,54E-05 | 1,92E-04 |
| 155 | hsa-miR-604 | 95 | 62 | 1,53 | 0,43 | 1,29E-04 | 1,01E-03 | 0,69 | 4,51E-04 | 2,66E-03 |
| 735 | hsa-miR-135a | 1 | 3 | 0,36 | -1,03 | 1,30E-04 | 1,01E-03 | 0,31 | 6,38E-06 | 9,81E-05 |
| 674 | hsa-miR-17* | 722 | 466 | 1,55 | 0,44 | 1,32E-04 | 1,01E-03 | 0,72 | 5,17E-04 | 2,98E-03 |
| 449 | hsa-miR-339-5p | 636 | 884 | 0,72 | -0,33 | 1,54E-04 | 1,17E-03 | 0,30 | 2,05E-04 | 1,48E-03 |
| 519 | hsa-miR-27a | 344 | 245 | 1,40 | 0,34 | 1,58E-04 | 1,20E-03 | 0,69 | 1,01E-04 | 8,45E-04 |
| 622 | hsa-miR-195 | 636 | 426 | 1,49 | 0,40 | 1,93E-04 | 1,43E-03 | 0,75 | 2,19E-05 | 2,59E-04 |
| 737 | hsa-miR-133b | 10 | 35 | 0,29 | -1,24 | 1,94E-04 | 1,43E-03 | 0,28 | 2,24E-05 | 2,60E-04 |
| 707 | hsa-miR-146b-3p | 72 | 46 | 1,58 | 0,46 | 1,92E-04 | 1,43E-03 | 0,69 | 1,10E-04 | 9,00E-04 |
| 839 | hsa-miR-1910 | 40 | 97 | 0,41 | -0,88 | 2,05E-04 | 1,50E-03 | 0,21 | 2,43E-05 | 2,79E-04 |
| 393 | hsa-miR-409-3p | 29 | 71 | 0,40 | -0,92 | 2,09E-04 | 1,52E-03 | 0,28 | 2,68E-05 | 3,00E-04 |
| 283 | hsa-miR-518f* | 126 | 77 | 1,64 | 0,49 | 2,21E-04 | 1,59E-03 | 0,69 | 1,14E-04 | 9,16E-04 |
| 386 | hsa-miR-422a | 141 | 250 | 0,56 | -0,57 | 2,31E-04 | 1,65E-03 | 0,30 | 1,77E-02 | 4,78E-02 |
| 452 | hsa-miR-338-3p | 141 | 74 | 1,92 | 0,65 | 2,62E-04 | 1,85E-03 | 0,75 | 2,13E-04 | 1,50E-03 |
| 7 | hsa-miR-96 | 175 | 118 | 1,49 | 0,40 | 2,72E-04 | 1,91E-03 | 0,72 | 2,22E-04 | 1,55E-03 |
| 521 | hsa-miR-26b | 463 | 307 | 1,51 | 0,41 | 2,89E-04 | 2,01E-03 | 0,67 | 7,87E-04 | 4,16E-03 |
| 287 | hsa-miR-518d-5p | 155 | 80 | 1,94 | 0,66 | 3,03E-04 | 2,08E-03 | 0,71 | 2,23E-02 | 5,75E-02 |
| 429 | hsa-miR-362-5p | 142 | 225 | 0,63 | -0,46 | 3,04E-04 | 2,08E-03 | 0,30 | 5,84E-04 | 3,29E-03 |
| 383 | hsa-miR-424 | 258 | 198 | 1,30 | 0,26 | 3,10E-04 | 2,11E-03 | 0,68 | 1,62E-03 | 7,14E-03 |
| 752 | hsa-miR-1305 | 88 | 56 | 1,57 | 0,45 | 3,15E-04 | 2,12E-03 | 0,71 | 1,21E-03 | 5,63E-03 |
| 868 | hsa-miR-10b* | 51 | 29 | 1,75 | 0,56 | 3,17E-04 | 2,12E-03 | 0,68 | 1,17E-02 | 3,41E-02 |
| 339 | hsa-miR-493 | 24 | 53 | 0,46 | -0,77 | 3,21E-04 | 2,13E-03 | 0,32 | 5,27E-03 | 1,78E-02 |
| 706 | hsa-miR-146b-5p | 126 | 105 | 1,20 | 0,18 | 3,28E-04 | 2,16E-03 | 0,67 | 7,25E-06 | 1,06E-04 |
| 625 | hsa-miR-193b* | 29 | 66 | 0,44 | -0,82 | 3,43E-04 | 2,24E-03 | 0,30 | 6,78E-05 | 6,09E-04 |
| 30 | hsa-miR-921 | 60 | 87 | 0,69 | -0,37 | 3,49E-04 | 2,26E-03 | 0,32 | 1,93E-02 | 5,12E-02 |
| 337 | hsa-miR-494 | 65 | 117 | 0,56 | -0,59 | 3,60E-04 | 2,32E-03 | 0,30 | 2,31E-03 | 9,56E-03 |
| 341 | hsa-miR-491-5p | 97 | 134 | 0,73 | -0,32 | 3,66E-04 | 2,34E-03 | 0,31 | 3,15E-02 | 7,54E-02 |
| 857 | hsa-miR-1201 | 63 | 34 | 1,84 | 0,61 | 3,78E-04 | 2,40E-03 | 0,65 | 3,90E-02 | 8,89E-02 |
| 266 | hsa-miR-520e | 1 | 14 | 0,07 | -2,63 | 3,98E-04 | 2,51E-03 | 0,33 | 2,53E-04 | 1,72E-03 |
| 660 | hsa-miR-183* | 105 | 173 | 0,61 | -0,50 | 4,04E-04 | 2,52E-03 | 0,30 | 4,57E-02 | 9,92E-02 |
| 745 | hsa-miR-130b* | 1 | 15 | 0,07 | -2,68 | 4,10E-04 | 2,54E-03 | 0,31 | 5,21E-05 | 5,16E-04 |
| 326 | hsa-miR-501-5p | 32 | 78 | 0,41 | -0,89 | 4,22E-04 | 2,60E-03 | 0,26 | 1,26E-05 | 1,62E-04 |
| 72 | hsa-miR-7-2* | 27 | 60 | 0,45 | -0,79 | 4,25E-04 | 2,60E-03 | 0,29 | 5,55E-03 | 1,86E-02 |
| 694 | hsa-miR-150* | 92 | 129 | 0,71 | -0,34 | 4,34E-04 | 2,64E-03 | 0,31 | 1,71E-03 | 7,46E-03 |
| 317 | hsa-miR-508-3p | 1 | 16 | 0,06 | -2,77 | 4,47E-04 | 2,68E-03 | 0,30 | 2,89E-05 | 3,15E-04 |
| 522 | hsa-miR-28a-2* | 1 | 2 | 0,64 | -0,44 | 4,44E-04 | 2,68E-03 | 0,33 | 3,30E-05 | 3,46E-04 |
| 416 | hsa-miR-373 | 1 | 21 | 0,05 | -3,05 | 4,55E-04 | 2,70E-03 | 0,33 | 7,99E-04 | 4,20E-03 |
| 572 | hsa-miR-211 | 1 | 11 | 0,09 | -2,39 | 4,68E-04 | 2,77E-03 | 0,31 | 7,34E-05 | 6,39E-04 |
| 464 | hsa-miR-325 | 52 | 15 | 3,53 | 1,26 | 4,93E-04 | 2,89E-03 | 0,72 | 1,78E-05 | 2,19E-04 |
| 493 | hsa-miR-302c | 1 | 15 | 0,07 | -2,72 | 4,97E-04 | 2,89E-03 | 0,31 | 2,96E-04 | 1,98E-03 |
| 697 | hsa-miR-149 | 24 | 59 | 0,41 | -0,88 | 5,15E-04 | 2,98E-03 | 0,31 | 6,37E-03 | 2,05E-02 |
| 23 | hsa-miR-92b* | 129 | 206 | 0,63 | -0,47 | 5,19E-04 | 2,98E-03 | 0,31 | 6,41E-04 | 3,54E-03 |
| 52 | hsa-miR-875-3p | 51 | 15 | 3,35 | 1,21 | 5,29E-04 | 3,02E-03 | 0,67 | 1,35E-03 | 6,10E-03 |
| 305 | hsa-miR-513c | 5 | 25 | 0,20 | -1,62 | 5,56E-04 | 3,12E-03 | 0,31 | 3,46E-04 | 2,19E-03 |
| 791 | hsa-miR-1272 | 134 | 88 | 1,52 | 0,42 | 5,58E-04 | 3,12E-03 | 0,69 | 1,31E-03 | 6,05E-03 |
| 888 | hsa-let-7i | 654 | 411 | 1,59 | 0,46 | 5,56E-04 | 3,12E-03 | 0,66 | 3,24E-04 | 2,12E-03 |
| 246 | hsa-miR-541 | 108 | 62 | 1,75 | 0,56 | 5,72E-04 | 3,18E-03 | 0,70 | 3,27E-05 | 3,46E-04 |
| 106 | hsa-miR-647 | 71 | 49 | 1,43 | 0,36 | 5,76E-04 | 3,18E-03 | 0,67 | 3,23E-02 | 7,69E-02 |

FIG. 5 (Continued)

| | | | | | | | | | |
|---|---|---|---|---|---|---|---|---|---|
| 890 | hsa-let-7g | 478 | 303 | 1,58 | 0,46 | 5,78E-04 | 3,18E-03 | 0,65 | 2,51E-02 | 6,35E-02 |
| 324 | hsa-miR-502-5p | 13 | 36 | 0,34 | -1,07 | 6,57E-04 | 3,58E-03 | 0,32 | 2,15E-03 | 9,20E-03 |
| 193 | hsa-miR-571 | 47 | 73 | 0,64 | -0,44 | 6,88E-04 | 3,73E-03 | 0,31 | 1,11E-03 | 5,31E-03 |
| 179 | hsa-miR-582-5p | 25 | 44 | 0,57 | -0,57 | 6,97E-04 | 3,75E-03 | 0,33 | 1,87E-03 | 8,14E-03 |
| 620 | hsa-miR-196a | 1 | 31 | 0,03 | -3,45 | 7,11E-04 | 3,81E-03 | 0,28 | 4,62E-06 | 7,61E-05 |
| 465 | hsa-miR-324-5p | 356 | 461 | 0,77 | -0,26 | 7,49E-04 | 3,96E-03 | 0,30 | 5,20E-03 | 1,78E-02 |
| 896 | hsa-let-7d* | 74 | 114 | 0,65 | -0,43 | 7,48E-04 | 3,96E-03 | 0,31 | 3,54E-04 | 2,22E-03 |
| 129 | hsa-miR-626 | 31 | 1 | 31,01 | 3,43 | 7,62E-04 | 4,01E-03 | 0,72 | 4,46E-06 | 7,54E-05 |
| 367 | hsa-miR-450a | 1 | 24 | 0,04 | -3,19 | 7,87E-04 | 4,11E-03 | 0,27 | 2,55E-06 | 5,23E-05 |
| 187 | hsa-miR-576-3p | 1 | 12 | 0,08 | -2,47 | 8,53E-04 | 4,42E-03 | 0,32 | 2,44E-04 | 1,68E-03 |
| 809 | hsa-miR-125a-5p | 205 | 375 | 0,55 | -0,61 | 8,57E-04 | 4,42E-03 | 0,33 | 5,84E-02 | 1,21E-01 |
| 512 | hsa-miR-296-5p | 243 | 382 | 0,64 | -0,45 | 9,53E-04 | 4,89E-03 | 0,32 | 4,29E-03 | 1,54E-02 |
| 54 | hsa-miR-873 | 69 | 40 | 1,69 | 0,53 | 9,77E-04 | 4,98E-03 | 0,68 | 2,22E-03 | 9,37E-03 |
| 244 | hsa-miR-542-3p | 80 | 44 | 1,82 | 0,60 | 9,99E-04 | 5,07E-03 | 0,66 | 1,02E-02 | 3,07E-02 |
| 344 | hsa-miR-490-3p | 87 | 49 | 1,78 | 0,57 | 1,01E-03 | 5,09E-03 | 0,69 | 3,56E-02 | 8,37E-02 |
| 588 | hsa-miR-204 | 1 | 1 | 1,00 | 0,00 | 1,03E-03 | 5,14E-03 | 0,33 | 6,03E-05 | 5,71E-04 |
| 529 | hsa-miR-24 | 1863 | 1322 | 1,41 | 0,34 | 1,04E-03 | 5,21E-03 | 0,67 | 6,99E-04 | 3,81E-03 |
| 70 | hsa-miR-744 | 617 | 952 | 0,65 | -0,43 | 1,07E-03 | 5,28E-03 | 0,27 | 7,57E-05 | 6,53E-04 |
| 22 | hsa-miR-93 | 3708 | 2868 | 1,29 | 0,26 | 1,07E-03 | 5,29E-03 | 0,67 | 3,62E-03 | 2,26E-03 |
| 874 | hsa-miR-106b | 11844 | 8961 | 1,32 | 0,28 | 1,18E-03 | 5,77E-03 | 0,65 | 1,33E-03 | 6,10E-03 |
| 741 | hsa-miR-1322 | 90 | 60 | 1,50 | 0,41 | 1,22E-03 | 5,92E-03 | 0,67 | 7,75E-03 | 2,45E-02 |
| 439 | hsa-miR-346 | 60 | 74 | 0,81 | -0,21 | 1,26E-03 | 6,09E-03 | 0,34 | 3,29E-02 | 7,80E-02 |
| 693 | hsa-miR-151-3p | 573 | 698 | 0,82 | -0,20 | 1,30E-03 | 6,25E-03 | 0,32 | 1,15E-03 | 5,42E-03 |
| 371 | hsa-miR-449b | 33 | 43 | 0,76 | -0,28 | 1,34E-03 | 6,43E-03 | 0,35 | 2,94E-03 | 1,16E-02 |
| 58 | hsa-miR-769-3p | 8 | 42 | 0,20 | -1,63 | 1,44E-03 | 6,85E-03 | 0,31 | 1,34E-03 | 6,10E-03 |
| 738 | hsa-miR-133a | 50 | 76 | 0,66 | -0,42 | 1,55E-03 | 7,36E-03 | 0,34 | 2,67E-03 | 1,08E-02 |
| 682 | hsa-miR-15a | 3376 | 3149 | 1,07 | 0,07 | 1,61E-03 | 7,57E-03 | 0,62 | 2,24E-03 | 9,41E-03 |
| 21 | hsa-miR-93* | 1029 | 1427 | 0,72 | -0,33 | 1,65E-03 | 7,67E-03 | 0,29 | 1,88E-04 | 1,38E-03 |
| 260 | hsa-miR-522* | 140 | 93 | 1,51 | 0,41 | 1,64E-03 | 7,67E-03 | 0,70 | 9,24E-05 | 7,81E-04 |
| 253 | hsa-miR-526a | 147 | 73 | 2,02 | 0,70 | 1,68E-03 | 7,74E-03 | 0,71 | 3,46E-05 | 3,50E-04 |
| 49 | hsa-miR-876-5p | 34 | 18 | 1,92 | 0,65 | 1,68E-03 | 7,74E-03 | 0,64 | 2,43E-02 | 6,19E-02 |
| 435 | hsa-miR-34b* | 43 | 24 | 1,78 | 0,58 | 1,74E-03 | 7,98E-03 | 0,67 | 1,34E-03 | 6,10E-03 |
| 827 | hsa-miR-1244 | 1 | 4 | 0,28 | -1,26 | 1,80E-03 | 8,23E-03 | 0,34 | 1,56E-04 | 1,20E-03 |
| 705 | hsa-miR-147 | 33 | 58 | 0,56 | -0,58 | 1,82E-03 | 8,24E-03 | 0,35 | 4,90E-02 | 1,05E-01 |
| 118 | hsa-miR-635 | 108 | 73 | 1,49 | 0,40 | 1,84E-03 | 8,28E-03 | 0,72 | 5,13E-04 | 2,98E-03 |
| 355 | hsa-miR-483-5p | 162 | 240 | 0,67 | -0,39 | 1,87E-03 | 8,38E-03 | 0,30 | 3,02E-04 | 2,00E-03 |
| 793 | hsa-miR-1270 | 23 | 73 | 0,32 | -1,15 | 1,88E-03 | 8,41E-03 | 0,24 | 2,42E-06 | 5,08E-05 |
| 431 | hsa-miR-361-5p | 426 | 678 | 0,63 | -0,46 | 1,91E-03 | 8,46E-03 | 0,30 | 8,55E-02 | 1,63E-01 |
| 116 | hsa-miR-637 | 12 | 43 | 0,29 | -1,24 | 1,91E-03 | 8,46E-03 | 0,33 | 3,37E-03 | 1,29E-02 |
| 879 | hsa-miR-103-as | 145 | 114 | 1,27 | 0,24 | 1,93E-03 | 8,47E-03 | 0,64 | 4,41E-02 | 9,71E-02 |
| 385 | hsa-miR-423-3p | 1062 | 1287 | 0,82 | -0,19 | 2,05E-03 | 8,96E-03 | 0,35 | 4,45E-02 | 9,76E-02 |
| 400 | hsa-miR-379* | 57 | 40 | 1,41 | 0,34 | 2,07E-03 | 9,03E-03 | 0,66 | 2,82E-03 | 6,92E-02 |
| 743 | hsa-miR-132* | 1 | 2 | 0,60 | -0,51 | 2,16E-03 | 9,37E-03 | 0,32 | 2,17E-05 | 2,59E-04 |
| 491 | hsa-miR-302d | 1 | 1 | 1,00 | 0,00 | 2,20E-03 | 9,49E-03 | 0,35 | 2,75E-04 | 1,85E-03 |
| 111 | hsa-miR-642 | 27 | 63 | 0,43 | -0,84 | 2,26E-03 | 9,70E-03 | 0,30 | 9,42E-04 | 4,68E-03 |
| 227 | hsa-miR-548h | 1 | 32 | 0,04 | -3,16 | 2,28E-03 | 9,72E-03 | 0,34 | 2,81E-03 | 1,13E-02 |
| 663 | hsa-miR-1826 | 177 | 153 | 1,16 | 0,15 | 2,37E-03 | 1,00E-02 | 0,64 | 9,20E-03 | 2,79E-02 |
| 852 | hsa-miR-1206 | 58 | 13 | 4,44 | 1,49 | 2,43E-03 | 1,02E-02 | 0,72 | 2,99E-05 | 3,23E-04 |
| 720 | hsa-miR-141* | 84 | 67 | 1,26 | 0,23 | 2,44E-03 | 1,02E-02 | 0,67 | 5,23E-03 | 1,78E-02 |
| 136 | hsa-miR-621 | 354 | 172 | 2,05 | 0,72 | 2,59E-03 | 1,08E-02 | 0,71 | 5,18E-04 | 2,98E-03 |
| 199 | hsa-miR-564 | 158 | 101 | 1,57 | 0,45 | 2,58E-03 | 1,08E-02 | 0,66 | 2,18E-02 | 5,63E-02 |
| 158 | hsa-miR-601 | 1 | 27 | 0,04 | -3,30 | 2,64E-03 | 1,10E-02 | 0,34 | 1,08E-03 | 5,22E-03 |
| 884 | hsa-miR-100* | 73 | 47 | 1,56 | 0,44 | 2,72E-03 | 1,12E-02 | 0,67 | 6,91E-05 | 6,14E-04 |
| 93 | hsa-miR-659 | 79 | 97 | 0,81 | -0,21 | 2,72E-03 | 1,12E-02 | 0,33 | 8,76E-04 | 4,44E-03 |
| 532 | hsa-miR-23a* | 3 | 40 | 0,08 | -2,49 | 2,75E-03 | 1,12E-02 | 0,32 | 4,49E-04 | 2,66E-03 |
| 710 | hsa-miR-1469 | 165 | 230 | 0,72 | -0,33 | 2,78E-03 | 1,13E-02 | 0,30 | 6,17E-03 | 2,01E-02 |
| 501 | hsa-miR-29c* | 1 | 21 | 0,05 | -3,05 | 2,78E-03 | 1,13E-02 | 0,35 | 5,28E-03 | 1,78E-02 |
| 69 | hsa-miR-744* | 39 | 60 | 0,65 | -0,43 | 2,91E-03 | 1,17E-02 | 0,37 | 1,83E-01 | 2,88E-01 |
| 43 | hsa-miR-886-5p | 78 | 115 | 0,68 | -0,38 | 2,93E-03 | 1,18E-02 | 0,32 | 3,31E-01 | 4,60E-01 |
| 632 | hsa-miR-1915 | 594 | 1086 | 0,55 | -0,60 | 3,07E-03 | 1,23E-02 | 0,28 | 2,46E-05 | 2,79E-04 |
| 864 | hsa-miR-1181 | 186 | 231 | 0,81 | -0,21 | 3,09E-03 | 1,23E-02 | 0,31 | 2,05E-03 | 8,83E-03 |
| 838 | hsa-miR-1228* | 1118 | 1676 | 0,67 | -0,40 | 3,10E-03 | 1,23E-02 | 0,31 | 1,12E-03 | 5,33E-03 |
| 859 | hsa-miR-1197 | 39 | 3 | 11,91 | 2,48 | 3,12E-03 | 1,23E-02 | 0,73 | 7,33E-07 | 1,71E-05 |
| 115 | hsa-miR-638 | 314 | 510 | 0,62 | -0,48 | 3,13E-03 | 1,23E-02 | 0,32 | 6,39E-04 | 3,54E-03 |
| 748 | hsa-miR-130a | 1456 | 1118 | 1,30 | 0,26 | 3,14E-03 | 1,23E-02 | 0,67 | 5,62E-03 | 1,87E-02 |
| 652 | hsa-miR-188-3p | 136 | 114 | 1,21 | 0,19 | 3,26E-03 | 1,27E-02 | 0,67 | 3,79E-04 | 2,33E-03 |
| 867 | hsa-miR-1178 | 19 | 52 | 0,37 | -0,98 | 3,37E-03 | 1,30E-02 | 0,33 | 5,23E-03 | 1,78E-02 |
| 442 | hsa-miR-342-3p | 3909 | 4417 | 0,89 | -0,12 | 3,41E-03 | 1,31E-02 | 0,36 | 2,67E-03 | 1,08E-02 |
| 804 | hsa-miR-126* | 1 | 7 | 0,15 | -1,90 | 3,60E-03 | 1,38E-02 | 0,42 | 6,08E-02 | 1,25E-01 |
| 551 | hsa-miR-219-2-3p | 1 | 8 | 0,13 | -2,04 | 3,75E-03 | 1,43E-02 | 0,36 | 1,91E-03 | 8,27E-03 |
| 47 | hsa-miR-877* | 77 | 110 | 0,70 | -0,36 | 3,86E-03 | 1,46E-02 | 0,35 | 3,87E-04 | 2,36E-03 |
| 48 | hsa-miR-877 | 69 | 112 | 0,61 | -0,49 | 3,98E-03 | 1,50E-02 | 0,36 | 5,04E-01 | 6,28E-01 |
| 861 | hsa-miR-1184 | 201 | 127 | 1,59 | 0,46 | 4,00E-03 | 1,51E-02 | 0,68 | 4,31E-04 | 2,60E-03 |
| 325 | hsa-miR-502-3p | 710 | 871 | 0,81 | -0,21 | 4,02E-03 | 1,51E-02 | 0,36 | 4,18E-03 | 1,51E-02 |
| 760 | hsa-miR-1296 | 47 | 66 | 0,71 | -0,34 | 4,13E-03 | 1,54E-02 | 0,32 | 2,58E-03 | 1,05E-02 |
| 832 | hsa-miR-1237 | 89 | 125 | 0,71 | -0,34 | 4,17E-03 | 1,55E-02 | 0,35 | 7,75E-03 | 2,45E-02 |
| 177 | hsa-miR-584 | 96 | 184 | 0,52 | -0,65 | 4,23E-03 | 1,56E-02 | 0,35 | 7,50E-02 | 1,48E-01 |
| 66 | hsa-miR-760 | 39 | 68 | 0,57 | -0,56 | 4,23E-03 | 1,56E-02 | 0,36 | 3,53E-02 | 8,32E-02 |
| 664 | hsa-miR-1825 | 48 | 72 | 0,67 | -0,40 | 4,29E-03 | 1,58E-02 | 0,37 | 3,65E-02 | 8,55E-02 |
| 101 | hsa-miR-652 | 1215 | 1511 | 0,80 | -0,22 | 4,50E-03 | 1,64E-02 | 0,35 | 1,36E-02 | 3,84E-02 |
| 482 | hsa-miR-30c-1* | 35 | 14 | 2,53 | 0,93 | 4,55E-03 | 1,66E-02 | 0,63 | 8,70E-03 | 2,68E-02 |
| 257 | hsa-miR-524-3p | 19 | 40 | 0,46 | -0,77 | 4,58E-03 | 1,66E-02 | 0,37 | 7,86E-02 | 1,54E-01 |

FIG. 5 (Continued)

| 845 | hsa-miR-1224-5p | 31 | 48 | 0,65 | -0,43 | 4,60E-03 | 1,66E-02 | 0,36 | 4,71E-03 | 1,64E-02 |
|---|---|---|---|---|---|---|---|---|---|---|
| 53 | hsa-miR-874 | 161 | 205 | 0,79 | -0,24 | 4,72E-03 | 1,70E-02 | 0,31 | 3,26E-03 | 1,26E-02 |
| 891 | hsa-let-7f-2* | 8 | 18 | 0,46 | -0,77 | 4,75E-03 | 1,70E-02 | 0,44 | 3,12E-01 | 4,39E-01 |
| 406 | hsa-miR-376c | 81 | 111 | 0,73 | -0,31 | 4,98E-03 | 1,77E-02 | 0,37 | 8,95E-02 | 1,68E-01 |
| 176 | hsa-miR-585 | 12 | 42 | 0,29 | -1,24 | 5,97E-03 | 2,12E-02 | 0,38 | 5,11E-02 | 1,09E-01 |
| 35 | hsa-miR-892a | 3 | 6 | 0,46 | -0,77 | 6,02E-03 | 2,13E-02 | 0,42 | 1,11E-01 | 2,02E-01 |
| 152 | hsa-miR-607 | 82 | 63 | 1,30 | 0,27 | 6,04E-03 | 2,13E-02 | 0,69 | 2,14E-04 | 1,50E-03 |
| 505 | hsa-miR-29b | 412 | 358 | 1,15 | 0,14 | 6,13E-03 | 2,15E-02 | 0,64 | 1,31E-02 | 3,76E-02 |
| 275 | hsa-miR-519e | 1 | 1 | 1,00 | 0,00 | 6,57E-03 | 2,29E-02 | 0,42 | 4,27E-02 | 9,49E-02 |
| 41 | hsa-miR-888 | 54 | 74 | 0,73 | -0,31 | 6,61E-03 | 2,30E-02 | 0,36 | 4,45E-03 | 1,58E-02 |
| 321 | hsa-miR-505 | 23 | 52 | 0,45 | -0,79 | 6,82E-03 | 2,34E-02 | 0,30 | 5,73E-04 | 3,25E-03 |
| 196 | hsa-miR-568 | 72 | 40 | 1,80 | 0,59 | 6,79E-03 | 2,34E-02 | 0,66 | 2,71E-02 | 6,73E-02 |
| 159 | hsa-miR-600 | 67 | 41 | 1,64 | 0,50 | 6,80E-03 | 2,34E-02 | 0,64 | 5,79E-02 | 1,21E-01 |
| 292 | hsa-miR-518a-5p | 170 | 126 | 1,35 | 0,30 | 7,00E-03 | 2,39E-02 | 0,69 | 4,76E-03 | 1,65E-02 |
| 250 | hsa-miR-527 | 158 | 114 | 1,39 | 0,33 | 7,13E-03 | 2,43E-02 | 0,65 | 2,79E-01 | 4,00E-01 |
| 225 | hsa-miR-548j | 1 | 1 | 1,00 | 0,00 | 7,25E-03 | 2,46E-02 | 0,41 | 4,24E-02 | 9,45E-02 |
| 238 | hsa-miR-548a-3p | 77 | 49 | 1,57 | 0,45 | 7,53E-03 | 2,55E-02 | 0,64 | 2,67E-01 | 3,87E-01 |
| 904 | hsa-let-7a | 1335 | 910 | 1,47 | 0,38 | 7,63E-03 | 2,57E-02 | 0,61 | 1,08E-02 | 3,22E-02 |
| 668 | hsa-miR-181c* | 66 | 89 | 0,74 | -0,30 | 7,72E-03 | 2,59E-02 | 0,36 | 1,07E-02 | 3,19E-02 |
| 820 | hsa-miR-1251 | 128 | 95 | 1,35 | 0,30 | 7,88E-03 | 2,62E-02 | 0,67 | 3,98E-03 | 1,46E-02 |
| 347 | hsa-miR-488 | 1 | 13 | 0,08 | -2,57 | 7,88E-03 | 2,62E-02 | 0,35 | 2,48E-03 | 1,02E-02 |
| 643 | hsa-miR-1909* | 31 | 50 | 0,62 | -0,48 | 7,97E-03 | 2,64E-02 | 0,35 | 6,08E-02 | 1,25E-01 |
| 87 | hsa-miR-664 | 240 | 370 | 0,65 | -0,43 | 8,16E-03 | 2,69E-02 | 0,36 | 5,91E-02 | 1,22E-01 |
| 525 | hsa-miR-25* | 62 | 72 | 0,85 | -0,16 | 8,41E-03 | 2,76E-02 | 0,37 | 4,81E-01 | 6,07E-01 |
| 603 | hsa-miR-199b-5p | 12 | 35 | 0,33 | -1,10 | 8,42E-03 | 2,76E-02 | 0,37 | 2,25E-02 | 5,78E-02 |
| 516 | hsa-miR-27b* | 71 | 52 | 1,38 | 0,32 | 8,54E-03 | 2,79E-02 | 0,67 | 9,97E-04 | 4,91E-03 |
| 354 | hsa-miR-484 | 6753 | 7956 | 0,85 | -0,16 | 8,65E-03 | 2,81E-02 | 0,34 | 8,11E-03 | 2,54E-02 |
| 507 | hsa-miR-29a | 714 | 579 | 1,23 | 0,21 | 8,73E-03 | 2,83E-02 | 0,65 | 3,44E-03 | 1,30E-02 |
| 646 | hsa-miR-190 | 1 | 16 | 0,06 | -2,77 | 8,93E-03 | 2,87E-02 | 0,36 | 3,22E-03 | 1,26E-02 |
| 192 | hsa-miR-572 | 63 | 73 | 0,87 | -0,14 | 8,91E-03 | 2,87E-02 | 0,37 | 1,15E-02 | 3,37E-02 |
| 90 | hsa-miR-662 | 48 | 75 | 0,65 | -0,44 | 9,29E-03 | 2,98E-02 | 0,35 | 1,80E-02 | 4,85E-02 |
| 578 | hsa-miR-20a* | 152 | 88 | 1,72 | 0,54 | 9,39E-03 | 2,98E-02 | 0,73 | 1,13E-03 | 5,38E-03 |
| 833 | hsa-miR-1236 | 13 | 47 | 0,28 | -1,26 | 9,41E-03 | 2,98E-02 | 0,33 | 3,23E-03 | 1,26E-02 |
| 824 | hsa-miR-1247 | 67 | 99 | 0,68 | -0,39 | 9,44E-03 | 2,98E-02 | 0,34 | 1,71E-01 | 2,73E-01 |
| 604 | hsa-miR-199b-3p | 112 | 70 | 1,59 | 0,46 | 9,39E-03 | 2,98E-02 | 0,65 | 6,92E-03 | 2,22E-02 |
| 648 | hsa-miR-18b | 221 | 192 | 1,15 | 0,14 | 9,54E-03 | 3,00E-02 | 0,61 | 5,86E-03 | 1,84E-02 |
| 100 | hsa-miR-653 | 33 | 50 | 0,66 | -0,41 | 9,75E-03 | 3,06E-02 | 0,36 | 1,53E-03 | 6,78E-03 |
| 59 | hsa-miR-767-5p | 170 | 113 | 1,50 | 0,41 | 1,02E-02 | 3,19E-02 | 0,70 | 1,85E-04 | 1,38E-03 |
| 94 | hsa-miR-658 | 39 | 62 | 0,63 | -0,46 | 1,02E-02 | 3,19E-02 | 0,36 | 1,82E-02 | 4,88E-02 |
| 239 | hsa-miR-545* | 24 | 1 | 23,71 | 3,17 | 1,04E-02 | 3,23E-02 | 0,69 | 4,19E-06 | 7,38E-05 |
| 212 | hsa-miR-551b* | 35 | 41 | 0,85 | -0,16 | 1,08E-02 | 3,33E-02 | 0,41 | 2,36E-01 | 3,52E-01 |
| 778 | hsa-miR-1281 | 77 | 122 | 0,64 | -0,45 | 1,09E-02 | 3,36E-02 | 0,36 | 8,55E-02 | 1,63E-01 |
| 858 | hsa-miR-1200 | 88 | 56 | 1,57 | 0,45 | 1,10E-02 | 3,38E-02 | 0,66 | 3,96E-04 | 2,41E-03 |
| 134 | hsa-miR-623 | 57 | 73 | 0,77 | -0,26 | 1,11E-02 | 3,39E-02 | 0,34 | 3,03E-02 | 7,37E-02 |
| 560 | hsa-miR-214* | 61 | 52 | 1,17 | 0,16 | 1,12E-02 | 3,39E-02 | 0,63 | 1,36E-02 | 3,84E-02 |
| 228 | hsa-miR-548g | 31 | 50 | 0,63 | -0,47 | 1,11E-02 | 3,39E-02 | 0,41 | 6,52E-02 | 1,31E-01 |
| 373 | hsa-miR-448 | 98 | 71 | 1,38 | 0,32 | 1,15E-02 | 3,49E-02 | 0,64 | 2,07E-01 | 3,20E-01 |
| 31 | hsa-miR-920 | 26 | 39 | 0,67 | -0,40 | 1,16E-02 | 3,50E-02 | 0,37 | 2,05E-02 | 5,40E-02 |
| 688 | hsa-miR-1538 | 81 | 104 | 0,78 | -0,25 | 1,17E-02 | 3,53E-02 | 0,42 | 1,82E-01 | 2,88E-01 |
| 853 | hsa-miR-1205 | 75 | 56 | 1,35 | 0,30 | 1,19E-02 | 3,56E-02 | 0,62 | 6,16E-02 | 1,26E-01 |
| 481 | hsa-miR-30c-2* | 25 | 54 | 0,45 | -0,79 | 1,20E-02 | 3,57E-02 | 0,36 | 1,55E-02 | 4,25E-02 |
| 825 | hsa-miR-1246 | 1 | 14 | 0,07 | -2,61 | 1,26E-02 | 3,73E-02 | 0,34 | 9,45E-04 | 4,68E-03 |
| 780 | hsa-miR-128 | 596 | 474 | 1,26 | 0,23 | 1,26E-02 | 3,75E-02 | 0,64 | 1,40E-03 | 6,29E-03 |
| 186 | hsa-miR-576-5p | 1 | 1 | 1,00 | 0,00 | 1,27E-02 | 3,75E-02 | 0,44 | 6,41E-02 | 1,30E-01 |
| 327 | hsa-miR-501-3p | 334 | 416 | 0,80 | -0,22 | 1,28E-02 | 3,77E-02 | 0,34 | 3,07E-03 | 1,22E-02 |
| 456 | hsa-miR-335 | 463 | 369 | 1,25 | 0,23 | 1,29E-02 | 3,78E-02 | 0,64 | 4,43E-03 | 1,58E-02 |
| 894 | hsa-let-7e* | 3 | 20 | 0,16 | -1,86 | 1,31E-02 | 3,82E-02 | 0,38 | 3,91E-02 | 8,90E-02 |
| 510 | hsa-miR-298 | 121 | 103 | 1,17 | 0,16 | 1,31E-02 | 3,83E-02 | 0,58 | 6,95E-01 | 7,86E-01 |
| 508 | hsa-miR-299-5p | 23 | 47 | 0,50 | -0,70 | 1,33E-02 | 3,87E-02 | 0,31 | 8,06E-04 | 4,20E-03 |
| 504 | hsa-miR-29b-1* | 1 | 11 | 0,09 | -2,39 | 1,36E-02 | 3,91E-02 | 0,35 | 1,50E-03 | 6,67E-03 |
| 784 | hsa-miR-1276 | 37 | 54 | 0,69 | -0,37 | 1,35E-02 | 3,91E-02 | 0,38 | 1,27E-01 | 2,22E-01 |
| 68 | hsa-miR-758 | 15 | 47 | 0,32 | -1,15 | 1,37E-02 | 3,93E-02 | 0,34 | 1,08E-03 | 5,14E-03 |
| 783 | hsa-miR-1277 | 58 | 38 | 1,54 | 0,43 | 1,37E-02 | 3,93E-02 | 0,64 | 3,45E-04 | 2,19E-03 |
| 761 | hsa-miR-129-5p | 21 | 34 | 0,62 | -0,48 | 1,39E-02 | 3,96E-02 | 0,40 | 1,28E-01 | 2,22E-01 |
| 733 | hsa-miR-135b | 1 | 11 | 0,09 | -2,39 | 1,41E-02 | 4,00E-02 | 0,36 | 3,40E-03 | 1,29E-02 |
| 210 | hsa-miR-553 | 1 | 1 | 1,14 | 0,13 | 1,41E-02 | 4,00E-02 | 0,44 | 2,10E-01 | 3,23E-01 |
| 409 | hsa-miR-376a | 92 | 65 | 1,40 | 0,34 | 1,42E-02 | 4,01E-02 | 0,64 | 2,58E-03 | 1,05E-02 |
| 520 | hsa-miR-26b* | 3 | 14 | 0,20 | -1,63 | 1,44E-02 | 4,05E-02 | 0,38 | 2,77E-02 | 6,85E-02 |
| 405 | hsa-miR-377 | 118 | 89 | 1,32 | 0,28 | 1,49E-02 | 4,19E-02 | 0,65 | 2,05E-02 | 5,39E-02 |
| 80 | hsa-miR-675 | 156 | 197 | 0,79 | -0,23 | 1,51E-02 | 4,24E-02 | 0,37 | 1,12E-02 | 3,31E-02 |
| 124 | hsa-miR-629* | 96 | 126 | 0,76 | -0,27 | 1,52E-02 | 4,24E-02 | 0,37 | 3,74E-01 | 5,05E-01 |
| 259 | hsa-miR-523 | 90 | 54 | 1,65 | 0,50 | 1,55E-02 | 4,30E-02 | 0,69 | 9,36E-02 | 1,74E-01 |
| 822 | hsa-miR-1249 | 75 | 130 | 0,57 | -0,56 | 1,57E-02 | 4,35E-02 | 0,35 | 1,40E-02 | 3,93E-02 |
| 57 | hsa-miR-769-5p | 13 | 20 | 0,64 | -0,44 | 1,60E-02 | 4,43E-02 | 0,38 | 6,33E-03 | 2,05E-02 |
| 296 | hsa-miR-517a | 24 | 13 | 1,90 | 0,64 | 1,62E-02 | 4,45E-02 | 0,61 | 1,17E-01 | 2,09E-01 |
| 178 | hsa-miR-583 | 37 | 50 | 0,74 | -0,30 | 1,64E-02 | 4,50E-02 | 0,41 | 2,18E-01 | 3,33E-01 |
| 485 | hsa-miR-30b | 7334 | 6418 | 1,14 | 0,13 | 1,65E-02 | 4,51E-02 | 0,60 | 1,17E-01 | 2,09E-01 |
| 548 | hsa-miR-22* | 45 | 86 | 0,52 | -0,65 | 1,72E-02 | 4,69E-02 | 0,36 | 1,42E-02 | 3,96E-02 |
| 756 | hsa-miR-1301 | 206 | 173 | 1,19 | 0,17 | 1,74E-02 | 4,74E-02 | 0,65 | 1,05E-02 | 3,15E-02 |
| 38 | hsa-miR-890 | 22 | 39 | 0,55 | -0,59 | 1,78E-02 | 4,82E-02 | 0,39 | 3,17E-02 | 7,57E-02 |
| 492 | hsa-miR-302c* | 13 | 22 | 0,60 | -0,52 | 1,79E-02 | 4,82E-02 | 0,42 | 3,08E-01 | 4,34E-01 |
| 524 | hsa-miR-26a | 7334 | 6753 | 1,09 | 0,08 | 1,80E-02 | 4,85E-02 | 0,62 | 2,66E-02 | 6,65E-02 |

FIG. 5 (Continued)

| 458 | hsa-miR-331-3p | 860 | 1118 | 0,77 | -0,26 | 1,83E-02 | 4,91E-02 | 0,38 | 3,35E-01 | 4,63E-01 |
| 659 | hsa-miR-184 | 21 | 30 | 0,68 | -0,38 | 1,84E-02 | 4,92E-02 | 0,37 | 1,29E-02 | 3,71E-02 |

Figure 6

| Signature | miRNA-identifiers | Acc | Spec | Sens |
|---|---|---|---|---|
| SNP-1 | hsa-miR-144*, hsa-miR-148a | 87,0% | 87,8% | 86,2% |
| SNP-2 | hsa-miR-148a, hsa-miR-20b | 86,8% | 89,0% | 84,5% |
| SNP-3 | hsa-miR-20b, hsa-miR-891b | 83,1% | 85,0% | 81,2% |
| SNP-4 | hsa-miR-891b, hsa-miR-144 | 83,1% | 86,1% | 80,2% |
| SNP-5 | hsa-miR-144, hsa-miR-148b | 72,0% | 66,6% | 77,3% |
| SNP-6 | hsa-miR-148b, hsa-miR-301a | 78,4% | 74,4% | 82,5% |
| SNP-7 | hsa-miR-301a, hsa-miR-33a | 81,7% | 80,2% | 83,3% |
| SNP-8 | hsa-miR-33a, hsa-miR-20a | 81,8% | 77,0% | 86,5% |
| SNP-9 | hsa-miR-20a, hsa-miR-423-5p | 82,0% | 87,0% | 76,9% |
| SNP-10 | hsa-miR-423-5p, hsa-miR-556-5p | 78,9% | 83,2% | 74,6% |
| SNP-11 | hsa-miR-556-5p, hsa-miR-374b | 81,7% | 88,2% | 75,3% |
| SNP-12 | hsa-miR-374b, hsa-miR-101 | 72,6% | 73,8% | 71,5% |
| SNP-13 | hsa-miR-101, hsa-miR-455-3p | 80,0% | 86,7% | 73,4% |
| SNP-14 | hsa-miR-455-3p, hsa-miR-1245 | 75,3% | 80,8% | 69,8% |
| SNP-15 | hsa-miR-1245, hsa-miR-374a | 81,1% | 80,8% | 81,4% |
| SNP-16 | hsa-miR-374a, hsa-miR-1283 | 80,9% | 85,8% | 76,1% |
| SNP-17 | hsa-miR-1283, hsa-miR-15b | 77,1% | 85,7% | 68,6% |
| SNP-18 | hsa-miR-15b, hsa-miR-33b | 77,9% | 73,7% | 82,1% |
| SNP-19 | hsa-miR-33b, hsa-miR-363 | 78,2% | 81,4% | 75,0% |
| SNP-20 | hsa-miR-363, hsa-miR-320a | 72,3% | 86,2% | 58,5% |
| SNP-21 | hsa-miR-320a, hsa-miR-1226 | 75,0% | 76,2% | 73,8% |
| SNP-22 | hsa-miR-1226, hsa-miR-21* | 75,4% | 70,9% | 79,9% |
| SNP-23 | hsa-miR-21*, hsa-miR-574-3p | 80,7% | 89,3% | 72,1% |
| SNP-24 | hsa-miR-574-3p, hsa-miR-21 | 72,7% | 77,6% | 67,8% |
| SNP-25 | hsa-miR-21, hsa-miR-191 | 76,5% | 73,1% | 79,9% |
| SNP-26 | hsa-miR-191, hsa-miR-380* | 75,6% | 74,3% | 77,0% |
| SNP-27 | hsa-miR-380*, hsa-miR-517* | 70,6% | 68,6% | 72,6% |
| SNP-28 | hsa-miR-144*, hsa-miR-20b | 82,9% | 74,7% | 91,1% |
| SNP-29 | hsa-miR-148a, hsa-miR-891b | 83,3% | 83,9% | 82,6% |
| SNP-30 | hsa-miR-20b, hsa-miR-144 | 77,0% | 73,4% | 80,6% |
| SNP-31 | hsa-miR-891b, hsa-miR-148b | 79,4% | 82,7% | 76,2% |
| SNP-32 | hsa-miR-144, hsa-miR-301a | 76,4% | 66,3% | 86,5% |
| SNP-33 | hsa-miR-148b, hsa-miR-33a | 79,0% | 76,0% | 81,9% |
| SNP-34 | hsa-miR-301a, hsa-miR-20a | 75,3% | 63,9% | 86,6% |
| SNP-35 | hsa-miR-33a, hsa-miR-423-5p | 83,1% | 87,2% | 79,0% |
| SNP-36 | hsa-miR-20a, hsa-miR-556-5p | 77,4% | 72,6% | 82,2% |
| SNP-37 | hsa-miR-423-5p, hsa-miR-374b | 79,8% | 87,6% | 72,0% |
| SNP-38 | hsa-miR-556-5p, hsa-miR-101 | 78,0% | 75,0% | 81,0% |
| SNP-39 | hsa-miR-374b, hsa-miR-455-3p | 84,4% | 89,7% | 79,0% |
| SNP-40 | hsa-miR-101, hsa-miR-1245 | 78,9% | 77,7% | 80,1% |
| SNP-41 | hsa-miR-455-3p, hsa-miR-374a | 85,1% | 87,3% | 83,0% |
| SNP-42 | hsa-miR-1245, hsa-miR-1283 | 77,7% | 81,7% | 73,8% |
| SNP-43 | hsa-miR-374a, hsa-miR-15b | 81,0% | 81,6% | 80,3% |
| SNP-44 | hsa-miR-1283, hsa-miR-33b | 80,4% | 80,8% | 80,1% |
| SNP-45 | hsa-miR-15b, hsa-miR-363 | 78,4% | 79,7% | 77,1% |
| SNP-46 | hsa-miR-33b, hsa-miR-320a | 74,6% | 77,4% | 71,7% |
| SNP-47 | hsa-miR-363, hsa-miR-1226 | 74,0% | 71,8% | 76,2% |
| SNP-48 | hsa-miR-320a, hsa-miR-21* | 77,8% | 85,4% | 70,2% |
| SNP-49 | hsa-miR-1226, hsa-miR-574-3p | 70,6% | 69,2% | 72,0% |
| SNP-50 | hsa-miR-21*, hsa-miR-21 | 78,0% | 76,9% | 79,2% |
| SNP-51 | hsa-miR-574-3p, hsa-miR-191 | 79,0% | 87,4% | 70,6% |

FIG. 6 (Continued)

| SNP-52 | hsa-miR-21, hsa-miR-380* | 78,6% | 74,5% | 82,7% |
|---|---|---|---|---|
| SNP-53 | hsa-miR-191, hsa-miR-517* | 73,8% | 72,3% | 75,4% |
| SNP-54 | hsa-miR-144*, hsa-miR-891b | 86,0% | 84,3% | 87,8% |
| SNP-55 | hsa-miR-148a, hsa-miR-144 | 83,7% | 82,4% | 85,0% |
| SNP-56 | hsa-miR-20b, hsa-miR-148b | 78,9% | 76,4% | 81,4% |
| SNP-57 | hsa-miR-891b, hsa-miR-301a | 84,7% | 87,4% | 82,0% |
| SNP-58 | hsa-miR-144, hsa-miR-33a | 81,2% | 77,5% | 84,8% |
| SNP-59 | hsa-miR-148b, hsa-miR-20a | 74,8% | 70,1% | 79,5% |
| SNP-60 | hsa-miR-301a, hsa-miR-423-5p | 83,3% | 86,7% | 79,8% |
| SNP-61 | hsa-miR-33a, hsa-miR-556-5p | 79,8% | 75,2% | 84,4% |
| SNP-62 | hsa-miR-20a, hsa-miR-374b | 76,3% | 71,2% | 81,4% |
| SNP-63 | hsa-miR-423-5p, hsa-miR-101 | 79,4% | 85,4% | 73,5% |
| SNP-64 | hsa-miR-556-5p, hsa-miR-455-3p | 77,7% | 78,8% | 76,6% |
| SNP-65 | hsa-miR-374b, hsa-miR-1245 | 82,4% | 84,2% | 80,6% |
| SNP-66 | hsa-miR-101, hsa-miR-374a | 71,8% | 71,9% | 71,6% |
| SNP-67 | hsa-miR-455-3p, hsa-miR-1283 | 79,8% | 82,4% | 77,1% |
| SNP-68 | hsa-miR-1245, hsa-miR-15b | 76,5% | 80,9% | 72,2% |
| SNP-69 | hsa-miR-374a, hsa-miR-33b | 81,5% | 76,6% | 86,3% |
| SNP-70 | hsa-miR-1283, hsa-miR-363 | 80,5% | 91,3% | 69,7% |
| SNP-71 | hsa-miR-15b, hsa-miR-320a | 70,5% | 79,8% | 61,1% |
| SNP-72 | hsa-miR-33b, hsa-miR-1226 | 77,5% | 65,0% | 90,0% |
| SNP-73 | hsa-miR-363, hsa-miR-21* | 79,0% | 85,4% | 72,6% |
| SNP-74 | hsa-miR-320a, hsa-miR-574-3p | 70,7% | 81,5% | 59,9% |
| SNP-75 | hsa-miR-1226, hsa-miR-21 | 76,1% | 69,6% | 82,6% |
| SNP-76 | hsa-miR-21*, hsa-miR-191 | 78,4% | 77,3% | 79,4% |
| SNP-77 | hsa-miR-574-3p, hsa-miR-380* | 73,8% | 81,3% | 66,4% |
| SNP-78 | hsa-miR-21, hsa-miR-517* | 81,8% | 80,5% | 83,1% |
| SNP-79 | hsa-miR-144*, hsa-miR-148a, hsa-miR-20b | 87,8% | 88,8% | 86,7% |
| SNP-80 | hsa-miR-148a, hsa-miR-20b, hsa-miR-891b | 90,0% | 90,2% | 89,8% |
| SNP-81 | hsa-miR-20b, hsa-miR-891b, hsa-miR-144 | 86,3% | 87,4% | 85,2% |
| SNP-82 | hsa-miR-891b, hsa-miR-144, hsa-miR-148b | 82,8% | 84,4% | 81,2% |
| SNP-83 | hsa-miR-144, hsa-miR-148b, hsa-miR-301a | 75,1% | 68,2% | 82,1% |
| SNP-84 | hsa-miR-148b, hsa-miR-301a, hsa-miR-33a | 82,6% | 83,6% | 81,7% |
| SNP-85 | hsa-miR-301a, hsa-miR-33a, hsa-miR-20a | 80,8% | 79,7% | 82,0% |
| SNP-86 | hsa-miR-33a, hsa-miR-20a, hsa-miR-423-5p | 84,3% | 86,2% | 82,5% |
| SNP-87 | hsa-miR-20a, hsa-miR-423-5p, hsa-miR-556-5p | 82,8% | 86,3% | 79,3% |
| SNP-88 | hsa-miR-423-5p, hsa-miR-556-5p, hsa-miR-374b | 82,3% | 86,6% | 78,0% |
| SNP-89 | hsa-miR-556-5p, hsa-miR-374b, hsa-miR-101 | 82,8% | 84,1% | 81,5% |
| SNP-90 | hsa-miR-374b, hsa-miR-101, hsa-miR-455-3p | 84,7% | 87,5% | 81,8% |
| SNP-91 | hsa-miR-101, hsa-miR-455-3p, hsa-miR-1245 | 84,3% | 86,0% | 82,6% |
| SNP-92 | hsa-miR-455-3p, hsa-miR-1245, hsa-miR-374a | 80,6% | 83,4% | 77,9% |
| SNP-93 | hsa-miR-1245, hsa-miR-374a, hsa-miR-1283 | 79,6% | 81,7% | 77,6% |
| SNP-94 | hsa-miR-374a, hsa-miR-1283, hsa-miR-15b | 80,9% | 85,4% | 76,4% |
| SNP-95 | hsa-miR-1283, hsa-miR-15b, hsa-miR-33b | 82,8% | 87,1% | 78,4% |
| SNP-96 | hsa-miR-15b, hsa-miR-33b, hsa-miR-363 | 78,5% | 79,8% | 77,2% |
| SNP-97 | hsa-miR-33b, hsa-miR-363, hsa-miR-320a | 74,8% | 80,4% | 69,3% |
| SNP-98 | hsa-miR-363, hsa-miR-320a, hsa-miR-1226 | 74,2% | 75,4% | 73,0% |
| SNP-99 | hsa-miR-320a, hsa-miR-1226, hsa-miR-21* | 76,7% | 74,5% | 79,0% |
| SNP-100 | hsa-miR-1226, hsa-miR-21*, hsa-miR-574-3p | 77,6% | 76,2% | 79,0% |
| SNP-101 | hsa-miR-21*, hsa-miR-574-3p, hsa-miR-21 | 81,4% | 89,5% | 73,3% |
| SNP-102 | hsa-miR-574-3p, hsa-miR-21, hsa-miR-191 | 78,8% | 85,5% | 72,2% |
| SNP-103 | hsa-miR-21, hsa-miR-191, hsa-miR-380* | 80,4% | 80,8% | 79,9% |
| SNP-104 | hsa-miR-191, hsa-miR-380*, hsa-miR-517* | 76,4% | 72,4% | 80,4% |
| SNP-105 | hsa-miR-144*, hsa-miR-148a, hsa-miR-891b | 89,8% | 86,8% | 92,8% |

FIG. 6 (Continued)

| SNP-106 | hsa-miR-148a, hsa-miR-20b, hsa-miR-144 | 86,0% | 86,8% | 85,3% |
|---|---|---|---|---|
| SNP-107 | hsa-miR-20b, hsa-miR-891b, hsa-miR-148b | 84,3% | 86,1% | 82,6% |
| SNP-108 | hsa-miR-891b, hsa-miR-144, hsa-miR-301a | 84,6% | 87,0% | 82,2% |
| SNP-109 | hsa-miR-144, hsa-miR-148b, hsa-miR-33a | 79,4% | 77,7% | 81,1% |
| SNP-110 | hsa-miR-148b, hsa-miR-301a, hsa-miR-20a | 76,2% | 70,6% | 81,8% |
| SNP-111 | hsa-miR-301a, hsa-miR-33a, hsa-miR-423-5p | 84,1% | 85,6% | 82,6% |
| SNP-112 | hsa-miR-33a, hsa-miR-20a, hsa-miR-556-5p | 81,0% | 78,3% | 83,7% |
| SNP-113 | hsa-miR-20a, hsa-miR-423-5p, hsa-miR-374b | 82,0% | 85,1% | 78,8% |
| SNP-114 | hsa-miR-423-5p, hsa-miR-556-5p, hsa-miR-101 | 82,4% | 83,3% | 81,4% |
| SNP-115 | hsa-miR-556-5p, hsa-miR-374b, hsa-miR-455-3p | 84,1% | 88,5% | 79,7% |
| SNP-116 | hsa-miR-374b, hsa-miR-101, hsa-miR-1245 | 81,9% | 82,6% | 81,2% |
| SNP-117 | hsa-miR-101, hsa-miR-455-3p, hsa-miR-374a | 84,0% | 87,8% | 80,2% |
| SNP-118 | hsa-miR-455-3p, hsa-miR-1245, hsa-miR-1283 | 79,5% | 84,8% | 74,2% |
| SNP-119 | hsa-miR-1245, hsa-miR-374a, hsa-miR-15b | 80,4% | 81,1% | 79,6% |
| SNP-120 | hsa-miR-374a, hsa-miR-1283, hsa-miR-33b | 83,2% | 83,5% | 83,0% |
| SNP-121 | hsa-miR-1283, hsa-miR-15b, hsa-miR-363 | 80,1% | 91,0% | 69,2% |
| SNP-122 | hsa-miR-15b, hsa-miR-33b, hsa-miR-320a | 74,8% | 78,3% | 71,2% |
| SNP-123 | hsa-miR-33b, hsa-miR-363, hsa-miR-1226 | 77,8% | 76,1% | 79,6% |
| SNP-124 | hsa-miR-363, hsa-miR-320a, hsa-miR-21* | 79,2% | 83,8% | 74,6% |
| SNP-125 | hsa-miR-320a, hsa-miR-1226, hsa-miR-574-3p | 72,2% | 74,3% | 70,1% |
| SNP-126 | hsa-miR-1226, hsa-miR-21*, hsa-miR-21 | 80,6% | 81,1% | 80,2% |
| SNP-127 | hsa-miR-21*, hsa-miR-574-3p, hsa-miR-191 | 82,9% | 90,0% | 75,8% |
| SNP-128 | hsa-miR-574-3p, hsa-miR-21, hsa-miR-380* | 75,5% | 76,9% | 74,2% |
| SNP-129 | hsa-miR-21, hsa-miR-191, hsa-miR-517* | 82,6% | 80,9% | 84,4% |
| SNP-130 | hsa-miR-144*, hsa-miR-20b, hsa-miR-891b | 87,8% | 85,8% | 89,8% |
| SNP-131 | hsa-miR-148a, hsa-miR-891b, hsa-miR-144 | 85,5% | 83,0% | 87,9% |
| SNP-132 | hsa-miR-20b, hsa-miR-144, hsa-miR-148b | 79,5% | 73,5% | 85,5% |
| SNP-133 | hsa-miR-891b, hsa-miR-148b, hsa-miR-301a | 83,6% | 86,7% | 80,4% |
| SNP-134 | hsa-miR-144, hsa-miR-301a, hsa-miR-33a | 79,8% | 77,8% | 81,8% |
| SNP-135 | hsa-miR-148b, hsa-miR-33a, hsa-miR-20a | 80,7% | 77,8% | 83,5% |
| SNP-136 | hsa-miR-301a, hsa-miR-20a, hsa-miR-423-5p | 83,1% | 86,5% | 79,8% |
| SNP-137 | hsa-miR-33a, hsa-miR-423-5p, hsa-miR-556-5p | 83,6% | 84,9% | 82,3% |
| SNP-138 | hsa-miR-20a, hsa-miR-556-5p, hsa-miR-374b | 81,7% | 82,9% | 80,5% |
| SNP-139 | hsa-miR-423-5p, hsa-miR-374b, hsa-miR-101 | 78,4% | 83,5% | 73,2% |
| SNP-140 | hsa-miR-556-5p, hsa-miR-101, hsa-miR-455-3p | 82,9% | 87,4% | 78,5% |
| SNP-141 | hsa-miR-374b, hsa-miR-455-3p, hsa-miR-1245 | 86,8% | 93,3% | 80,2% |
| SNP-142 | hsa-miR-101, hsa-miR-1245, hsa-miR-374a | 81,6% | 82,4% | 80,7% |
| SNP-143 | hsa-miR-455-3p, hsa-miR-374a, hsa-miR-1283 | 83,9% | 85,5% | 82,2% |
| SNP-144 | hsa-miR-1245, hsa-miR-1283, hsa-miR-15b | 81,9% | 87,5% | 76,3% |
| SNP-145 | hsa-miR-374a, hsa-miR-15b, hsa-miR-33b | 82,4% | 81,6% | 83,2% |
| SNP-146 | hsa-miR-1283, hsa-miR-33b, hsa-miR-363 | 83,1% | 89,0% | 77,1% |
| SNP-147 | hsa-miR-15b, hsa-miR-363, hsa-miR-320a | 74,0% | 84,7% | 63,4% |
| SNP-148 | hsa-miR-33b, hsa-miR-320a, hsa-miR-1226 | 74,2% | 70,2% | 78,2% |
| SNP-149 | hsa-miR-363, hsa-miR-1226, hsa-miR-21* | 78,7% | 81,6% | 75,8% |
| SNP-150 | hsa-miR-320a, hsa-miR-21*, hsa-miR-574-3p | 81,8% | 90,8% | 72,9% |
| SNP-151 | hsa-miR-1226, hsa-miR-574-3p, hsa-miR-21 | 76,2% | 72,2% | 80,2% |
| SNP-152 | hsa-miR-21*, hsa-miR-21, hsa-miR-191 | 83,4% | 82,8% | 84,1% |
| SNP-153 | hsa-miR-574-3p, hsa-miR-191, hsa-miR-380* | 78,2% | 83,7% | 72,8% |
| SNP-154 | hsa-miR-21, hsa-miR-380*, hsa-miR-517* | 81,3% | 79,7% | 83,0% |
| SNP-155 | hsa-miR-144*, hsa-miR-20b, hsa-miR-144 | 84,9% | 77,9% | 91,8% |
| SNP-156 | hsa-miR-148a, hsa-miR-891b, hsa-miR-148b | 82,8% | 85,8% | 79,8% |
| SNP-157 | hsa-miR-20b, hsa-miR-144, hsa-miR-301a | 77,6% | 69,7% | 85,4% |
| SNP-158 | hsa-miR-891b, hsa-miR-148b, hsa-miR-33a | 78,7% | 79,4% | 77,9% |
| SNP-159 | hsa-miR-144, hsa-miR-301a, hsa-miR-20a | 76,2% | 65,8% | 86,5% |

FIG. 6 (Continued)

| SNP-160 | hsa-miR-148b, hsa-miR-33a, hsa-miR-423-5p | 83,2% | 88,7% | 77,6% |
|---|---|---|---|---|
| SNP-161 | hsa-miR-301a, hsa-miR-20a, hsa-miR-556-5p | 77,7% | 72,2% | 83,3% |
| SNP-162 | hsa-miR-33a, hsa-miR-423-5p, hsa-miR-374b | 86,4% | 89,7% | 83,0% |
| SNP-163 | hsa-miR-20a, hsa-miR-556-5p, hsa-miR-101 | 78,9% | 75,4% | 82,4% |
| SNP-164 | hsa-miR-423-5p, hsa-miR-374b, hsa-miR-455-3p | 84,1% | 88,2% | 79,9% |
| SNP-165 | hsa-miR-556-5p, hsa-miR-101, hsa-miR-1245 | 80,1% | 76,8% | 83,4% |
| SNP-166 | hsa-miR-374b, hsa-miR-455-3p, hsa-miR-374a | 84,4% | 88,3% | 80,4% |
| SNP-167 | hsa-miR-101, hsa-miR-1245, hsa-miR-1283 | 79,6% | 81,7% | 77,5% |
| SNP-168 | hsa-miR-455-3p, hsa-miR-374a, hsa-miR-15b | 83,4% | 87,8% | 79,1% |
| SNP-169 | hsa-miR-1245, hsa-miR-1283, hsa-miR-33b | 77,6% | 82,1% | 73,0% |
| SNP-170 | hsa-miR-374a, hsa-miR-15b, hsa-miR-363 | 79,4% | 82,1% | 76,6% |
| SNP-171 | hsa-miR-1283, hsa-miR-33b, hsa-miR-320a | 81,4% | 86,7% | 76,0% |
| SNP-172 | hsa-miR-15b, hsa-miR-363, hsa-miR-1226 | 77,6% | 78,7% | 76,5% |
| SNP-173 | hsa-miR-33b, hsa-miR-320a, hsa-miR-21* | 79,2% | 78,2% | 80,1% |
| SNP-174 | hsa-miR-363, hsa-miR-1226, hsa-miR-574-3p | 74,4% | 71,2% | 77,6% |
| SNP-175 | hsa-miR-320a, hsa-miR-21*, hsa-miR-21 | 80,2% | 81,5% | 78,9% |
| SNP-176 | hsa-miR-1226, hsa-miR-574-3p, hsa-miR-191 | 80,0% | 78,3% | 81,8% |
| SNP-177 | hsa-miR-21*, hsa-miR-21, hsa-miR-380* | 81,5% | 83,4% | 79,6% |
| SNP-178 | hsa-miR-574-3p, hsa-miR-191, hsa-miR-517* | 80,2% | 90,0% | 70,4% |
| SNP-179 | hsa-miR-144*, hsa-miR-148a, hsa-miR-144 | 85,9% | 84,5% | 87,3% |
| SNP-180 | hsa-miR-148a, hsa-miR-20b, hsa-miR-148b | 86,5% | 87,9% | 85,1% |
| SNP-181 | hsa-miR-20b, hsa-miR-891b, hsa-miR-301a | 83,3% | 85,4% | 81,2% |
| SNP-182 | hsa-miR-891b, hsa-miR-144, hsa-miR-33a | 83,0% | 87,0% | 79,0% |
| SNP-183 | hsa-miR-144, hsa-miR-148b, hsa-miR-20a | 76,3% | 68,3% | 84,2% |
| SNP-184 | hsa-miR-148b, hsa-miR-301a, hsa-miR-423-5p | 81,7% | 85,9% | 77,5% |
| SNP-185 | hsa-miR-301a, hsa-miR-33a, hsa-miR-556-5p | 79,9% | 78,2% | 81,5% |
| SNP-186 | hsa-miR-33a, hsa-miR-20a, hsa-miR-374b | 85,6% | 88,5% | 82,6% |
| SNP-187 | hsa-miR-20a, hsa-miR-423-5p, hsa-miR-101 | 81,9% | 87,1% | 76,7% |
| SNP-188 | hsa-miR-423-5p, hsa-miR-556-5p, hsa-miR-455-3p | 81,9% | 84,5% | 79,3% |
| SNP-189 | hsa-miR-556-5p, hsa-miR-374b, hsa-miR-1245 | 80,4% | 79,9% | 80,9% |
| SNP-190 | hsa-miR-374b, hsa-miR-101, hsa-miR-374a | 74,1% | 70,5% | 77,8% |
| SNP-191 | hsa-miR-101, hsa-miR-455-3p, hsa-miR-1283 | 83,9% | 87,3% | 80,6% |
| SNP-192 | hsa-miR-455-3p, hsa-miR-1245, hsa-miR-15b | 76,8% | 80,4% | 73,1% |
| SNP-193 | hsa-miR-1245, hsa-miR-374a, hsa-miR-33b | 81,3% | 78,9% | 83,7% |
| SNP-194 | hsa-miR-374a, hsa-miR-1283, hsa-miR-363 | 80,6% | 90,1% | 71,1% |
| SNP-195 | hsa-miR-1283, hsa-miR-15b, hsa-miR-320a | 82,9% | 96,1% | 69,8% |
| SNP-196 | hsa-miR-15b, hsa-miR-33b, hsa-miR-1226 | 78,3% | 72,6% | 84,0% |
| SNP-197 | hsa-miR-33b, hsa-miR-363, hsa-miR-21* | 81,1% | 85,3% | 76,9% |
| SNP-198 | hsa-miR-363, hsa-miR-320a, hsa-miR-574-3p | 74,5% | 82,4% | 66,6% |
| SNP-199 | hsa-miR-320a, hsa-miR-1226, hsa-miR-21 | 75,4% | 72,8% | 77,9% |
| SNP-200 | hsa-miR-1226, hsa-miR-21*, hsa-miR-191 | 79,6% | 77,8% | 81,5% |
| SNP-201 | hsa-miR-21*, hsa-miR-574-3p, hsa-miR-380* | 79,1% | 85,4% | 72,7% |
| SNP-202 | hsa-miR-574-3p, hsa-miR-21, hsa-miR-517* | 78,5% | 85,8% | 71,3% |
| SNP-203 | hsa-miR-144*, hsa-miR-891b, hsa-miR-144 | 85,3% | 83,0% | 87,6% |
| SNP-204 | hsa-miR-148a, hsa-miR-144, hsa-miR-148b | 81,6% | 82,6% | 80,6% |
| SNP-205 | hsa-miR-20b, hsa-miR-148b, hsa-miR-301a | 77,6% | 73,9% | 81,4% |
| SNP-206 | hsa-miR-891b, hsa-miR-301a, hsa-miR-33a | 81,0% | 83,5% | 78,4% |
| SNP-207 | hsa-miR-144, hsa-miR-33a, hsa-miR-20a | 81,2% | 76,4% | 85,9% |
| SNP-208 | hsa-miR-148b, hsa-miR-20a, hsa-miR-423-5p | 82,8% | 88,2% | 77,5% |
| SNP-209 | hsa-miR-301a, hsa-miR-423-5p, hsa-miR-556-5p | 83,0% | 85,7% | 80,4% |
| SNP-210 | hsa-miR-33a, hsa-miR-556-5p, hsa-miR-374b | 86,4% | 89,0% | 83,8% |
| SNP-211 | hsa-miR-20a, hsa-miR-374b, hsa-miR-101 | 76,3% | 70,6% | 82,1% |
| SNP-212 | hsa-miR-423-5p, hsa-miR-101, hsa-miR-455-3p | 88,5% | 89,6% | 87,4% |
| SNP-213 | hsa-miR-556-5p, hsa-miR-455-3p, hsa-miR-1245 | 79,1% | 76,2% | 81,9% |

FIG. 6 (Continued)

| | | | | |
|---|---|---|---|---|
| SNP-214 | hsa-miR-374b, hsa-miR-1245, hsa-miR-374a | 80,0% | 80,2% | 79,7% |
| SNP-215 | hsa-miR-101, hsa-miR-374a, hsa-miR-1283 | 80,6% | 82,0% | 79,2% |
| SNP-216 | hsa-miR-455-3p, hsa-miR-1283, hsa-miR-15b | 82,0% | 88,7% | 75,3% |
| SNP-217 | hsa-miR-1245, hsa-miR-15b, hsa-miR-33b | 78,4% | 79,7% | 77,0% |
| SNP-218 | hsa-miR-374a, hsa-miR-33b, hsa-miR-363 | 79,3% | 77,0% | 81,5% |
| SNP-219 | hsa-miR-1283, hsa-miR-363, hsa-miR-320a | 83,5% | 95,9% | 71,0% |
| SNP-220 | hsa-miR-15b, hsa-miR-320a, hsa-miR-1226 | 73,9% | 75,8% | 72,0% |
| SNP-221 | hsa-miR-33b, hsa-miR-1226, hsa-miR-21* | 78,7% | 69,5% | 87,8% |
| SNP-222 | hsa-miR-363, hsa-miR-21*, hsa-miR-574-3p | 80,6% | 91,4% | 69,9% |
| SNP-223 | hsa-miR-320a, hsa-miR-574-3p, hsa-miR-21 | 71,9% | 78,4% | 65,4% |
| SNP-224 | hsa-miR-1226, hsa-miR-21, hsa-miR-191 | 81,6% | 80,0% | 83,2% |
| SNP-225 | hsa-miR-21*, hsa-miR-191, hsa-miR-380* | 77,6% | 79,0% | 76,2% |
| SNP-226 | hsa-miR-574-3p, hsa-miR-380*, hsa-miR-517* | 75,8% | 82,6% | 69,0% |
| SNP-227 | hsa-miR-144, hsa-miR-20a | 74,1% | 67,3% | 80,9% |
| SNP-228 | hsa-miR-374b, hsa-miR-374a | 76,3% | 69,0% | 83,6% |
| SNP-229 | hsa-miR-374a, hsa-miR-21 | 72,1% | 67,4% | 76,9% |
| SNP-230 | hsa-miR-21, hsa-miR-320b | 69,7% | 72,2% | 67,1% |
| SNP-231 | hsa-miR-320b, hsa-miR-720 | 75,1% | 85,5% | 64,7% |
| SNP-232 | hsa-miR-720, hsa-miR-197 | 70,0% | 75,9% | 64,2% |
| SNP-233 | hsa-miR-197, hsa-miR-621 | 73,5% | 68,6% | 78,4% |
| SNP-234 | hsa-miR-621, hsa-miR-148b | 72,8% | 65,3% | 80,4% |
| SNP-235 | hsa-miR-301a, hsa-miR-101 | 73,6% | 77,7% | 69,5% |
| SNP-236 | hsa-miR-455-3p, hsa-miR-33b | 81,0% | 83,0% | 79,0% |
| SNP-237 | hsa-miR-33b, hsa-miR-15b | 77,0% | 73,4% | 80,6% |
| SNP-238 | hsa-miR-517*, hsa-miR-18a | 70,0% | 62,8% | 77,3% |
| SNP-239 | hsa-miR-18a, hsa-miR-152 | 71,5% | 65,1% | 77,9% |
| SNP-240 | hsa-miR-152, hsa-let-7i* | 76,7% | 70,4% | 83,0% |
| SNP-241 | hsa-let-7i*, hsa-miR-320d | 77,6% | 73,8% | 81,4% |
| SNP-242 | hsa-miR-20b, hsa-miR-20a | 76,1% | 76,4% | 75,8% |
| SNP-243 | hsa-miR-144, hsa-miR-423-5p | 84,3% | 89,3% | 79,4% |
| SNP-244 | hsa-miR-423-5p, hsa-miR-374a | 81,5% | 88,6% | 74,3% |
| SNP-245 | hsa-miR-374b, hsa-miR-21 | 71,2% | 63,6% | 78,8% |
| SNP-246 | hsa-miR-374a, hsa-miR-320b | 72,2% | 75,3% | 69,0% |
| SNP-247 | hsa-miR-21, hsa-miR-720 | 74,8% | 81,0% | 68,6% |
| SNP-248 | hsa-miR-320b, hsa-miR-197 | 72,9% | 74,7% | 71,1% |
| SNP-249 | hsa-miR-720, hsa-miR-621 | 73,0% | 70,2% | 75,8% |
| SNP-250 | hsa-miR-197, hsa-miR-148b | 76,1% | 70,6% | 81,7% |
| SNP-251 | hsa-miR-621, hsa-miR-301a | 73,0% | 63,8% | 82,2% |
| SNP-252 | hsa-miR-148b, hsa-miR-101 | 70,5% | 74,0% | 67,0% |
| SNP-253 | hsa-miR-301a, hsa-miR-455-3p | 80,1% | 77,4% | 82,9% |
| SNP-254 | hsa-miR-101, hsa-miR-33b | 81,5% | 84,0% | 79,0% |
| SNP-255 | hsa-miR-455-3p, hsa-miR-15b | 77,1% | 79,0% | 75,3% |
| SNP-256 | hsa-miR-363, hsa-miR-574-3p | 76,7% | 81,4% | 72,1% |
| SNP-257 | hsa-miR-320a, hsa-miR-191 | 83,0% | 81,8% | 84,2% |
| SNP-258 | hsa-miR-574-3p, hsa-miR-517* | 76,8% | 87,5% | 66,1% |
| SNP-259 | hsa-miR-191, hsa-miR-18a | 71,2% | 71,1% | 71,2% |
| SNP-260 | hsa-miR-517*, hsa-miR-152 | 71,0% | 64,6% | 77,4% |
| SNP-261 | hsa-miR-18a, hsa-let-7i* | 75,9% | 69,1% | 82,6% |
| SNP-262 | hsa-miR-152, hsa-miR-320d | 74,9% | 75,3% | 74,5% |
| SNP-263 | hsa-miR-144*, hsa-miR-144 | 86,0% | 78,4% | 93,6% |
| SNP-264 | hsa-miR-148a, hsa-miR-20a | 86,1% | 87,5% | 84,6% |
| SNP-265 | hsa-miR-20b, hsa-miR-423-5p | 82,6% | 89,4% | 75,8% |
| SNP-266 | hsa-miR-144, hsa-miR-374b | 77,8% | 74,1% | 81,5% |
| SNP-267 | hsa-miR-20a, hsa-miR-374a | 74,0% | 72,0% | 76,0% |

FIG. 6 (Continued)

| SNP-268 | hsa-miR-423-5p, hsa-miR-21 | 81,1% | 85,4% | 76,7% |
|---|---|---|---|---|
| SNP-269 | hsa-miR-374b, hsa-miR-320b | 70,3% | 65,3% | 75,3% |
| SNP-270 | hsa-miR-374a, hsa-miR-720 | 73,7% | 75,4% | 72,0% |
| SNP-271 | hsa-miR-21, hsa-miR-197 | 75,0% | 74,2% | 75,8% |
| SNP-272 | hsa-miR-320b, hsa-miR-621 | 74,7% | 82,1% | 67,4% |
| SNP-273 | hsa-miR-720, hsa-miR-148b | 73,0% | 78,7% | 67,4% |
| SNP-274 | hsa-miR-197, hsa-miR-301a | 74,9% | 66,8% | 83,0% |
| SNP-275 | hsa-miR-621, hsa-miR-101 | 73,8% | 70,4% | 77,1% |
| SNP-276 | hsa-miR-148b, hsa-miR-455-3p | 76,3% | 86,6% | 66,0% |
| SNP-277 | hsa-miR-301a, hsa-miR-33b | 76,4% | 67,8% | 85,0% |
| SNP-278 | hsa-miR-101, hsa-miR-15b | 75,7% | 80,7% | 70,6% |
| SNP-279 | hsa-miR-455-3p, hsa-miR-363 | 80,0% | 90,5% | 69,4% |
| SNP-280 | hsa-miR-15b, hsa-miR-574-3p | 73,7% | 75,8% | 71,5% |
| SNP-281 | hsa-miR-363, hsa-miR-191 | 80,6% | 83,0% | 78,1% |
| SNP-282 | hsa-miR-320a, hsa-miR-517* | 74,9% | 87,4% | 62,4% |
| SNP-283 | hsa-miR-574-3p, hsa-miR-18a | 71,9% | 75,1% | 68,6% |
| SNP-284 | hsa-miR-191, hsa-miR-152 | 72,5% | 69,8% | 75,2% |
| SNP-285 | hsa-miR-517*, hsa-let-7i* | 70,9% | 61,1% | 80,7% |
| SNP-286 | hsa-miR-18a, hsa-miR-320d | 71,6% | 81,6% | 61,5% |
| SNP-287 | hsa-miR-20b, hsa-miR-144, hsa-miR-20a | 76,3% | 70,6% | 81,9% |
| SNP-288 | hsa-miR-144, hsa-miR-20a, hsa-miR-423-5p | 83,6% | 86,1% | 81,2% |
| SNP-289 | hsa-miR-423-5p, hsa-miR-374b, hsa-miR-374a | 81,5% | 88,1% | 75,0% |
| SNP-290 | hsa-miR-374b, hsa-miR-374a, hsa-miR-21 | 75,0% | 66,2% | 83,8% |
| SNP-291 | hsa-miR-374a, hsa-miR-21, hsa-miR-320b | 70,8% | 68,0% | 73,5% |
| SNP-292 | hsa-miR-21, hsa-miR-320b, hsa-miR-720 | 73,4% | 79,3% | 67,5% |
| SNP-293 | hsa-miR-320b, hsa-miR-720, hsa-miR-197 | 74,1% | 81,8% | 66,5% |
| SNP-294 | hsa-miR-720, hsa-miR-197, hsa-miR-621 | 71,6% | 74,0% | 69,1% |
| SNP-295 | hsa-miR-197, hsa-miR-621, hsa-miR-148b | 77,9% | 74,1% | 81,8% |
| SNP-296 | hsa-miR-621, hsa-miR-148b, hsa-miR-301a | 79,0% | 72,8% | 85,2% |
| SNP-297 | hsa-miR-148b, hsa-miR-301a, hsa-miR-101 | 73,8% | 73,0% | 74,6% |
| SNP-298 | hsa-miR-301a, hsa-miR-101, hsa-miR-455-3p | 80,7% | 83,0% | 78,3% |
| SNP-299 | hsa-miR-101, hsa-miR-455-3p, hsa-miR-33b | 84,9% | 88,8% | 81,0% |
| SNP-300 | hsa-miR-455-3p, hsa-miR-33b, hsa-miR-15b | 79,6% | 81,6% | 77,5% |
| SNP-301 | hsa-miR-33b, hsa-miR-15b, hsa-miR-363 | 78,8% | 80,4% | 77,2% |
| SNP-302 | hsa-miR-320a, hsa-miR-574-3p, hsa-miR-191 | 83,5% | 83,4% | 83,7% |
| SNP-303 | hsa-miR-191, hsa-miR-517*, hsa-miR-18a | 74,8% | 72,9% | 76,7% |
| SNP-304 | hsa-miR-517*, hsa-miR-18a, hsa-miR-152 | 74,0% | 68,3% | 79,8% |
| SNP-305 | hsa-miR-18a, hsa-miR-152, hsa-let-7i* | 77,5% | 73,4% | 81,5% |
| SNP-306 | hsa-miR-152, hsa-let-7i*, hsa-miR-320d | 79,0% | 76,1% | 81,9% |
| SNP-307 | hsa-miR-148a, hsa-miR-20b, hsa-miR-20a | 87,0% | 88,7% | 85,3% |
| SNP-308 | hsa-miR-20b, hsa-miR-144, hsa-miR-423-5p | 84,5% | 88,1% | 81,0% |
| SNP-309 | hsa-miR-144, hsa-miR-20a, hsa-miR-374b | 82,2% | 76,6% | 87,7% |
| SNP-310 | hsa-miR-20a, hsa-miR-423-5p, hsa-miR-374a | 82,1% | 88,0% | 76,2% |
| SNP-311 | hsa-miR-423-5p, hsa-miR-374b, hsa-miR-21 | 79,8% | 86,4% | 73,3% |
| SNP-312 | hsa-miR-374b, hsa-miR-374a, hsa-miR-320b | 74,4% | 69,4% | 79,4% |
| SNP-313 | hsa-miR-374a, hsa-miR-21, hsa-miR-720 | 74,4% | 75,4% | 73,5% |
| SNP-314 | hsa-miR-21, hsa-miR-320b, hsa-miR-197 | 71,6% | 71,0% | 72,1% |
| SNP-315 | hsa-miR-320b, hsa-miR-720, hsa-miR-621 | 76,3% | 83,5% | 69,1% |
| SNP-316 | hsa-miR-720, hsa-miR-197, hsa-miR-148b | 75,8% | 74,2% | 77,4% |
| SNP-317 | hsa-miR-197, hsa-miR-621, hsa-miR-301a | 73,5% | 67,0% | 80,0% |
| SNP-318 | hsa-miR-621, hsa-miR-148b, hsa-miR-101 | 76,9% | 77,1% | 76,6% |
| SNP-319 | hsa-miR-148b, hsa-miR-301a, hsa-miR-455-3p | 78,8% | 82,0% | 75,7% |
| SNP-320 | hsa-miR-301a, hsa-miR-101, hsa-miR-33b | 80,5% | 80,3% | 80,7% |
| SNP-321 | hsa-miR-101, hsa-miR-455-3p, hsa-miR-15b | 83,6% | 87,1% | 80,2% |

FIG. 6 (Continued)

| SNP-322 | hsa-miR-455-3p, hsa-miR-33b, hsa-miR-363 | 80,5% | 89,1% | 71,9% |
|---|---|---|---|---|
| SNP-323 | hsa-miR-33b, hsa-miR-15b, hsa-miR-320a | 74,9% | 79,2% | 70,6% |
| SNP-324 | hsa-miR-15b, hsa-miR-363, hsa-miR-574-3p | 76,0% | 80,5% | 71,5% |
| SNP-325 | hsa-miR-363, hsa-miR-320a, hsa-miR-191 | 81,4% | 83,9% | 79,0% |
| SNP-326 | hsa-miR-320a, hsa-miR-574-3p, hsa-miR-517* | 79,6% | 87,7% | 71,4% |
| SNP-327 | hsa-miR-574-3p, hsa-miR-191, hsa-miR-18a | 77,4% | 84,1% | 70,8% |
| SNP-328 | hsa-miR-191, hsa-miR-517*, hsa-miR-152 | 76,6% | 75,0% | 78,2% |
| SNP-329 | hsa-miR-517*, hsa-miR-18a, hsa-let-7i* | 74,9% | 67,0% | 82,9% |
| SNP-330 | hsa-miR-18a, hsa-miR-152, hsa-miR-320d | 75,9% | 79,6% | 72,2% |
| SNP-331 | hsa-miR-148a, hsa-miR-144, hsa-miR-20a | 85,3% | 85,2% | 85,4% |
| SNP-332 | hsa-miR-20b, hsa-miR-20a, hsa-miR-423-5p | 83,4% | 89,1% | 77,7% |
| SNP-333 | hsa-miR-144, hsa-miR-423-5p, hsa-miR-374b | 83,0% | 85,7% | 80,3% |
| SNP-334 | hsa-miR-20a, hsa-miR-374b, hsa-miR-374a | 77,2% | 72,0% | 82,3% |
| SNP-335 | hsa-miR-423-5p, hsa-miR-374a, hsa-miR-21 | 81,8% | 85,8% | 77,9% |
| SNP-336 | hsa-miR-374b, hsa-miR-21, hsa-miR-320b | 71,2% | 67,5% | 75,0% |
| SNP-337 | hsa-miR-374a, hsa-miR-320b, hsa-miR-720 | 75,4% | 81,9% | 69,0% |
| SNP-338 | hsa-miR-21, hsa-miR-720, hsa-miR-197 | 72,1% | 75,7% | 68,5% |
| SNP-339 | hsa-miR-320b, hsa-miR-197, hsa-miR-621 | 78,3% | 75,1% | 81,5% |
| SNP-340 | hsa-miR-720, hsa-miR-621, hsa-miR-148b | 78,0% | 79,8% | 76,2% |
| SNP-341 | hsa-miR-197, hsa-miR-148b, hsa-miR-301a | 78,8% | 73,2% | 84,3% |
| SNP-342 | hsa-miR-621, hsa-miR-301a, hsa-miR-101 | 74,7% | 68,6% | 80,9% |
| SNP-343 | hsa-miR-148b, hsa-miR-101, hsa-miR-455-3p | 81,3% | 85,9% | 76,7% |
| SNP-344 | hsa-miR-301a, hsa-miR-455-3p, hsa-miR-33b | 82,0% | 82,7% | 81,2% |
| SNP-345 | hsa-miR-101, hsa-miR-33b, hsa-miR-15b | 80,6% | 79,6% | 81,6% |
| SNP-346 | hsa-miR-455-3p, hsa-miR-15b, hsa-miR-363 | 81,6% | 93,0% | 70,2% |
| SNP-347 | hsa-miR-15b, hsa-miR-320a, hsa-miR-574-3p | 70,4% | 76,9% | 63,8% |
| SNP-348 | hsa-miR-363, hsa-miR-574-3p, hsa-miR-191 | 82,2% | 86,2% | 78,2% |
| SNP-349 | hsa-miR-320a, hsa-miR-191, hsa-miR-517* | 83,1% | 84,7% | 81,4% |
| SNP-350 | hsa-miR-574-3p, hsa-miR-517*, hsa-miR-18a | 74,8% | 83,8% | 65,8% |
| SNP-351 | hsa-miR-191, hsa-miR-18a, hsa-miR-152 | 72,9% | 71,1% | 74,6% |
| SNP-352 | hsa-miR-517*, hsa-miR-152, hsa-let-7i* | 75,2% | 69,0% | 81,4% |
| SNP-353 | hsa-miR-18a, hsa-let-7i*, hsa-miR-320d | 78,9% | 80,3% | 77,4% |
| SNP-354 | hsa-miR-144*, hsa-miR-20b, hsa-miR-20a | 83,3% | 75,2% | 91,4% |
| SNP-355 | hsa-miR-148a, hsa-miR-144, hsa-miR-423-5p | 90,5% | 91,0% | 90,1% |
| SNP-356 | hsa-miR-20b, hsa-miR-20a, hsa-miR-374b | 77,2% | 75,8% | 78,7% |
| SNP-357 | hsa-miR-144, hsa-miR-423-5p, hsa-miR-374a | 83,7% | 86,5% | 80,9% |
| SNP-358 | hsa-miR-20a, hsa-miR-374b, hsa-miR-21 | 76,8% | 69,6% | 83,9% |
| SNP-359 | hsa-miR-423-5p, hsa-miR-374a, hsa-miR-320b | 80,5% | 88,6% | 72,4% |
| SNP-360 | hsa-miR-374b, hsa-miR-21, hsa-miR-720 | 73,3% | 78,5% | 68,1% |
| SNP-361 | hsa-miR-374a, hsa-miR-320b, hsa-miR-197 | 78,5% | 81,8% | 75,2% |
| SNP-362 | hsa-miR-21, hsa-miR-720, hsa-miR-621 | 76,2% | 76,8% | 75,7% |
| SNP-363 | hsa-miR-320b, hsa-miR-197, hsa-miR-148b | 78,5% | 75,5% | 81,5% |
| SNP-364 | hsa-miR-720, hsa-miR-621, hsa-miR-301a | 75,5% | 70,6% | 80,5% |
| SNP-365 | hsa-miR-197, hsa-miR-148b, hsa-miR-101 | 75,3% | 76,2% | 74,4% |
| SNP-366 | hsa-miR-621, hsa-miR-301a, hsa-miR-455-3p | 78,8% | 76,7% | 81,0% |
| SNP-367 | hsa-miR-148b, hsa-miR-101, hsa-miR-33b | 82,2% | 82,5% | 81,9% |
| SNP-368 | hsa-miR-301a, hsa-miR-455-3p, hsa-miR-15b | 78,6% | 81,3% | 76,0% |
| SNP-369 | hsa-miR-101, hsa-miR-33b, hsa-miR-363 | 82,2% | 85,6% | 78,9% |
| SNP-370 | hsa-miR-455-3p, hsa-miR-15b, hsa-miR-320a | 79,2% | 87,4% | 71,0% |
| SNP-371 | hsa-miR-33b, hsa-miR-363, hsa-miR-574-3p | 78,6% | 82,2% | 75,0% |
| SNP-372 | hsa-miR-15b, hsa-miR-320a, hsa-miR-191 | 80,4% | 80,4% | 80,3% |
| SNP-373 | hsa-miR-363, hsa-miR-574-3p, hsa-miR-517* | 80,8% | 92,2% | 69,5% |
| SNP-374 | hsa-miR-320a, hsa-miR-191, hsa-miR-18a | 81,9% | 79,7% | 84,1% |
| SNP-375 | hsa-miR-574-3p, hsa-miR-517*, hsa-miR-152 | 74,8% | 80,6% | 69,0% |

FIG. 6 (Continued)

| SNP-376 | hsa-miR-191, hsa-miR-18a, hsa-let-7i* | 74,9% | 71,8% | 78,0% |
|---|---|---|---|---|
| SNP-377 | hsa-miR-517*, hsa-miR-152, hsa-miR-320d | 75,3% | 73,9% | 76,6% |
| SNP-378 | hsa-miR-144*, hsa-miR-148a, hsa-miR-20a | 85,6% | 85,5% | 85,6% |
| SNP-379 | hsa-miR-148a, hsa-miR-20b, hsa-miR-423-5p | 90,4% | 91,0% | 89,8% |
| SNP-380 | hsa-miR-20b, hsa-miR-144, hsa-miR-374b | 79,3% | 76,4% | 82,2% |
| SNP-381 | hsa-miR-144, hsa-miR-20a, hsa-miR-374a | 77,7% | 73,3% | 82,1% |
| SNP-382 | hsa-miR-20a, hsa-miR-423-5p, hsa-miR-21 | 84,8% | 89,1% | 80,5% |
| SNP-383 | hsa-miR-423-5p, hsa-miR-374b, hsa-miR-320b | 77,0% | 84,7% | 69,4% |
| SNP-384 | hsa-miR-374b, hsa-miR-374a, hsa-miR-720 | 75,0% | 74,0% | 75,9% |
| SNP-385 | hsa-miR-374a, hsa-miR-21, hsa-miR-197 | 75,4% | 76,6% | 74,1% |
| SNP-386 | hsa-miR-21, hsa-miR-320b, hsa-miR-621 | 77,1% | 77,0% | 77,1% |
| SNP-387 | hsa-miR-320b, hsa-miR-720, hsa-miR-148b | 76,0% | 84,6% | 67,3% |
| SNP-388 | hsa-miR-720, hsa-miR-197, hsa-miR-301a | 72,0% | 71,2% | 72,8% |
| SNP-389 | hsa-miR-197, hsa-miR-621, hsa-miR-101 | 75,8% | 77,4% | 74,1% |
| SNP-390 | hsa-miR-621, hsa-miR-148b, hsa-miR-455-3p | 76,1% | 76,9% | 75,4% |
| SNP-391 | hsa-miR-148b, hsa-miR-301a, hsa-miR-33b | 81,7% | 79,4% | 84,0% |
| SNP-392 | hsa-miR-301a, hsa-miR-101, hsa-miR-15b | 78,4% | 75,4% | 81,4% |
| SNP-393 | hsa-miR-101, hsa-miR-455-3p, hsa-miR-363 | 85,2% | 89,0% | 81,4% |
| SNP-394 | hsa-miR-455-3p, hsa-miR-33b, hsa-miR-320a | 82,6% | 84,0% | 81,1% |
| SNP-395 | hsa-miR-33b, hsa-miR-15b, hsa-miR-574-3p | 76,9% | 78,3% | 75,5% |
| SNP-396 | hsa-miR-15b, hsa-miR-363, hsa-miR-191 | 80,3% | 82,6% | 78,0% |
| SNP-397 | hsa-miR-363, hsa-miR-320a, hsa-miR-517* | 79,0% | 87,0% | 71,0% |
| SNP-398 | hsa-miR-320a, hsa-miR-574-3p, hsa-miR-18a | 74,1% | 79,3% | 69,0% |
| SNP-399 | hsa-miR-574-3p, hsa-miR-191, hsa-miR-152 | 80,8% | 87,2% | 74,3% |
| SNP-400 | hsa-miR-191, hsa-miR-517*, hsa-let-7i* | 77,0% | 75,2% | 78,9% |
| SNP-401 | hsa-miR-517*, hsa-miR-18a, hsa-miR-320d | 71,1% | 75,1% | 67,0% |
| SNP-402 | hsa-miR-144*, hsa-miR-144, hsa-miR-20a | 84,0% | 75,5% | 92,5% |
| SNP-403 | hsa-miR-148a, hsa-miR-20a, hsa-miR-423-5p | 90,4% | 89,2% | 91,7% |
| SNP-404 | hsa-miR-20b, hsa-miR-423-5p, hsa-miR-374b | 83,7% | 85,9% | 81,5% |
| SNP-405 | hsa-miR-144, hsa-miR-374b, hsa-miR-374a | 79,7% | 74,3% | 85,0% |
| SNP-406 | hsa-miR-20a, hsa-miR-374a, hsa-miR-21 | 75,7% | 69,0% | 82,3% |
| SNP-407 | hsa-miR-423-5p, hsa-miR-21, hsa-miR-320b | 80,3% | 85,6% | 75,0% |
| SNP-408 | hsa-miR-374b, hsa-miR-320b, hsa-miR-720 | 74,2% | 79,5% | 68,9% |
| SNP-409 | hsa-miR-374a, hsa-miR-720, hsa-miR-197 | 76,2% | 76,9% | 75,4% |
| SNP-410 | hsa-miR-21, hsa-miR-197, hsa-miR-621 | 75,4% | 73,5% | 77,4% |
| SNP-411 | hsa-miR-320b, hsa-miR-621, hsa-miR-148b | 77,5% | 80,6% | 74,5% |
| SNP-412 | hsa-miR-720, hsa-miR-148b, hsa-miR-301a | 75,8% | 78,0% | 73,6% |
| SNP-413 | hsa-miR-197, hsa-miR-301a, hsa-miR-101 | 73,1% | 76,6% | 69,6% |
| SNP-414 | hsa-miR-621, hsa-miR-101, hsa-miR-455-3p | 84,1% | 86,4% | 81,8% |
| SNP-415 | hsa-miR-148b, hsa-miR-455-3p, hsa-miR-33b | 80,7% | 87,1% | 74,3% |
| SNP-416 | hsa-miR-301a, hsa-miR-33b, hsa-miR-15b | 79,9% | 75,0% | 84,8% |
| SNP-417 | hsa-miR-101, hsa-miR-15b, hsa-miR-363 | 75,6% | 82,0% | 69,3% |
| SNP-418 | hsa-miR-455-3p, hsa-miR-363, hsa-miR-320a | 78,3% | 85,5% | 71,1% |
| SNP-419 | hsa-miR-33b, hsa-miR-320a, hsa-miR-574-3p | 74,7% | 74,9% | 74,5% |
| SNP-420 | hsa-miR-15b, hsa-miR-574-3p, hsa-miR-191 | 76,5% | 80,6% | 72,3% |
| SNP-421 | hsa-miR-363, hsa-miR-191, hsa-miR-517* | 83,6% | 88,2% | 79,0% |
| SNP-422 | hsa-miR-320a, hsa-miR-517*, hsa-miR-18a | 74,0% | 79,1% | 68,9% |
| SNP-423 | hsa-miR-574-3p, hsa-miR-18a, hsa-miR-152 | 71,4% | 70,3% | 72,5% |
| SNP-424 | hsa-miR-191, hsa-miR-152, hsa-let-7i* | 76,1% | 75,4% | 76,8% |
| SNP-425 | hsa-miR-517*, hsa-let-7i*, hsa-miR-320d | 77,2% | 72,8% | 81,5% |
| SNP-426 | hsa-miR-21, hsa-miR-548p | 79,5% | 71,9% | 87,0% |
| SNP-427 | hsa-miR-548p, hsa-miR-1180 | 67,6% | 60,1% | 75,0% |
| SNP-428 | hsa-miR-1180, hsa-miR-320b | 74,1% | 79,2% | 69,0% |
| SNP-429 | hsa-miR-197, hsa-miR-328 | 73,6% | 78,5% | 68,8% |

FIG. 6 (Continued)

| SNP-430 | hsa-miR-328, hsa-miR-526a | 67,0% | 71,3% | 62,6% |
|---|---|---|---|---|
| SNP-431 | hsa-miR-526a, hsa-miR-621 | 68,5% | 64,4% | 72,6% |
| SNP-432 | hsa-miR-20b, hsa-miR-33a | 83,8% | 81,4% | 86,2% |
| SNP-433 | hsa-miR-374a, hsa-miR-548p | 82,2% | 72,2% | 92,2% |
| SNP-434 | hsa-miR-21, hsa-miR-1180 | 77,5% | 71,4% | 83,5% |
| SNP-435 | hsa-miR-548p, hsa-miR-320b | 77,2% | 84,2% | 70,1% |
| SNP-436 | hsa-miR-1180, hsa-miR-720 | 72,6% | 73,4% | 71,9% |
| SNP-437 | hsa-miR-720, hsa-miR-328 | 72,4% | 72,1% | 72,6% |
| SNP-438 | hsa-miR-197, hsa-miR-526a | 74,5% | 73,8% | 75,2% |
| SNP-439 | hsa-miR-328, hsa-miR-621 | 69,0% | 63,8% | 74,1% |
| SNP-440 | hsa-miR-526a, hsa-miR-148b | 73,4% | 74,0% | 72,7% |
| SNP-441 | hsa-miR-148a, hsa-miR-33a | 85,3% | 84,7% | 85,9% |
| SNP-442 | hsa-miR-33a, hsa-miR-374b | 86,7% | 88,6% | 84,9% |
| SNP-443 | hsa-miR-374b, hsa-miR-548p | 84,4% | 82,2% | 86,6% |
| SNP-444 | hsa-miR-374a, hsa-miR-1180 | 79,3% | 82,7% | 75,9% |
| SNP-445 | hsa-miR-548p, hsa-miR-720 | 67,4% | 63,0% | 71,9% |
| SNP-446 | hsa-miR-1180, hsa-miR-197 | 76,1% | 83,0% | 69,2% |
| SNP-447 | hsa-miR-320b, hsa-miR-328 | 79,6% | 82,2% | 77,0% |
| SNP-448 | hsa-miR-720, hsa-miR-526a | 71,8% | 79,4% | 64,2% |
| SNP-449 | hsa-miR-328, hsa-miR-148b | 75,5% | 72,6% | 78,4% |
| SNP-450 | hsa-miR-526a, hsa-miR-301a | 72,9% | 68,1% | 77,8% |
| SNP-451 | hsa-miR-15b, hsa-miR-1226 | 73,4% | 74,5% | 72,2% |
| SNP-452 | hsa-miR-20b, hsa-miR-144, hsa-miR-33a | 82,1% | 78,8% | 85,4% |
| SNP-453 | hsa-miR-374a, hsa-miR-21, hsa-miR-548p | 81,0% | 69,9% | 92,1% |
| SNP-454 | hsa-miR-21, hsa-miR-548p, hsa-miR-1180 | 82,0% | 76,2% | 87,8% |
| SNP-455 | hsa-miR-548p, hsa-miR-1180, hsa-miR-320b | 75,8% | 79,6% | 72,0% |
| SNP-456 | hsa-miR-1180, hsa-miR-320b, hsa-miR-720 | 77,6% | 80,8% | 74,3% |
| SNP-457 | hsa-miR-720, hsa-miR-197, hsa-miR-328 | 76,0% | 78,9% | 73,1% |
| SNP-458 | hsa-miR-197, hsa-miR-328, hsa-miR-526a | 76,1% | 73,7% | 78,5% |
| SNP-459 | hsa-miR-328, hsa-miR-526a, hsa-miR-621 | 68,4% | 65,4% | 71,3% |
| SNP-460 | hsa-miR-526a, hsa-miR-621, hsa-miR-148b | 72,3% | 69,5% | 75,1% |
| SNP-461 | hsa-miR-148a, hsa-miR-20b, hsa-miR-33a | 89,3% | 89,1% | 89,5% |
| SNP-462 | hsa-miR-144, hsa-miR-33a, hsa-miR-423-5p | 85,9% | 87,7% | 84,1% |
| SNP-463 | hsa-miR-374b, hsa-miR-374a, hsa-miR-548p | 83,2% | 80,2% | 86,2% |
| SNP-464 | hsa-miR-374a, hsa-miR-21, hsa-miR-1180 | 79,2% | 81,0% | 77,4% |
| SNP-465 | hsa-miR-21, hsa-miR-548p, hsa-miR-320b | 80,9% | 79,8% | 82,0% |
| SNP-466 | hsa-miR-548p, hsa-miR-1180, hsa-miR-720 | 71,6% | 67,9% | 75,2% |
| SNP-467 | hsa-miR-1180, hsa-miR-320b, hsa-miR-197 | 79,5% | 85,5% | 73,4% |
| SNP-468 | hsa-miR-320b, hsa-miR-720, hsa-miR-328 | 79,0% | 86,0% | 72,1% |
| SNP-469 | hsa-miR-720, hsa-miR-197, hsa-miR-526a | 73,2% | 80,4% | 66,1% |
| SNP-470 | hsa-miR-197, hsa-miR-328, hsa-miR-621 | 75,5% | 74,7% | 76,3% |
| SNP-471 | hsa-miR-328, hsa-miR-526a, hsa-miR-148b | 75,3% | 70,0% | 80,6% |
| SNP-472 | hsa-miR-526a, hsa-miR-621, hsa-miR-301a | 74,8% | 73,4% | 76,2% |
| SNP-473 | hsa-miR-148a, hsa-miR-144, hsa-miR-33a | 85,6% | 86,8% | 84,3% |
| SNP-474 | hsa-miR-20b, hsa-miR-33a, hsa-miR-20a | 82,3% | 78,3% | 86,3% |
| SNP-475 | hsa-miR-374b, hsa-miR-21, hsa-miR-548p | 83,1% | 77,4% | 88,8% |
| SNP-476 | hsa-miR-374a, hsa-miR-548p, hsa-miR-1180 | 79,6% | 78,9% | 80,2% |
| SNP-477 | hsa-miR-21, hsa-miR-1180, hsa-miR-320b | 78,4% | 76,6% | 80,3% |
| SNP-478 | hsa-miR-548p, hsa-miR-320b, hsa-miR-720 | 77,4% | 84,9% | 70,0% |
| SNP-479 | hsa-miR-1180, hsa-miR-720, hsa-miR-197 | 78,3% | 85,0% | 71,6% |
| SNP-480 | hsa-miR-320b, hsa-miR-197, hsa-miR-328 | 79,7% | 81,8% | 77,6% |
| SNP-481 | hsa-miR-720, hsa-miR-328, hsa-miR-526a | 75,4% | 77,9% | 72,9% |
| SNP-482 | hsa-miR-197, hsa-miR-526a, hsa-miR-621 | 72,8% | 69,9% | 75,6% |
| SNP-483 | hsa-miR-328, hsa-miR-621, hsa-miR-148b | 75,2% | 68,1% | 82,3% |

FIG. 6 (Continued)

| SNP-484 | hsa-miR-526a, hsa-miR-148b, hsa-miR-301a | 74,6% | 74,0% | 75,3% |
|---|---|---|---|---|
| SNP-485 | hsa-miR-144*, hsa-miR-20b, hsa-miR-33a | 86,4% | 85,2% | 87,6% |
| SNP-486 | hsa-miR-20b, hsa-miR-33a, hsa-miR-423-5p | 83,1% | 85,8% | 80,4% |
| SNP-487 | hsa-miR-33a, hsa-miR-423-5p, hsa-miR-374a | 86,0% | 88,3% | 83,8% |
| SNP-488 | hsa-miR-423-5p, hsa-miR-374a, hsa-miR-548p | 84,4% | 88,1% | 80,7% |
| SNP-489 | hsa-miR-374b, hsa-miR-21, hsa-miR-1180 | 83,8% | 83,5% | 84,0% |
| SNP-490 | hsa-miR-374a, hsa-miR-548p, hsa-miR-320b | 78,5% | 76,6% | 80,3% |
| SNP-491 | hsa-miR-21, hsa-miR-1180, hsa-miR-720 | 77,8% | 75,4% | 80,2% |
| SNP-492 | hsa-miR-548p, hsa-miR-320b, hsa-miR-197 | 80,9% | 79,5% | 82,3% |
| SNP-493 | hsa-miR-1180, hsa-miR-720, hsa-miR-328 | 73,6% | 74,2% | 73,0% |
| SNP-494 | hsa-miR-320b, hsa-miR-197, hsa-miR-526a | 72,8% | 73,8% | 71,8% |
| SNP-495 | hsa-miR-720, hsa-miR-328, hsa-miR-621 | 72,3% | 72,6% | 72,0% |
| SNP-496 | hsa-miR-197, hsa-miR-526a, hsa-miR-148b | 77,0% | 79,2% | 74,7% |
| SNP-497 | hsa-miR-328, hsa-miR-621, hsa-miR-301a | 74,3% | 66,6% | 82,0% |
| SNP-498 | hsa-miR-526a, hsa-miR-148b, hsa-miR-101 | 79,5% | 80,8% | 78,2% |
| SNP-499 | hsa-miR-144*, hsa-miR-148a, hsa-miR-33a | 87,2% | 88,2% | 86,2% |
| SNP-500 | hsa-miR-144, hsa-miR-33a, hsa-miR-374b | 86,6% | 88,9% | 84,4% |
| SNP-501 | hsa-miR-33a, hsa-miR-20a, hsa-miR-374a | 83,6% | 83,4% | 83,7% |
| SNP-502 | hsa-miR-423-5p, hsa-miR-374b, hsa-miR-548p | 83,2% | 87,8% | 78,6% |
| SNP-503 | hsa-miR-374b, hsa-miR-374a, hsa-miR-1180 | 83,4% | 85,5% | 81,2% |
| SNP-504 | hsa-miR-21, hsa-miR-548p, hsa-miR-720 | 78,6% | 73,3% | 83,8% |
| SNP-505 | hsa-miR-548p, hsa-miR-1180, hsa-miR-197 | 76,0% | 75,0% | 77,0% |
| SNP-506 | hsa-miR-1180, hsa-miR-320b, hsa-miR-328 | 79,8% | 81,9% | 77,7% |
| SNP-507 | hsa-miR-320b, hsa-miR-720, hsa-miR-526a | 78,0% | 87,4% | 68,6% |
| SNP-508 | hsa-miR-197, hsa-miR-328, hsa-miR-148b | 78,4% | 78,2% | 78,6% |
| SNP-509 | hsa-miR-328, hsa-miR-526a, hsa-miR-301a | 79,0% | 75,7% | 82,2% |
| SNP-510 | hsa-miR-526a, hsa-miR-621, hsa-miR-101 | 77,1% | 74,8% | 79,4% |
| SNP-511 | hsa-miR-33b, hsa-miR-15b, hsa-miR-1226 | 77,0% | 70,6% | 83,4% |
| SNP-512 | hsa-miR-144*, hsa-miR-144, hsa-miR-33a | 85,2% | 84,2% | 86,1% |
| SNP-513 | hsa-miR-148a, hsa-miR-33a, hsa-miR-20a | 88,2% | 89,8% | 86,7% |
| SNP-514 | hsa-miR-33a, hsa-miR-374b, hsa-miR-374a | 85,0% | 85,8% | 84,1% |
| SNP-515 | hsa-miR-423-5p, hsa-miR-21, hsa-miR-548p | 83,6% | 84,2% | 83,0% |
| SNP-516 | hsa-miR-374b, hsa-miR-548p, hsa-miR-1180 | 83,4% | 84,3% | 82,4% |
| SNP-517 | hsa-miR-374a, hsa-miR-1180, hsa-miR-320b | 80,2% | 84,0% | 76,5% |
| SNP-518 | hsa-miR-548p, hsa-miR-720, hsa-miR-197 | 72,7% | 73,7% | 71,7% |
| SNP-519 | hsa-miR-1180, hsa-miR-197, hsa-miR-328 | 75,2% | 81,9% | 68,4% |
| SNP-520 | hsa-miR-320b, hsa-miR-328, hsa-miR-526a | 78,5% | 79,9% | 77,0% |
| SNP-521 | hsa-miR-720, hsa-miR-526a, hsa-miR-621 | 70,7% | 76,4% | 65,0% |
| SNP-522 | hsa-miR-328, hsa-miR-148b, hsa-miR-301a | 77,0% | 72,2% | 81,7% |
| SNP-523 | hsa-miR-526a, hsa-miR-301a, hsa-miR-101 | 78,0% | 79,2% | 76,8% |
| SNP-524 | hsa-miR-15b, hsa-miR-1226, hsa-miR-574-3p | 73,9% | 75,5% | 72,2% |
| SNP-525 | hsa-miR-148a, hsa-miR-423-5p | 87,6% | 85,2% | 90,1% |
| SNP-526 | hsa-miR-423-5p, hsa-miR-20b | 82,3% | 89,1% | 75,4% |
| SNP-527 | hsa-miR-148b, hsa-miR-374b | 80,4% | 80,2% | 80,7% |
| SNP-528 | hsa-miR-374a, hsa-miR-455-3p | 84,7% | 87,4% | 82,0% |
| SNP-529 | hsa-miR-455-3p, hsa-miR-519b-5p | 79,4% | 79,4% | 79,4% |
| SNP-530 | hsa-miR-519b-5p, hsa-miR-20a | 77,1% | 71,2% | 83,0% |
| SNP-531 | hsa-miR-20a, hsa-miR-33a | 81,2% | 75,9% | 86,5% |
| SNP-532 | hsa-miR-33a, hsa-miR-1245 | 77,2% | 80,7% | 73,6% |
| SNP-533 | hsa-miR-1245, hsa-let-7i* | 76,5% | 78,5% | 74,6% |
| SNP-534 | hsa-let-7i*, hsa-miR-556-5p | 75,9% | 70,5% | 81,4% |
| SNP-535 | hsa-miR-556-5p, hsa-miR-320c | 77,7% | 80,9% | 74,5% |
| SNP-536 | hsa-miR-320c, hsa-miR-301a | 74,7% | 74,2% | 75,1% |
| SNP-537 | hsa-miR-33b, hsa-miR-574-3p | 75,0% | 71,1% | 78,9% |

FIG. 6 (Continued)

| SNP-538 | hsa-miR-574-3p, hsa-let-7b* | 76,4% | 88,6% | 64,1% |
|---|---|---|---|---|
| SNP-539 | hsa-let-7b*, hsa-miR-197 | 75,5% | 67,4% | 83,5% |
| SNP-540 | hsa-miR-197, hsa-miR-363 | 75,8% | 76,6% | 75,1% |
| SNP-541 | hsa-miR-1226, hsa-miR-1283 | 76,6% | 71,7% | 81,6% |
| SNP-542 | hsa-miR-1283, hsa-miR-720 | 75,6% | 78,0% | 73,1% |
| SNP-543 | hsa-miR-144*, hsa-miR-423-5p | 85,8% | 83,1% | 88,6% |
| SNP-544 | hsa-miR-423-5p, hsa-miR-891b | 83,1% | 88,8% | 77,4% |
| SNP-545 | hsa-miR-148b, hsa-miR-374a | 78,3% | 78,1% | 78,6% |
| SNP-546 | hsa-miR-374a, hsa-miR-519b-5p | 82,4% | 83,6% | 81,3% |
| SNP-547 | hsa-miR-455-3p, hsa-miR-20a | 78,6% | 78,2% | 79,0% |
| SNP-548 | hsa-miR-519b-5p, hsa-miR-33a | 78,4% | 75,8% | 80,9% |
| SNP-549 | hsa-miR-20a, hsa-miR-1245 | 74,6% | 75,2% | 74,1% |
| SNP-550 | hsa-miR-33a, hsa-let-7i* | 79,0% | 70,2% | 87,8% |
| SNP-551 | hsa-miR-1245, hsa-miR-556-5p | 76,0% | 72,2% | 79,7% |
| SNP-552 | hsa-let-7i*, hsa-miR-320c | 76,2% | 73,2% | 79,1% |
| SNP-553 | hsa-miR-556-5p, hsa-miR-301a | 76,9% | 74,7% | 79,1% |
| SNP-554 | hsa-miR-320c, hsa-miR-101 | 69,1% | 74,4% | 63,8% |
| SNP-555 | hsa-miR-101, hsa-miR-574-3p | 74,0% | 81,1% | 66,9% |
| SNP-556 | hsa-miR-33b, hsa-let-7b* | 80,7% | 75,2% | 86,2% |
| SNP-557 | hsa-miR-574-3p, hsa-miR-197 | 75,6% | 79,1% | 72,0% |
| SNP-558 | hsa-let-7b*, hsa-miR-363 | 82,2% | 91,3% | 73,1% |
| SNP-559 | hsa-miR-197, hsa-miR-320a | 76,8% | 79,6% | 73,9% |
| SNP-560 | hsa-miR-320a, hsa-miR-1283 | 79,8% | 91,0% | 68,6% |
| SNP-561 | hsa-miR-1226, hsa-miR-720 | 76,1% | 70,0% | 82,2% |
| SNP-562 | hsa-miR-423-5p, hsa-miR-144 | 84,3% | 88,6% | 80,0% |
| SNP-563 | hsa-miR-891b, hsa-miR-374b | 85,7% | 89,1% | 82,3% |
| SNP-564 | hsa-miR-144, hsa-miR-374a | 75,2% | 70,9% | 79,5% |
| SNP-565 | hsa-miR-374b, hsa-miR-519b-5p | 83,8% | 83,7% | 84,0% |
| SNP-566 | hsa-miR-374a, hsa-miR-20a | 73,6% | 71,4% | 75,8% |
| SNP-567 | hsa-miR-455-3p, hsa-miR-33a | 79,0% | 77,0% | 81,0% |
| SNP-568 | hsa-miR-519b-5p, hsa-miR-1245 | 74,2% | 75,4% | 73,0% |
| SNP-569 | hsa-miR-20a, hsa-let-7i* | 78,0% | 71,0% | 85,0% |
| SNP-570 | hsa-miR-1245, hsa-miR-320c | 78,9% | 81,8% | 76,0% |
| SNP-571 | hsa-let-7i*, hsa-miR-301a | 77,4% | 68,6% | 86,3% |
| SNP-572 | hsa-miR-320c, hsa-miR-33b | 77,5% | 76,3% | 78,6% |
| SNP-573 | hsa-miR-301a, hsa-miR-574-3p | 75,2% | 76,6% | 73,8% |
| SNP-574 | hsa-miR-101, hsa-let-7b* | 78,1% | 83,3% | 73,0% |
| SNP-575 | hsa-miR-33b, hsa-miR-197 | 76,1% | 73,3% | 79,0% |
| SNP-576 | hsa-miR-574-3p, hsa-miR-363 | 75,8% | 80,2% | 71,5% |
| SNP-577 | hsa-let-7b*, hsa-miR-320a | 75,8% | 86,7% | 64,8% |
| SNP-578 | hsa-miR-197, hsa-miR-1226 | 77,4% | 69,4% | 85,4% |
| SNP-579 | hsa-miR-363, hsa-miR-1283 | 80,7% | 91,5% | 69,8% |
| SNP-580 | hsa-miR-320a, hsa-miR-720 | 73,6% | 89,5% | 57,6% |
| SNP-581 | hsa-miR-144*, hsa-miR-148a, hsa-miR-423-5p | 87,6% | 88,9% | 86,2% |
| SNP-582 | hsa-miR-148a, hsa-miR-423-5p, hsa-miR-20b | 90,6% | 91,0% | 90,2% |
| SNP-583 | hsa-miR-423-5p, hsa-miR-20b, hsa-miR-891b | 84,9% | 88,0% | 81,8% |
| SNP-584 | hsa-miR-144, hsa-miR-148b, hsa-miR-374b | 80,0% | 79,6% | 80,3% |
| SNP-585 | hsa-miR-148b, hsa-miR-374b, hsa-miR-374a | 80,1% | 79,5% | 80,6% |
| SNP-586 | hsa-miR-374b, hsa-miR-374a, hsa-miR-455-3p | 84,7% | 89,4% | 80,0% |
| SNP-587 | hsa-miR-374a, hsa-miR-455-3p, hsa-miR-519b-5p | 81,4% | 83,7% | 79,2% |
| SNP-588 | hsa-miR-455-3p, hsa-miR-519b-5p, hsa-miR-20a | 79,6% | 77,0% | 82,2% |
| SNP-589 | hsa-miR-519b-5p, hsa-miR-20a, hsa-miR-33a | 80,8% | 79,2% | 82,4% |
| SNP-590 | hsa-miR-20a, hsa-miR-33a, hsa-miR-1245 | 76,7% | 75,2% | 78,2% |
| SNP-591 | hsa-miR-33a, hsa-miR-1245, hsa-let-7i* | 79,2% | 81,5% | 77,0% |

FIG. 6 (Continued)

| | | | | |
|---|---|---|---|---|
| SNP-592 | hsa-miR-1245, hsa-let-7i*, hsa-miR-556-5p | 78,0% | 73,7% | 82,3% |
| SNP-593 | hsa-let-7i*, hsa-miR-556-5p, hsa-miR-320c | 79,0% | 81,5% | 76,5% |
| SNP-594 | hsa-miR-556-5p, hsa-miR-320c, hsa-miR-301a | 79,4% | 83,2% | 75,5% |
| SNP-595 | hsa-miR-320c, hsa-miR-301a, hsa-miR-101 | 71,6% | 73,4% | 69,8% |
| SNP-596 | hsa-miR-101, hsa-miR-33b, hsa-miR-574-3p | 83,4% | 87,8% | 79,1% |
| SNP-597 | hsa-miR-33b, hsa-miR-574-3p, hsa-let-7b* | 81,0% | 81,1% | 80,9% |
| SNP-598 | hsa-miR-574-3p, hsa-let-7b*, hsa-miR-197 | 77,7% | 78,1% | 77,4% |
| SNP-599 | hsa-let-7b*, hsa-miR-197, hsa-miR-363 | 83,2% | 85,4% | 81,0% |
| SNP-600 | hsa-miR-197, hsa-miR-363, hsa-miR-320a | 76,5% | 79,5% | 73,4% |
| SNP-601 | hsa-miR-320a, hsa-miR-1226, hsa-miR-1283 | 77,9% | 80,5% | 75,3% |
| SNP-602 | hsa-miR-1226, hsa-miR-1283, hsa-miR-720 | 78,0% | 74,5% | 81,6% |
| SNP-603 | hsa-miR-148a, hsa-miR-423-5p, hsa-miR-891b | 86,2% | 88,9% | 83,6% |
| SNP-604 | hsa-miR-423-5p, hsa-miR-20b, hsa-miR-144 | 84,2% | 87,8% | 80,5% |
| SNP-605 | hsa-miR-891b, hsa-miR-144, hsa-miR-374b | 84,1% | 87,0% | 81,3% |
| SNP-606 | hsa-miR-144, hsa-miR-148b, hsa-miR-374a | 81,0% | 79,7% | 82,4% |
| SNP-607 | hsa-miR-148b, hsa-miR-374b, hsa-miR-455-3p | 82,6% | 85,5% | 79,8% |
| SNP-608 | hsa-miR-374b, hsa-miR-374a, hsa-miR-519b-5p | 83,2% | 82,2% | 84,1% |
| SNP-609 | hsa-miR-374a, hsa-miR-455-3p, hsa-miR-20a | 83,8% | 84,0% | 83,7% |
| SNP-610 | hsa-miR-455-3p, hsa-miR-519b-5p, hsa-miR-33a | 81,2% | 81,4% | 81,0% |
| SNP-611 | hsa-miR-519b-5p, hsa-miR-20a, hsa-miR-1245 | 74,4% | 72,0% | 76,9% |
| SNP-612 | hsa-miR-20a, hsa-miR-33a, hsa-let-7i* | 81,5% | 76,0% | 87,0% |
| SNP-613 | hsa-miR-33a, hsa-miR-1245, hsa-miR-556-5p | 78,6% | 77,1% | 80,2% |
| SNP-614 | hsa-miR-1245, hsa-let-7i*, hsa-miR-320c | 79,0% | 81,3% | 76,6% |
| SNP-615 | hsa-let-7i*, hsa-miR-556-5p, hsa-miR-301a | 76,6% | 72,2% | 81,0% |
| SNP-616 | hsa-miR-556-5p, hsa-miR-320c, hsa-miR-101 | 77,2% | 75,4% | 79,0% |
| SNP-617 | hsa-miR-320c, hsa-miR-301a, hsa-miR-33b | 76,9% | 73,9% | 79,9% |
| SNP-618 | hsa-miR-301a, hsa-miR-101, hsa-miR-574-3p | 76,0% | 83,5% | 68,5% |
| SNP-619 | hsa-miR-101, hsa-miR-33b, hsa-let-7b* | 85,3% | 86,0% | 84,6% |
| SNP-620 | hsa-miR-33b, hsa-miR-574-3p, hsa-miR-197 | 79,0% | 80,2% | 77,8% |
| SNP-621 | hsa-miR-574-3p, hsa-let-7b*, hsa-miR-363 | 78,9% | 91,4% | 66,4% |
| SNP-622 | hsa-let-7b*, hsa-miR-197, hsa-miR-320a | 78,4% | 81,8% | 75,1% |
| SNP-623 | hsa-miR-197, hsa-miR-363, hsa-miR-1226 | 78,8% | 77,5% | 80,0% |
| SNP-624 | hsa-miR-363, hsa-miR-320a, hsa-miR-1283 | 82,7% | 94,9% | 70,5% |
| SNP-625 | hsa-miR-320a, hsa-miR-1226, hsa-miR-720 | 74,8% | 74,0% | 75,6% |
| SNP-626 | hsa-miR-144*, hsa-miR-423-5p, hsa-miR-20b | 87,0% | 84,0% | 89,9% |
| SNP-627 | hsa-miR-423-5p, hsa-miR-891b, hsa-miR-144 | 85,5% | 87,5% | 83,4% |
| SNP-628 | hsa-miR-891b, hsa-miR-148b, hsa-miR-374b | 85,0% | 88,1% | 81,8% |
| SNP-629 | hsa-miR-148b, hsa-miR-374a, hsa-miR-455-3p | 83,4% | 84,3% | 82,6% |
| SNP-630 | hsa-miR-374b, hsa-miR-455-3p, hsa-miR-519b-5p | 85,5% | 89,5% | 81,5% |
| SNP-631 | hsa-miR-374a, hsa-miR-519b-5p, hsa-miR-20a | 81,2% | 82,1% | 80,2% |
| SNP-632 | hsa-miR-455-3p, hsa-miR-20a, hsa-miR-33a | 83,5% | 83,0% | 84,0% |
| SNP-633 | hsa-miR-519b-5p, hsa-miR-33a, hsa-miR-1245 | 76,7% | 76,5% | 77,0% |
| SNP-634 | hsa-miR-20a, hsa-miR-1245, hsa-let-7i* | 78,2% | 75,1% | 81,4% |
| SNP-635 | hsa-miR-33a, hsa-let-7i*, hsa-miR-556-5p | 80,8% | 78,1% | 83,6% |
| SNP-636 | hsa-miR-1245, hsa-miR-556-5p, hsa-miR-320c | 75,7% | 76,0% | 75,4% |
| SNP-637 | hsa-let-7i*, hsa-miR-320c, hsa-miR-301a | 78,8% | 77,8% | 79,7% |
| SNP-638 | hsa-miR-556-5p, hsa-miR-301a, hsa-miR-101 | 77,2% | 72,4% | 82,1% |
| SNP-639 | hsa-miR-320c, hsa-miR-101, hsa-miR-33b | 81,6% | 84,2% | 79,0% |
| SNP-640 | hsa-miR-301a, hsa-miR-33b, hsa-miR-574-3p | 75,3% | 74,2% | 76,4% |
| SNP-641 | hsa-miR-101, hsa-miR-574-3p, hsa-let-7b* | 78,1% | 84,0% | 72,2% |
| SNP-642 | hsa-miR-33b, hsa-let-7b*, hsa-miR-197 | 79,8% | 73,4% | 86,2% |
| SNP-643 | hsa-miR-574-3p, hsa-miR-197, hsa-miR-363 | 75,4% | 79,9% | 70,9% |
| SNP-644 | hsa-let-7b*, hsa-miR-363, hsa-miR-320a | 80,0% | 89,8% | 70,2% |
| SNP-645 | hsa-miR-197, hsa-miR-320a, hsa-miR-1226 | 80,3% | 76,7% | 83,9% |

FIG. 6 (Continued)

| | | | | |
|---|---|---|---|---|
| SNP-646 | hsa-miR-363, hsa-miR-1226, hsa-miR-1283 | 79,4% | 85,3% | 73,6% |
| SNP-647 | hsa-miR-320a, hsa-miR-1283, hsa-miR-720 | 79,2% | 89,3% | 69,0% |
| SNP-648 | hsa-miR-144*, hsa-miR-423-5p, hsa-miR-891b | 87,2% | 85,5% | 89,0% |
| SNP-649 | hsa-miR-423-5p, hsa-miR-891b, hsa-miR-148b | 82,6% | 86,7% | 78,5% |
| SNP-650 | hsa-miR-891b, hsa-miR-148b, hsa-miR-374a | 83,8% | 85,8% | 81,9% |
| SNP-651 | hsa-miR-144, hsa-miR-374b, hsa-miR-455-3p | 83,9% | 84,3% | 83,4% |
| SNP-652 | hsa-miR-148b, hsa-miR-374a, hsa-miR-519b-5p | 79,1% | 80,2% | 78,1% |
| SNP-653 | hsa-miR-374b, hsa-miR-455-3p, hsa-miR-20a | 84,2% | 85,7% | 82,6% |
| SNP-654 | hsa-miR-374a, hsa-miR-519b-5p, hsa-miR-33a | 81,1% | 81,1% | 81,0% |
| SNP-655 | hsa-miR-455-3p, hsa-miR-20a, hsa-miR-1245 | 77,6% | 75,7% | 79,5% |
| SNP-656 | hsa-miR-519b-5p, hsa-miR-33a, hsa-let-7i* | 80,1% | 75,6% | 84,6% |
| SNP-657 | hsa-miR-20a, hsa-miR-1245, hsa-miR-556-5p | 74,4% | 68,7% | 80,0% |
| SNP-658 | hsa-miR-33a, hsa-let-7i*, hsa-miR-320c | 81,7% | 80,7% | 82,6% |
| SNP-659 | hsa-miR-1245, hsa-miR-556-5p, hsa-miR-301a | 75,5% | 72,0% | 79,0% |
| SNP-660 | hsa-let-7i*, hsa-miR-320c, hsa-miR-101 | 79,0% | 81,2% | 76,7% |
| SNP-661 | hsa-miR-556-5p, hsa-miR-301a, hsa-miR-33b | 77,4% | 73,8% | 80,9% |
| SNP-662 | hsa-miR-320c, hsa-miR-101, hsa-miR-574-3p | 75,7% | 83,1% | 68,3% |
| SNP-663 | hsa-miR-301a, hsa-miR-33b, hsa-let-7b* | 83,3% | 82,2% | 84,5% |
| SNP-664 | hsa-miR-101, hsa-miR-574-3p, hsa-miR-197 | 76,3% | 83,8% | 68,8% |
| SNP-665 | hsa-miR-33b, hsa-let-7b*, hsa-miR-363 | 82,7% | 87,5% | 77,9% |
| SNP-666 | hsa-miR-574-3p, hsa-miR-197, hsa-miR-320a | 80,6% | 85,7% | 75,6% |
| SNP-667 | hsa-let-7b*, hsa-miR-363, hsa-miR-1226 | 81,7% | 86,9% | 76,6% |
| SNP-668 | hsa-miR-197, hsa-miR-320a, hsa-miR-1283 | 78,8% | 84,7% | 72,8% |
| SNP-669 | hsa-miR-363, hsa-miR-1226, hsa-miR-720 | 74,9% | 72,4% | 77,4% |
| SNP-670 | hsa-miR-148a, hsa-miR-423-5p, hsa-miR-144 | 90,2% | 90,8% | 89,7% |
| SNP-671 | hsa-miR-423-5p, hsa-miR-20b, hsa-miR-148b | 86,6% | 86,8% | 86,5% |
| SNP-672 | hsa-miR-20b, hsa-miR-891b, hsa-miR-374b | 85,5% | 88,4% | 82,6% |
| SNP-673 | hsa-miR-891b, hsa-miR-144, hsa-miR-374a | 86,8% | 90,8% | 82,9% |
| SNP-674 | hsa-miR-144, hsa-miR-148b, hsa-miR-455-3p | 77,5% | 76,2% | 78,8% |
| SNP-675 | hsa-miR-148b, hsa-miR-374b, hsa-miR-519b-5p | 83,2% | 83,7% | 82,8% |
| SNP-676 | hsa-miR-374b, hsa-miR-374a, hsa-miR-20a | 77,8% | 72,6% | 83,1% |
| SNP-677 | hsa-miR-374a, hsa-miR-455-3p, hsa-miR-33a | 86,4% | 90,1% | 82,7% |
| SNP-678 | hsa-miR-455-3p, hsa-miR-519b-5p, hsa-miR-1245 | 76,1% | 78,3% | 73,8% |
| SNP-679 | hsa-miR-519b-5p, hsa-miR-20a, hsa-let-7i* | 81,1% | 77,1% | 85,1% |
| SNP-680 | hsa-miR-20a, hsa-miR-33a, hsa-miR-556-5p | 81,2% | 78,6% | 83,8% |
| SNP-681 | hsa-miR-33a, hsa-miR-1245, hsa-miR-320c | 78,6% | 80,7% | 76,6% |
| SNP-682 | hsa-miR-1245, hsa-let-7i*, hsa-miR-301a | 76,2% | 74,1% | 78,2% |
| SNP-683 | hsa-let-7i*, hsa-miR-556-5p, hsa-miR-101 | 80,6% | 77,3% | 84,0% |
| SNP-684 | hsa-miR-556-5p, hsa-miR-320c, hsa-miR-33b | 79,2% | 77,0% | 81,5% |
| SNP-685 | hsa-miR-320c, hsa-miR-301a, hsa-miR-574-3p | 76,2% | 81,4% | 71,1% |
| SNP-686 | hsa-miR-301a, hsa-miR-101, hsa-let-7b* | 81,3% | 84,2% | 78,3% |
| SNP-687 | hsa-miR-101, hsa-miR-33b, hsa-miR-197 | 78,0% | 82,5% | 73,4% |
| SNP-688 | hsa-miR-33b, hsa-miR-574-3p, hsa-miR-363 | 77,6% | 81,5% | 73,6% |
| SNP-689 | hsa-miR-574-3p, hsa-let-7b*, hsa-miR-320a | 79,8% | 92,0% | 67,7% |
| SNP-690 | hsa-let-7b*, hsa-miR-197, hsa-miR-1226 | 76,4% | 71,1% | 81,8% |
| SNP-691 | hsa-miR-197, hsa-miR-363, hsa-miR-1283 | 78,6% | 85,8% | 71,5% |
| SNP-692 | hsa-miR-363, hsa-miR-320a, hsa-miR-720 | 70,4% | 82,1% | 58,8% |
| SNP-693 | hsa-miR-423-5p, hsa-miR-144, hsa-miR-148b | 84,0% | 88,9% | 79,1% |
| SNP-694 | hsa-miR-20b, hsa-miR-148b, hsa-miR-374b | 83,4% | 81,0% | 85,8% |
| SNP-695 | hsa-miR-891b, hsa-miR-374b, hsa-miR-374a | 85,9% | 88,5% | 83,4% |
| SNP-696 | hsa-miR-144, hsa-miR-374a, hsa-miR-455-3p | 82,6% | 79,8% | 85,4% |
| SNP-697 | hsa-miR-148b, hsa-miR-455-3p, hsa-miR-519b-5p | 80,5% | 84,2% | 76,8% |
| SNP-698 | hsa-miR-374b, hsa-miR-519b-5p, hsa-miR-20a | 83,4% | 83,2% | 83,7% |
| SNP-699 | hsa-miR-374a, hsa-miR-20a, hsa-miR-33a | 83,2% | 83,4% | 82,9% |

FIG. 6 (Continued)

| SNP-700 | hsa-miR-455-3p, hsa-miR-33a, hsa-miR-1245 | 76,8% | 79,7% | 74,0% |
|---|---|---|---|---|
| SNP-701 | hsa-miR-519b-5p, hsa-miR-1245, hsa-let-7i* | 76,4% | 73,7% | 79,0% |
| SNP-702 | hsa-miR-20a, hsa-let-7i*, hsa-miR-556-5p | 77,4% | 69,8% | 85,0% |
| SNP-703 | hsa-miR-33a, hsa-miR-556-5p, hsa-miR-320c | 78,9% | 81,6% | 76,2% |
| SNP-704 | hsa-miR-1245, hsa-miR-320c, hsa-miR-301a | 76,5% | 78,4% | 74,6% |
| SNP-705 | hsa-let-7i*, hsa-miR-301a, hsa-miR-101 | 78,4% | 77,0% | 79,8% |
| SNP-706 | hsa-miR-556-5p, hsa-miR-101, hsa-miR-33b | 83,1% | 81,4% | 84,9% |
| SNP-707 | hsa-miR-320c, hsa-miR-33b, hsa-miR-574-3p | 76,4% | 80,2% | 72,6% |
| SNP-708 | hsa-miR-301a, hsa-miR-574-3p, hsa-let-7b* | 76,1% | 82,3% | 69,8% |
| SNP-709 | hsa-miR-101, hsa-let-7b*, hsa-miR-197 | 79,2% | 79,4% | 79,1% |
| SNP-710 | hsa-miR-33b, hsa-miR-197, hsa-miR-363 | 79,4% | 79,5% | 79,4% |
| SNP-711 | hsa-miR-574-3p, hsa-miR-363, hsa-miR-320a | 73,5% | 81,3% | 65,7% |
| SNP-712 | hsa-let-7b*, hsa-miR-320a, hsa-miR-1226 | 75,7% | 80,6% | 70,7% |
| SNP-713 | hsa-miR-197, hsa-miR-1226, hsa-miR-1283 | 81,9% | 70,5% | 93,3% |
| SNP-714 | hsa-miR-363, hsa-miR-1283, hsa-miR-720 | 76,6% | 82,4% | 70,8% |
| SNP-715 | hsa-miR-423-5p, hsa-miR-148a | 87,6% | 85,1% | 90,0% |
| SNP-716 | hsa-miR-20b, hsa-miR-1245 | 81,4% | 78,0% | 84,9% |
| SNP-717 | hsa-miR-1245, hsa-miR-144 | 79,0% | 73,0% | 85,0% |
| SNP-718 | hsa-miR-20a, hsa-miR-496 | 73,4% | 81,7% | 65,1% |
| SNP-719 | hsa-miR-496, hsa-miR-320c | 72,8% | 87,4% | 58,3% |
| SNP-720 | hsa-miR-101, hsa-miR-374b | 72,9% | 72,9% | 72,9% |
| SNP-721 | hsa-miR-374b, hsa-miR-1283 | 81,7% | 83,7% | 79,8% |
| SNP-722 | hsa-miR-1283, hsa-miR-891b | 81,3% | 82,2% | 80,5% |
| SNP-723 | hsa-miR-891b, hsa-miR-574-3p | 79,7% | 84,5% | 74,9% |
| SNP-724 | hsa-miR-574-3p, hsa-miR-367 | 73,8% | 82,9% | 64,6% |
| SNP-725 | hsa-miR-367, hsa-miR-21 | 72,4% | 74,9% | 69,9% |
| SNP-726 | hsa-miR-21, hsa-miR-374a | 72,5% | 66,0% | 79,0% |
| SNP-727 | hsa-miR-374a, hsa-let-7b* | 81,3% | 84,2% | 78,5% |
| SNP-728 | hsa-miR-320a, hsa-miR-320b | 68,6% | 83,5% | 53,7% |
| SNP-729 | hsa-miR-720, hsa-miR-519b-5p | 74,2% | 82,6% | 65,8% |
| SNP-730 | hsa-miR-519b-5p, hsa-miR-320d | 75,8% | 78,1% | 73,6% |
| SNP-731 | hsa-miR-320d, hsa-let-7i* | 77,0% | 72,3% | 81,7% |
| SNP-732 | hsa-let-7i*, hsa-miR-363 | 82,2% | 86,3% | 78,1% |
| SNP-733 | hsa-miR-363, hsa-miR-301a | 78,6% | 78,8% | 78,3% |
| SNP-734 | hsa-miR-148a, hsa-miR-1245 | 79,1% | 83,5% | 74,6% |
| SNP-735 | hsa-miR-1245, hsa-miR-148b | 76,2% | 85,0% | 67,4% |
| SNP-736 | hsa-miR-148b, hsa-miR-496 | 77,0% | 80,7% | 73,2% |
| SNP-737 | hsa-miR-20a, hsa-miR-320c | 70,9% | 76,8% | 65,0% |
| SNP-738 | hsa-miR-496, hsa-miR-101 | 74,5% | 80,7% | 68,2% |
| SNP-739 | hsa-miR-320c, hsa-miR-374b | 75,8% | 76,3% | 75,4% |
| SNP-740 | hsa-miR-101, hsa-miR-1283 | 76,5% | 80,4% | 72,6% |
| SNP-741 | hsa-miR-374b, hsa-miR-891b | 86,3% | 90,1% | 82,6% |
| SNP-742 | hsa-miR-1283, hsa-miR-574-3p | 76,3% | 84,9% | 67,7% |
| SNP-743 | hsa-miR-891b, hsa-miR-367 | 81,2% | 83,0% | 79,3% |
| SNP-744 | hsa-miR-367, hsa-miR-374a | 75,6% | 75,0% | 76,1% |
| SNP-745 | hsa-miR-21, hsa-let-7b* | 80,3% | 86,4% | 74,2% |
| SNP-746 | hsa-miR-374a, hsa-miR-320a | 71,0% | 84,5% | 57,6% |
| SNP-747 | hsa-let-7b*, hsa-miR-320b | 74,7% | 79,4% | 70,0% |
| SNP-748 | hsa-miR-320b, hsa-miR-519b-5p | 77,0% | 82,9% | 71,0% |
| SNP-749 | hsa-miR-720, hsa-miR-320d | 70,9% | 83,3% | 58,6% |
| SNP-750 | hsa-miR-519b-5p, hsa-let-7i* | 73,1% | 70,4% | 75,8% |
| SNP-751 | hsa-miR-320d, hsa-miR-363 | 75,2% | 83,0% | 67,5% |
| SNP-752 | hsa-miR-363, hsa-miR-455-3p | 79,6% | 89,4% | 69,8% |
| SNP-753 | hsa-miR-423-5p, hsa-miR-1245 | 82,1% | 87,3% | 77,0% |

FIG. 6 (Continued)

| SNP-754 | hsa-miR-1245, hsa-miR-20a | 74,9% | 75,4% | 74,3% |
|---|---|---|---|---|
| SNP-755 | hsa-miR-144, hsa-miR-496 | 75,1% | 75,1% | 75,0% |
| SNP-756 | hsa-miR-148b, hsa-miR-320c | 73,5% | 72,6% | 74,4% |
| SNP-757 | hsa-miR-20a, hsa-miR-101 | 74,2% | 78,7% | 69,7% |
| SNP-758 | hsa-miR-496, hsa-miR-374b | 75,2% | 72,6% | 77,8% |
| SNP-759 | hsa-miR-320c, hsa-miR-1283 | 77,0% | 84,2% | 69,9% |
| SNP-760 | hsa-miR-101, hsa-miR-891b | 79,9% | 81,4% | 78,3% |
| SNP-761 | hsa-miR-374b, hsa-miR-574-3p | 72,2% | 68,5% | 75,8% |
| SNP-762 | hsa-miR-1283, hsa-miR-367 | 74,1% | 77,7% | 70,6% |
| SNP-763 | hsa-miR-891b, hsa-miR-21 | 86,0% | 91,7% | 80,4% |
| SNP-764 | hsa-miR-574-3p, hsa-miR-374a | 75,0% | 81,5% | 68,6% |
| SNP-765 | hsa-miR-367, hsa-let-7b* | 75,5% | 74,8% | 76,2% |
| SNP-766 | hsa-miR-21, hsa-miR-320a | 67,0% | 75,9% | 58,0% |
| SNP-767 | hsa-let-7b*, hsa-miR-720 | 75,2% | 82,9% | 67,6% |
| SNP-768 | hsa-miR-320a, hsa-miR-519b-5p | 79,2% | 88,0% | 70,3% |
| SNP-769 | hsa-miR-320b, hsa-miR-320d | 69,9% | 74,6% | 65,2% |
| SNP-770 | hsa-miR-720, hsa-let-7i* | 72,9% | 76,7% | 69,0% |
| SNP-771 | hsa-miR-519b-5p, hsa-miR-363 | 83,0% | 90,2% | 75,9% |
| SNP-772 | hsa-miR-320d, hsa-miR-301a | 73,0% | 67,2% | 78,9% |
| SNP-773 | hsa-let-7i*, hsa-miR-455-3p | 73,0% | 71,8% | 74,2% |
| SNP-774 | hsa-miR-144*, hsa-miR-423-5p, hsa-miR-148a | 87,9% | 89,8% | 86,1% |
| SNP-775 | hsa-miR-423-5p, hsa-miR-148a, hsa-miR-20b | 90,5% | 90,9% | 90,2% |
| SNP-776 | hsa-miR-148a, hsa-miR-20b, hsa-miR-1245 | 87,0% | 86,6% | 87,4% |
| SNP-777 | hsa-miR-20b, hsa-miR-1245, hsa-miR-144 | 80,6% | 73,4% | 87,9% |
| SNP-778 | hsa-miR-1245, hsa-miR-144, hsa-miR-148b | 77,2% | 75,8% | 78,7% |
| SNP-779 | hsa-miR-148b, hsa-miR-20a, hsa-miR-496 | 79,0% | 81,4% | 76,7% |
| SNP-780 | hsa-miR-20a, hsa-miR-496, hsa-miR-320c | 78,7% | 88,4% | 69,0% |
| SNP-781 | hsa-miR-496, hsa-miR-320c, hsa-miR-101 | 78,2% | 87,8% | 68,6% |
| SNP-782 | hsa-miR-320c, hsa-miR-101, hsa-miR-374b | 73,6% | 73,7% | 73,4% |
| SNP-783 | hsa-miR-101, hsa-miR-374b, hsa-miR-1283 | 83,1% | 81,0% | 85,2% |
| SNP-784 | hsa-miR-374b, hsa-miR-1283, hsa-miR-891b | 87,6% | 88,5% | 86,6% |
| SNP-785 | hsa-miR-1283, hsa-miR-891b, hsa-miR-574-3p | 80,2% | 81,7% | 78,6% |
| SNP-786 | hsa-miR-891b, hsa-miR-574-3p, hsa-miR-367 | 81,4% | 84,3% | 78,5% |
| SNP-787 | hsa-miR-574-3p, hsa-miR-367, hsa-miR-21 | 72,5% | 79,6% | 65,4% |
| SNP-788 | hsa-miR-367, hsa-miR-21, hsa-miR-374a | 76,3% | 78,1% | 74,6% |
| SNP-789 | hsa-miR-21, hsa-miR-374a, hsa-let-7b* | 82,6% | 88,2% | 77,0% |
| SNP-790 | hsa-miR-374a, hsa-let-7b*, hsa-miR-320a | 78,9% | 84,3% | 73,5% |
| SNP-791 | hsa-let-7b*, hsa-miR-320a, hsa-miR-320b | 75,7% | 86,4% | 65,0% |
| SNP-792 | hsa-miR-320a, hsa-miR-320b, hsa-miR-720 | 74,5% | 89,0% | 60,0% |
| SNP-793 | hsa-miR-320b, hsa-miR-720, hsa-miR-519b-5p | 80,4% | 91,8% | 68,9% |
| SNP-794 | hsa-miR-720, hsa-miR-519b-5p, hsa-miR-320d | 77,2% | 86,7% | 67,7% |
| SNP-795 | hsa-miR-519b-5p, hsa-miR-320d, hsa-let-7i* | 77,7% | 78,1% | 77,3% |
| SNP-796 | hsa-miR-320d, hsa-let-7i*, hsa-miR-363 | 82,6% | 87,7% | 77,4% |
| SNP-797 | hsa-let-7i*, hsa-miR-363, hsa-miR-301a | 83,7% | 89,4% | 78,0% |
| SNP-798 | hsa-miR-363, hsa-miR-301a, hsa-miR-455-3p | 81,5% | 87,8% | 75,3% |
| SNP-799 | hsa-miR-423-5p, hsa-miR-148a, hsa-miR-1245 | 86,7% | 87,4% | 85,9% |
| SNP-800 | hsa-miR-20b, hsa-miR-1245, hsa-miR-148b | 82,1% | 78,2% | 85,9% |
| SNP-801 | hsa-miR-1245, hsa-miR-144, hsa-miR-20a | 79,1% | 71,5% | 86,7% |
| SNP-802 | hsa-miR-144, hsa-miR-148b, hsa-miR-496 | 76,8% | 76,6% | 76,9% |
| SNP-803 | hsa-miR-148b, hsa-miR-20a, hsa-miR-320c | 74,2% | 71,3% | 77,2% |
| SNP-804 | hsa-miR-20a, hsa-miR-496, hsa-miR-101 | 77,4% | 81,4% | 73,4% |
| SNP-805 | hsa-miR-496, hsa-miR-320c, hsa-miR-374b | 74,2% | 78,7% | 69,7% |
| SNP-806 | hsa-miR-320c, hsa-miR-101, hsa-miR-1283 | 77,7% | 77,3% | 78,1% |
| SNP-807 | hsa-miR-101, hsa-miR-374b, hsa-miR-891b | 85,4% | 86,3% | 84,5% |

FIG. 6 (Continued)

| SNP-808 | hsa-miR-374b, hsa-miR-1283, hsa-miR-574-3p | 82,4% | 87,3% | 77,4% |
|---|---|---|---|---|
| SNP-809 | hsa-miR-1283, hsa-miR-891b, hsa-miR-367 | 83,4% | 81,5% | 85,3% |
| SNP-810 | hsa-miR-891b, hsa-miR-574-3p, hsa-miR-21 | 87,3% | 91,0% | 83,6% |
| SNP-811 | hsa-miR-574-3p, hsa-miR-367, hsa-miR-374a | 76,5% | 81,9% | 71,0% |
| SNP-812 | hsa-miR-367, hsa-miR-21, hsa-let-7b* | 80,7% | 82,1% | 79,3% |
| SNP-813 | hsa-miR-21, hsa-miR-374a, hsa-miR-320a | 72,0% | 74,7% | 69,3% |
| SNP-814 | hsa-miR-374a, hsa-let-7b*, hsa-miR-320b | 80,7% | 83,0% | 78,4% |
| SNP-815 | hsa-let-7b*, hsa-miR-320a, hsa-miR-720 | 81,4% | 88,3% | 74,5% |
| SNP-816 | hsa-miR-320a, hsa-miR-320b, hsa-miR-519b-5p | 79,2% | 88,4% | 70,0% |
| SNP-817 | hsa-miR-320b, hsa-miR-720, hsa-miR-320d | 75,3% | 85,0% | 65,6% |
| SNP-818 | hsa-miR-720, hsa-miR-519b-5p, hsa-let-7i* | 76,3% | 83,3% | 69,4% |
| SNP-819 | hsa-miR-519b-5p, hsa-miR-320d, hsa-miR-363 | 81,8% | 88,8% | 74,8% |
| SNP-820 | hsa-miR-320d, hsa-let-7i*, hsa-miR-301a | 81,6% | 79,2% | 84,0% |
| SNP-821 | hsa-let-7i*, hsa-miR-363, hsa-miR-455-3p | 83,2% | 92,0% | 74,5% |
| SNP-822 | hsa-miR-423-5p, hsa-miR-20b, hsa-miR-1245 | 88,7% | 88,2% | 89,3% |
| SNP-823 | hsa-miR-148a, hsa-miR-1245, hsa-miR-144 | 84,6% | 84,2% | 85,0% |
| SNP-824 | hsa-miR-1245, hsa-miR-148b, hsa-miR-20a | 76,8% | 79,4% | 74,2% |
| SNP-825 | hsa-miR-144, hsa-miR-20a, hsa-miR-496 | 76,5% | 72,7% | 80,3% |
| SNP-826 | hsa-miR-148b, hsa-miR-496, hsa-miR-320c | 78,0% | 85,6% | 70,5% |
| SNP-827 | hsa-miR-20a, hsa-miR-320c, hsa-miR-101 | 73,4% | 76,7% | 70,2% |
| SNP-828 | hsa-miR-496, hsa-miR-101, hsa-miR-374b | 76,9% | 79,4% | 74,4% |
| SNP-829 | hsa-miR-320c, hsa-miR-374b, hsa-miR-1283 | 79,6% | 82,5% | 76,6% |
| SNP-830 | hsa-miR-101, hsa-miR-1283, hsa-miR-891b | 83,0% | 83,8% | 82,3% |
| SNP-831 | hsa-miR-374b, hsa-miR-891b, hsa-miR-574-3p | 85,9% | 89,0% | 82,8% |
| SNP-832 | hsa-miR-1283, hsa-miR-574-3p, hsa-miR-367 | 76,8% | 82,6% | 71,0% |
| SNP-833 | hsa-miR-891b, hsa-miR-367, hsa-miR-21 | 84,8% | 89,4% | 80,3% |
| SNP-834 | hsa-miR-574-3p, hsa-miR-21, hsa-miR-374a | 76,6% | 81,6% | 71,5% |
| SNP-835 | hsa-miR-367, hsa-miR-374a, hsa-let-7b* | 80,4% | 79,4% | 81,5% |
| SNP-836 | hsa-miR-21, hsa-let-7b*, hsa-miR-320a | 81,0% | 89,9% | 72,2% |
| SNP-837 | hsa-miR-374a, hsa-miR-320a, hsa-miR-320b | 71,5% | 81,0% | 62,0% |
| SNP-838 | hsa-let-7b*, hsa-miR-320b, hsa-miR-720 | 78,2% | 86,1% | 70,2% |
| SNP-839 | hsa-miR-320a, hsa-miR-720, hsa-miR-519b-5p | 82,6% | 92,7% | 72,4% |
| SNP-840 | hsa-miR-320b, hsa-miR-519b-5p, hsa-miR-320d | 75,2% | 80,5% | 69,9% |
| SNP-841 | hsa-miR-720, hsa-miR-320d, hsa-let-7i* | 77,9% | 88,4% | 67,4% |
| SNP-842 | hsa-miR-519b-5p, hsa-let-7i*, hsa-miR-363 | 85,4% | 94,8% | 76,1% |
| SNP-843 | hsa-miR-320d, hsa-miR-363, hsa-miR-301a | 76,2% | 75,8% | 76,6% |
| SNP-844 | hsa-let-7i*, hsa-miR-301a, hsa-miR-455-3p | 81,5% | 79,2% | 83,8% |
| SNP-845 | hsa-miR-144*, hsa-miR-148a, hsa-miR-1245 | 87,4% | 85,9% | 88,9% |
| SNP-846 | hsa-miR-148a, hsa-miR-1245, hsa-miR-148b | 84,2% | 91,2% | 77,3% |
| SNP-847 | hsa-miR-1245, hsa-miR-148b, hsa-miR-496 | 78,6% | 80,9% | 76,4% |
| SNP-848 | hsa-miR-144, hsa-miR-20a, hsa-miR-320c | 74,7% | 71,3% | 78,1% |
| SNP-849 | hsa-miR-148b, hsa-miR-496, hsa-miR-101 | 76,5% | 83,6% | 69,4% |
| SNP-850 | hsa-miR-20a, hsa-miR-320c, hsa-miR-374b | 76,7% | 71,4% | 81,9% |
| SNP-851 | hsa-miR-496, hsa-miR-101, hsa-miR-1283 | 82,4% | 82,3% | 82,4% |
| SNP-852 | hsa-miR-320c, hsa-miR-374b, hsa-miR-891b | 83,4% | 87,0% | 79,8% |
| SNP-853 | hsa-miR-101, hsa-miR-1283, hsa-miR-574-3p | 79,8% | 87,3% | 72,2% |
| SNP-854 | hsa-miR-374b, hsa-miR-891b, hsa-miR-367 | 85,8% | 88,2% | 83,4% |
| SNP-855 | hsa-miR-1283, hsa-miR-574-3p, hsa-miR-21 | 79,2% | 87,1% | 71,2% |
| SNP-856 | hsa-miR-891b, hsa-miR-367, hsa-miR-374a | 83,8% | 84,2% | 83,3% |
| SNP-857 | hsa-miR-574-3p, hsa-miR-21, hsa-let-7b* | 77,4% | 87,4% | 67,4% |
| SNP-858 | hsa-miR-367, hsa-miR-374a, hsa-miR-320a | 75,4% | 82,3% | 68,5% |
| SNP-859 | hsa-miR-21, hsa-let-7b*, hsa-miR-320b | 78,8% | 83,9% | 73,6% |
| SNP-860 | hsa-miR-374a, hsa-miR-320a, hsa-miR-720 | 72,0% | 84,9% | 59,0% |
| SNP-861 | hsa-let-7b*, hsa-miR-320b, hsa-miR-519b-5p | 80,2% | 84,5% | 76,0% |

FIG. 6 (Continued)

| SNP-862 | hsa-miR-320a, hsa-miR-720, hsa-miR-320d | 74,7% | 91,7% | 57,8% |
|---|---|---|---|---|
| SNP-863 | hsa-miR-320b, hsa-miR-519b-5p, hsa-let-7i* | 78,8% | 79,7% | 77,9% |
| SNP-864 | hsa-miR-720, hsa-miR-320d, hsa-miR-363 | 71,6% | 78,6% | 64,6% |
| SNP-865 | hsa-miR-519b-5p, hsa-let-7i*, hsa-miR-301a | 75,9% | 77,4% | 74,4% |
| SNP-866 | hsa-miR-320d, hsa-miR-363, hsa-miR-455-3p | 77,5% | 85,4% | 69,5% |
| SNP-867 | hsa-miR-144*, hsa-miR-423-5p, hsa-miR-1245 | 85,6% | 78,3% | 92,9% |
| SNP-868 | hsa-miR-423-5p, hsa-miR-148a, hsa-miR-144 | 89,9% | 89,8% | 90,0% |
| SNP-869 | hsa-miR-20b, hsa-miR-1245, hsa-miR-20a | 80,1% | 77,4% | 82,7% |
| SNP-870 | hsa-miR-1245, hsa-miR-144, hsa-miR-496 | 80,4% | 78,9% | 82,0% |
| SNP-871 | hsa-miR-144, hsa-miR-148b, hsa-miR-320c | 73,3% | 67,4% | 79,2% |
| SNP-872 | hsa-miR-148b, hsa-miR-20a, hsa-miR-101 | 74,9% | 73,4% | 76,4% |
| SNP-873 | hsa-miR-20a, hsa-miR-496, hsa-miR-374b | 79,6% | 77,2% | 82,1% |
| SNP-874 | hsa-miR-496, hsa-miR-320c, hsa-miR-1283 | 80,3% | 80,9% | 79,8% |
| SNP-875 | hsa-miR-320c, hsa-miR-101, hsa-miR-891b | 79,5% | 83,6% | 75,4% |
| SNP-876 | hsa-miR-101, hsa-miR-374b, hsa-miR-574-3p | 72,8% | 72,2% | 73,4% |
| SNP-877 | hsa-miR-374b, hsa-miR-1283, hsa-miR-367 | 83,3% | 80,3% | 86,2% |
| SNP-878 | hsa-miR-1283, hsa-miR-891b, hsa-miR-21 | 88,3% | 88,7% | 87,9% |
| SNP-879 | hsa-miR-891b, hsa-miR-574-3p, hsa-miR-374a | 84,4% | 87,0% | 81,8% |
| SNP-880 | hsa-miR-574-3p, hsa-miR-367, hsa-let-7b* | 76,0% | 82,2% | 69,8% |
| SNP-881 | hsa-miR-367, hsa-miR-21, hsa-miR-320a | 75,0% | 83,0% | 66,9% |
| SNP-882 | hsa-miR-21, hsa-miR-374a, hsa-miR-320b | 69,8% | 67,7% | 71,9% |
| SNP-883 | hsa-miR-374a, hsa-let-7b*, hsa-miR-720 | 77,2% | 82,7% | 71,6% |
| SNP-884 | hsa-let-7b*, hsa-miR-320a, hsa-miR-519b-5p | 80,2% | 89,1% | 71,3% |
| SNP-885 | hsa-miR-320a, hsa-miR-320b, hsa-miR-320d | 68,9% | 81,3% | 56,6% |
| SNP-886 | hsa-miR-320b, hsa-miR-720, hsa-let-7i* | 78,3% | 87,5% | 69,0% |
| SNP-887 | hsa-miR-720, hsa-miR-519b-5p, hsa-miR-363 | 81,9% | 90,4% | 73,4% |
| SNP-888 | hsa-miR-519b-5p, hsa-miR-320d, hsa-miR-301a | 77,5% | 79,6% | 75,4% |
| SNP-889 | hsa-miR-320d, hsa-let-7i*, hsa-miR-455-3p | 78,2% | 78,7% | 77,8% |
| SNP-890 | hsa-miR-144*, hsa-miR-20b, hsa-miR-1245 | 84,8% | 77,4% | 92,2% |
| SNP-891 | hsa-miR-423-5p, hsa-miR-1245, hsa-miR-144 | 85,5% | 88,3% | 82,6% |
| SNP-892 | hsa-miR-20b, hsa-miR-148b, hsa-miR-20a | 78,5% | 73,6% | 83,4% |
| SNP-893 | hsa-miR-1245, hsa-miR-20a, hsa-miR-496 | 76,7% | 74,5% | 79,0% |
| SNP-894 | hsa-miR-144, hsa-miR-496, hsa-miR-320c | 78,5% | 86,7% | 70,2% |
| SNP-895 | hsa-miR-148b, hsa-miR-320c, hsa-miR-101 | 70,9% | 71,3% | 70,6% |
| SNP-896 | hsa-miR-20a, hsa-miR-101, hsa-miR-374b | 75,9% | 69,8% | 82,1% |
| SNP-897 | hsa-miR-496, hsa-miR-374b, hsa-miR-1283 | 82,8% | 85,8% | 79,9% |
| SNP-898 | hsa-miR-320c, hsa-miR-1283, hsa-miR-891b | 83,4% | 86,9% | 80,0% |
| SNP-899 | hsa-miR-101, hsa-miR-891b, hsa-miR-574-3p | 84,6% | 89,7% | 79,5% |
| SNP-900 | hsa-miR-374b, hsa-miR-574-3p, hsa-miR-367 | 74,9% | 79,7% | 70,1% |
| SNP-901 | hsa-miR-1283, hsa-miR-367, hsa-miR-21 | 80,6% | 82,7% | 78,4% |
| SNP-902 | hsa-miR-891b, hsa-miR-21, hsa-miR-374a | 84,6% | 88,3% | 80,9% |
| SNP-903 | hsa-miR-574-3p, hsa-miR-374a, hsa-let-7b* | 75,6% | 80,1% | 71,0% |
| SNP-904 | hsa-miR-367, hsa-let-7b*, hsa-miR-320a | 78,7% | 85,9% | 71,5% |
| SNP-905 | hsa-miR-21, hsa-miR-320a, hsa-miR-320b | 69,2% | 75,4% | 63,1% |
| SNP-906 | hsa-let-7b*, hsa-miR-720, hsa-miR-519b-5p | 77,8% | 82,1% | 73,4% |
| SNP-907 | hsa-miR-320a, hsa-miR-519b-5p, hsa-miR-320d | 78,4% | 86,9% | 70,0% |
| SNP-908 | hsa-miR-320b, hsa-miR-320d, hsa-let-7i* | 77,0% | 76,6% | 77,4% |
| SNP-909 | hsa-miR-720, hsa-let-7i*, hsa-miR-363 | 78,4% | 81,8% | 75,0% |
| SNP-910 | hsa-miR-519b-5p, hsa-miR-363, hsa-miR-301a | 82,8% | 89,5% | 76,0% |
| SNP-911 | hsa-miR-320d, hsa-miR-301a, hsa-miR-455-3p | 81,2% | 81,5% | 80,8% |

SEQUENCE LISTING

<160> NUMBER OF SEQ ID NOS: 962

<210> SEQ ID NO 1
<211> LENGTH: 22
<212> TYPE: RNA
<213> ORGANISM: Homo sapiens

<400> SEQUENCE: 1
caagcucgug ucugugdgguc cg                                              22

<210> SEQ ID NO 2
<211> LENGTH: 22
<212> TYPE: RNA
<213> ORGANISM: Homo sapiens

<400> SEQUENCE: 2
cacccguaga accgaccuug cg                                               22

<210> SEQ ID NO 3
<211> LENGTH: 22
<212> TYPE: RNA
<213> ORGANISM: Homo sapiens

<400> SEQUENCE: 3
caagcucgcu ucuauggguc ug                                               22

<210> SEQ ID NO 4
<211> LENGTH: 22
<212> TYPE: RNA
<213> ORGANISM: Homo sapiens

<400> SEQUENCE: 4
aacccguaga uccgaucuug ug                                               22

<210> SEQ ID NO 5
<211> LENGTH: 22
<212> TYPE: RNA
<213> ORGANISM: Homo sapiens

<400> SEQUENCE: 5
ugagguagua aguuguauug uu                                               22

<210> SEQ ID NO 6
<211> LENGTH: 22
<212> TYPE: RNA
<213> ORGANISM: Homo sapiens

<400> SEQUENCE: 6
aaucaugugc agugccaaua ug                                               22

<210> SEQ ID NO 7
<211> LENGTH: 23
<212> TYPE: RNA
<213> ORGANISM: Homo sapiens

<400> SEQUENCE: 7
uuuggcacua gcacauuuuu gcu                                              23

<210> SEQ ID NO 8
<211> LENGTH: 22
<212> TYPE: RNA
<213> ORGANISM: Homo sapiens

<400> SEQUENCE: 8

-continued uucaacggguauuuauugagca                                          22

<210> SEQ ID NO 9
<211> LENGTH: 22
<212> TYPE: RNA
<213> ORGANISM: Homo sapiens

<400> SEQUENCE: 9 aaauuauuguacaucggaugag                                          22

<210> SEQ ID NO 10
<211> LENGTH: 21
<212> TYPE: RNA
<213> ORGANISM: Homo sapiens

<400> SEQUENCE: 10 cugacuguugccguccuccag                                           21

<210> SEQ ID NO 11
<211> LENGTH: 22
<212> TYPE: RNA
<213> ORGANISM: Homo sapiens

<400> SEQUENCE: 11 ucuucucuguuuuggccaugug                                          22

<210> SEQ ID NO 12
<211> LENGTH: 23
<212> TYPE: RNA
<213> ORGANISM: Homo sapiens

<400> SEQUENCE: 12 cacccggcugugugcacaugugc                                         23

<210> SEQ ID NO 13
<211> LENGTH: 21
<212> TYPE: RNA
<213> ORGANISM: Homo sapiens

<400> SEQUENCE: 13 aaggcagggcccccgcucccc                                           21

<210> SEQ ID NO 14
<211> LENGTH: 24
<212> TYPE: RNA
<213> ORGANISM: Homo sapiens

<400> SEQUENCE: 14 ugggagcugaggcucugggggug                                         24

<210> SEQ ID NO 15
<211> LENGTH: 22
<212> TYPE: RNA
<213> ORGANISM: Homo sapiens

<400> SEQUENCE: 15 ugcccuuaaaggugaacccagu                                          22

<210> SEQ ID NO 16
<211> LENGTH: 22
<212> TYPE: RNA
<213> ORGANISM: Homo sapiens

```
<400> SEQUENCE: 16
auccgcgcuc ugacucucug cc                                          22

<210> SEQ ID NO 17
<211> LENGTH: 22
<212> TYPE: RNA
<213> ORGANISM: Homo sapiens

<400> SEQUENCE: 17
acaguagagg gaggaaucgc ag                                          22

<210> SEQ ID NO 18
<211> LENGTH: 23
<212> TYPE: RNA
<213> ORGANISM: Homo sapiens

<400> SEQUENCE: 18
ccaguuaccg cuuccgcuac cgc                                         23

<210> SEQ ID NO 19
<211> LENGTH: 22
<212> TYPE: RNA
<213> ORGANISM: Homo sapiens

<400> SEQUENCE: 19
ugucuacuac uggagacacu gg                                          22

<210> SEQ ID NO 20
<211> LENGTH: 22
<212> TYPE: RNA
<213> ORGANISM: Homo sapiens

<400> SEQUENCE: 20
ugugcgcagg gagaccucuc cc                                          22

<210> SEQ ID NO 21
<211> LENGTH: 22
<212> TYPE: RNA
<213> ORGANISM: Homo sapiens

<400> SEQUENCE: 21
acugcugagc uagcacuucc cg                                          22

<210> SEQ ID NO 22
<211> LENGTH: 23
<212> TYPE: RNA
<213> ORGANISM: Homo sapiens

<400> SEQUENCE: 22
caaagugcug uucgugcagg uag                                         23

<210> SEQ ID NO 23
<211> LENGTH: 22
<212> TYPE: RNA
<213> ORGANISM: Homo sapiens

<400> SEQUENCE: 23
agggacggga cgcggugcag ug                                          22

<210> SEQ ID NO 24
<211> LENGTH: 22
<212> TYPE: RNA
<213> ORGANISM: Homo sapiens
```

-continued

```
<400> SEQUENCE: 24
uauugcacuc gucccggccu cc                                              22

<210> SEQ ID NO 25
<211> LENGTH: 22
<212> TYPE: RNA
<213> ORGANISM: Homo sapiens

<400> SEQUENCE: 25
ggguggggau uuguugcauu ac                                              22

<210> SEQ ID NO 26
<211> LENGTH: 23
<212> TYPE: RNA
<213> ORGANISM: Homo sapiens

<400> SEQUENCE: 26
agguugggau cgguugcaau gcu                                             23

<210> SEQ ID NO 27
<211> LENGTH: 22
<212> TYPE: RNA
<213> ORGANISM: Homo sapiens

<400> SEQUENCE: 27
uauugcacuu gucccggccu gu                                              22

<210> SEQ ID NO 28
<211> LENGTH: 20
<212> TYPE: RNA
<213> ORGANISM: Homo sapiens

<400> SEQUENCE: 28
agagucuugu gaugucuugc                                                 20

<210> SEQ ID NO 29
<211> LENGTH: 23
<212> TYPE: RNA
<213> ORGANISM: Homo sapiens

<400> SEQUENCE: 29
gcagcagaga auaggacuac guc                                             23

<210> SEQ ID NO 30
<211> LENGTH: 25
<212> TYPE: RNA
<213> ORGANISM: Homo sapiens

<400> SEQUENCE: 30
cuagugaggg acagaaccag gauuc                                           25

<210> SEQ ID NO 31
<211> LENGTH: 20
<212> TYPE: RNA
<213> ORGANISM: Homo sapiens

<400> SEQUENCE: 31
ggggagcugu ggaagcagua                                                 20

<210> SEQ ID NO 32
<211> LENGTH: 22
<212> TYPE: RNA
```

```
<213> ORGANISM: Homo sapiens

<400> SEQUENCE: 32
auaaagcuag auaaccgaaa gu                                              22

<210> SEQ ID NO 33
<211> LENGTH: 23
<212> TYPE: RNA
<213> ORGANISM: Homo sapiens

<400> SEQUENCE: 33
ucuuugguua ucuagcugua uga                                             23

<210> SEQ ID NO 34
<211> LENGTH: 22
<212> TYPE: RNA
<213> ORGANISM: Homo sapiens

<400> SEQUENCE: 34
cacuggcucc uuucugggua ga                                              22

<210> SEQ ID NO 35
<211> LENGTH: 21
<212> TYPE: RNA
<213> ORGANISM: Homo sapiens

<400> SEQUENCE: 35
cacugugucc uuucugcgua g                                               21

<210> SEQ ID NO 36
<211> LENGTH: 22
<212> TYPE: RNA
<213> ORGANISM: Homo sapiens

<400> SEQUENCE: 36
ugcaacuuac cugagucauu ga                                              22

<210> SEQ ID NO 37
<211> LENGTH: 22
<212> TYPE: RNA
<213> ORGANISM: Homo sapiens

<400> SEQUENCE: 37
ugcaacgaac cugagccacu ga                                              22

<210> SEQ ID NO 38
<211> LENGTH: 21
<212> TYPE: RNA
<213> ORGANISM: Homo sapiens

<400> SEQUENCE: 38
uacuuggaaa ggcaucaguu g                                               21

<210> SEQ ID NO 39
<211> LENGTH: 21
<212> TYPE: RNA
<213> ORGANISM: Homo sapiens

<400> SEQUENCE: 39
uuaauaucgg acaaccauug u                                               21

<210> SEQ ID NO 40
<211> LENGTH: 22
```

```
<212> TYPE: RNA
<213> ORGANISM: Homo sapiens

<400> SEQUENCE: 40
gacugacacc ucuuugggug aa                                        22

<210> SEQ ID NO 41
<211> LENGTH: 21
<212> TYPE: RNA
<213> ORGANISM: Homo sapiens

<400> SEQUENCE: 41
uacucaaaaa gcugucaguc a                                         21

<210> SEQ ID NO 42
<211> LENGTH: 22
<212> TYPE: RNA
<213> ORGANISM: Homo sapiens

<400> SEQUENCE: 42
gugaacgggc gccaucccga gg                                        22

<210> SEQ ID NO 43
<211> LENGTH: 23
<212> TYPE: RNA
<213> ORGANISM: Homo sapiens

<400> SEQUENCE: 43
cgggucggag uuagcucaag cgg                                       23

<210> SEQ ID NO 44
<211> LENGTH: 21
<212> TYPE: RNA
<213> ORGANISM: Homo sapiens

<400> SEQUENCE: 44
cgcgggugcu uacugacccu u                                         21

<210> SEQ ID NO 45
<211> LENGTH: 22
<212> TYPE: RNA
<213> ORGANISM: Homo sapiens

<400> SEQUENCE: 45
uccauuacac uacccugccu cu                                        22

<210> SEQ ID NO 46
<211> LENGTH: 22
<212> TYPE: RNA
<213> ORGANISM: Homo sapiens

<400> SEQUENCE: 46
aggcagcggg guguagugga ua                                        22

<210> SEQ ID NO 47
<211> LENGTH: 21
<212> TYPE: RNA
<213> ORGANISM: Homo sapiens

<400> SEQUENCE: 47
uccucuucuc ccuccuccca g                                         21

<210> SEQ ID NO 48
```

```
<211> LENGTH: 20
<212> TYPE: RNA
<213> ORGANISM: Homo sapiens

<400> SEQUENCE: 48
guagaggaga uggcgcaggg                                                   20

<210> SEQ ID NO 49
<211> LENGTH: 22
<212> TYPE: RNA
<213> ORGANISM: Homo sapiens

<400> SEQUENCE: 49
uggauuucuu ugugaaucac ca                                                22

<210> SEQ ID NO 50
<211> LENGTH: 22
<212> TYPE: RNA
<213> ORGANISM: Homo sapiens

<400> SEQUENCE: 50
uggugguuua caaaguaauu ca                                                22

<210> SEQ ID NO 51
<211> LENGTH: 22
<212> TYPE: RNA
<213> ORGANISM: Homo sapiens

<400> SEQUENCE: 51
uauaccucag uuuuaucagg ug                                                22

<210> SEQ ID NO 52
<211> LENGTH: 21
<212> TYPE: RNA
<213> ORGANISM: Homo sapiens

<400> SEQUENCE: 52
ccuggaaaca cugagguugu g                                                 21

<210> SEQ ID NO 53
<211> LENGTH: 22
<212> TYPE: RNA
<213> ORGANISM: Homo sapiens

<400> SEQUENCE: 53
cugcccuggc ccgagggacc ga                                                22

<210> SEQ ID NO 54
<211> LENGTH: 21
<212> TYPE: RNA
<213> ORGANISM: Homo sapiens

<400> SEQUENCE: 54
gcaggaacuu gugagucucc u                                                 21

<210> SEQ ID NO 55
<211> LENGTH: 23
<212> TYPE: RNA
<213> ORGANISM: Homo sapiens

<400> SEQUENCE: 55
caguaacaaa gauucauccu ugu                                               23
```

```
<210> SEQ ID NO 56
<211> LENGTH: 23
<212> TYPE: RNA
<213> ORGANISM: Homo sapiens

<400> SEQUENCE: 56
uccaguacca cgugucaggg cca                                          23

<210> SEQ ID NO 57
<211> LENGTH: 22
<212> TYPE: RNA
<213> ORGANISM: Homo sapiens

<400> SEQUENCE: 57
ugagaccucu ggguucugag cu                                           22

<210> SEQ ID NO 58
<211> LENGTH: 23
<212> TYPE: RNA
<213> ORGANISM: Homo sapiens

<400> SEQUENCE: 58
cugggaucuc cggggucuug guu                                          23

<210> SEQ ID NO 59
<211> LENGTH: 23
<212> TYPE: RNA
<213> ORGANISM: Homo sapiens

<400> SEQUENCE: 59
ugcaccaugg uugucugagc aug                                          23

<210> SEQ ID NO 60
<211> LENGTH: 23
<212> TYPE: RNA
<213> ORGANISM: Homo sapiens

<400> SEQUENCE: 60
ucugcucaua ccccaugguu ucu                                          23

<210> SEQ ID NO 61
<211> LENGTH: 22
<212> TYPE: RNA
<213> ORGANISM: Homo sapiens

<400> SEQUENCE: 61
acuccagccc cacagccuca gc                                           22

<210> SEQ ID NO 62
<211> LENGTH: 21
<212> TYPE: RNA
<213> ORGANISM: Homo sapiens

<400> SEQUENCE: 62
uggaggagaa ggaaggugau g                                            21

<210> SEQ ID NO 63
<211> LENGTH: 22
<212> TYPE: RNA
<213> ORGANISM: Homo sapiens

<400> SEQUENCE: 63
gcaggugcuc acuuguccuc cu                                           22
```

```
<210> SEQ ID NO 64
<211> LENGTH: 22
<212> TYPE: RNA
<213> ORGANISM: Homo sapiens

<400> SEQUENCE: 64 ggggcuggggg ccggggccga gc                                            22

<210> SEQ ID NO 65
<211> LENGTH: 22
<212> TYPE: RNA
<213> ORGANISM: Homo sapiens

<400> SEQUENCE: 65
gcagcagggu gaaacugaca ca                                             22

<210> SEQ ID NO 66
<211> LENGTH: 20
<212> TYPE: RNA
<213> ORGANISM: Homo sapiens

<400> SEQUENCE: 66
cggcucuggg ucugugggga                                                20

<210> SEQ ID NO 67
<211> LENGTH: 22
<212> TYPE: RNA
<213> ORGANISM: Homo sapiens

<400> SEQUENCE: 67
gcagagugca aacaauuuug ac                                             22

<210> SEQ ID NO 68
<211> LENGTH: 22
<212> TYPE: RNA
<213> ORGANISM: Homo sapiens

<400> SEQUENCE: 68
uuugugaccu gguccacuaa cc                                             22

<210> SEQ ID NO 69
<211> LENGTH: 22
<212> TYPE: RNA
<213> ORGANISM: Homo sapiens

<400> SEQUENCE: 69
cuguugccac uaaccucaac cu                                             22

<210> SEQ ID NO 70
<211> LENGTH: 22
<212> TYPE: RNA
<213> ORGANISM: Homo sapiens

<400> SEQUENCE: 70
ugcggggcua gggcuaacag ca                                             22

<210> SEQ ID NO 71
<211> LENGTH: 17
<212> TYPE: RNA
<213> ORGANISM: Homo sapiens

<400> SEQUENCE: 71
ucucgcuggg gccucca                                                   17
```

-continued

<210> SEQ ID NO 72
<211> LENGTH: 22
<212> TYPE: RNA
<213> ORGANISM: Homo sapiens

<400> SEQUENCE: 72
caacaaaucc cagucuaccu aa                                              22

<210> SEQ ID NO 73
<211> LENGTH: 21
<212> TYPE: RNA
<213> ORGANISM: Homo sapiens

<400> SEQUENCE: 73
cuuccgcccc gccgggcguc g                                               21

<210> SEQ ID NO 74
<211> LENGTH: 22
<212> TYPE: RNA
<213> ORGANISM: Homo sapiens

<400> SEQUENCE: 74
gggacccagg gagagacgua ag                                              22

<210> SEQ ID NO 75
<211> LENGTH: 22
<212> TYPE: RNA
<213> ORGANISM: Homo sapiens

<400> SEQUENCE: 75
caacaaauca cagucugcca ua                                              22

<210> SEQ ID NO 76
<211> LENGTH: 22
<212> TYPE: RNA
<213> ORGANISM: Homo sapiens

<400> SEQUENCE: 76
caacuagacu gugagcuucu ag                                              22

<210> SEQ ID NO 77
<211> LENGTH: 23
<212> TYPE: RNA
<213> ORGANISM: Homo sapiens

<400> SEQUENCE: 77
aaggagcuua caaucuagcu ggg                                             23

<210> SEQ ID NO 78
<211> LENGTH: 23
<212> TYPE: RNA
<213> ORGANISM: Homo sapiens

<400> SEQUENCE: 78
uggaagacua gugauuuugu ugu                                             23

<210> SEQ ID NO 79
<211> LENGTH: 20
<212> TYPE: RNA
<213> ORGANISM: Homo sapiens

<400> SEQUENCE: 79
cuguaugccc ucaccgcuca                                                20

<210> SEQ ID NO 80
<211> LENGTH: 23
<212> TYPE: RNA
<213> ORGANISM: Homo sapiens

<400> SEQUENCE: 80
uggugcggag agggcccaca gug                                            23

<210> SEQ ID NO 81
<211> LENGTH: 23
<212> TYPE: RNA
<213> ORGANISM: Homo sapiens

<400> SEQUENCE: 81
aggaagcccu ggaggggcug gag                                            23

<210> SEQ ID NO 82
<211> LENGTH: 21
<212> TYPE: RNA
<213> ORGANISM: Homo sapiens

<400> SEQUENCE: 82
uccgguucuc agggcuccac c                                              21

<210> SEQ ID NO 83
<211> LENGTH: 20
<212> TYPE: RNA
<213> ORGANISM: Homo sapiens

<400> SEQUENCE: 83
gucccugagu guaugggug                                                 20

<210> SEQ ID NO 84
<211> LENGTH: 23
<212> TYPE: RNA
<213> ORGANISM: Homo sapiens

<400> SEQUENCE: 84
ugucacucgg cucggcccac uac                                            23

<210> SEQ ID NO 85
<211> LENGTH: 20
<212> TYPE: RNA
<213> ORGANISM: Homo sapiens

<400> SEQUENCE: 85
accaggaggc ugaggcccu                                                 20

<210> SEQ ID NO 86
<211> LENGTH: 24
<212> TYPE: RNA
<213> ORGANISM: Homo sapiens

<400> SEQUENCE: 86
acuggcuagg gaaaaugauu ggau                                           24

<210> SEQ ID NO 87
<211> LENGTH: 23
<212> TYPE: RNA
<213> ORGANISM: Homo sapiens

<400> SEQUENCE: 87
uauucauuua uccccagccu aca                                              23

<210> SEQ ID NO 88
<211> LENGTH: 22
<212> TYPE: RNA
<213> ORGANISM: Homo sapiens

<400> SEQUENCE: 88
gguggcccgg ccgugccuga gg                                               22

<210> SEQ ID NO 89
<211> LENGTH: 22
<212> TYPE: RNA
<213> ORGANISM: Homo sapiens

<400> SEQUENCE: 89
aggcggggcg ccgcgggacc gc                                               22

<210> SEQ ID NO 90
<211> LENGTH: 21
<212> TYPE: RNA
<213> ORGANISM: Homo sapiens

<400> SEQUENCE: 90
ucccacguug uggcccagca g                                                21

<210> SEQ ID NO 91
<211> LENGTH: 24
<212> TYPE: RNA
<213> ORGANISM: Homo sapiens

<400> SEQUENCE: 91
ugccuggguc ucuggccugc gcgu                                             24

<210> SEQ ID NO 92
<211> LENGTH: 22
<212> TYPE: RNA
<213> ORGANISM: Homo sapiens

<400> SEQUENCE: 92
uacccauugc auaucggagu ug                                               22

<210> SEQ ID NO 93
<211> LENGTH: 22
<212> TYPE: RNA
<213> ORGANISM: Homo sapiens

<400> SEQUENCE: 93
cuugguucag ggaggguccc ca                                               22

<210> SEQ ID NO 94
<211> LENGTH: 25
<212> TYPE: RNA
<213> ORGANISM: Homo sapiens

<400> SEQUENCE: 94
ggcggaggga aguagguccg uuggu                                            25

<210> SEQ ID NO 95
<211> LENGTH: 23
<212> TYPE: RNA
<213> ORGANISM: Homo sapiens

```
<400> SEQUENCE: 95
ggcagguucu cacccucucu agg                                              23

<210> SEQ ID NO 96
<211> LENGTH: 21
<212> TYPE: RNA
<213> ORGANISM: Homo sapiens

<400> SEQUENCE: 96
aauauuauac agucaaccuc u                                                21

<210> SEQ ID NO 97
<211> LENGTH: 22
<212> TYPE: RNA
<213> ORGANISM: Homo sapiens

<400> SEQUENCE: 97
auaauacaug guuaaccucu uu                                               22

<210> SEQ ID NO 98
<211> LENGTH: 22
<212> TYPE: RNA
<213> ORGANISM: Homo sapiens

<400> SEQUENCE: 98 ugguggccg cagaacaugu gc                                                22

<210> SEQ ID NO 99
<211> LENGTH: 22
<212> TYPE: RNA
<213> ORGANISM: Homo sapiens

<400> SEQUENCE: 99
uaugucugcu gaccaucacc uu                                               22

<210> SEQ ID NO 100
<211> LENGTH: 21
<212> TYPE: RNA
<213> ORGANISM: Homo sapiens

<400> SEQUENCE: 100
guguugaaac aaucucuacu g                                                21

<210> SEQ ID NO 101
<211> LENGTH: 21
<212> TYPE: RNA
<213> ORGANISM: Homo sapiens

<400> SEQUENCE: 101
aauggcgcca cuaggguugu g                                                21

<210> SEQ ID NO 102
<211> LENGTH: 22
<212> TYPE: RNA
<213> ORGANISM: Homo sapiens

<400> SEQUENCE: 102
uuuaggauaa gcuugacuuu ug                                               22

<210> SEQ ID NO 103
<211> LENGTH: 21
<212> TYPE: RNA
<213> ORGANISM: Homo sapiens
```

```
<400> SEQUENCE: 103
aggaggcagc gcucucagga c                                         21

<210> SEQ ID NO 104
<211> LENGTH: 22
<212> TYPE: RNA
<213> ORGANISM: Homo sapiens

<400> SEQUENCE: 104
aaaccugugu uguucaagag uc                                        22

<210> SEQ ID NO 105
<211> LENGTH: 19
<212> TYPE: RNA
<213> ORGANISM: Homo sapiens

<400> SEQUENCE: 105
aagugugcag ggcacuggu                                            19

<210> SEQ ID NO 106
<211> LENGTH: 21
<212> TYPE: RNA
<213> ORGANISM: Homo sapiens

<400> SEQUENCE: 106
guggcugcac ucacuuccuu c                                         21

<210> SEQ ID NO 107
<211> LENGTH: 19
<212> TYPE: RNA
<213> ORGANISM: Homo sapiens

<400> SEQUENCE: 107
aagcagcugc cucugaggc                                            19

<210> SEQ ID NO 108
<211> LENGTH: 19
<212> TYPE: RNA
<213> ORGANISM: Homo sapiens

<400> SEQUENCE: 108
ucuaggcugg uacugcuga                                            19

<210> SEQ ID NO 109
<211> LENGTH: 19
<212> TYPE: RNA
<213> ORGANISM: Homo sapiens

<400> SEQUENCE: 109
aguguggcuu ucuuagagc                                            19

<210> SEQ ID NO 110
<211> LENGTH: 22
<212> TYPE: RNA
<213> ORGANISM: Homo sapiens

<400> SEQUENCE: 110
acuuguaugc uagcucaggu ag                                        22

<210> SEQ ID NO 111
<211> LENGTH: 22
<212> TYPE: RNA
```

```
<213> ORGANISM: Homo sapiens

<400> SEQUENCE: 111
gucccucucc aaaugugucu ug                                              22

<210> SEQ ID NO 112
<211> LENGTH: 24
<212> TYPE: RNA
<213> ORGANISM: Homo sapiens

<400> SEQUENCE: 112
aaagacauag gauagaguca ccuc                                            24

<210> SEQ ID NO 113
<211> LENGTH: 21
<212> TYPE: RNA
<213> ORGANISM: Homo sapiens

<400> SEQUENCE: 113
augauccagg aaccugccuc u                                               21

<210> SEQ ID NO 114
<211> LENGTH: 23
<212> TYPE: RNA
<213> ORGANISM: Homo sapiens

<400> SEQUENCE: 114
aucgcugcgg uugcgagcgc ugu                                             23

<210> SEQ ID NO 115
<211> LENGTH: 25
<212> TYPE: RNA
<213> ORGANISM: Homo sapiens

<400> SEQUENCE: 115
agggaucgcg ggcggguggc ggccu                                           25

<210> SEQ ID NO 116
<211> LENGTH: 24
<212> TYPE: RNA
<213> ORGANISM: Homo sapiens

<400> SEQUENCE: 116 acuggggcu uucgggcucu gcgu                                             24

<210> SEQ ID NO 117
<211> LENGTH: 23
<212> TYPE: RNA
<213> ORGANISM: Homo sapiens

<400> SEQUENCE: 117
ugugcuugcu cgucccgccc gca                                             23

<210> SEQ ID NO 118
<211> LENGTH: 23
<212> TYPE: RNA
<213> ORGANISM: Homo sapiens

<400> SEQUENCE: 118
acuugggcac ugaaacaaug ucc                                             23

<210> SEQ ID NO 119
<211> LENGTH: 22
```

```
<212> TYPE: RNA
<213> ORGANISM: Homo sapiens

<400> SEQUENCE: 119
aaccagcacc ccaacuuugg ac                                              22

<210> SEQ ID NO 120
<211> LENGTH: 23
<212> TYPE: RNA
<213> ORGANISM: Homo sapiens

<400> SEQUENCE: 120
cuaauaguau cuaccacaau aaa                                             23

<210> SEQ ID NO 121
<211> LENGTH: 19
<212> TYPE: RNA
<213> ORGANISM: Homo sapiens

<400> SEQUENCE: 121
gugucugcuu ccuguggga                                                  19

<210> SEQ ID NO 122
<211> LENGTH: 21
<212> TYPE: RNA
<213> ORGANISM: Homo sapiens

<400> SEQUENCE: 122
agaccuggcc cagaccucag c                                               21

<210> SEQ ID NO 123
<211> LENGTH: 22
<212> TYPE: RNA
<213> ORGANISM: Homo sapiens

<400> SEQUENCE: 123
aguauucugu accagggaag gu                                              22

<210> SEQ ID NO 124
<211> LENGTH: 22
<212> TYPE: RNA
<213> ORGANISM: Homo sapiens

<400> SEQUENCE: 124
guucucccaa cguaagccca gc                                              22

<210> SEQ ID NO 125
<211> LENGTH: 21
<212> TYPE: RNA
<213> ORGANISM: Homo sapiens

<400> SEQUENCE: 125
uggguuuacg uugggagaac u                                               21

<210> SEQ ID NO 126
<211> LENGTH: 22
<212> TYPE: RNA
<213> ORGANISM: Homo sapiens

<400> SEQUENCE: 126
augcugacau auuuacuaga gg                                              22

<210> SEQ ID NO 127
```

```
<211> LENGTH: 21
<212> TYPE: RNA
<213> ORGANISM: Homo sapiens

<400> SEQUENCE: 127
ucuaguaaga guggcagucg a                                              21

<210> SEQ ID NO 128
<211> LENGTH: 22
<212> TYPE: RNA
<213> ORGANISM: Homo sapiens

<400> SEQUENCE: 128
gugagucucu aagaaaagag ga                                             22

<210> SEQ ID NO 129
<211> LENGTH: 19
<212> TYPE: RNA
<213> ORGANISM: Homo sapiens

<400> SEQUENCE: 129
agcugucuga aaaugucuu                                                 19

<210> SEQ ID NO 130
<211> LENGTH: 22
<212> TYPE: RNA
<213> ORGANISM: Homo sapiens

<400> SEQUENCE: 130
gacuauagaa cuuccccccu ca                                             22

<210> SEQ ID NO 131
<211> LENGTH: 21
<212> TYPE: RNA
<213> ORGANISM: Homo sapiens

<400> SEQUENCE: 131 aggggggaaag uucuauaguc c                                             21

<210> SEQ ID NO 132
<211> LENGTH: 22
<212> TYPE: RNA
<213> ORGANISM: Homo sapiens

<400> SEQUENCE: 132
uaguaccagu accuuguguu ca                                             22

<210> SEQ ID NO 133
<211> LENGTH: 21
<212> TYPE: RNA
<213> ORGANISM: Homo sapiens

<400> SEQUENCE: 133
cacaagguau ugguauuacc u                                              21

<210> SEQ ID NO 134
<211> LENGTH: 23
<212> TYPE: RNA
<213> ORGANISM: Homo sapiens

<400> SEQUENCE: 134
aucccuugca ggggcuguug ggu                                            23
```

-continued

```
<210> SEQ ID NO 135
<211> LENGTH: 21
<212> TYPE: RNA
<213> ORGANISM: Homo sapiens

<400> SEQUENCE: 135
acagucugcu gagguuggag c                                             21

<210> SEQ ID NO 136
<211> LENGTH: 21
<212> TYPE: RNA
<213> ORGANISM: Homo sapiens

<400> SEQUENCE: 136
ggcuagcaac agcgcuuacc u                                             21

<210> SEQ ID NO 137
<211> LENGTH: 20
<212> TYPE: RNA
<213> ORGANISM: Homo sapiens

<400> SEQUENCE: 137
auggagauag auauagaaau                                               20

<210> SEQ ID NO 138
<211> LENGTH: 24
<212> TYPE: RNA
<213> ORGANISM: Homo sapiens

<400> SEQUENCE: 138
gaccuggaca uguuugugcc cagu                                          24

<210> SEQ ID NO 139
<211> LENGTH: 23
<212> TYPE: RNA
<213> ORGANISM: Homo sapiens

<400> SEQUENCE: 139
aaacucuacu uguccuucug agu                                           23

<210> SEQ ID NO 140
<211> LENGTH: 22
<212> TYPE: RNA
<213> ORGANISM: Homo sapiens

<400> SEQUENCE: 140
agacuuccca uuugaaggug gc                                            22

<210> SEQ ID NO 141
<211> LENGTH: 22
<212> TYPE: RNA
<213> ORGANISM: Homo sapiens

<400> SEQUENCE: 141
acucaaaacc cuucagugac uu                                            22

<210> SEQ ID NO 142
<211> LENGTH: 22
<212> TYPE: RNA
<213> ORGANISM: Homo sapiens

<400> SEQUENCE: 142
agucauugga ggguuugagc ag                                            22
```

```
<210> SEQ ID NO 143
<211> LENGTH: 22
<212> TYPE: RNA
<213> ORGANISM: Homo sapiens

<400> SEQUENCE: 143
gggggucccc ggugcucgga uc                                      22

<210> SEQ ID NO 144
<211> LENGTH: 22
<212> TYPE: RNA
<213> ORGANISM: Homo sapiens

<400> SEQUENCE: 144
uccgagccug ggucucccuc uu                                      22

<210> SEQ ID NO 145
<211> LENGTH: 23
<212> TYPE: RNA
<213> ORGANISM: Homo sapiens

<400> SEQUENCE: 145
gaacgccugu ucuugccagg ugg                                     23

<210> SEQ ID NO 146
<211> LENGTH: 20
<212> TYPE: RNA
<213> ORGANISM: Homo sapiens

<400> SEQUENCE: 146
aggaauguuc cuucuuugcc                                         20

<210> SEQ ID NO 147
<211> LENGTH: 25
<212> TYPE: RNA
<213> ORGANISM: Homo sapiens

<400> SEQUENCE: 147
gcugggcagg gcuucugagc uccuu                                   25

<210> SEQ ID NO 148
<211> LENGTH: 23
<212> TYPE: RNA
<213> ORGANISM: Homo sapiens

<400> SEQUENCE: 148
gcgaggaccc cucggggucu gac                                     23

<210> SEQ ID NO 149
<211> LENGTH: 21
<212> TYPE: RNA
<213> ORGANISM: Homo sapiens

<400> SEQUENCE: 149
ugagcuaaau gugugcuggg a                                       21

<210> SEQ ID NO 150
<211> LENGTH: 20
<212> TYPE: RNA
<213> ORGANISM: Homo sapiens

<400> SEQUENCE: 150
agggguguuc ucucaucucu                                         20
```

<210> SEQ ID NO 151
<211> LENGTH: 25
<212> TYPE: RNA
<213> ORGANISM: Homo sapiens

<400> SEQUENCE: 151 aggggguggug uugggacagc uccgu                                    25

<210> SEQ ID NO 152
<211> LENGTH: 21
<212> TYPE: RNA
<213> ORGANISM: Homo sapiens

<400> SEQUENCE: 152
guucaaaucc agaucuauaa c                                         21

<210> SEQ ID NO 153
<211> LENGTH: 21
<212> TYPE: RNA
<213> ORGANISM: Homo sapiens

<400> SEQUENCE: 153
aaacuacuga aaaucaaaga u                                         21

<210> SEQ ID NO 154
<211> LENGTH: 23
<212> TYPE: RNA
<213> ORGANISM: Homo sapiens

<400> SEQUENCE: 154
uaaaucccau ggugccuucu ccu                                       23

<210> SEQ ID NO 155
<211> LENGTH: 19
<212> TYPE: RNA
<213> ORGANISM: Homo sapiens

<400> SEQUENCE: 155
aggcugcgga auucaggac                                            19

<210> SEQ ID NO 156
<211> LENGTH: 22
<212> TYPE: RNA
<213> ORGANISM: Homo sapiens

<400> SEQUENCE: 156
cacacacugc aauuacuuuu gc                                        22

<210> SEQ ID NO 157
<211> LENGTH: 23
<212> TYPE: RNA
<213> ORGANISM: Homo sapiens

<400> SEQUENCE: 157
gacacgggcg acagcugcgg ccc                                       23

<210> SEQ ID NO 158
<211> LENGTH: 22
<212> TYPE: RNA
<213> ORGANISM: Homo sapiens

<400> SEQUENCE: 158
uggucuagga uuguuggagg ag                                         22

<210> SEQ ID NO 159
<211> LENGTH: 23
<212> TYPE: RNA
<213> ORGANISM: Homo sapiens

<400> SEQUENCE: 159
acuuacagac aagagccuug cuc                                        23

<210> SEQ ID NO 160
<211> LENGTH: 20
<212> TYPE: RNA
<213> ORGANISM: Homo sapiens

<400> SEQUENCE: 160
guugugucag uuuaucaaac                                            20

<210> SEQ ID NO 161
<211> LENGTH: 22
<212> TYPE: RNA
<213> ORGANISM: Homo sapiens

<400> SEQUENCE: 161
uacgucaucg uugucaucgu ca                                         22

<210> SEQ ID NO 162
<211> LENGTH: 22
<212> TYPE: RNA
<213> ORGANISM: Homo sapiens

<400> SEQUENCE: 162
ugugucacuc gaugaccacu gu                                         22

<210> SEQ ID NO 163
<211> LENGTH: 21
<212> TYPE: RNA
<213> ORGANISM: Homo sapiens

<400> SEQUENCE: 163
aagccugccc ggcuccucgg g                                          21

<210> SEQ ID NO 164
<211> LENGTH: 21
<212> TYPE: RNA
<213> ORGANISM: Homo sapiens

<400> SEQUENCE: 164
gaagugugcc gugguguguc u                                          21

<210> SEQ ID NO 165
<211> LENGTH: 25
<212> TYPE: RNA
<213> ORGANISM: Homo sapiens

<400> SEQUENCE: 165
aggcaccagc caggcauugc ucagc                                      25

<210> SEQ ID NO 166
<211> LENGTH: 19
<212> TYPE: RNA
<213> ORGANISM: Homo sapiens

<400> SEQUENCE: 166

```
ugucucugcu gggguuucu                                           19

<210> SEQ ID NO 167
<211> LENGTH: 22
<212> TYPE: RNA
<213> ORGANISM: Homo sapiens

<400> SEQUENCE: 167
uugugucaau augcgaugau gu                                       22

<210> SEQ ID NO 168
<211> LENGTH: 20
<212> TYPE: RNA
<213> ORGANISM: Homo sapiens

<400> SEQUENCE: 168
agaccauggg uucucauugu                                          20

<210> SEQ ID NO 169
<211> LENGTH: 22
<212> TYPE: RNA
<213> ORGANISM: Homo sapiens

<400> SEQUENCE: 169
gagcuuauuc auaaaagugc ag                                       22

<210> SEQ ID NO 170
<211> LENGTH: 21
<212> TYPE: RNA
<213> ORGANISM: Homo sapiens

<400> SEQUENCE: 170
uaauuuuaug uauaagcuag u                                        21

<210> SEQ ID NO 171
<211> LENGTH: 24
<212> TYPE: RNA
<213> ORGANISM: Homo sapiens

<400> SEQUENCE: 171
ucagaacaaa ugccgguucc caga                                     24

<210> SEQ ID NO 172
<211> LENGTH: 22
<212> TYPE: RNA
<213> ORGANISM: Homo sapiens

<400> SEQUENCE: 172
ugagaaccac gucugcucug ag                                       22

<210> SEQ ID NO 173
<211> LENGTH: 21
<212> TYPE: RNA
<213> ORGANISM: Homo sapiens

<400> SEQUENCE: 173
uuggccacaa uggguuagaa c                                        21

<210> SEQ ID NO 174
<211> LENGTH: 21
<212> TYPE: RNA
<213> ORGANISM: Homo sapiens
```

```
<400> SEQUENCE: 174
uuuccauagg ugaugaguca c                                          21

<210> SEQ ID NO 175
<211> LENGTH: 22
<212> TYPE: RNA
<213> ORGANISM: Homo sapiens

<400> SEQUENCE: 175
uaugcauugu auuuuaggu cc                                          22

<210> SEQ ID NO 176
<211> LENGTH: 19
<212> TYPE: RNA
<213> ORGANISM: Homo sapiens

<400> SEQUENCE: 176
ugggcguauc uguaugcua                                             19

<210> SEQ ID NO 177
<211> LENGTH: 22
<212> TYPE: RNA
<213> ORGANISM: Homo sapiens

<400> SEQUENCE: 177
uuaugguuug ccugggacug ag                                         22

<210> SEQ ID NO 178
<211> LENGTH: 21
<212> TYPE: RNA
<213> ORGANISM: Homo sapiens

<400> SEQUENCE: 178
caaagaggaa ggucccauua c                                          21

<210> SEQ ID NO 179
<211> LENGTH: 23
<212> TYPE: RNA
<213> ORGANISM: Homo sapiens

<400> SEQUENCE: 179
uuacaguugu ucaaccaguu acu                                        23

<210> SEQ ID NO 180
<211> LENGTH: 22
<212> TYPE: RNA
<213> ORGANISM: Homo sapiens

<400> SEQUENCE: 180
uaacugguug aacaacugaa cc                                         22

<210> SEQ ID NO 181
<211> LENGTH: 21
<212> TYPE: RNA
<213> ORGANISM: Homo sapiens

<400> SEQUENCE: 181
ucuuguguuc ucuagaucag u                                          21

<210> SEQ ID NO 182
<211> LENGTH: 22
<212> TYPE: RNA
<213> ORGANISM: Homo sapiens
```

-continued

<400> SEQUENCE: 182
uugagaauga ugaaucauua gg                                          22

<210> SEQ ID NO 183
<211> LENGTH: 23
<212> TYPE: RNA
<213> ORGANISM: Homo sapiens

<400> SEQUENCE: 183 uucauuggu auaaaccgcg auu                                          23

<210> SEQ ID NO 184
<211> LENGTH: 21
<212> TYPE: RNA
<213> ORGANISM: Homo sapiens

<400> SEQUENCE: 184
cuucuugugc ucuaggauug u                                           21

<210> SEQ ID NO 185
<211> LENGTH: 21
<212> TYPE: RNA
<213> ORGANISM: Homo sapiens

<400> SEQUENCE: 185
uagauaaaau auugguaccu g                                           21

<210> SEQ ID NO 186
<211> LENGTH: 22
<212> TYPE: RNA
<213> ORGANISM: Homo sapiens

<400> SEQUENCE: 186
auucuaauuu cuccacgucu uu                                          22

<210> SEQ ID NO 187
<211> LENGTH: 22
<212> TYPE: RNA
<213> ORGANISM: Homo sapiens

<400> SEQUENCE: 187
aagaugugga aaaauuggaa uc                                          22

<210> SEQ ID NO 188
<211> LENGTH: 19
<212> TYPE: RNA
<213> ORGANISM: Homo sapiens

<400> SEQUENCE: 188
gagccaguug gacaggagc                                              19

<210> SEQ ID NO 189
<211> LENGTH: 23
<212> TYPE: RNA
<213> ORGANISM: Homo sapiens

<400> SEQUENCE: 189
ugagugugug ugugugagug ugu                                         23

<210> SEQ ID NO 190
<211> LENGTH: 22
<212> TYPE: RNA

```
<213> ORGANISM: Homo sapiens

<400> SEQUENCE: 190
cacgcucaug cacacaccca ca                                          22

<210> SEQ ID NO 191
<211> LENGTH: 24
<212> TYPE: RNA
<213> ORGANISM: Homo sapiens

<400> SEQUENCE: 191
cugaagugau guguaacuga ucag                                        24

<210> SEQ ID NO 192
<211> LENGTH: 20
<212> TYPE: RNA
<213> ORGANISM: Homo sapiens

<400> SEQUENCE: 192
guccgcucgg cgguggccca                                             20

<210> SEQ ID NO 193
<211> LENGTH: 21
<212> TYPE: RNA
<213> ORGANISM: Homo sapiens

<400> SEQUENCE: 193
ugaguuggcc aucugaguga g                                           21

<210> SEQ ID NO 194
<211> LENGTH: 22
<212> TYPE: RNA
<213> ORGANISM: Homo sapiens

<400> SEQUENCE: 194
cgaaaacagc aauuaccuuu gc                                          22

<210> SEQ ID NO 195
<211> LENGTH: 21
<212> TYPE: RNA
<213> ORGANISM: Homo sapiens

<400> SEQUENCE: 195
aguuaaugaa uccuggaaag u                                           21

<210> SEQ ID NO 196
<211> LENGTH: 20
<212> TYPE: RNA
<213> ORGANISM: Homo sapiens

<400> SEQUENCE: 196
auguauaaau guauacacac                                             20

<210> SEQ ID NO 197
<211> LENGTH: 23
<212> TYPE: RNA
<213> ORGANISM: Homo sapiens

<400> SEQUENCE: 197
aguauguucu uccaggacag aac                                         23

<210> SEQ ID NO 198
<211> LENGTH: 19
```

```
<212> TYPE: RNA
<213> ORGANISM: Homo sapiens

<400> SEQUENCE: 198
gggcgccugu gaucccaac                                                19

<210> SEQ ID NO 199
<211> LENGTH: 19
<212> TYPE: RNA
<213> ORGANISM: Homo sapiens

<400> SEQUENCE: 199
aggcacggug ucagcaggc                                                19

<210> SEQ ID NO 200
<211> LENGTH: 19
<212> TYPE: RNA
<213> ORGANISM: Homo sapiens

<400> SEQUENCE: 200
agguugacau acguuuccc                                                19

<210> SEQ ID NO 201
<211> LENGTH: 20
<212> TYPE: RNA
<213> ORGANISM: Homo sapiens

<400> SEQUENCE: 201
aaaguagcug uaccauuugc                                               20

<210> SEQ ID NO 202
<211> LENGTH: 22
<212> TYPE: RNA
<213> ORGANISM: Homo sapiens

<400> SEQUENCE: 202
caaaguuuaa gauccuugaa gu                                            22

<210> SEQ ID NO 203
<211> LENGTH: 21
<212> TYPE: RNA
<213> ORGANISM: Homo sapiens

<400> SEQUENCE: 203
uaaaguaaau augcaccaaa a                                             21

<210> SEQ ID NO 204
<211> LENGTH: 19
<212> TYPE: RNA
<213> ORGANISM: Homo sapiens

<400> SEQUENCE: 204
ugagcugcug uaccaaaau                                                19

<210> SEQ ID NO 205
<211> LENGTH: 23
<212> TYPE: RNA
<213> ORGANISM: Homo sapiens

<400> SEQUENCE: 205
guuugcacgg gugggccuug ucu                                           23

<210> SEQ ID NO 206
```

```
<211> LENGTH: 22
<212> TYPE: RNA
<213> ORGANISM: Homo sapiens

<400> SEQUENCE: 206
gaugagcuca uuguaauaug ag                                              22

<210> SEQ ID NO 207
<211> LENGTH: 22
<212> TYPE: RNA
<213> ORGANISM: Homo sapiens

<400> SEQUENCE: 207
auauuaccau uagcucaucu uu                                              22

<210> SEQ ID NO 208
<211> LENGTH: 21
<212> TYPE: RNA
<213> ORGANISM: Homo sapiens

<400> SEQUENCE: 208
aggguaagcu gaaccucuga u                                               21

<210> SEQ ID NO 209
<211> LENGTH: 21
<212> TYPE: RNA
<213> ORGANISM: Homo sapiens

<400> SEQUENCE: 209
gcuaguccug acucagccag u                                               21

<210> SEQ ID NO 210
<211> LENGTH: 21
<212> TYPE: RNA
<213> ORGANISM: Homo sapiens

<400> SEQUENCE: 210
aaaacgguga gauuuuguuu u                                               21

<210> SEQ ID NO 211
<211> LENGTH: 21
<212> TYPE: RNA
<213> ORGANISM: Homo sapiens

<400> SEQUENCE: 211
aacaggugac ugguuagaca a                                               21

<210> SEQ ID NO 212
<211> LENGTH: 22
<212> TYPE: RNA
<213> ORGANISM: Homo sapiens

<400> SEQUENCE: 212
gaaaucaagc gugggugaga cc                                              22

<210> SEQ ID NO 213
<211> LENGTH: 21
<212> TYPE: RNA
<213> ORGANISM: Homo sapiens

<400> SEQUENCE: 213
gcgacccaua cuugguuuca g                                               21
```

```
<210> SEQ ID NO 214
<211> LENGTH: 21
<212> TYPE: RNA
<213> ORGANISM: Homo sapiens

<400> SEQUENCE: 214
gcgacccacu cuugguuucc a                                              21

<210> SEQ ID NO 215
<211> LENGTH: 22
<212> TYPE: RNA
<213> ORGANISM: Homo sapiens

<400> SEQUENCE: 215
ugucuuacuc ccucaggcac au                                             22

<210> SEQ ID NO 216
<211> LENGTH: 23
<212> TYPE: RNA
<213> ORGANISM: Homo sapiens

<400> SEQUENCE: 216
agugccugag ggaguaagag ccc                                            23

<210> SEQ ID NO 217
<211> LENGTH: 21
<212> TYPE: RNA
<213> ORGANISM: Homo sapiens

<400> SEQUENCE: 217
ugacaacuau ggaugagcuc u                                              21

<210> SEQ ID NO 218
<211> LENGTH: 22
<212> TYPE: RNA
<213> ORGANISM: Homo sapiens

<400> SEQUENCE: 218
gcuggugcaa aaguaauggc gg                                             22

<210> SEQ ID NO 219
<211> LENGTH: 22
<212> TYPE: RNA
<213> ORGANISM: Homo sapiens

<400> SEQUENCE: 219
uagcaaaaac ugcaguuacu uu                                             22

<210> SEQ ID NO 220
<211> LENGTH: 22
<212> TYPE: RNA
<213> ORGANISM: Homo sapiens

<400> SEQUENCE: 220
ccaaaacugc aguuacuuuu gc                                             22

<210> SEQ ID NO 221
<211> LENGTH: 22
<212> TYPE: RNA
<213> ORGANISM: Homo sapiens

<400> SEQUENCE: 221
caaaaguaau uguggauuuu gu                                             22
```

```
<210> SEQ ID NO 222
<211> LENGTH: 21
<212> TYPE: RNA
<213> ORGANISM: Homo sapiens

<400> SEQUENCE: 222
caaagguauu ugugguuuuu g                                              21

<210> SEQ ID NO 223
<211> LENGTH: 22
<212> TYPE: RNA
<213> ORGANISM: Homo sapiens

<400> SEQUENCE: 223
aaaaguauuu gcgguuuug uc                                              22

<210> SEQ ID NO 224
<211> LENGTH: 22
<212> TYPE: RNA
<213> ORGANISM: Homo sapiens

<400> SEQUENCE: 224
aaaaguacuu gcggauuuug cu                                             22

<210> SEQ ID NO 225
<211> LENGTH: 22
<212> TYPE: RNA
<213> ORGANISM: Homo sapiens

<400> SEQUENCE: 225
aaaaguaauu gcggucuuug gu                                             22

<210> SEQ ID NO 226
<211> LENGTH: 22
<212> TYPE: RNA
<213> ORGANISM: Homo sapiens

<400> SEQUENCE: 226
aaaaguaauu gcggauuuug cc                                             22

<210> SEQ ID NO 227
<211> LENGTH: 22
<212> TYPE: RNA
<213> ORGANISM: Homo sapiens

<400> SEQUENCE: 227
aaaaguaauc gcgguuuuug uc                                             22

<210> SEQ ID NO 228
<211> LENGTH: 22
<212> TYPE: RNA
<213> ORGANISM: Homo sapiens

<400> SEQUENCE: 228
aaaacuguaa uuacuuuugu ac                                             22

<210> SEQ ID NO 229
<211> LENGTH: 19
<212> TYPE: RNA
<213> ORGANISM: Homo sapiens

<400> SEQUENCE: 229
aaaaacugua auuacuuuu                                                 19
```

```
<210> SEQ ID NO 230
<211> LENGTH: 22
<212> TYPE: RNA
<213> ORGANISM: Homo sapiens

<400> SEQUENCE: 230
aaaaacugag acuacuuuug ca                                              22

<210> SEQ ID NO 231
<211> LENGTH: 22
<212> TYPE: RNA
<213> ORGANISM: Homo sapiens

<400> SEQUENCE: 231
aaaaguaauu gugguuuuug cc                                              22

<210> SEQ ID NO 232
<211> LENGTH: 22
<212> TYPE: RNA
<213> ORGANISM: Homo sapiens

<400> SEQUENCE: 232
caaaaaccac aguucuuuu gc                                               22

<210> SEQ ID NO 233
<211> LENGTH: 22
<212> TYPE: RNA
<213> ORGANISM: Homo sapiens

<400> SEQUENCE: 233
aaaaguaauu gcgguuuug cc                                               22

<210> SEQ ID NO 234
<211> LENGTH: 22
<212> TYPE: RNA
<213> ORGANISM: Homo sapiens

<400> SEQUENCE: 234
caaaaaucuc aauuacuuuu gc                                              22

<210> SEQ ID NO 235
<211> LENGTH: 22
<212> TYPE: RNA
<213> ORGANISM: Homo sapiens

<400> SEQUENCE: 235
aaaaguaauu gugguuuugg cc                                              22

<210> SEQ ID NO 236
<211> LENGTH: 22
<212> TYPE: RNA
<213> ORGANISM: Homo sapiens

<400> SEQUENCE: 236
caagaaccuc aguugcuuuu gu                                              22

<210> SEQ ID NO 237
<211> LENGTH: 22
<212> TYPE: RNA
<213> ORGANISM: Homo sapiens

<400> SEQUENCE: 237
```
aaaaguaauu gcgaguuuua cc                                            22

<210> SEQ ID NO 238
<211> LENGTH: 22
<212> TYPE: RNA
<213> ORGANISM: Homo sapiens

<400> SEQUENCE: 238
caaaacuggc aauuacuuuu gc                                            22

<210> SEQ ID NO 239
<211> LENGTH: 22
<212> TYPE: RNA
<213> ORGANISM: Homo sapiens

<400> SEQUENCE: 239
ucaguaaaug uuuauuagau ga                                            22

<210> SEQ ID NO 240
<211> LENGTH: 22
<212> TYPE: RNA
<213> ORGANISM: Homo sapiens

<400> SEQUENCE: 240
ucagcaaaca uuuauugugu gc                                            22

<210> SEQ ID NO 241
<211> LENGTH: 22
<212> TYPE: RNA
<213> ORGANISM: Homo sapiens

<400> SEQUENCE: 241
auucugcauu uuuagcaagu uc                                            22

<210> SEQ ID NO 242
<211> LENGTH: 22
<212> TYPE: RNA
<213> ORGANISM: Homo sapiens

<400> SEQUENCE: 242
aaacauucgc ggugcacuuc uu                                            22

<210> SEQ ID NO 243
<211> LENGTH: 23
<212> TYPE: RNA
<213> ORGANISM: Homo sapiens

<400> SEQUENCE: 243
ucggggauca ucaugucacg aga                                           23

<210> SEQ ID NO 244
<211> LENGTH: 22
<212> TYPE: RNA
<213> ORGANISM: Homo sapiens

<400> SEQUENCE: 244
ugugacagau ugauaacuga aa                                            22

<210> SEQ ID NO 245
<211> LENGTH: 25
<212> TYPE: RNA
<213> ORGANISM: Homo sapiens

<400> SEQUENCE: 245
aaaggauucu gcugucgguc ccacu                                            25

<210> SEQ ID NO 246
<211> LENGTH: 22
<212> TYPE: RNA
<213> ORGANISM: Homo sapiens

<400> SEQUENCE: 246 ugguggcac agaaucugga cu                                                22

<210> SEQ ID NO 247
<211> LENGTH: 22
<212> TYPE: RNA
<213> ORGANISM: Homo sapiens

<400> SEQUENCE: 247
ggagaaauua uccuuggugu gu                                               22

<210> SEQ ID NO 248
<211> LENGTH: 22
<212> TYPE: RNA
<213> ORGANISM: Homo sapiens

<400> SEQUENCE: 248
caugccuuga guguaggacc gu                                               22

<210> SEQ ID NO 249
<211> LENGTH: 22
<212> TYPE: RNA
<213> ORGANISM: Homo sapiens

<400> SEQUENCE: 249
ccucccacac ccaaggcuug ca                                               22

<210> SEQ ID NO 250
<211> LENGTH: 20
<212> TYPE: RNA
<213> ORGANISM: Homo sapiens

<400> SEQUENCE: 250
cugcaaaggg aagcccuuuc                                                  20

<210> SEQ ID NO 251
<211> LENGTH: 22
<212> TYPE: RNA
<213> ORGANISM: Homo sapiens

<400> SEQUENCE: 251
gaaagugcuu ccuuuuagag gc                                               22

<210> SEQ ID NO 252
<211> LENGTH: 23
<212> TYPE: RNA
<213> ORGANISM: Homo sapiens

<400> SEQUENCE: 252
cucuugaggg aagcacuuuc ugu                                              23

<210> SEQ ID NO 253
<211> LENGTH: 22
<212> TYPE: RNA
<213> ORGANISM: Homo sapiens -continued

<400> SEQUENCE: 253
cucuagaggg aagcacuuuc ug                                              22

<210> SEQ ID NO 254
<211> LENGTH: 21
<212> TYPE: RNA
<213> ORGANISM: Homo sapiens

<400> SEQUENCE: 254
cuccagaggg augcacuuuc u                                               21

<210> SEQ ID NO 255
<211> LENGTH: 22
<212> TYPE: RNA
<213> ORGANISM: Homo sapiens

<400> SEQUENCE: 255
gaaggcgcuu cccuuuagag cg                                              22

<210> SEQ ID NO 256
<211> LENGTH: 22
<212> TYPE: RNA
<213> ORGANISM: Homo sapiens

<400> SEQUENCE: 256
cuacaaaggg aagcacuuuc uc                                              22

<210> SEQ ID NO 257
<211> LENGTH: 21
<212> TYPE: RNA
<213> ORGANISM: Homo sapiens

<400> SEQUENCE: 257
gaaggcgcuu cccuuuggag u                                               21

<210> SEQ ID NO 258
<211> LENGTH: 22
<212> TYPE: RNA
<213> ORGANISM: Homo sapiens

<400> SEQUENCE: 258
cucuagaggg aagcgcuuuc ug                                              22

<210> SEQ ID NO 259
<211> LENGTH: 23
<212> TYPE: RNA
<213> ORGANISM: Homo sapiens

<400> SEQUENCE: 259
gaacgcgcuu cccuauagag ggu                                             23

<210> SEQ ID NO 260
<211> LENGTH: 22
<212> TYPE: RNA
<213> ORGANISM: Homo sapiens

<400> SEQUENCE: 260
cucuagaggg aagcgcuuuc ug                                              22

<210> SEQ ID NO 261
<211> LENGTH: 22
<212> TYPE: RNA
<213> ORGANISM: Homo sapiens

```
<400> SEQUENCE: 261
aaaauggauc ccuuuagagu gu                                        22

<210> SEQ ID NO 262
<211> LENGTH: 22
<212> TYPE: RNA
<213> ORGANISM: Homo sapiens

<400> SEQUENCE: 262
aacgcacuuc ccuuuagagu gu                                        22

<210> SEQ ID NO 263
<211> LENGTH: 22
<212> TYPE: RNA
<213> ORGANISM: Homo sapiens

<400> SEQUENCE: 263
acaaagugcu ucccuuuaga gu                                        22

<210> SEQ ID NO 264
<211> LENGTH: 24
<212> TYPE: RNA
<213> ORGANISM: Homo sapiens

<400> SEQUENCE: 264
acaaagugcu ucccuuuaga gugu                                      24

<210> SEQ ID NO 265
<211> LENGTH: 22
<212> TYPE: RNA
<213> ORGANISM: Homo sapiens

<400> SEQUENCE: 265
aagugcuucc uuuuagaggg uu                                        22

<210> SEQ ID NO 266
<211> LENGTH: 21
<212> TYPE: RNA
<213> ORGANISM: Homo sapiens

<400> SEQUENCE: 266
aaagugcuuc cuuuuugagg g                                         21

<210> SEQ ID NO 267
<211> LENGTH: 20
<212> TYPE: RNA
<213> ORGANISM: Homo sapiens

<400> SEQUENCE: 267
cuacaaaggg aagcccuuuc                                           20

<210> SEQ ID NO 268
<211> LENGTH: 22
<212> TYPE: RNA
<213> ORGANISM: Homo sapiens

<400> SEQUENCE: 268
aaagugcuuc ucuuuggugg gu                                        22

<210> SEQ ID NO 269
<211> LENGTH: 22
<212> TYPE: RNA
```

```
<213> ORGANISM: Homo sapiens

<400> SEQUENCE: 269
cucuagaggg aagcacuuuc ug                                              22

<210> SEQ ID NO 270
<211> LENGTH: 22
<212> TYPE: RNA
<213> ORGANISM: Homo sapiens

<400> SEQUENCE: 270
aaagugcuuc cuuuuagagg gu                                              22

<210> SEQ ID NO 271
<211> LENGTH: 21
<212> TYPE: RNA
<213> ORGANISM: Homo sapiens

<400> SEQUENCE: 271
aaagugcuuc cuuuuagagg g                                               21

<210> SEQ ID NO 272
<211> LENGTH: 21
<212> TYPE: RNA
<213> ORGANISM: Homo sapiens

<400> SEQUENCE: 272
cuccagaggg aaguacuuuc u                                               21

<210> SEQ ID NO 273
<211> LENGTH: 22
<212> TYPE: RNA
<213> ORGANISM: Homo sapiens

<400> SEQUENCE: 273
aaagugcuuc ccuuuggacu gu                                              22

<210> SEQ ID NO 274
<211> LENGTH: 22
<212> TYPE: RNA
<213> ORGANISM: Homo sapiens

<400> SEQUENCE: 274
uucuccaaaa gggagcacuu uc                                              22

<210> SEQ ID NO 275
<211> LENGTH: 22
<212> TYPE: RNA
<213> ORGANISM: Homo sapiens

<400> SEQUENCE: 275
aagugccucc uuuuagagug uu                                              22

<210> SEQ ID NO 276
<211> LENGTH: 22
<212> TYPE: RNA
<213> ORGANISM: Homo sapiens

<400> SEQUENCE: 276
caaagugccu cccuuuagag ug                                              22

<210> SEQ ID NO 277
<211> LENGTH: 22
```

```
<212> TYPE: RNA
<213> ORGANISM: Homo sapiens

<400> SEQUENCE: 277
cucuagaggg aagcgcuuuc ug                                              22

<210> SEQ ID NO 278
<211> LENGTH: 22
<212> TYPE: RNA
<213> ORGANISM: Homo sapiens

<400> SEQUENCE: 278
aaagugcauc uuuuuagagg au                                              22

<210> SEQ ID NO 279
<211> LENGTH: 22
<212> TYPE: RNA
<213> ORGANISM: Homo sapiens

<400> SEQUENCE: 279
cucuagaggg aagcgcuuuc ug                                              22

<210> SEQ ID NO 280
<211> LENGTH: 22
<212> TYPE: RNA
<213> ORGANISM: Homo sapiens

<400> SEQUENCE: 280
aaagugcauc cuuuuagagg uu                                              22

<210> SEQ ID NO 281
<211> LENGTH: 22
<212> TYPE: RNA
<213> ORGANISM: Homo sapiens

<400> SEQUENCE: 281
cucuagaggg aagcgcuuuc ug                                              22

<210> SEQ ID NO 282
<211> LENGTH: 22
<212> TYPE: RNA
<213> ORGANISM: Homo sapiens

<400> SEQUENCE: 282
aaagugcauc cuuuuagagu gu                                              22

<210> SEQ ID NO 283
<211> LENGTH: 22
<212> TYPE: RNA
<213> ORGANISM: Homo sapiens

<400> SEQUENCE: 283
cucuagaggg aagcacuuuc uc                                              22

<210> SEQ ID NO 284
<211> LENGTH: 21
<212> TYPE: RNA
<213> ORGANISM: Homo sapiens

<400> SEQUENCE: 284
gaaagcgcuu cucuuuagag g                                               21

<210> SEQ ID NO 285
```

```
<211> LENGTH: 22
<212> TYPE: RNA
<213> ORGANISM: Homo sapiens

<400> SEQUENCE: 285
cucuagaggg aagcgcuuuc ug                                            22

<210> SEQ ID NO 286
<211> LENGTH: 21
<212> TYPE: RNA
<213> ORGANISM: Homo sapiens

<400> SEQUENCE: 286
aaagcgcuuc ccuucagagu g                                             21

<210> SEQ ID NO 287
<211> LENGTH: 22
<212> TYPE: RNA
<213> ORGANISM: Homo sapiens

<400> SEQUENCE: 287
cucuagaggg aagcacuuuc ug                                            22

<210> SEQ ID NO 288
<211> LENGTH: 21
<212> TYPE: RNA
<213> ORGANISM: Homo sapiens

<400> SEQUENCE: 288
caaagcgcuu cccuuuggag c                                             21

<210> SEQ ID NO 289
<211> LENGTH: 23
<212> TYPE: RNA
<213> ORGANISM: Homo sapiens

<400> SEQUENCE: 289
ucucuggagg gaagcacuuu cug                                           23

<210> SEQ ID NO 290
<211> LENGTH: 23
<212> TYPE: RNA
<213> ORGANISM: Homo sapiens

<400> SEQUENCE: 290
caaagcgcuu cucuuuagag ugu                                           23

<210> SEQ ID NO 291
<211> LENGTH: 22
<212> TYPE: RNA
<213> ORGANISM: Homo sapiens

<400> SEQUENCE: 291
caaagcgcuc cccuuuagag gu                                            22

<210> SEQ ID NO 292
<211> LENGTH: 20
<212> TYPE: RNA
<213> ORGANISM: Homo sapiens

<400> SEQUENCE: 292
cugcaaaggg aagcccuuuc                                               20
```

```
<210> SEQ ID NO 293
<211> LENGTH: 22
<212> TYPE: RNA
<213> ORGANISM: Homo sapiens

<400> SEQUENCE: 293
gaaagcgcuu cccuuugcug ga                                              22

<210> SEQ ID NO 294
<211> LENGTH: 22
<212> TYPE: RNA
<213> ORGANISM: Homo sapiens

<400> SEQUENCE: 294
aucgugcauc cuuuuagagu gu                                              22

<210> SEQ ID NO 295
<211> LENGTH: 22
<212> TYPE: RNA
<213> ORGANISM: Homo sapiens

<400> SEQUENCE: 295
ucgugcaucc cuuuagagug uu                                              22

<210> SEQ ID NO 296
<211> LENGTH: 22
<212> TYPE: RNA
<213> ORGANISM: Homo sapiens

<400> SEQUENCE: 296
aucgugcauc ccuuuagagu gu                                              22

<210> SEQ ID NO 297
<211> LENGTH: 22
<212> TYPE: RNA
<213> ORGANISM: Homo sapiens

<400> SEQUENCE: 297
ccucuagaug gaagcacugu cu                                              22

<210> SEQ ID NO 298
<211> LENGTH: 18
<212> TYPE: RNA
<213> ORGANISM: Homo sapiens

<400> SEQUENCE: 298
ugcuuccuuu cagagggu                                                   18

<210> SEQ ID NO 299
<211> LENGTH: 22
<212> TYPE: RNA
<213> ORGANISM: Homo sapiens

<400> SEQUENCE: 299
aucuggaggu aagaagcacu uu                                              22

<210> SEQ ID NO 300
<211> LENGTH: 23
<212> TYPE: RNA
<213> ORGANISM: Homo sapiens

<400> SEQUENCE: 300
uucucgagga aagaagcacu uuc                                             23
```

```
<210> SEQ ID NO 301
<211> LENGTH: 18
<212> TYPE: RNA
<213> ORGANISM: Homo sapiens

<400> SEQUENCE: 301
ugcuuccuuu cagagggu                                                    18

<210> SEQ ID NO 302
<211> LENGTH: 24
<212> TYPE: RNA
<213> ORGANISM: Homo sapiens

<400> SEQUENCE: 302
uucuccaaaa gaaagcacuu ucug                                             24

<210> SEQ ID NO 303
<211> LENGTH: 22
<212> TYPE: RNA
<213> ORGANISM: Homo sapiens

<400> SEQUENCE: 303
gagugccuuc uuuuggagcg uu                                               22

<210> SEQ ID NO 304
<211> LENGTH: 21
<212> TYPE: RNA
<213> ORGANISM: Homo sapiens

<400> SEQUENCE: 304
auugacacuu cugugaguag a                                                21

<210> SEQ ID NO 305
<211> LENGTH: 22
<212> TYPE: RNA
<213> ORGANISM: Homo sapiens

<400> SEQUENCE: 305
uucucaagga ggugucguuu au                                               22

<210> SEQ ID NO 306
<211> LENGTH: 22
<212> TYPE: RNA
<213> ORGANISM: Homo sapiens

<400> SEQUENCE: 306
uucacaagga ggugucauuu au                                               22

<210> SEQ ID NO 307
<211> LENGTH: 18
<212> TYPE: RNA
<213> ORGANISM: Homo sapiens

<400> SEQUENCE: 307
uucacaggga ggugucau                                                    18

<210> SEQ ID NO 308
<211> LENGTH: 23
<212> TYPE: RNA
<213> ORGANISM: Homo sapiens

<400> SEQUENCE: 308
uaaauuucac cuuucugaga agg                                              23
```

<210> SEQ ID NO 309
<211> LENGTH: 23
<212> TYPE: RNA
<213> ORGANISM: Homo sapiens

<400> SEQUENCE: 309
cacucagccu ugagggcacu uuc                                                 23

<210> SEQ ID NO 310
<211> LENGTH: 22
<212> TYPE: RNA
<213> ORGANISM: Homo sapiens

<400> SEQUENCE: 310
aagugcuguc auagcugagg uc                                                  22

<210> SEQ ID NO 311
<211> LENGTH: 21
<212> TYPE: RNA
<213> ORGANISM: Homo sapiens

<400> SEQUENCE: 311
gugucuuuug cucugcaguc a                                                   21

<210> SEQ ID NO 312
<211> LENGTH: 22
<212> TYPE: RNA
<213> ORGANISM: Homo sapiens

<400> SEQUENCE: 312
uacucaggag aguggcaauc ac                                                  22

<210> SEQ ID NO 313
<211> LENGTH: 21
<212> TYPE: RNA
<213> ORGANISM: Homo sapiens

<400> SEQUENCE: 313
uacugcagac aguggcaauc a                                                   21

<210> SEQ ID NO 314
<211> LENGTH: 22
<212> TYPE: RNA
<213> ORGANISM: Homo sapiens

<400> SEQUENCE: 314
ugauugguac gucugugggu ag                                                  22

<210> SEQ ID NO 315
<211> LENGTH: 22
<212> TYPE: RNA
<213> ORGANISM: Homo sapiens

<400> SEQUENCE: 315
uacugcagac guggcaauca ug                                                  22

<210> SEQ ID NO 316
<211> LENGTH: 23
<212> TYPE: RNA
<213> ORGANISM: Homo sapiens

<400> SEQUENCE: 316
uacuccagag ggcgucacuc aug    23

<210> SEQ ID NO 317
<211> LENGTH: 23
<212> TYPE: RNA
<213> ORGANISM: Homo sapiens

<400> SEQUENCE: 317
ugauuguagc cuuuuggagu aga    23

<210> SEQ ID NO 318
<211> LENGTH: 21
<212> TYPE: RNA
<213> ORGANISM: Homo sapiens

<400> SEQUENCE: 318
uuuugcaccu uuuggaguga a    21

<210> SEQ ID NO 319
<211> LENGTH: 21
<212> TYPE: RNA
<213> ORGANISM: Homo sapiens

<400> SEQUENCE: 319
uaaggcaccc uucugaguag a    21

<210> SEQ ID NO 320
<211> LENGTH: 22
<212> TYPE: RNA
<213> ORGANISM: Homo sapiens

<400> SEQUENCE: 320
gggagccagg aaguauugau gu    22

<210> SEQ ID NO 321
<211> LENGTH: 22
<212> TYPE: RNA
<213> ORGANISM: Homo sapiens

<400> SEQUENCE: 321
cgucaacacu ugcugguuuc cu    22

<210> SEQ ID NO 322
<211> LENGTH: 22
<212> TYPE: RNA
<213> ORGANISM: Homo sapiens

<400> SEQUENCE: 322
agacccuggu cugcacucua uc    22

<210> SEQ ID NO 323
<211> LENGTH: 23
<212> TYPE: RNA
<213> ORGANISM: Homo sapiens

<400> SEQUENCE: 323
uagcagcggg aacaguucug cag    23

<210> SEQ ID NO 324
<211> LENGTH: 21
<212> TYPE: RNA
<213> ORGANISM: Homo sapiens

<400> SEQUENCE: 324
auccuugcua ucugggugcu a                                           21

<210> SEQ ID NO 325
<211> LENGTH: 22
<212> TYPE: RNA
<213> ORGANISM: Homo sapiens

<400> SEQUENCE: 325
aaugcaccug ggcaaggauu ca                                          22

<210> SEQ ID NO 326
<211> LENGTH: 22
<212> TYPE: RNA
<213> ORGANISM: Homo sapiens

<400> SEQUENCE: 326
aauccuuugu cccuggguga ga                                          22

<210> SEQ ID NO 327
<211> LENGTH: 22
<212> TYPE: RNA
<213> ORGANISM: Homo sapiens

<400> SEQUENCE: 327
aaugcacccg ggcaaggauu cu                                          22

<210> SEQ ID NO 328
<211> LENGTH: 22
<212> TYPE: RNA
<213> ORGANISM: Homo sapiens

<400> SEQUENCE: 328
augcaccugg gcaaggauuc ug                                          22

<210> SEQ ID NO 329
<211> LENGTH: 23
<212> TYPE: RNA
<213> ORGANISM: Homo sapiens

<400> SEQUENCE: 329
uaauccuugc uaccuggguga aga                                        23

<210> SEQ ID NO 330
<211> LENGTH: 21
<212> TYPE: RNA
<213> ORGANISM: Homo sapiens

<400> SEQUENCE: 330
uuaagacuug cagugauguu u                                           21

<210> SEQ ID NO 331
<211> LENGTH: 22
<212> TYPE: RNA
<213> ORGANISM: Homo sapiens

<400> SEQUENCE: 331
aacaucacag caagucugug cu                                          22

<210> SEQ ID NO 332
<211> LENGTH: 23
<212> TYPE: RNA
<213> ORGANISM: Homo sapiens

```
<400> SEQUENCE: 332
uuucaagcca gggggcguuu uuc                                        23

<210> SEQ ID NO 333
<211> LENGTH: 22
<212> TYPE: RNA
<213> ORGANISM: Homo sapiens

<400> SEQUENCE: 333
caaaccacac uguggguguua ga                                        22

<210> SEQ ID NO 334
<211> LENGTH: 21
<212> TYPE: RNA
<213> ORGANISM: Homo sapiens

<400> SEQUENCE: 334
cagcagcaca cuguggguuug u                                         21

<210> SEQ ID NO 335
<211> LENGTH: 22
<212> TYPE: RNA
<213> ORGANISM: Homo sapiens

<400> SEQUENCE: 335
ugaguauuac auggccaauc uc                                         22

<210> SEQ ID NO 336
<211> LENGTH: 22
<212> TYPE: RNA
<213> ORGANISM: Homo sapiens

<400> SEQUENCE: 336
aaacaaacau ggugcacuuc uu                                         22

<210> SEQ ID NO 337
<211> LENGTH: 22
<212> TYPE: RNA
<213> ORGANISM: Homo sapiens

<400> SEQUENCE: 337
ugaaacauac acgggaaacc uc                                         22

<210> SEQ ID NO 338
<211> LENGTH: 22
<212> TYPE: RNA
<213> ORGANISM: Homo sapiens

<400> SEQUENCE: 338
uuguacaugg uaggcuuuca uu                                         22

<210> SEQ ID NO 339
<211> LENGTH: 22
<212> TYPE: RNA
<213> ORGANISM: Homo sapiens

<400> SEQUENCE: 339
ugaaggucua cugugugcca gg                                         22

<210> SEQ ID NO 340
<211> LENGTH: 23
<212> TYPE: RNA
<213> ORGANISM: Homo sapiens
```

-continued

```
<400> SEQUENCE: 340
aggaccugcg ggacaagauu cuu                                        23

<210> SEQ ID NO 341
<211> LENGTH: 22
<212> TYPE: RNA
<213> ORGANISM: Homo sapiens

<400> SEQUENCE: 341 agugggggaac ccuuccauga gg                                        22

<210> SEQ ID NO 342
<211> LENGTH: 22
<212> TYPE: RNA
<213> ORGANISM: Homo sapiens

<400> SEQUENCE: 342
cuuaugcaag auucccuucu ac                                         22

<210> SEQ ID NO 343
<211> LENGTH: 20
<212> TYPE: RNA
<213> ORGANISM: Homo sapiens

<400> SEQUENCE: 343
ccauggaucu ccaggugggu                                            20

<210> SEQ ID NO 344
<211> LENGTH: 22
<212> TYPE: RNA
<213> ORGANISM: Homo sapiens

<400> SEQUENCE: 344
caaccuggag gacuccaugc ug                                         22

<210> SEQ ID NO 345
<211> LENGTH: 22
<212> TYPE: RNA
<213> ORGANISM: Homo sapiens

<400> SEQUENCE: 345
gugacaucac auauacggca gc                                         22

<210> SEQ ID NO 346
<211> LENGTH: 21
<212> TYPE: RNA
<213> ORGANISM: Homo sapiens

<400> SEQUENCE: 346
cccagauaau ggcacucuca a                                          21

<210> SEQ ID NO 347
<211> LENGTH: 21
<212> TYPE: RNA
<213> ORGANISM: Homo sapiens

<400> SEQUENCE: 347
uugaaaggcu auuucuuggu c                                          21

<210> SEQ ID NO 348
<211> LENGTH: 22
<212> TYPE: RNA
```

<213> ORGANISM: Homo sapiens

<400> SEQUENCE: 348
aaucguacag ggucauccac uu                                    22

<210> SEQ ID NO 349
<211> LENGTH: 22
<212> TYPE: RNA
<213> ORGANISM: Homo sapiens

<400> SEQUENCE: 349
aaucauacag ggacauccag uu                                    22

<210> SEQ ID NO 350
<211> LENGTH: 22
<212> TYPE: RNA
<213> ORGANISM: Homo sapiens

<400> SEQUENCE: 350
uccuguacug agcugccccg ag                                    22

<210> SEQ ID NO 351
<211> LENGTH: 21
<212> TYPE: RNA
<213> ORGANISM: Homo sapiens

<400> SEQUENCE: 351
cggggcagcu caguacagga u                                     21

<210> SEQ ID NO 352
<211> LENGTH: 22
<212> TYPE: RNA
<213> ORGANISM: Homo sapiens

<400> SEQUENCE: 352
agaggcuggc cgugaugaau uc                                    22

<210> SEQ ID NO 353
<211> LENGTH: 22
<212> TYPE: RNA
<213> ORGANISM: Homo sapiens

<400> SEQUENCE: 353
gucauacacg gcucuccucu cu                                    22

<210> SEQ ID NO 354
<211> LENGTH: 22
<212> TYPE: RNA
<213> ORGANISM: Homo sapiens

<400> SEQUENCE: 354
ucaggcucag uccccucccg au                                    22

<210> SEQ ID NO 355
<211> LENGTH: 22
<212> TYPE: RNA
<213> ORGANISM: Homo sapiens

<400> SEQUENCE: 355
aagacgggag gaaagaaggg ag                                    22

<210> SEQ ID NO 356
<211> LENGTH: 21

```
<212> TYPE: RNA
<213> ORGANISM: Homo sapiens

<400> SEQUENCE: 356
ucacuccucu cucccgucu u                                              21

<210> SEQ ID NO 357
<211> LENGTH: 22
<212> TYPE: RNA
<213> ORGANISM: Homo sapiens

<400> SEQUENCE: 357
uaugugccuu uggacuacau cg                                            22

<210> SEQ ID NO 358
<211> LENGTH: 21
<212> TYPE: RNA
<213> ORGANISM: Homo sapiens

<400> SEQUENCE: 358
gcaguccaug ggcauauaca c                                             21

<210> SEQ ID NO 359
<211> LENGTH: 22
<212> TYPE: RNA
<213> ORGANISM: Homo sapiens

<400> SEQUENCE: 359
acccuaucaa uauugucucu gc                                            22

<210> SEQ ID NO 360
<211> LENGTH: 23
<212> TYPE: RNA
<213> ORGANISM: Homo sapiens

<400> SEQUENCE: 360
uagugcaaua uugcuuauag ggu                                           23

<210> SEQ ID NO 361
<211> LENGTH: 23
<212> TYPE: RNA
<213> ORGANISM: Homo sapiens

<400> SEQUENCE: 361
agguuguccg uggugaguuc gca                                           23

<210> SEQ ID NO 362
<211> LENGTH: 22
<212> TYPE: RNA
<213> ORGANISM: Homo sapiens

<400> SEQUENCE: 362
cucaucugca aagaaguaag ug                                            22

<210> SEQ ID NO 363
<211> LENGTH: 22
<212> TYPE: RNA
<213> ORGANISM: Homo sapiens

<400> SEQUENCE: 363
aacuguuugc agaggaaacu ga                                            22

<210> SEQ ID NO 364
```

```
<211> LENGTH: 22
<212> TYPE: RNA
<213> ORGANISM: Homo sapiens

<400> SEQUENCE: 364
aaaccguuac cauuacugag uu                                                  22

<210> SEQ ID NO 365
<211> LENGTH: 22
<212> TYPE: RNA
<213> ORGANISM: Homo sapiens

<400> SEQUENCE: 365
uuuugcaaua uguuccugaa ua                                                  22

<210> SEQ ID NO 366
<211> LENGTH: 22
<212> TYPE: RNA
<213> ORGANISM: Homo sapiens

<400> SEQUENCE: 366
uugggaucau uuugcaucca ua                                                  22

<210> SEQ ID NO 367
<211> LENGTH: 22
<212> TYPE: RNA
<213> ORGANISM: Homo sapiens

<400> SEQUENCE: 367
uuuugcgaug uguuccuaau au                                                  22

<210> SEQ ID NO 368
<211> LENGTH: 23
<212> TYPE: RNA
<213> ORGANISM: Homo sapiens

<400> SEQUENCE: 368
uugcuaguug cacuccucuc ugu                                                 23

<210> SEQ ID NO 369
<211> LENGTH: 25
<212> TYPE: RNA
<213> ORGANISM: Homo sapiens

<400> SEQUENCE: 369
uaggcagugu auugcuagcg gcugu                                               25

<210> SEQ ID NO 370
<211> LENGTH: 22
<212> TYPE: RNA
<213> ORGANISM: Homo sapiens

<400> SEQUENCE: 370
cagccacaac uacccugcca cu                                                  22

<210> SEQ ID NO 371
<211> LENGTH: 22
<212> TYPE: RNA
<213> ORGANISM: Homo sapiens

<400> SEQUENCE: 371
aggcagugua uuguuagcug gc                                                  22
```

-continued

<210> SEQ ID NO 372
<211> LENGTH: 22
<212> TYPE: RNA
<213> ORGANISM: Homo sapiens

<400> SEQUENCE: 372
uggcagugua uuguuagcug gu                              22

<210> SEQ ID NO 373
<211> LENGTH: 22
<212> TYPE: RNA
<213> ORGANISM: Homo sapiens

<400> SEQUENCE: 373
uugcauaugu aggauguccc au                              22

<210> SEQ ID NO 374
<211> LENGTH: 22
<212> TYPE: RNA
<213> ORGANISM: Homo sapiens

<400> SEQUENCE: 374
aucaugaugg gcuccucggu gu                              22

<210> SEQ ID NO 375
<211> LENGTH: 21
<212> TYPE: RNA
<213> ORGANISM: Homo sapiens

<400> SEQUENCE: 375
cuggauggcu ccuccauguc u                               21

<210> SEQ ID NO 376
<211> LENGTH: 23
<212> TYPE: RNA
<213> ORGANISM: Homo sapiens

<400> SEQUENCE: 376
ucuuggagua ggucauuggg ugg                             23

<210> SEQ ID NO 377
<211> LENGTH: 22
<212> TYPE: RNA
<213> ORGANISM: Homo sapiens

<400> SEQUENCE: 377
caggucgucu ugcagggcuu cu                              22

<210> SEQ ID NO 378
<211> LENGTH: 21
<212> TYPE: RNA
<213> ORGANISM: Homo sapiens

<400> SEQUENCE: 378
ugucuugcag gccgucaugc a                               21

<210> SEQ ID NO 379
<211> LENGTH: 22
<212> TYPE: RNA
<213> ORGANISM: Homo sapiens

<400> SEQUENCE: 379
uaauacuguc ugguaaaacc gu                              22

```
<210> SEQ ID NO 380
<211> LENGTH: 22
<212> TYPE: RNA
<213> ORGANISM: Homo sapiens

<400> SEQUENCE: 380
aucgggaaug ucguguccgc cc                                              22

<210> SEQ ID NO 381
<211> LENGTH: 23
<212> TYPE: RNA
<213> ORGANISM: Homo sapiens

<400> SEQUENCE: 381
aaugacacga ucacucccgu uga                                             23

<210> SEQ ID NO 382
<211> LENGTH: 21
<212> TYPE: RNA
<213> ORGANISM: Homo sapiens

<400> SEQUENCE: 382
caaaacguga ggcgcugcua u                                               21

<210> SEQ ID NO 383
<211> LENGTH: 22
<212> TYPE: RNA
<213> ORGANISM: Homo sapiens

<400> SEQUENCE: 383
cagcagcaau ucauguuuug aa                                              22

<210> SEQ ID NO 384
<211> LENGTH: 23
<212> TYPE: RNA
<213> ORGANISM: Homo sapiens

<400> SEQUENCE: 384
ugaggggcag agagcgagac uuu                                             23

<210> SEQ ID NO 385
<211> LENGTH: 23
<212> TYPE: RNA
<213> ORGANISM: Homo sapiens

<400> SEQUENCE: 385
agcucggucu gaggccccuc agu                                             23

<210> SEQ ID NO 386
<211> LENGTH: 22
<212> TYPE: RNA
<213> ORGANISM: Homo sapiens

<400> SEQUENCE: 386
acuggacuua gggucagaag gc                                              22

<210> SEQ ID NO 387
<211> LENGTH: 23
<212> TYPE: RNA
<213> ORGANISM: Homo sapiens

<400> SEQUENCE: 387
aucaacagac auuaauuggg cgc                                             23
```

```
<210> SEQ ID NO 388
<211> LENGTH: 23
<212> TYPE: RNA
<213> ORGANISM: Homo sapiens

<400> SEQUENCE: 388
acuucaccug guccacuagc cgu                                              23

<210> SEQ ID NO 389
<211> LENGTH: 22
<212> TYPE: RNA
<213> ORGANISM: Homo sapiens

<400> SEQUENCE: 389
uauguaacac gguccacuaa cc                                               22

<210> SEQ ID NO 390
<211> LENGTH: 21
<212> TYPE: RNA
<213> ORGANISM: Homo sapiens

<400> SEQUENCE: 390
uaguagaccg uauagcguac g                                                21

<210> SEQ ID NO 391
<211> LENGTH: 21
<212> TYPE: RNA
<213> ORGANISM: Homo sapiens

<400> SEQUENCE: 391
aauauaacac agauggccug u                                                21

<210> SEQ ID NO 392
<211> LENGTH: 23
<212> TYPE: RNA
<213> ORGANISM: Homo sapiens

<400> SEQUENCE: 392
agguuacccg agcaacuuug cau                                              23

<210> SEQ ID NO 393
<211> LENGTH: 22
<212> TYPE: RNA
<213> ORGANISM: Homo sapiens

<400> SEQUENCE: 393
gaauguugcu cggugaaccc cu                                               22

<210> SEQ ID NO 394
<211> LENGTH: 20
<212> TYPE: RNA
<213> ORGANISM: Homo sapiens

<400> SEQUENCE: 394 auccuagaa auuguucaua                                                   20

<210> SEQ ID NO 395
<211> LENGTH: 22
<212> TYPE: RNA
<213> ORGANISM: Homo sapiens

<400> SEQUENCE: 395
```
agaucagaag gugauugugg cu                            22

<210> SEQ ID NO 396
<211> LENGTH: 22
<212> TYPE: RNA
<213> ORGANISM: Homo sapiens

<400> SEQUENCE: 396
gaaguuguuc gugguggauu cg                            22

<210> SEQ ID NO 397
<211> LENGTH: 22
<212> TYPE: RNA
<213> ORGANISM: Homo sapiens

<400> SEQUENCE: 397
uauacaaggg caagcucucu gu                            22

<210> SEQ ID NO 398
<211> LENGTH: 22
<212> TYPE: RNA
<213> ORGANISM: Homo sapiens

<400> SEQUENCE: 398
ugguugacca uagaacaugc gc                            22

<210> SEQ ID NO 399
<211> LENGTH: 22
<212> TYPE: RNA
<213> ORGANISM: Homo sapiens

<400> SEQUENCE: 399
uauguaauau gguccacauc uu                            22

<210> SEQ ID NO 400
<211> LENGTH: 22
<212> TYPE: RNA
<213> ORGANISM: Homo sapiens

<400> SEQUENCE: 400
uauguaacau gguccacuaa cu                            22

<210> SEQ ID NO 401
<211> LENGTH: 21
<212> TYPE: RNA
<213> ORGANISM: Homo sapiens

<400> SEQUENCE: 401
ugguagacua uggaacguag g                             21

<210> SEQ ID NO 402
<211> LENGTH: 22
<212> TYPE: RNA
<213> ORGANISM: Homo sapiens

<400> SEQUENCE: 402
cuccugacuc cagguccugu gu                            22

<210> SEQ ID NO 403
<211> LENGTH: 21
<212> TYPE: RNA
<213> ORGANISM: Homo sapiens

<400> SEQUENCE: 403

```
acuggacuug gagucagaag g                                      21

<210> SEQ ID NO 404
<211> LENGTH: 22
<212> TYPE: RNA
<213> ORGANISM: Homo sapiens

<400> SEQUENCE: 404
agagguugcc cuuggugaau uc                                     22

<210> SEQ ID NO 405
<211> LENGTH: 22
<212> TYPE: RNA
<213> ORGANISM: Homo sapiens

<400> SEQUENCE: 405
aucacacaaa ggcaacuuuu gu                                     22

<210> SEQ ID NO 406
<211> LENGTH: 21
<212> TYPE: RNA
<213> ORGANISM: Homo sapiens

<400> SEQUENCE: 406
aacauagagg aaauuccacg u                                      21

<210> SEQ ID NO 407
<211> LENGTH: 22
<212> TYPE: RNA
<213> ORGANISM: Homo sapiens

<400> SEQUENCE: 407
aucauagagg aaaauccaug uu                                     22

<210> SEQ ID NO 408
<211> LENGTH: 22
<212> TYPE: RNA
<213> ORGANISM: Homo sapiens

<400> SEQUENCE: 408
guagauucuc cuucuaugag ua                                     22

<210> SEQ ID NO 409
<211> LENGTH: 21
<212> TYPE: RNA
<213> ORGANISM: Homo sapiens

<400> SEQUENCE: 409
aucauagagg aaaauccacg u                                      21

<210> SEQ ID NO 410
<211> LENGTH: 22
<212> TYPE: RNA
<213> ORGANISM: Homo sapiens

<400> SEQUENCE: 410
uuuguucguu cggcucgcgu ga                                     22

<210> SEQ ID NO 411
<211> LENGTH: 22
<212> TYPE: RNA
<213> ORGANISM: Homo sapiens
```

```
<400> SEQUENCE: 411
cuuagcaggu uguauuauca uu                                            22

<210> SEQ ID NO 412
<211> LENGTH: 22
<212> TYPE: RNA
<213> ORGANISM: Homo sapiens

<400> SEQUENCE: 412
auauaauaca accugcuaag ug                                            22

<210> SEQ ID NO 413
<211> LENGTH: 22
<212> TYPE: RNA
<213> ORGANISM: Homo sapiens

<400> SEQUENCE: 413
cuuaucagau uguauuguaa uu                                            22

<210> SEQ ID NO 414
<211> LENGTH: 22
<212> TYPE: RNA
<213> ORGANISM: Homo sapiens

<400> SEQUENCE: 414
uuauaauaca accugauaag ug                                            22

<210> SEQ ID NO 415
<211> LENGTH: 22
<212> TYPE: RNA
<213> ORGANISM: Homo sapiens

<400> SEQUENCE: 415
acucaaaaug ggggcgcuuu cc                                            22

<210> SEQ ID NO 416
<211> LENGTH: 23
<212> TYPE: RNA
<213> ORGANISM: Homo sapiens

<400> SEQUENCE: 416
gaagugcuuc gauuuugggg ugu                                           23

<210> SEQ ID NO 417
<211> LENGTH: 23
<212> TYPE: RNA
<213> ORGANISM: Homo sapiens

<400> SEQUENCE: 417
aaagugcugc gacauuugag cgu                                           23

<210> SEQ ID NO 418
<211> LENGTH: 20
<212> TYPE: RNA
<213> ORGANISM: Homo sapiens

<400> SEQUENCE: 418
acucaaacug uggggggcacu                                              20

<210> SEQ ID NO 419
<211> LENGTH: 23
<212> TYPE: RNA
<213> ORGANISM: Homo sapiens
```

```
<400> SEQUENCE: 419
aagugccgcc aucuuugag ugu                                          23

<210> SEQ ID NO 420
<211> LENGTH: 22
<212> TYPE: RNA
<213> ORGANISM: Homo sapiens

<400> SEQUENCE: 420
gccugcuggg guggaaccug gu                                          22

<210> SEQ ID NO 421
<211> LENGTH: 22
<212> TYPE: RNA
<213> ORGANISM: Homo sapiens

<400> SEQUENCE: 421
agaucgaccg uguuauauuc gc                                          22

<210> SEQ ID NO 422
<211> LENGTH: 21
<212> TYPE: RNA
<213> ORGANISM: Homo sapiens

<400> SEQUENCE: 422
aauaauacau gguugaucuu u                                           21

<210> SEQ ID NO 423
<211> LENGTH: 22
<212> TYPE: RNA
<213> ORGANISM: Homo sapiens

<400> SEQUENCE: 423
acuguugcua auaugcaacu cu                                          22

<210> SEQ ID NO 424
<211> LENGTH: 22
<212> TYPE: RNA
<213> ORGANISM: Homo sapiens

<400> SEQUENCE: 424
aauugcacuu uagcaauggu ga                                          22

<210> SEQ ID NO 425
<211> LENGTH: 22
<212> TYPE: RNA
<213> ORGANISM: Homo sapiens

<400> SEQUENCE: 425
agggacuuuc aggggcagcu gu                                          22

<210> SEQ ID NO 426
<211> LENGTH: 22
<212> TYPE: RNA
<213> ORGANISM: Homo sapiens

<400> SEQUENCE: 426
uaaugccccu aaaaauccuu au                                          22

<210> SEQ ID NO 427
<211> LENGTH: 22
<212> TYPE: RNA
```

```
<213> ORGANISM: Homo sapiens

<400> SEQUENCE: 427
cggguggauc acgaugcaau uu                                              22

<210> SEQ ID NO 428
<211> LENGTH: 22
<212> TYPE: RNA
<213> ORGANISM: Homo sapiens

<400> SEQUENCE: 428
aauugcacgg uauccaucug ua                                              22

<210> SEQ ID NO 429
<211> LENGTH: 24
<212> TYPE: RNA
<213> ORGANISM: Homo sapiens

<400> SEQUENCE: 429
aauccuugga accuaggugu gagu                                            24

<210> SEQ ID NO 430
<211> LENGTH: 22
<212> TYPE: RNA
<213> ORGANISM: Homo sapiens

<400> SEQUENCE: 430
aacacaccua uucaaggauu ca                                              22

<210> SEQ ID NO 431
<211> LENGTH: 22
<212> TYPE: RNA
<213> ORGANISM: Homo sapiens

<400> SEQUENCE: 431
uuaucagaau cuccaggggu ac                                              22

<210> SEQ ID NO 432
<211> LENGTH: 23
<212> TYPE: RNA
<213> ORGANISM: Homo sapiens

<400> SEQUENCE: 432 uccccaggu gugauucuga uuu                                              23

<210> SEQ ID NO 433
<211> LENGTH: 23
<212> TYPE: RNA
<213> ORGANISM: Homo sapiens

<400> SEQUENCE: 433
aggcagugua guuagcugau ugc                                             23

<210> SEQ ID NO 434
<211> LENGTH: 22
<212> TYPE: RNA
<213> ORGANISM: Homo sapiens

<400> SEQUENCE: 434
aaucacuaac cacacggcca gg                                              22

<210> SEQ ID NO 435
<211> LENGTH: 23
```

```
<212> TYPE: RNA
<213> ORGANISM: Homo sapiens

<400> SEQUENCE: 435
uaggcagugu cauuagcuga uug                                    23

<210> SEQ ID NO 436
<211> LENGTH: 22
<212> TYPE: RNA
<213> ORGANISM: Homo sapiens

<400> SEQUENCE: 436
caaucacuaa cuccacugcc au                                     22

<210> SEQ ID NO 437
<211> LENGTH: 22
<212> TYPE: RNA
<213> ORGANISM: Homo sapiens

<400> SEQUENCE: 437
caaucagcaa guauacugcc cu                                     22

<210> SEQ ID NO 438
<211> LENGTH: 22
<212> TYPE: RNA
<213> ORGANISM: Homo sapiens

<400> SEQUENCE: 438
uggcaguguc uuagcugguu gu                                     22

<210> SEQ ID NO 439
<211> LENGTH: 23
<212> TYPE: RNA
<213> ORGANISM: Homo sapiens

<400> SEQUENCE: 439
ugucugcccg caugccugcc ucu                                    23

<210> SEQ ID NO 440
<211> LENGTH: 22
<212> TYPE: RNA
<213> ORGANISM: Homo sapiens

<400> SEQUENCE: 440
gcugacuccu aguccagggc uc                                     22

<210> SEQ ID NO 441
<211> LENGTH: 21
<212> TYPE: RNA
<213> ORGANISM: Homo sapiens

<400> SEQUENCE: 441
aggggugcua ucugugauug a                                      21

<210> SEQ ID NO 442
<211> LENGTH: 23
<212> TYPE: RNA
<213> ORGANISM: Homo sapiens

<400> SEQUENCE: 442
ucucacacag aaaucgcacc cgu                                    23

<210> SEQ ID NO 443
```

<211> LENGTH: 22
<212> TYPE: RNA
<213> ORGANISM: Homo sapiens

<400> SEQUENCE: 443
uccgucucag uuacuuuaua gc                                            22

<210> SEQ ID NO 444
<211> LENGTH: 22
<212> TYPE: RNA
<213> ORGANISM: Homo sapiens

<400> SEQUENCE: 444
uuauaaagca augagacuga uu                                            22

<210> SEQ ID NO 445
<211> LENGTH: 22
<212> TYPE: RNA
<213> ORGANISM: Homo sapiens

<400> SEQUENCE: 445
cagugccucg gcagugcagc cc                                            22

<210> SEQ ID NO 446
<211> LENGTH: 20
<212> TYPE: RNA
<213> ORGANISM: Homo sapiens

<400> SEQUENCE: 446
gugcauugcu guugcauugc                                               20

<210> SEQ ID NO 447
<211> LENGTH: 22
<212> TYPE: RNA
<213> ORGANISM: Homo sapiens

<400> SEQUENCE: 447
caauguuucc acagugcauc ac                                            22

<210> SEQ ID NO 448
<211> LENGTH: 21
<212> TYPE: RNA
<213> ORGANISM: Homo sapiens

<400> SEQUENCE: 448
gugcauugua guugcauugc a                                             21

<210> SEQ ID NO 449
<211> LENGTH: 23
<212> TYPE: RNA
<213> ORGANISM: Homo sapiens

<400> SEQUENCE: 449
ucccuguccu ccaggagcuc acg                                           23

<210> SEQ ID NO 450
<211> LENGTH: 23
<212> TYPE: RNA
<213> ORGANISM: Homo sapiens

<400> SEQUENCE: 450
ugagcgccuc gacgacagag ccg                                           23

```
<210> SEQ ID NO 451
<211> LENGTH: 22
<212> TYPE: RNA
<213> ORGANISM: Homo sapiens

<400> SEQUENCE: 451
aacaauaucc uggugcugag ug                                              22

<210> SEQ ID NO 452
<211> LENGTH: 22
<212> TYPE: RNA
<213> ORGANISM: Homo sapiens

<400> SEQUENCE: 452
uccagcauca gugauuuugu ug                                              22

<210> SEQ ID NO 453
<211> LENGTH: 21
<212> TYPE: RNA
<213> ORGANISM: Homo sapiens

<400> SEQUENCE: 453
gaacggcuuc auacaggagu u                                               21

<210> SEQ ID NO 454
<211> LENGTH: 22
<212> TYPE: RNA
<213> ORGANISM: Homo sapiens

<400> SEQUENCE: 454
cuccuauaug augccuuucu uc                                              22

<210> SEQ ID NO 455
<211> LENGTH: 22
<212> TYPE: RNA
<213> ORGANISM: Homo sapiens

<400> SEQUENCE: 455
uuuuucauua uugcuccuga cc                                              22

<210> SEQ ID NO 456
<211> LENGTH: 23
<212> TYPE: RNA
<213> ORGANISM: Homo sapiens

<400> SEQUENCE: 456
ucaagagcaa uaacgaaaaa ugu                                             23

<210> SEQ ID NO 457
<211> LENGTH: 22
<212> TYPE: RNA
<213> ORGANISM: Homo sapiens

<400> SEQUENCE: 457
cuagguaugg ucccagggau cc                                              22

<210> SEQ ID NO 458
<211> LENGTH: 21
<212> TYPE: RNA
<213> ORGANISM: Homo sapiens

<400> SEQUENCE: 458
gccccugggc cuauccuaga a                                               21
```

```
<210> SEQ ID NO 459
<211> LENGTH: 22
<212> TYPE: RNA
<213> ORGANISM: Homo sapiens

<400> SEQUENCE: 459 ucucuggcc ugugucuuag gc                                             22

<210> SEQ ID NO 460
<211> LENGTH: 23
<212> TYPE: RNA
<213> ORGANISM: Homo sapiens

<400> SEQUENCE: 460
gcaaagcaca cggccugcag aga                                           23

<210> SEQ ID NO 461
<211> LENGTH: 22
<212> TYPE: RNA
<213> ORGANISM: Homo sapiens

<400> SEQUENCE: 461
aacacaccug guuaaccucu uu                                            22

<210> SEQ ID NO 462
<211> LENGTH: 22
<212> TYPE: RNA
<213> ORGANISM: Homo sapiens

<400> SEQUENCE: 462
cuggcccucu cugcccuucc gu                                            22

<210> SEQ ID NO 463
<211> LENGTH: 20
<212> TYPE: RNA
<213> ORGANISM: Homo sapiens

<400> SEQUENCE: 463
ccucugggcc cuuccuccag                                               20

<210> SEQ ID NO 464
<211> LENGTH: 23
<212> TYPE: RNA
<213> ORGANISM: Homo sapiens

<400> SEQUENCE: 464
ccuaguaggu guccaguaag ugu                                           23

<210> SEQ ID NO 465
<211> LENGTH: 23
<212> TYPE: RNA
<213> ORGANISM: Homo sapiens

<400> SEQUENCE: 465 cgcaucccu agggcauugg ugu                                            23

<210> SEQ ID NO 466
<211> LENGTH: 20
<212> TYPE: RNA
<213> ORGANISM: Homo sapiens

<400> SEQUENCE: 466
acugccccag gugcugcugg                                               20
```

```
<210> SEQ ID NO 467
<211> LENGTH: 22
<212> TYPE: RNA
<213> ORGANISM: Homo sapiens

<400> SEQUENCE: 467
aggugguccg uggcgcguuc gc                                            22

<210> SEQ ID NO 468
<211> LENGTH: 21
<212> TYPE: RNA
<213> ORGANISM: Homo sapiens

<400> SEQUENCE: 468
cacauuacac ggucgaccuc u                                             21

<210> SEQ ID NO 469
<211> LENGTH: 19
<212> TYPE: RNA
<213> ORGANISM: Homo sapiens

<400> SEQUENCE: 469
aaaagcuggg uugagagga                                                19

<210> SEQ ID NO 470
<211> LENGTH: 20
<212> TYPE: RNA
<213> ORGANISM: Homo sapiens

<400> SEQUENCE: 470
aaaagcuggg uugagagggu                                               20

<210> SEQ ID NO 471
<211> LENGTH: 22
<212> TYPE: RNA
<213> ORGANISM: Homo sapiens

<400> SEQUENCE: 471
aaaagcuggg uugagagggc aa                                            22

<210> SEQ ID NO 472
<211> LENGTH: 22
<212> TYPE: RNA
<213> ORGANISM: Homo sapiens

<400> SEQUENCE: 472
aaaagcuggg uugagagggc ga                                            22

<210> SEQ ID NO 473
<211> LENGTH: 22
<212> TYPE: RNA
<213> ORGANISM: Homo sapiens

<400> SEQUENCE: 473
caauuuagug ugugugauau uu                                            22

<210> SEQ ID NO 474
<211> LENGTH: 22
<212> TYPE: RNA
<213> ORGANISM: Homo sapiens

<400> SEQUENCE: 474
```
uauugcacau uacuaaguug ca                                               22

<210> SEQ ID NO 475
<211> LENGTH: 22
<212> TYPE: RNA
<213> ORGANISM: Homo sapiens

<400> SEQUENCE: 475
ugcuaugcca acauauugcc au                                               22

<210> SEQ ID NO 476
<211> LENGTH: 21
<212> TYPE: RNA
<213> ORGANISM: Homo sapiens

<400> SEQUENCE: 476
aggcaagaug cuggcauagc u                                                21

<210> SEQ ID NO 477
<211> LENGTH: 22
<212> TYPE: RNA
<213> ORGANISM: Homo sapiens

<400> SEQUENCE: 477
cuuucagucg gauguuuaca gc                                               22

<210> SEQ ID NO 478
<211> LENGTH: 22
<212> TYPE: RNA
<213> ORGANISM: Homo sapiens

<400> SEQUENCE: 478
uguaaacauc cuugacugga ag                                               22

<210> SEQ ID NO 479
<211> LENGTH: 22
<212> TYPE: RNA
<213> ORGANISM: Homo sapiens

<400> SEQUENCE: 479
cuuucaguca gauguuugcu gc                                               22

<210> SEQ ID NO 480
<211> LENGTH: 22
<212> TYPE: RNA
<213> ORGANISM: Homo sapiens

<400> SEQUENCE: 480
uguaaacauc cccgacugga ag                                               22

<210> SEQ ID NO 481
<211> LENGTH: 22
<212> TYPE: RNA
<213> ORGANISM: Homo sapiens

<400> SEQUENCE: 481
cugggagaag gcuguuuacu cu                                               22

<210> SEQ ID NO 482
<211> LENGTH: 22
<212> TYPE: RNA
<213> ORGANISM: Homo sapiens

<400> SEQUENCE: 482
cugggagagg guuguuuacu cc                                          22

<210> SEQ ID NO 483
<211> LENGTH: 23
<212> TYPE: RNA
<213> ORGANISM: Homo sapiens

<400> SEQUENCE: 483
uguaaacauc cuacacucuc agc                                         23

<210> SEQ ID NO 484
<211> LENGTH: 22
<212> TYPE: RNA
<213> ORGANISM: Homo sapiens

<400> SEQUENCE: 484
cugggaggug gauguuuacu uc                                          22

<210> SEQ ID NO 485
<211> LENGTH: 22
<212> TYPE: RNA
<213> ORGANISM: Homo sapiens

<400> SEQUENCE: 485
uguaaacauc cuacacucag cu                                          22

<210> SEQ ID NO 486
<211> LENGTH: 22
<212> TYPE: RNA
<213> ORGANISM: Homo sapiens

<400> SEQUENCE: 486
cuuucagucg gauguuugca gc                                          22

<210> SEQ ID NO 487
<211> LENGTH: 22
<212> TYPE: RNA
<213> ORGANISM: Homo sapiens

<400> SEQUENCE: 487
uguaaacauc cucgacugga ag                                          22

<210> SEQ ID NO 488
<211> LENGTH: 17
<212> TYPE: RNA
<213> ORGANISM: Homo sapiens

<400> SEQUENCE: 488
uaauugcuuc cauguuu                                                17

<210> SEQ ID NO 489
<211> LENGTH: 17
<212> TYPE: RNA
<213> ORGANISM: Homo sapiens

<400> SEQUENCE: 489
uaagugcuuc caugcuu                                                17

<210> SEQ ID NO 490
<211> LENGTH: 22
<212> TYPE: RNA
<213> ORGANISM: Homo sapiens -continued

<400> SEQUENCE: 490
acuuuaacau ggaggcacuu gc                                    22

<210> SEQ ID NO 491
<211> LENGTH: 23
<212> TYPE: RNA
<213> ORGANISM: Homo sapiens

<400> SEQUENCE: 491
uaagugcuuc cauguuugag ugu                                   23

<210> SEQ ID NO 492
<211> LENGTH: 22
<212> TYPE: RNA
<213> ORGANISM: Homo sapiens

<400> SEQUENCE: 492
uuuaacaugg ggguaccugc ug                                    22

<210> SEQ ID NO 493
<211> LENGTH: 23
<212> TYPE: RNA
<213> ORGANISM: Homo sapiens

<400> SEQUENCE: 493
uaagugcuuc cauguuucag ugg                                   23

<210> SEQ ID NO 494
<211> LENGTH: 22
<212> TYPE: RNA
<213> ORGANISM: Homo sapiens

<400> SEQUENCE: 494
acuuuaacau ggaagugcuu uc                                    22

<210> SEQ ID NO 495
<211> LENGTH: 23
<212> TYPE: RNA
<213> ORGANISM: Homo sapiens

<400> SEQUENCE: 495
uaagugcuuc cauguuuuag uag                                   23

<210> SEQ ID NO 496
<211> LENGTH: 23
<212> TYPE: RNA
<213> ORGANISM: Homo sapiens

<400> SEQUENCE: 496
acuuaaacgu ggauguacuu gcu                                   23

<210> SEQ ID NO 497
<211> LENGTH: 23
<212> TYPE: RNA
<213> ORGANISM: Homo sapiens

<400> SEQUENCE: 497
uaagugcuuc cauguuuugg uga                                   23

<210> SEQ ID NO 498
<211> LENGTH: 23
<212> TYPE: RNA
<213> ORGANISM: Homo sapiens

```
<400> SEQUENCE: 498
cagugcaaug auauugucaa agc                                           23

<210> SEQ ID NO 499
<211> LENGTH: 23
<212> TYPE: RNA
<213> ORGANISM: Homo sapiens

<400> SEQUENCE: 499
cagugcaaua guauugucaa agc                                           23

<210> SEQ ID NO 500
<211> LENGTH: 22
<212> TYPE: RNA
<213> ORGANISM: Homo sapiens

<400> SEQUENCE: 500
uauacaaggg cagacucucu cu                                            22

<210> SEQ ID NO 501
<211> LENGTH: 22
<212> TYPE: RNA
<213> ORGANISM: Homo sapiens

<400> SEQUENCE: 501
ugaccgauuu cuccuggugu uc                                            22

<210> SEQ ID NO 502
<211> LENGTH: 22
<212> TYPE: RNA
<213> ORGANISM: Homo sapiens

<400> SEQUENCE: 502
uagcaccauu ugaaaucggu ua                                            22

<210> SEQ ID NO 503
<211> LENGTH: 22
<212> TYPE: RNA
<213> ORGANISM: Homo sapiens

<400> SEQUENCE: 503
cugguuucac augguggcuu ag                                            22

<210> SEQ ID NO 504
<211> LENGTH: 24
<212> TYPE: RNA
<213> ORGANISM: Homo sapiens

<400> SEQUENCE: 504
gcugguuuca uauggugguu uaga                                          24

<210> SEQ ID NO 505
<211> LENGTH: 23
<212> TYPE: RNA
<213> ORGANISM: Homo sapiens

<400> SEQUENCE: 505
uagcaccauu ugaaaucagu guu                                           23

<210> SEQ ID NO 506
<211> LENGTH: 22
<212> TYPE: RNA
```

```
<213> ORGANISM: Homo sapiens

<400> SEQUENCE: 506
acugauuucu uuugguguuc ag                                              22

<210> SEQ ID NO 507
<211> LENGTH: 22
<212> TYPE: RNA
<213> ORGANISM: Homo sapiens

<400> SEQUENCE: 507
uagcaccauc ugaaaucggu ua                                              22

<210> SEQ ID NO 508
<211> LENGTH: 22
<212> TYPE: RNA
<213> ORGANISM: Homo sapiens

<400> SEQUENCE: 508
ugguuuaccg ucccacauac au                                              22

<210> SEQ ID NO 509
<211> LENGTH: 22
<212> TYPE: RNA
<213> ORGANISM: Homo sapiens

<400> SEQUENCE: 509 uauguggau gguaaaccgc uu                                               22

<210> SEQ ID NO 510
<211> LENGTH: 24
<212> TYPE: RNA
<213> ORGANISM: Homo sapiens

<400> SEQUENCE: 510
agcagaagca gggagguucu ccca                                            24

<210> SEQ ID NO 511
<211> LENGTH: 21
<212> TYPE: RNA
<213> ORGANISM: Homo sapiens

<400> SEQUENCE: 511
auguaugugu gcaugugcau g                                               21

<210> SEQ ID NO 512
<211> LENGTH: 21
<212> TYPE: RNA
<213> ORGANISM: Homo sapiens

<400> SEQUENCE: 512 agggccccc cucaauccug u                                                21

<210> SEQ ID NO 513
<211> LENGTH: 22
<212> TYPE: RNA
<213> ORGANISM: Homo sapiens

<400> SEQUENCE: 513
gaggguuggg uggaggcucu cc                                              22

<210> SEQ ID NO 514
<211> LENGTH: 22
```

```
<212> TYPE: RNA
<213> ORGANISM: Homo sapiens

<400> SEQUENCE: 514
aaggagcuca cagucuauug ag                                              22

<210> SEQ ID NO 515
<211> LENGTH: 22
<212> TYPE: RNA
<213> ORGANISM: Homo sapiens

<400> SEQUENCE: 515
cacuagauug ugagcuccug ga                                              22

<210> SEQ ID NO 516
<211> LENGTH: 22
<212> TYPE: RNA
<213> ORGANISM: Homo sapiens

<400> SEQUENCE: 516
agagcuuagc ugauugguga ac                                              22

<210> SEQ ID NO 517
<211> LENGTH: 21
<212> TYPE: RNA
<213> ORGANISM: Homo sapiens

<400> SEQUENCE: 517
uucacagugg cuaaguucug c                                               21

<210> SEQ ID NO 518
<211> LENGTH: 22
<212> TYPE: RNA
<213> ORGANISM: Homo sapiens

<400> SEQUENCE: 518
agggcuuagc ugcuugugag ca                                              22

<210> SEQ ID NO 519
<211> LENGTH: 21
<212> TYPE: RNA
<213> ORGANISM: Homo sapiens

<400> SEQUENCE: 519
uucacagugg cuaaguuccg c                                               21

<210> SEQ ID NO 520
<211> LENGTH: 22
<212> TYPE: RNA
<213> ORGANISM: Homo sapiens

<400> SEQUENCE: 520
ccuguucucc auuacuuggc uc                                              22

<210> SEQ ID NO 521
<211> LENGTH: 21
<212> TYPE: RNA
<213> ORGANISM: Homo sapiens

<400> SEQUENCE: 521
uucaaguaau ucaggauagg u                                               21

<210> SEQ ID NO 522
```

```
<211> LENGTH: 22
<212> TYPE: RNA
<213> ORGANISM: Homo sapiens

<400> SEQUENCE: 522
ccuauucuug auuacuuguu uc                                              22

<210> SEQ ID NO 523
<211> LENGTH: 22
<212> TYPE: RNA
<213> ORGANISM: Homo sapiens

<400> SEQUENCE: 523
ccuauucuug guuacuugca cg                                              22

<210> SEQ ID NO 524
<211> LENGTH: 22
<212> TYPE: RNA
<213> ORGANISM: Homo sapiens

<400> SEQUENCE: 524
uucaaguaau ccaggauagg cu                                              22

<210> SEQ ID NO 525
<211> LENGTH: 21
<212> TYPE: RNA
<213> ORGANISM: Homo sapiens

<400> SEQUENCE: 525
aggcggagac uugggcaauu g                                               21

<210> SEQ ID NO 526
<211> LENGTH: 22
<212> TYPE: RNA
<213> ORGANISM: Homo sapiens

<400> SEQUENCE: 526
cauugcacuu gucucggucu ga                                              22

<210> SEQ ID NO 527
<211> LENGTH: 22
<212> TYPE: RNA
<213> ORGANISM: Homo sapiens

<400> SEQUENCE: 527
ugccuacuga gcugaaacac ag                                              22

<210> SEQ ID NO 528
<211> LENGTH: 22
<212> TYPE: RNA
<213> ORGANISM: Homo sapiens

<400> SEQUENCE: 528
ugccuacuga gcugauauca gu                                              22

<210> SEQ ID NO 529
<211> LENGTH: 22
<212> TYPE: RNA
<213> ORGANISM: Homo sapiens

<400> SEQUENCE: 529
uggcucaguu cagcaggaac ag                                              22
```

```
<210> SEQ ID NO 530
<211> LENGTH: 22
<212> TYPE: RNA
<213> ORGANISM: Homo sapiens

<400> SEQUENCE: 530
uggguuccug gcaugcugau uu                                              22

<210> SEQ ID NO 531
<211> LENGTH: 21
<212> TYPE: RNA
<213> ORGANISM: Homo sapiens

<400> SEQUENCE: 531
aucacauugc cagggauuac c                                               21

<210> SEQ ID NO 532
<211> LENGTH: 22
<212> TYPE: RNA
<213> ORGANISM: Homo sapiens

<400> SEQUENCE: 532
gggguuccug gggaugggau uu                                              22

<210> SEQ ID NO 533
<211> LENGTH: 21
<212> TYPE: RNA
<213> ORGANISM: Homo sapiens

<400> SEQUENCE: 533
aucacauugc cagggauuuc c                                               21

<210> SEQ ID NO 534
<211> LENGTH: 22
<212> TYPE: RNA
<213> ORGANISM: Homo sapiens

<400> SEQUENCE: 534
gagagcagug uguuugccu gg                                               22

<210> SEQ ID NO 535
<211> LENGTH: 21
<212> TYPE: RNA
<213> ORGANISM: Homo sapiens

<400> SEQUENCE: 535
ugacagcgcc cugccuggcu c                                               21

<210> SEQ ID NO 536
<211> LENGTH: 22
<212> TYPE: RNA
<213> ORGANISM: Homo sapiens

<400> SEQUENCE: 536
ucugcaagug ucagaggcga gg                                              22

<210> SEQ ID NO 537
<211> LENGTH: 23
<212> TYPE: RNA
<213> ORGANISM: Homo sapiens

<400> SEQUENCE: 537
aaaauggugc ccuagugacu aca                                             23
```

```
<210> SEQ ID NO 538
<211> LENGTH: 21
<212> TYPE: RNA
<213> ORGANISM: Homo sapiens

<400> SEQUENCE: 538
caagucacua gugguuccgu u                                              21

<210> SEQ ID NO 539
<211> LENGTH: 22
<212> TYPE: RNA
<213> ORGANISM: Homo sapiens

<400> SEQUENCE: 539
cguguauuug acaagcugag uu                                             22

<210> SEQ ID NO 540
<211> LENGTH: 22
<212> TYPE: RNA
<213> ORGANISM: Homo sapiens

<400> SEQUENCE: 540
ugucaguuug ucaaauaccc ca                                             22

<210> SEQ ID NO 541
<211> LENGTH: 22
<212> TYPE: RNA
<213> ORGANISM: Homo sapiens

<400> SEQUENCE: 541
cucaguagcc aguguagauc cu                                             22

<210> SEQ ID NO 542
<211> LENGTH: 21
<212> TYPE: RNA
<213> ORGANISM: Homo sapiens

<400> SEQUENCE: 542
agcuacaucu ggcuacuggg u                                              21

<210> SEQ ID NO 543
<211> LENGTH: 22
<212> TYPE: RNA
<213> ORGANISM: Homo sapiens

<400> SEQUENCE: 543
accuggcaua caauguagau uu                                             22

<210> SEQ ID NO 544
<211> LENGTH: 23
<212> TYPE: RNA
<213> ORGANISM: Homo sapiens

<400> SEQUENCE: 544
agcuacauug ucugcugggu uuc                                            23

<210> SEQ ID NO 545
<211> LENGTH: 22
<212> TYPE: RNA
<213> ORGANISM: Homo sapiens

<400> SEQUENCE: 545
acacagggcu guugugaaga cu                                             22
```

-continued

<210> SEQ ID NO 546
<211> LENGTH: 21
<212> TYPE: RNA
<213> ORGANISM: Homo sapiens

<400> SEQUENCE: 546
ccaccaccgu gucugacacu u                                              21

<210> SEQ ID NO 547
<211> LENGTH: 21
<212> TYPE: RNA
<213> ORGANISM: Homo sapiens

<400> SEQUENCE: 547
ccacaccgua ucugacacuu u                                              21

<210> SEQ ID NO 548
<211> LENGTH: 22
<212> TYPE: RNA
<213> ORGANISM: Homo sapiens

<400> SEQUENCE: 548
aguucuucag uggcaagcuu ua                                             22

<210> SEQ ID NO 549
<211> LENGTH: 22
<212> TYPE: RNA
<213> ORGANISM: Homo sapiens

<400> SEQUENCE: 549
aagcugccag uugaagaacu gu                                             22

<210> SEQ ID NO 550
<211> LENGTH: 21
<212> TYPE: RNA
<213> ORGANISM: Homo sapiens

<400> SEQUENCE: 550
ugauugucca aacgcaauuc u                                              21

<210> SEQ ID NO 551
<211> LENGTH: 22
<212> TYPE: RNA
<213> ORGANISM: Homo sapiens

<400> SEQUENCE: 551
agaauugugg cuggacaucu gu                                             22

<210> SEQ ID NO 552
<211> LENGTH: 22
<212> TYPE: RNA
<213> ORGANISM: Homo sapiens

<400> SEQUENCE: 552
agaguugagu cuggacgucc cg                                             22

<210> SEQ ID NO 553
<211> LENGTH: 22
<212> TYPE: RNA
<213> ORGANISM: Homo sapiens

<400> SEQUENCE: 553
caugguucug ucaagcaccg cg                                        22

<210> SEQ ID NO 554
<211> LENGTH: 22
<212> TYPE: RNA
<213> ORGANISM: Homo sapiens

<400> SEQUENCE: 554
augguuccgu caagcaccau gg                                        22

<210> SEQ ID NO 555
<211> LENGTH: 21
<212> TYPE: RNA
<213> ORGANISM: Homo sapiens

<400> SEQUENCE: 555
uugugcuuga ucuaaccaug u                                         21

<210> SEQ ID NO 556
<211> LENGTH: 23
<212> TYPE: RNA
<213> ORGANISM: Homo sapiens

<400> SEQUENCE: 556
uacugcauca ggaacugauu gga                                       23

<210> SEQ ID NO 557
<211> LENGTH: 22
<212> TYPE: RNA
<213> ORGANISM: Homo sapiens

<400> SEQUENCE: 557
aaaucucugc aggcaaaugu ga                                        22

<210> SEQ ID NO 558
<211> LENGTH: 22
<212> TYPE: RNA
<213> ORGANISM: Homo sapiens

<400> SEQUENCE: 558
uaaucucagc uggcaacugu ga                                        22

<210> SEQ ID NO 559
<211> LENGTH: 21
<212> TYPE: RNA
<213> ORGANISM: Homo sapiens

<400> SEQUENCE: 559
augaccuaug aauugacaga c                                         21

<210> SEQ ID NO 560
<211> LENGTH: 22
<212> TYPE: RNA
<213> ORGANISM: Homo sapiens

<400> SEQUENCE: 560
ugccugucua cacuugcugu gc                                        22

<210> SEQ ID NO 561
<211> LENGTH: 22
<212> TYPE: RNA
<213> ORGANISM: Homo sapiens

<400> SEQUENCE: 561
acagcaggca cagacaggca gu                                             22

<210> SEQ ID NO 562
<211> LENGTH: 21
<212> TYPE: RNA
<213> ORGANISM: Homo sapiens

<400> SEQUENCE: 562
uaacagucuc cagucacggc c                                              21

<210> SEQ ID NO 563
<211> LENGTH: 21
<212> TYPE: RNA
<213> ORGANISM: Homo sapiens

<400> SEQUENCE: 563
uguucucuuu gccaaggaca g                                              21

<210> SEQ ID NO 564
<211> LENGTH: 21
<212> TYPE: RNA
<213> ORGANISM: Homo sapiens

<400> SEQUENCE: 564
ccucccaugc caagaacucc c                                              21

<210> SEQ ID NO 565
<211> LENGTH: 21
<212> TYPE: RNA
<213> ORGANISM: Homo sapiens

<400> SEQUENCE: 565
gguucuuagc auaggagguc u                                              21

<210> SEQ ID NO 566
<211> LENGTH: 22
<212> TYPE: RNA
<213> ORGANISM: Homo sapiens

<400> SEQUENCE: 566
caucagaauu cauggaggcu ag                                             22

<210> SEQ ID NO 567
<211> LENGTH: 22
<212> TYPE: RNA
<213> ORGANISM: Homo sapiens

<400> SEQUENCE: 567
agcuuccaug acuccugaug ga                                             22

<210> SEQ ID NO 568
<211> LENGTH: 21
<212> TYPE: RNA
<213> ORGANISM: Homo sapiens

<400> SEQUENCE: 568
cgagccucaa gcaagggacu u                                              21

<210> SEQ ID NO 569
<211> LENGTH: 22
<212> TYPE: RNA
<213> ORGANISM: Homo sapiens

```
<400> SEQUENCE: 569
uagucccuuc cuugaagcgg uc                                        22

<210> SEQ ID NO 570
<211> LENGTH: 21
<212> TYPE: RNA
<213> ORGANISM: Homo sapiens

<400> SEQUENCE: 570
auuugugcuu ggcucuguca c                                         21

<210> SEQ ID NO 571
<211> LENGTH: 22
<212> TYPE: RNA
<213> ORGANISM: Homo sapiens

<400> SEQUENCE: 571
uuggggaaac ggccgcugag ug                                        22

<210> SEQ ID NO 572
<211> LENGTH: 22
<212> TYPE: RNA
<213> ORGANISM: Homo sapiens

<400> SEQUENCE: 572
uucccuuugu cauccuucgc cu                                        22

<210> SEQ ID NO 573
<211> LENGTH: 22
<212> TYPE: RNA
<213> ORGANISM: Homo sapiens

<400> SEQUENCE: 573
cugugcgugu gacagcggcu ga                                        22

<210> SEQ ID NO 574
<211> LENGTH: 21
<212> TYPE: RNA
<213> ORGANISM: Homo sapiens

<400> SEQUENCE: 574
caacaccagu cgaugggcug u                                         21

<210> SEQ ID NO 575
<211> LENGTH: 22
<212> TYPE: RNA
<213> ORGANISM: Homo sapiens

<400> SEQUENCE: 575
uagcuuauca gacugauguu ga                                        22

<210> SEQ ID NO 576
<211> LENGTH: 22
<212> TYPE: RNA
<213> ORGANISM: Homo sapiens

<400> SEQUENCE: 576
acuguaguau gggcacuucc ag                                        22

<210> SEQ ID NO 577
<211> LENGTH: 23
<212> TYPE: RNA
<213> ORGANISM: Homo sapiens
```

-continued

```
<400> SEQUENCE: 577
caaagugcuc auagugcagg uag                                           23

<210> SEQ ID NO 578
<211> LENGTH: 22
<212> TYPE: RNA
<213> ORGANISM: Homo sapiens

<400> SEQUENCE: 578
acugcauuau gagcacuuaa ag                                            22

<210> SEQ ID NO 579
<211> LENGTH: 23
<212> TYPE: RNA
<213> ORGANISM: Homo sapiens

<400> SEQUENCE: 579
uaaagugcuu auagugcagg uag                                           23

<210> SEQ ID NO 580
<211> LENGTH: 22
<212> TYPE: RNA
<213> ORGANISM: Homo sapiens

<400> SEQUENCE: 580
auaagacgaa caaaagguuu gu                                            22

<210> SEQ ID NO 581
<211> LENGTH: 22
<212> TYPE: RNA
<213> ORGANISM: Homo sapiens

<400> SEQUENCE: 581
auaagacgag caaaaagcuu gu                                            22

<210> SEQ ID NO 582
<211> LENGTH: 22
<212> TYPE: RNA
<213> ORGANISM: Homo sapiens

<400> SEQUENCE: 582
uggaauguaa ggaagugugu gg                                            22

<210> SEQ ID NO 583
<211> LENGTH: 23
<212> TYPE: RNA
<213> ORGANISM: Homo sapiens

<400> SEQUENCE: 583
cuguaauaua aauuuaauuu auu                                           23

<210> SEQ ID NO 584
<211> LENGTH: 23
<212> TYPE: RNA
<213> ORGANISM: Homo sapiens

<400> SEQUENCE: 584
guguuaauua aaccucuauu uac                                           23

<210> SEQ ID NO 585
<211> LENGTH: 20
<212> TYPE: RNA
```

-continued

```
<213> ORGANISM: Homo sapiens

<400> SEQUENCE: 585
uguuuugaua acaguaaugu                                           20

<210> SEQ ID NO 586
<211> LENGTH: 21
<212> TYPE: RNA
<213> ORGANISM: Homo sapiens

<400> SEQUENCE: 586
gauuucagug gagugaaguu c                                         21

<210> SEQ ID NO 587
<211> LENGTH: 22
<212> TYPE: RNA
<213> ORGANISM: Homo sapiens

<400> SEQUENCE: 587
uccuucauuc caccggaguc ug                                        22

<210> SEQ ID NO 588
<211> LENGTH: 22
<212> TYPE: RNA
<213> ORGANISM: Homo sapiens

<400> SEQUENCE: 588
uucccuuugu cauccuaugc cu                                        22

<210> SEQ ID NO 589
<211> LENGTH: 22
<212> TYPE: RNA
<213> ORGANISM: Homo sapiens

<400> SEQUENCE: 589
gugaaauguu uaggaccacu ag                                        22

<210> SEQ ID NO 590
<211> LENGTH: 22
<212> TYPE: RNA
<213> ORGANISM: Homo sapiens

<400> SEQUENCE: 590
uuccuaugca uauacuucuu ug                                        22

<210> SEQ ID NO 591
<211> LENGTH: 20
<212> TYPE: RNA
<213> ORGANISM: Homo sapiens

<400> SEQUENCE: 591
agagguauag ggcaugggaa                                           20

<210> SEQ ID NO 592
<211> LENGTH: 22
<212> TYPE: RNA
<213> ORGANISM: Homo sapiens

<400> SEQUENCE: 592
cgucuuaccc agcaguguuu gg                                        22

<210> SEQ ID NO 593
<211> LENGTH: 23
```

<212> TYPE: RNA
<213> ORGANISM: Homo sapiens

<400> SEQUENCE: 593
uaauacugcc ggguaaugau gga                                          23

<210> SEQ ID NO 594
<211> LENGTH: 22
<212> TYPE: RNA
<213> ORGANISM: Homo sapiens

<400> SEQUENCE: 594
caucuuacug ggcagcauug ga                                           22

<210> SEQ ID NO 595
<211> LENGTH: 22
<212> TYPE: RNA
<213> ORGANISM: Homo sapiens

<400> SEQUENCE: 595
uaauacugcc ugguaaugau ga                                           22

<210> SEQ ID NO 596
<211> LENGTH: 22
<212> TYPE: RNA
<213> ORGANISM: Homo sapiens

<400> SEQUENCE: 596
caucuuaccg gacagugcug ga                                           22

<210> SEQ ID NO 597
<211> LENGTH: 22
<212> TYPE: RNA
<213> ORGANISM: Homo sapiens

<400> SEQUENCE: 597
uaacacuguc ugguaacgau gu                                           22

<210> SEQ ID NO 598
<211> LENGTH: 22
<212> TYPE: RNA
<213> ORGANISM: Homo sapiens

<400> SEQUENCE: 598
aguuuugcag guuugcauuu ca                                           22

<210> SEQ ID NO 599
<211> LENGTH: 23
<212> TYPE: RNA
<213> ORGANISM: Homo sapiens

<400> SEQUENCE: 599
aguuuugcag guuugcaucc agc                                          23

<210> SEQ ID NO 600
<211> LENGTH: 23
<212> TYPE: RNA
<213> ORGANISM: Homo sapiens

<400> SEQUENCE: 600
ugugcaaauc caugcaaaac uga                                          23

<210> SEQ ID NO 601

```
<211> LENGTH: 22
<212> TYPE: RNA
<213> ORGANISM: Homo sapiens

<400> SEQUENCE: 601
aguuuugcau aguugcacua ca                                              22

<210> SEQ ID NO 602
<211> LENGTH: 23
<212> TYPE: RNA
<213> ORGANISM: Homo sapiens

<400> SEQUENCE: 602
ugugcaaauc uaugcaaaac uga                                             23

<210> SEQ ID NO 603
<211> LENGTH: 23
<212> TYPE: RNA
<213> ORGANISM: Homo sapiens

<400> SEQUENCE: 603
cccaguguuu agacuaucug uuc                                             23

<210> SEQ ID NO 604
<211> LENGTH: 22
<212> TYPE: RNA
<213> ORGANISM: Homo sapiens

<400> SEQUENCE: 604
acaguagucu gcacauuggu ua                                              22

<210> SEQ ID NO 605
<211> LENGTH: 23
<212> TYPE: RNA
<213> ORGANISM: Homo sapiens

<400> SEQUENCE: 605
cccaguguuc agacuaccug uuc                                             23

<210> SEQ ID NO 606
<211> LENGTH: 22
<212> TYPE: RNA
<213> ORGANISM: Homo sapiens

<400> SEQUENCE: 606
acaguagucu gcacauuggu ua                                              22

<210> SEQ ID NO 607
<211> LENGTH: 22
<212> TYPE: RNA
<213> ORGANISM: Homo sapiens

<400> SEQUENCE: 607
gguccagagg ggagauaggu uc                                              22

<210> SEQ ID NO 608
<211> LENGTH: 22
<212> TYPE: RNA
<213> ORGANISM: Homo sapiens

<400> SEQUENCE: 608
cucccacugc uucacuugac ua                                              22
```

```
<210> SEQ ID NO 609
<211> LENGTH: 21
<212> TYPE: RNA
<213> ORGANISM: Homo sapiens

<400> SEQUENCE: 609
gguuuggucc uagccuuucu a                                          21

<210> SEQ ID NO 610
<211> LENGTH: 22
<212> TYPE: RNA
<213> ORGANISM: Homo sapiens

<400> SEQUENCE: 610
gauuagggug cuuagcuguu aa                                         22

<210> SEQ ID NO 611
<211> LENGTH: 20
<212> TYPE: RNA
<213> ORGANISM: Homo sapiens

<400> SEQUENCE: 611
ccuccugccc uccuugcugu                                            20

<210> SEQ ID NO 612
<211> LENGTH: 25
<212> TYPE: RNA
<213> ORGANISM: Homo sapiens

<400> SEQUENCE: 612
cccccacaac cgcgcuugac uagcu                                      25

<210> SEQ ID NO 613
<211> LENGTH: 23
<212> TYPE: RNA
<213> ORGANISM: Homo sapiens

<400> SEQUENCE: 613
ugguuguagu ccgugcgaga aua                                        23

<210> SEQ ID NO 614
<211> LENGTH: 19
<212> TYPE: RNA
<213> ORGANISM: Homo sapiens

<400> SEQUENCE: 614
accgugcaaa gguagcaua                                             19

<210> SEQ ID NO 615
<211> LENGTH: 22
<212> TYPE: RNA
<213> ORGANISM: Homo sapiens

<400> SEQUENCE: 615
ucaggccagg cacaguggcu ca                                         22

<210> SEQ ID NO 616
<211> LENGTH: 22
<212> TYPE: RNA
<213> ORGANISM: Homo sapiens

<400> SEQUENCE: 616
uucaccaccu ucuccaccca gc                                         22
```

```
<210> SEQ ID NO 617
<211> LENGTH: 22
<212> TYPE: RNA
<213> ORGANISM: Homo sapiens

<400> SEQUENCE: 617
ucgacagcac gacacugccu uc                                              22

<210> SEQ ID NO 618
<211> LENGTH: 22
<212> TYPE: RNA
<213> ORGANISM: Homo sapiens

<400> SEQUENCE: 618
uagguaguuu ccuguuguug gg                                              22

<210> SEQ ID NO 619
<211> LENGTH: 22
<212> TYPE: RNA
<213> ORGANISM: Homo sapiens

<400> SEQUENCE: 619
cggcaacaag aaacugccug ag                                              22

<210> SEQ ID NO 620
<211> LENGTH: 22
<212> TYPE: RNA
<213> ORGANISM: Homo sapiens

<400> SEQUENCE: 620
uagguaguuu cauguuguug gg                                              22

<210> SEQ ID NO 621
<211> LENGTH: 22
<212> TYPE: RNA
<213> ORGANISM: Homo sapiens

<400> SEQUENCE: 621
ccaauauugg cugugcugcu cc                                              22

<210> SEQ ID NO 622
<211> LENGTH: 21
<212> TYPE: RNA
<213> ORGANISM: Homo sapiens

<400> SEQUENCE: 622
uagcagcaca gaaauauugg c                                               21

<210> SEQ ID NO 623
<211> LENGTH: 22
<212> TYPE: RNA
<213> ORGANISM: Homo sapiens

<400> SEQUENCE: 623 ccagugggge ugcuguuauc ug                                              22

<210> SEQ ID NO 624
<211> LENGTH: 22
<212> TYPE: RNA
<213> ORGANISM: Homo sapiens

<400> SEQUENCE: 624
uguaacagca acuccaugug ga                                              22
```

```
<210> SEQ ID NO 625
<211> LENGTH: 22
<212> TYPE: RNA
<213> ORGANISM: Homo sapiens

<400> SEQUENCE: 625
cgggguuuug agggcgagau ga                                              22

<210> SEQ ID NO 626
<211> LENGTH: 22
<212> TYPE: RNA
<213> ORGANISM: Homo sapiens

<400> SEQUENCE: 626
aacuggcccu caaagucccg cu                                              22

<210> SEQ ID NO 627
<211> LENGTH: 22
<212> TYPE: RNA
<213> ORGANISM: Homo sapiens

<400> SEQUENCE: 627
ugggucuuug cgggcgagau ga                                              22

<210> SEQ ID NO 628
<211> LENGTH: 22
<212> TYPE: RNA
<213> ORGANISM: Homo sapiens

<400> SEQUENCE: 628
aacuggccua caaagucccca gu                                             22

<210> SEQ ID NO 629
<211> LENGTH: 22
<212> TYPE: RNA
<213> ORGANISM: Homo sapiens

<400> SEQUENCE: 629
cugccaauuc cauaggucac ag                                              22

<210> SEQ ID NO 630
<211> LENGTH: 21
<212> TYPE: RNA
<213> ORGANISM: Homo sapiens

<400> SEQUENCE: 630
cugaccuaug aauugacagc c                                               21

<210> SEQ ID NO 631
<211> LENGTH: 22
<212> TYPE: RNA
<213> ORGANISM: Homo sapiens

<400> SEQUENCE: 631
accuugccuu gcugcccggg cc                                              22

<210> SEQ ID NO 632
<211> LENGTH: 20
<212> TYPE: RNA
<213> ORGANISM: Homo sapiens

<400> SEQUENCE: 632
```

-continued ccccagggcg acgcggcggg                    20

<210> SEQ ID NO 633
<211> LENGTH: 22
<212> TYPE: RNA
<213> ORGANISM: Homo sapiens

<400> SEQUENCE: 633
ggaggggucc cgcacuggga gg                 22

<210> SEQ ID NO 634
<211> LENGTH: 22
<212> TYPE: RNA
<213> ORGANISM: Homo sapiens

<400> SEQUENCE: 634
cccugugccc ggcccacuuc ug                 22

<210> SEQ ID NO 635
<211> LENGTH: 22
<212> TYPE: RNA
<213> ORGANISM: Homo sapiens

<400> SEQUENCE: 635
ucugcccccu ccgcugcugc ca                 22

<210> SEQ ID NO 636
<211> LENGTH: 22
<212> TYPE: RNA
<213> ORGANISM: Homo sapiens

<400> SEQUENCE: 636
uacccagagc augcagugug aa                 22

<210> SEQ ID NO 637
<211> LENGTH: 20
<212> TYPE: RNA
<213> ORGANISM: Homo sapiens

<400> SEQUENCE: 637
caccaggcau uguggucucc                    20

<210> SEQ ID NO 638
<211> LENGTH: 23
<212> TYPE: RNA
<213> ORGANISM: Homo sapiens

<400> SEQUENCE: 638
ugaguaccgc caugucuguu ggg                23

<210> SEQ ID NO 639
<211> LENGTH: 21
<212> TYPE: RNA
<213> ORGANISM: Homo sapiens

<400> SEQUENCE: 639
ccaguccugu gccugccgcc u                  21

<210> SEQ ID NO 640
<211> LENGTH: 22
<212> TYPE: RNA
<213> ORGANISM: Homo sapiens

<400> SEQUENCE: 640

```
gcugcgcuug gauuucgucc cc                                        22

<210> SEQ ID NO 641
<211> LENGTH: 23
<212> TYPE: RNA
<213> ORGANISM: Homo sapiens

<400> SEQUENCE: 641
caacggaauc ccaaaagcag cug                                       23

<210> SEQ ID NO 642
<211> LENGTH: 21
<212> TYPE: RNA
<213> ORGANISM: Homo sapiens

<400> SEQUENCE: 642
ugauauguuu gauauugggu u                                         21

<210> SEQ ID NO 643
<211> LENGTH: 21
<212> TYPE: RNA
<213> ORGANISM: Homo sapiens

<400> SEQUENCE: 643
ugagugccgg ugccugcccu g                                         21

<210> SEQ ID NO 644
<211> LENGTH: 22
<212> TYPE: RNA
<213> ORGANISM: Homo sapiens

<400> SEQUENCE: 644
cgcaggggcc gggugcucac cg                                        22

<210> SEQ ID NO 645
<211> LENGTH: 21
<212> TYPE: RNA
<213> ORGANISM: Homo sapiens

<400> SEQUENCE: 645
cggcggggac ggcgauuggu c                                         21

<210> SEQ ID NO 646
<211> LENGTH: 22
<212> TYPE: RNA
<213> ORGANISM: Homo sapiens

<400> SEQUENCE: 646
ugauauguuu gauauauuag gu                                        22

<210> SEQ ID NO 647
<211> LENGTH: 22
<212> TYPE: RNA
<213> ORGANISM: Homo sapiens

<400> SEQUENCE: 647
ugcccuaaau gccccuucug gc                                        22

<210> SEQ ID NO 648
<211> LENGTH: 23
<212> TYPE: RNA
<213> ORGANISM: Homo sapiens
```

-continued

```
<400> SEQUENCE: 648
uaaggugcau cuagugcagu uag                                        23

<210> SEQ ID NO 649
<211> LENGTH: 23
<212> TYPE: RNA
<213> ORGANISM: Homo sapiens

<400> SEQUENCE: 649
acugcccuaa gugcuccuuc ugg                                        23

<210> SEQ ID NO 650
<211> LENGTH: 23
<212> TYPE: RNA
<213> ORGANISM: Homo sapiens

<400> SEQUENCE: 650
uaaggugcau cuagugcaga uag                                        23

<210> SEQ ID NO 651
<211> LENGTH: 21
<212> TYPE: RNA
<213> ORGANISM: Homo sapiens

<400> SEQUENCE: 651
caucccuugc augguggagg g                                          21

<210> SEQ ID NO 652
<211> LENGTH: 21
<212> TYPE: RNA
<213> ORGANISM: Homo sapiens

<400> SEQUENCE: 652
cucccacaug caggguuugc a                                          21

<210> SEQ ID NO 653
<211> LENGTH: 22
<212> TYPE: RNA
<213> ORGANISM: Homo sapiens

<400> SEQUENCE: 653
ggcuacaaca caggacccgg gc                                         22

<210> SEQ ID NO 654
<211> LENGTH: 22
<212> TYPE: RNA
<213> ORGANISM: Homo sapiens

<400> SEQUENCE: 654
ucgugucuug uguugcagcc gg                                         22

<210> SEQ ID NO 655
<211> LENGTH: 22
<212> TYPE: RNA
<213> ORGANISM: Homo sapiens

<400> SEQUENCE: 655
gcccaaaggu gaauuuuuug gg                                         22

<210> SEQ ID NO 656
<211> LENGTH: 22
<212> TYPE: RNA
<213> ORGANISM: Homo sapiens
```

-continued

```
<400> SEQUENCE: 656
caaagaauuc uccuuuuggg cu                                          22

<210> SEQ ID NO 657
<211> LENGTH: 22
<212> TYPE: RNA
<213> ORGANISM: Homo sapiens

<400> SEQUENCE: 657
aggggcuggc uuuccucugg uc                                          22

<210> SEQ ID NO 658
<211> LENGTH: 22
<212> TYPE: RNA
<213> ORGANISM: Homo sapiens

<400> SEQUENCE: 658
uggagagaaa ggcaguuccu ga                                          22

<210> SEQ ID NO 659
<211> LENGTH: 22
<212> TYPE: RNA
<213> ORGANISM: Homo sapiens

<400> SEQUENCE: 659
uggacggaga acugauaagg gu                                          22

<210> SEQ ID NO 660
<211> LENGTH: 22
<212> TYPE: RNA
<213> ORGANISM: Homo sapiens

<400> SEQUENCE: 660
gugaauuacc gaagggccau aa                                          22

<210> SEQ ID NO 661
<211> LENGTH: 22
<212> TYPE: RNA
<213> ORGANISM: Homo sapiens

<400> SEQUENCE: 661
uauggcacug guagaauuca cu                                          22

<210> SEQ ID NO 662
<211> LENGTH: 18
<212> TYPE: RNA
<213> ORGANISM: Homo sapiens

<400> SEQUENCE: 662
ugaggcagua gauugaau                                               18

<210> SEQ ID NO 663
<211> LENGTH: 27
<212> TYPE: RNA
<213> ORGANISM: Homo sapiens

<400> SEQUENCE: 663
auugaucauc gacacuucga acgcaau                                     27

<210> SEQ ID NO 664
<211> LENGTH: 18
<212> TYPE: RNA
```

```
<213> ORGANISM: Homo sapiens

<400> SEQUENCE: 664
uccagugccc uccucucc                                                    18

<210> SEQ ID NO 665
<211> LENGTH: 21
<212> TYPE: RNA
<213> ORGANISM: Homo sapiens

<400> SEQUENCE: 665
ugguucuaga cuugccaacu a                                                21

<210> SEQ ID NO 666
<211> LENGTH: 24
<212> TYPE: RNA
<213> ORGANISM: Homo sapiens

<400> SEQUENCE: 666
uuuggcaaug guagaacuca cacu                                             24

<210> SEQ ID NO 667
<211> LENGTH: 23
<212> TYPE: RNA
<213> ORGANISM: Homo sapiens

<400> SEQUENCE: 667
aacauucauu guguucgguug ggu                                             23

<210> SEQ ID NO 668
<211> LENGTH: 22
<212> TYPE: RNA
<213> ORGANISM: Homo sapiens

<400> SEQUENCE: 668
aaccaucgac cguugagugg ac                                               22

<210> SEQ ID NO 669
<211> LENGTH: 22
<212> TYPE: RNA
<213> ORGANISM: Homo sapiens

<400> SEQUENCE: 669
aacauucaac cugucggug agu                                               22

<210> SEQ ID NO 670
<211> LENGTH: 23
<212> TYPE: RNA
<213> ORGANISM: Homo sapiens

<400> SEQUENCE: 670
aacauucauu gcugucggug ggu                                              23

<210> SEQ ID NO 671
<211> LENGTH: 22
<212> TYPE: RNA
<213> ORGANISM: Homo sapiens

<400> SEQUENCE: 671
accacugacc guugacugua cc                                               22

<210> SEQ ID NO 672
<211> LENGTH: 22
```

```
<212> TYPE: RNA
<213> ORGANISM: Homo sapiens

<400> SEQUENCE: 672
accaucgacc guugauugua cc                                         22

<210> SEQ ID NO 673
<211> LENGTH: 23
<212> TYPE: RNA
<213> ORGANISM: Homo sapiens

<400> SEQUENCE: 673
aacauucaac gcugucggug agu                                        23

<210> SEQ ID NO 674
<211> LENGTH: 22
<212> TYPE: RNA
<213> ORGANISM: Homo sapiens

<400> SEQUENCE: 674
acugcaguga aggcacuugu ag                                         22

<210> SEQ ID NO 675
<211> LENGTH: 23
<212> TYPE: RNA
<213> ORGANISM: Homo sapiens

<400> SEQUENCE: 675
caaagugcuu acagugcagg uag                                        23

<210> SEQ ID NO 676
<211> LENGTH: 22
<212> TYPE: RNA
<213> ORGANISM: Homo sapiens

<400> SEQUENCE: 676
ccaauauuac ugugcugcuu ua                                         22

<210> SEQ ID NO 677
<211> LENGTH: 22
<212> TYPE: RNA
<213> ORGANISM: Homo sapiens

<400> SEQUENCE: 677
ccaguauuaa cugugcugcu ga                                         22

<210> SEQ ID NO 678
<211> LENGTH: 22
<212> TYPE: RNA
<213> ORGANISM: Homo sapiens

<400> SEQUENCE: 678
uagcagcacg uaaauauugg cg                                         22

<210> SEQ ID NO 679
<211> LENGTH: 22
<212> TYPE: RNA
<213> ORGANISM: Homo sapiens

<400> SEQUENCE: 679
cgaaucauua uuugcugcuc ua                                         22

<210> SEQ ID NO 680
```

```
<211> LENGTH: 22
<212> TYPE: RNA
<213> ORGANISM: Homo sapiens

<400> SEQUENCE: 680
uagcagcaca ucaugguuua ca                                              22

<210> SEQ ID NO 681
<211> LENGTH: 22
<212> TYPE: RNA
<213> ORGANISM: Homo sapiens

<400> SEQUENCE: 681
caggccauau ugugcugccu ca                                              22

<210> SEQ ID NO 682
<211> LENGTH: 22
<212> TYPE: RNA
<213> ORGANISM: Homo sapiens

<400> SEQUENCE: 682
uagcagcaca uaaugguuug ug                                              22

<210> SEQ ID NO 683
<211> LENGTH: 22
<212> TYPE: RNA
<213> ORGANISM: Homo sapiens

<400> SEQUENCE: 683
cuccuacaua uuagcauuaa ca                                              22

<210> SEQ ID NO 684
<211> LENGTH: 23
<212> TYPE: RNA
<213> ORGANISM: Homo sapiens

<400> SEQUENCE: 684
uuaaugcuaa ucgugauagg ggu                                             23

<210> SEQ ID NO 685
<211> LENGTH: 22
<212> TYPE: RNA
<213> ORGANISM: Homo sapiens

<400> SEQUENCE: 685
aaucauacac gguugaccua uu                                              22

<210> SEQ ID NO 686
<211> LENGTH: 22
<212> TYPE: RNA
<213> ORGANISM: Homo sapiens

<400> SEQUENCE: 686
uagguuaucc guguugccuu cg                                              22

<210> SEQ ID NO 687
<211> LENGTH: 21
<212> TYPE: RNA
<213> ORGANISM: Homo sapiens

<400> SEQUENCE: 687
uccugcgcgu cccagaugcc c                                               21
```

<210> SEQ ID NO 688
<211> LENGTH: 23
<212> TYPE: RNA
<213> ORGANISM: Homo sapiens

<400> SEQUENCE: 688
cggcccgggc ugcugcuguu ccu                                    23

<210> SEQ ID NO 689
<211> LENGTH: 22
<212> TYPE: RNA
<213> ORGANISM: Homo sapiens

<400> SEQUENCE: 689
aaaaccgucu aguuacaguu gu                                     22

<210> SEQ ID NO 690
<211> LENGTH: 22
<212> TYPE: RNA
<213> ORGANISM: Homo sapiens

<400> SEQUENCE: 690
uugcauaguc acaaaaguga uc                                     22

<210> SEQ ID NO 691
<211> LENGTH: 21
<212> TYPE: RNA
<213> ORGANISM: Homo sapiens

<400> SEQUENCE: 691
ucagugcaug acagaacuug g                                      21

<210> SEQ ID NO 692
<211> LENGTH: 21
<212> TYPE: RNA
<213> ORGANISM: Homo sapiens

<400> SEQUENCE: 692
ucgaggagcu cacagucuag u                                      21

<210> SEQ ID NO 693
<211> LENGTH: 21
<212> TYPE: RNA
<213> ORGANISM: Homo sapiens

<400> SEQUENCE: 693
cuagacugaa gcuccuugag g                                      21

<210> SEQ ID NO 694
<211> LENGTH: 22
<212> TYPE: RNA
<213> ORGANISM: Homo sapiens

<400> SEQUENCE: 694
cugguacagg ccuggggggac ag                                    22

<210> SEQ ID NO 695
<211> LENGTH: 22
<212> TYPE: RNA
<213> ORGANISM: Homo sapiens

<400> SEQUENCE: 695
ucucccaacc cuuguaccag ug                                     22

```
<210> SEQ ID NO 696
<211> LENGTH: 21
<212> TYPE: RNA
<213> ORGANISM: Homo sapiens

<400> SEQUENCE: 696
agggagggac gggggcugug c                                              21

<210> SEQ ID NO 697
<211> LENGTH: 23
<212> TYPE: RNA
<213> ORGANISM: Homo sapiens

<400> SEQUENCE: 697
ucuggcuccg ugucuucacu ccc                                            23

<210> SEQ ID NO 698
<211> LENGTH: 22
<212> TYPE: RNA
<213> ORGANISM: Homo sapiens

<400> SEQUENCE: 698
aaguucuguu auacacucag gc                                             22

<210> SEQ ID NO 699
<211> LENGTH: 22
<212> TYPE: RNA
<213> ORGANISM: Homo sapiens

<400> SEQUENCE: 699
ucagugcauc acagaacuuu gu                                             22

<210> SEQ ID NO 700
<211> LENGTH: 22
<212> TYPE: RNA
<213> ORGANISM: Homo sapiens

<400> SEQUENCE: 700
aaaguucuga gacacuccga cu                                             22

<210> SEQ ID NO 701
<211> LENGTH: 22
<212> TYPE: RNA
<213> ORGANISM: Homo sapiens

<400> SEQUENCE: 701
ucagugcacu acagaacuuu gu                                             22

<210> SEQ ID NO 702
<211> LENGTH: 22
<212> TYPE: RNA
<213> ORGANISM: Homo sapiens

<400> SEQUENCE: 702
gugugcggaa augcuucugc ua                                             22

<210> SEQ ID NO 703
<211> LENGTH: 22
<212> TYPE: RNA
<213> ORGANISM: Homo sapiens

<400> SEQUENCE: 703
gcccgcgugu ggagccaggu gu                                             22
```

<210> SEQ ID NO 704
<211> LENGTH: 21
<212> TYPE: RNA
<213> ORGANISM: Homo sapiens

<400> SEQUENCE: 704
gcccuccgcc cgugcacccc g                                            21

<210> SEQ ID NO 705
<211> LENGTH: 20
<212> TYPE: RNA
<213> ORGANISM: Homo sapiens

<400> SEQUENCE: 705
guguguggaa augcuucugc                                              20

<210> SEQ ID NO 706
<211> LENGTH: 22
<212> TYPE: RNA
<213> ORGANISM: Homo sapiens

<400> SEQUENCE: 706
ugagaacuga auuccauagg cu                                           22

<210> SEQ ID NO 707
<211> LENGTH: 22
<212> TYPE: RNA
<213> ORGANISM: Homo sapiens

<400> SEQUENCE: 707
ugcccugugg acucaguucu gg                                           22

<210> SEQ ID NO 708
<211> LENGTH: 22
<212> TYPE: RNA
<213> ORGANISM: Homo sapiens

<400> SEQUENCE: 708
ccucugaaau ucaguucuuc ag                                           22

<210> SEQ ID NO 709
<211> LENGTH: 22
<212> TYPE: RNA
<213> ORGANISM: Homo sapiens

<400> SEQUENCE: 709
ugagaacuga auuccauggg uu                                           22

<210> SEQ ID NO 710
<211> LENGTH: 22
<212> TYPE: RNA
<213> ORGANISM: Homo sapiens

<400> SEQUENCE: 710
cucggcgcgg ggcgcgggcu cc                                           22

<210> SEQ ID NO 711
<211> LENGTH: 21
<212> TYPE: RNA
<213> ORGANISM: Homo sapiens

<400> SEQUENCE: 711
cuccguuugc cuguuucgcu g                                           21

<210> SEQ ID NO 712
<211> LENGTH: 22
<212> TYPE: RNA
<213> ORGANISM: Homo sapiens

<400> SEQUENCE: 712
ggauuccugg aaauacuguu cu                                          22

<210> SEQ ID NO 713
<211> LENGTH: 23
<212> TYPE: RNA
<213> ORGANISM: Homo sapiens

<400> SEQUENCE: 713
guccaguuuu cccaggaauc ccu                                         23

<210> SEQ ID NO 714
<211> LENGTH: 22
<212> TYPE: RNA
<213> ORGANISM: Homo sapiens

<400> SEQUENCE: 714
ggauaucauc auauacugua ag                                          22

<210> SEQ ID NO 715
<211> LENGTH: 20
<212> TYPE: RNA
<213> ORGANISM: Homo sapiens

<400> SEQUENCE: 715
uacaguauag augauguacu                                             20

<210> SEQ ID NO 716
<211> LENGTH: 22
<212> TYPE: RNA
<213> ORGANISM: Homo sapiens

<400> SEQUENCE: 716
ggugcagugc ugcaucucug gu                                          22

<210> SEQ ID NO 717
<211> LENGTH: 21
<212> TYPE: RNA
<213> ORGANISM: Homo sapiens

<400> SEQUENCE: 717
ugagaugaag cacuguagcu c                                           21

<210> SEQ ID NO 718
<211> LENGTH: 21
<212> TYPE: RNA
<213> ORGANISM: Homo sapiens

<400> SEQUENCE: 718
cauaaaguag aaagcacuac u                                           21

<210> SEQ ID NO 719
<211> LENGTH: 23
<212> TYPE: RNA
<213> ORGANISM: Homo sapiens

<400> SEQUENCE: 719
uguaguguuu ccuacuuuau gga    23

<210> SEQ ID NO 720
<211> LENGTH: 22
<212> TYPE: RNA
<213> ORGANISM: Homo sapiens

<400> SEQUENCE: 720
caucuuccag uacaguguug ga    22

<210> SEQ ID NO 721
<211> LENGTH: 22
<212> TYPE: RNA
<213> ORGANISM: Homo sapiens

<400> SEQUENCE: 721
uaacacuguc ugguaaagau gg    22

<210> SEQ ID NO 722
<211> LENGTH: 22
<212> TYPE: RNA
<213> ORGANISM: Homo sapiens

<400> SEQUENCE: 722
cagugguuuu acccuauggu ag    22

<210> SEQ ID NO 723
<211> LENGTH: 21
<212> TYPE: RNA
<213> ORGANISM: Homo sapiens

<400> SEQUENCE: 723
uaccacaggg uagaaccacg g    21

<210> SEQ ID NO 724
<211> LENGTH: 22
<212> TYPE: RNA
<213> ORGANISM: Homo sapiens

<400> SEQUENCE: 724
ucuacagugc acgugucucc ag    22

<210> SEQ ID NO 725
<211> LENGTH: 22
<212> TYPE: RNA
<213> ORGANISM: Homo sapiens

<400> SEQUENCE: 725
ggagacgcgg cccuguugga gu    22

<210> SEQ ID NO 726
<211> LENGTH: 22
<212> TYPE: RNA
<213> ORGANISM: Homo sapiens

<400> SEQUENCE: 726
gcuauuucac gacaccaggg uu    22

<210> SEQ ID NO 727
<211> LENGTH: 22
<212> TYPE: RNA
<213> ORGANISM: Homo sapiens

```
<400> SEQUENCE: 727
gcuacuucac aacaccaggg cc                                              22

<210> SEQ ID NO 728
<211> LENGTH: 23
<212> TYPE: RNA
<213> ORGANISM: Homo sapiens

<400> SEQUENCE: 728
agcugguguu gugaaucagg ccg                                             23

<210> SEQ ID NO 729
<211> LENGTH: 23
<212> TYPE: RNA
<213> ORGANISM: Homo sapiens

<400> SEQUENCE: 729
uuauugcuua agaauacgcg uag                                             23

<210> SEQ ID NO 730
<211> LENGTH: 22
<212> TYPE: RNA
<213> ORGANISM: Homo sapiens

<400> SEQUENCE: 730
caucaucguc ucaaugagu cu                                               22

<210> SEQ ID NO 731
<211> LENGTH: 23
<212> TYPE: RNA
<213> ORGANISM: Homo sapiens

<400> SEQUENCE: 731
acuccauuug uuuugaugau gga                                             23

<210> SEQ ID NO 732
<211> LENGTH: 22
<212> TYPE: RNA
<213> ORGANISM: Homo sapiens

<400> SEQUENCE: 732
auguagggcu aaaagccaug gg                                              22

<210> SEQ ID NO 733
<211> LENGTH: 23
<212> TYPE: RNA
<213> ORGANISM: Homo sapiens

<400> SEQUENCE: 733
uauggcuuuu cauuccuaug uga                                             23

<210> SEQ ID NO 734
<211> LENGTH: 22
<212> TYPE: RNA
<213> ORGANISM: Homo sapiens

<400> SEQUENCE: 734
uauagggauu ggagccgugg cg                                              22

<210> SEQ ID NO 735
<211> LENGTH: 23
<212> TYPE: RNA
<213> ORGANISM: Homo sapiens
```

```
<400> SEQUENCE: 735
uauggcuuuu uauuccuaug uga                                            23

<210> SEQ ID NO 736
<211> LENGTH: 22
<212> TYPE: RNA
<213> ORGANISM: Homo sapiens

<400> SEQUENCE: 736
ugugacuggu ugaccagagg gg                                             22

<210> SEQ ID NO 737
<211> LENGTH: 22
<212> TYPE: RNA
<213> ORGANISM: Homo sapiens

<400> SEQUENCE: 737
uuuggucccc uucaaccagc ua                                             22

<210> SEQ ID NO 738
<211> LENGTH: 22
<212> TYPE: RNA
<213> ORGANISM: Homo sapiens

<400> SEQUENCE: 738
uuuggucccc uucaaccagc ug                                             22

<210> SEQ ID NO 739
<211> LENGTH: 24
<212> TYPE: RNA
<213> ORGANISM: Homo sapiens

<400> SEQUENCE: 739
ccagacagaa uucuaugcac uuuc                                           24

<210> SEQ ID NO 740
<211> LENGTH: 22
<212> TYPE: RNA
<213> ORGANISM: Homo sapiens

<400> SEQUENCE: 740
ucaaaacuga ggggcauuuu cu                                             22

<210> SEQ ID NO 741
<211> LENGTH: 19
<212> TYPE: RNA
<213> ORGANISM: Homo sapiens

<400> SEQUENCE: 741
gaugaugcug cugaugcug                                                 19

<210> SEQ ID NO 742
<211> LENGTH: 18
<212> TYPE: RNA
<213> ORGANISM: Homo sapiens

<400> SEQUENCE: 742
cagggaggug aaugugau                                                  18

<210> SEQ ID NO 743
<211> LENGTH: 22
<212> TYPE: RNA
```

```
<213> ORGANISM: Homo sapiens

<400> SEQUENCE: 743
accguggcuu ucgauuguua cu                                          22

<210> SEQ ID NO 744
<211> LENGTH: 22
<212> TYPE: RNA
<213> ORGANISM: Homo sapiens

<400> SEQUENCE: 744
uaacagucua cagccauggu cg                                          22

<210> SEQ ID NO 745
<211> LENGTH: 21
<212> TYPE: RNA
<213> ORGANISM: Homo sapiens

<400> SEQUENCE: 745
acucuuuccc uguugcacua c                                           21

<210> SEQ ID NO 746
<211> LENGTH: 22
<212> TYPE: RNA
<213> ORGANISM: Homo sapiens

<400> SEQUENCE: 746
cagugcaaug augaaagggc au                                          22

<210> SEQ ID NO 747
<211> LENGTH: 22
<212> TYPE: RNA
<213> ORGANISM: Homo sapiens

<400> SEQUENCE: 747
uucacauugu gcuacugucu gc                                          22

<210> SEQ ID NO 748
<211> LENGTH: 22
<212> TYPE: RNA
<213> ORGANISM: Homo sapiens

<400> SEQUENCE: 748
cagugcaaug uuaaaagggc au                                          22

<210> SEQ ID NO 749
<211> LENGTH: 18
<212> TYPE: RNA
<213> ORGANISM: Homo sapiens

<400> SEQUENCE: 749 gcauggugg uucagugg                                                18

<210> SEQ ID NO 750
<211> LENGTH: 22
<212> TYPE: RNA
<213> ORGANISM: Homo sapiens

<400> SEQUENCE: 750
acucggcgug gcgucggucg ug                                          22

<210> SEQ ID NO 751
<211> LENGTH: 18
```

```
<212> TYPE: RNA
<213> ORGANISM: Homo sapiens

<400> SEQUENCE: 751
acguuggcuc ugguggug                                                       18

<210> SEQ ID NO 752
<211> LENGTH: 22
<212> TYPE: RNA
<213> ORGANISM: Homo sapiens

<400> SEQUENCE: 752
uuuucaacuc uaaugggaga ga                                                  22

<210> SEQ ID NO 753
<211> LENGTH: 22
<212> TYPE: RNA
<213> ORGANISM: Homo sapiens

<400> SEQUENCE: 753
uuugaggcua cagugagaug ug                                                  22

<210> SEQ ID NO 754
<211> LENGTH: 22
<212> TYPE: RNA
<213> ORGANISM: Homo sapiens

<400> SEQUENCE: 754
uuuagagacg gggucuugcu cu                                                  22

<210> SEQ ID NO 755
<211> LENGTH: 21
<212> TYPE: RNA
<213> ORGANISM: Homo sapiens

<400> SEQUENCE: 755
uugggacaua cuuaugcuaa a                                                   21

<210> SEQ ID NO 756
<211> LENGTH: 24
<212> TYPE: RNA
<213> ORGANISM: Homo sapiens

<400> SEQUENCE: 756
uugcagcugc cugggaguga cuuc                                                24

<210> SEQ ID NO 757
<211> LENGTH: 22
<212> TYPE: RNA
<213> ORGANISM: Homo sapiens

<400> SEQUENCE: 757
uucuggaauu cugugugagg ga                                                  22

<210> SEQ ID NO 758
<211> LENGTH: 22
<212> TYPE: RNA
<213> ORGANISM: Homo sapiens

<400> SEQUENCE: 758
uucauucggc uguccagaug ua                                                  22

<210> SEQ ID NO 759
```

```
<211> LENGTH: 17
<212> TYPE: RNA
<213> ORGANISM: Homo sapiens

<400> SEQUENCE: 759
uucaaguaau ucaggug                                                      17

<210> SEQ ID NO 760
<211> LENGTH: 22
<212> TYPE: RNA
<213> ORGANISM: Homo sapiens

<400> SEQUENCE: 760
uuagggcccu ggcuccaucu cc                                                22

<210> SEQ ID NO 761
<211> LENGTH: 21
<212> TYPE: RNA
<213> ORGANISM: Homo sapiens

<400> SEQUENCE: 761
cuuuuugcgg ucugggcuug c                                                 21

<210> SEQ ID NO 762
<211> LENGTH: 21
<212> TYPE: RNA
<213> ORGANISM: Homo sapiens

<400> SEQUENCE: 762
uuaggccgca gaucugggug a                                                 21

<210> SEQ ID NO 763
<211> LENGTH: 22
<212> TYPE: RNA
<213> ORGANISM: Homo sapiens

<400> SEQUENCE: 763
ugugagguug gcauuguugu cu                                                22

<210> SEQ ID NO 764
<211> LENGTH: 22
<212> TYPE: RNA
<213> ORGANISM: Homo sapiens

<400> SEQUENCE: 764
aagcccuuac cccaaaaagc au                                                22

<210> SEQ ID NO 765
<211> LENGTH: 22
<212> TYPE: RNA
<213> ORGANISM: Homo sapiens

<400> SEQUENCE: 765
uggguggucu ggagauuugu gc                                                22

<210> SEQ ID NO 766
<211> LENGTH: 25
<212> TYPE: RNA
<213> ORGANISM: Homo sapiens

<400> SEQUENCE: 766
ugggaacggg uuccggcaga cgcug                                             25
```

```
<210> SEQ ID NO 767
<211> LENGTH: 24
<212> TYPE: RNA
<213> ORGANISM: Homo sapiens

<400> SEQUENCE: 767
uggcccugac ugaagaccag cagu                                          24

<210> SEQ ID NO 768
<211> LENGTH: 19
<212> TYPE: RNA
<213> ORGANISM: Homo sapiens

<400> SEQUENCE: 768
uggauuuuug gaucaggga                                                19

<210> SEQ ID NO 769
<211> LENGTH: 22
<212> TYPE: RNA
<213> ORGANISM: Homo sapiens

<400> SEQUENCE: 769
aagcccuuac cccaaaaagu au                                            22

<210> SEQ ID NO 770
<211> LENGTH: 23
<212> TYPE: RNA
<213> ORGANISM: Homo sapiens

<400> SEQUENCE: 770
uggaguccag gaaucugcau uuu                                           23

<210> SEQ ID NO 771
<211> LENGTH: 21
<212> TYPE: RNA
<213> ORGANISM: Homo sapiens

<400> SEQUENCE: 771
uggacugccc ugaucuggag a                                             21

<210> SEQ ID NO 772
<211> LENGTH: 22
<212> TYPE: RNA
<213> ORGANISM: Homo sapiens

<400> SEQUENCE: 772
ugcuggauca gugguucgag uc                                            22

<210> SEQ ID NO 773
<211> LENGTH: 21
<212> TYPE: RNA
<213> ORGANISM: Homo sapiens

<400> SEQUENCE: 773
ugcaggacca agaugagccc u                                             21

<210> SEQ ID NO 774
<211> LENGTH: 22
<212> TYPE: RNA
<213> ORGANISM: Homo sapiens

<400> SEQUENCE: 774
ucugggcaac aaagugagac cu                                            22
```

```
<210> SEQ ID NO 775
<211> LENGTH: 22
<212> TYPE: RNA
<213> ORGANISM: Homo sapiens

<400> SEQUENCE: 775
ucuauacaga cccuggcuuu uc                                              22

<210> SEQ ID NO 776
<211> LENGTH: 22
<212> TYPE: RNA
<213> ORGANISM: Homo sapiens

<400> SEQUENCE: 776
ucuacaaagg aaagcgcuuu cu                                              22

<210> SEQ ID NO 777
<211> LENGTH: 20
<212> TYPE: RNA
<213> ORGANISM: Homo sapiens

<400> SEQUENCE: 777
ucguuugccu uuucugcuu                                                  20

<210> SEQ ID NO 778
<211> LENGTH: 17
<212> TYPE: RNA
<213> ORGANISM: Homo sapiens

<400> SEQUENCE: 778
ucgccuccuc cucuccc                                                    17

<210> SEQ ID NO 779
<211> LENGTH: 17
<212> TYPE: RNA
<213> ORGANISM: Homo sapiens

<400> SEQUENCE: 779
ucccaccgcu gccaccc                                                    17

<210> SEQ ID NO 780
<211> LENGTH: 21
<212> TYPE: RNA
<213> ORGANISM: Homo sapiens

<400> SEQUENCE: 780
ucacagugaa ccggucucuu u                                               21

<210> SEQ ID NO 781
<211> LENGTH: 17
<212> TYPE: RNA
<213> ORGANISM: Homo sapiens

<400> SEQUENCE: 781
ucauauugcu ucuuucu                                                    17

<210> SEQ ID NO 782
<211> LENGTH: 22
<212> TYPE: RNA
<213> ORGANISM: Homo sapiens

<400> SEQUENCE: 782
uaguacugug cauaucaucu au                                              22
```

```
<210> SEQ ID NO 783
<211> LENGTH: 22
<212> TYPE: RNA
<213> ORGANISM: Homo sapiens

<400> SEQUENCE: 783
uacguagaua uauauguauu uu                                              22

<210> SEQ ID NO 784
<211> LENGTH: 20
<212> TYPE: RNA
<213> ORGANISM: Homo sapiens

<400> SEQUENCE: 784
uaaagagccc uguggagaca                                                 20

<210> SEQ ID NO 785
<211> LENGTH: 22
<212> TYPE: RNA
<213> ORGANISM: Homo sapiens

<400> SEQUENCE: 785
cugaagcuca gagggcucug au                                              22

<210> SEQ ID NO 786
<211> LENGTH: 17
<212> TYPE: RNA
<213> ORGANISM: Homo sapiens

<400> SEQUENCE: 786 guggggggaga ggcuguc                                                   17

<210> SEQ ID NO 787
<211> LENGTH: 17
<212> TYPE: RNA
<213> ORGANISM: Homo sapiens

<400> SEQUENCE: 787
ucccuguucg ggcgcca                                                    17

<210> SEQ ID NO 788
<211> LENGTH: 18
<212> TYPE: RNA
<213> ORGANISM: Homo sapiens

<400> SEQUENCE: 788
gucccuguuc aggcgcca                                                   18

<210> SEQ ID NO 789
<211> LENGTH: 22
<212> TYPE: RNA
<213> ORGANISM: Homo sapiens

<400> SEQUENCE: 789
ucggauccgu cugagcuugg cu                                              22

<210> SEQ ID NO 790
<211> LENGTH: 25
<212> TYPE: RNA
<213> ORGANISM: Homo sapiens

<400> SEQUENCE: 790
```
gggcgacaaa gcaagacucu uucuu 25

<210> SEQ ID NO 791
<211> LENGTH: 26
<212> TYPE: RNA
<213> ORGANISM: Homo sapiens

<400> SEQUENCE: 791
gaugaugaug gcagcaaauu cugaaa 26

<210> SEQ ID NO 792
<211> LENGTH: 22
<212> TYPE: RNA
<213> ORGANISM: Homo sapiens

<400> SEQUENCE: 792
cuuggcaccu agcaagcacu ca 22

<210> SEQ ID NO 793
<211> LENGTH: 23
<212> TYPE: RNA
<213> ORGANISM: Homo sapiens

<400> SEQUENCE: 793
cuggagauau ggaagagcug ugu 23

<210> SEQ ID NO 794
<211> LENGTH: 22
<212> TYPE: RNA
<213> ORGANISM: Homo sapiens

<400> SEQUENCE: 794
cuggacugag ccgugcuacu gg 22

<210> SEQ ID NO 795
<211> LENGTH: 18
<212> TYPE: RNA
<213> ORGANISM: Homo sapiens

<400> SEQUENCE: 795
cgggcguggu ggugggggg 18

<210> SEQ ID NO 796
<211> LENGTH: 21
<212> TYPE: RNA
<213> ORGANISM: Homo sapiens

<400> SEQUENCE: 796
ccuguugaag uguaaucccc a 21

<210> SEQ ID NO 797
<211> LENGTH: 23
<212> TYPE: RNA
<213> ORGANISM: Homo sapiens

<400> SEQUENCE: 797
ccucagggcu guagaacagg gcu 23

<210> SEQ ID NO 798
<211> LENGTH: 22
<212> TYPE: RNA
<213> ORGANISM: Homo sapiens

<400> SEQUENCE: 798
caggaugugg ucaaguguug uu                                       22

<210> SEQ ID NO 799
<211> LENGTH: 23
<212> TYPE: RNA
<213> ORGANISM: Homo sapiens

<400> SEQUENCE: 799
caagucuuau uugagcaccu guu                                      23

<210> SEQ ID NO 800
<211> LENGTH: 22
<212> TYPE: RNA
<213> ORGANISM: Homo sapiens

<400> SEQUENCE: 800
augguacccu ggcauacuga gu                                       22

<210> SEQ ID NO 801
<211> LENGTH: 22
<212> TYPE: RNA
<213> ORGANISM: Homo sapiens

<400> SEQUENCE: 801
augggugaau uuguagaagg au                                       22

<210> SEQ ID NO 802
<211> LENGTH: 19
<212> TYPE: RNA
<213> ORGANISM: Homo sapiens

<400> SEQUENCE: 802
auggauaagg cuuuggcuu                                           19

<210> SEQ ID NO 803
<211> LENGTH: 18
<212> TYPE: RNA
<213> ORGANISM: Homo sapiens

<400> SEQUENCE: 803
aucccaccuc ugccacca                                            18

<210> SEQ ID NO 804
<211> LENGTH: 21
<212> TYPE: RNA
<213> ORGANISM: Homo sapiens

<400> SEQUENCE: 804
cauuauuacu uuugguacgc g                                        21

<210> SEQ ID NO 805
<211> LENGTH: 22
<212> TYPE: RNA
<213> ORGANISM: Homo sapiens

<400> SEQUENCE: 805
ucguaccgug aguaauaaug cg                                       22

<210> SEQ ID NO 806
<211> LENGTH: 22
<212> TYPE: RNA
<213> ORGANISM: Homo sapiens

```
<400> SEQUENCE: 806
ucacaaguca ggcucuuggg ac                                                  22

<210> SEQ ID NO 807
<211> LENGTH: 22
<212> TYPE: RNA
<213> ORGANISM: Homo sapiens

<400> SEQUENCE: 807
acggguuagg cucuugggag cu                                                  22

<210> SEQ ID NO 808
<211> LENGTH: 22
<212> TYPE: RNA
<213> ORGANISM: Homo sapiens

<400> SEQUENCE: 808
ucccugagac ccuaacuugu ga                                                  22

<210> SEQ ID NO 809
<211> LENGTH: 24
<212> TYPE: RNA
<213> ORGANISM: Homo sapiens

<400> SEQUENCE: 809
ucccugagac ccuuuaaccu guga                                                24

<210> SEQ ID NO 810
<211> LENGTH: 22
<212> TYPE: RNA
<213> ORGANISM: Homo sapiens

<400> SEQUENCE: 810
acaggugagg uucuugggag cc                                                  22

<210> SEQ ID NO 811
<211> LENGTH: 21
<212> TYPE: RNA
<213> ORGANISM: Homo sapiens

<400> SEQUENCE: 811
auauaugaug acuuagcuuu u                                                   21

<210> SEQ ID NO 812
<211> LENGTH: 21
<212> TYPE: RNA
<213> ORGANISM: Homo sapiens

<400> SEQUENCE: 812
aguuaggauu aggucgugga a                                                   21

<210> SEQ ID NO 813
<211> LENGTH: 21
<212> TYPE: RNA
<213> ORGANISM: Homo sapiens

<400> SEQUENCE: 813
agugaaugau ggguucugac c                                                   21

<210> SEQ ID NO 814
<211> LENGTH: 22
<212> TYPE: RNA
<213> ORGANISM: Homo sapiens
```

```
<400> SEQUENCE: 814
aggcauugac uucucacuag cu                                              22

<210> SEQ ID NO 815
<211> LENGTH: 22
<212> TYPE: RNA
<213> ORGANISM: Homo sapiens

<400> SEQUENCE: 815
cggaugagca aagaaagugg uu                                              22

<210> SEQ ID NO 816
<211> LENGTH: 23
<212> TYPE: RNA
<213> ORGANISM: Homo sapiens

<400> SEQUENCE: 816
aggaugagca aagaaaguag auu                                             23

<210> SEQ ID NO 817
<211> LENGTH: 24
<212> TYPE: RNA
<213> ORGANISM: Homo sapiens

<400> SEQUENCE: 817
agccuggaag cuggagccug cagu                                            24

<210> SEQ ID NO 818
<211> LENGTH: 21
<212> TYPE: RNA
<213> ORGANISM: Homo sapiens

<400> SEQUENCE: 818
agagaagaag aucagccugc a                                               21

<210> SEQ ID NO 819
<211> LENGTH: 22
<212> TYPE: RNA
<213> ORGANISM: Homo sapiens

<400> SEQUENCE: 819
agaaggaaau ugaauucauu ua                                              22

<210> SEQ ID NO 820
<211> LENGTH: 21
<212> TYPE: RNA
<213> ORGANISM: Homo sapiens

<400> SEQUENCE: 820
acucuagcug ccaaaggcgc u                                               21

<210> SEQ ID NO 821
<211> LENGTH: 21
<212> TYPE: RNA
<213> ORGANISM: Homo sapiens

<400> SEQUENCE: 821
acggugcugg auguggccuu u                                               21

<210> SEQ ID NO 822
<211> LENGTH: 22
<212> TYPE: RNA
```

```
<213> ORGANISM: Homo sapiens

<400> SEQUENCE: 822
acgcccuucc ccccuucuu ca                                             22

<210> SEQ ID NO 823
<211> LENGTH: 27
<212> TYPE: RNA
<213> ORGANISM: Homo sapiens

<400> SEQUENCE: 823
accuucuugu auaagcacug ugcuaaa                                       27

<210> SEQ ID NO 824
<211> LENGTH: 22
<212> TYPE: RNA
<213> ORGANISM: Homo sapiens

<400> SEQUENCE: 824
acccgucccg uucgucccccg ga                                           22

<210> SEQ ID NO 825
<211> LENGTH: 19
<212> TYPE: RNA
<213> ORGANISM: Homo sapiens

<400> SEQUENCE: 825
aauggauuuu uggagcagg                                                19

<210> SEQ ID NO 826
<211> LENGTH: 21
<212> TYPE: RNA
<213> ORGANISM: Homo sapiens

<400> SEQUENCE: 826
aagugaucua aaggccuaca u                                             21

<210> SEQ ID NO 827
<211> LENGTH: 26
<212> TYPE: RNA
<213> ORGANISM: Homo sapiens

<400> SEQUENCE: 827
aaguaguugg uuuguaugag augguu                                        26

<210> SEQ ID NO 828
<211> LENGTH: 22
<212> TYPE: RNA
<213> ORGANISM: Homo sapiens

<400> SEQUENCE: 828
aacuggauca auuauaggag ug                                            22

<210> SEQ ID NO 829
<211> LENGTH: 22
<212> TYPE: RNA
<213> ORGANISM: Homo sapiens

<400> SEQUENCE: 829
cguguucaca gcggaccuug au                                            22

<210> SEQ ID NO 830
<211> LENGTH: 20
```

```
<212> TYPE: RNA
<213> ORGANISM: Homo sapiens

<400> SEQUENCE: 830
uaaggcacgc ggugaaugcc                                              20

<210> SEQ ID NO 831
<211> LENGTH: 20
<212> TYPE: RNA
<213> ORGANISM: Homo sapiens

<400> SEQUENCE: 831
cuuccucguc ugucugcccc                                              20

<210> SEQ ID NO 832
<211> LENGTH: 21
<212> TYPE: RNA
<213> ORGANISM: Homo sapiens

<400> SEQUENCE: 832
uccuucugcu ccgucccca g                                             21

<210> SEQ ID NO 833
<211> LENGTH: 22
<212> TYPE: RNA
<213> ORGANISM: Homo sapiens

<400> SEQUENCE: 833
ccucuucccc uugucucucc ag                                           22

<210> SEQ ID NO 834
<211> LENGTH: 22
<212> TYPE: RNA
<213> ORGANISM: Homo sapiens

<400> SEQUENCE: 834
ucggccugac cacccacccc ac                                           22

<210> SEQ ID NO 835
<211> LENGTH: 20
<212> TYPE: RNA
<213> ORGANISM: Homo sapiens

<400> SEQUENCE: 835
ugagcccugu ccucccgcag                                              20

<210> SEQ ID NO 836
<211> LENGTH: 20
<212> TYPE: RNA
<213> ORGANISM: Homo sapiens

<400> SEQUENCE: 836
gugucugggc ggacagcugc                                              20

<210> SEQ ID NO 837
<211> LENGTH: 23
<212> TYPE: RNA
<213> ORGANISM: Homo sapiens

<400> SEQUENCE: 837
cucucaccac ugcccuccca cag                                          23

<210> SEQ ID NO 838
```

-continued

<211> LENGTH: 21
<212> TYPE: RNA
<213> ORGANISM: Homo sapiens

<400> SEQUENCE: 838
gugggcgggg gcaggugugu g                                              21

<210> SEQ ID NO 839
<211> LENGTH: 20
<212> TYPE: RNA
<213> ORGANISM: Homo sapiens

<400> SEQUENCE: 839
ucacaccugc cucgcccccc                                                20

<210> SEQ ID NO 840
<211> LENGTH: 20
<212> TYPE: RNA
<213> ORGANISM: Homo sapiens

<400> SEQUENCE: 840
cgugccaccc uuuuccccag                                                20

<210> SEQ ID NO 841
<211> LENGTH: 26
<212> TYPE: RNA
<213> ORGANISM: Homo sapiens

<400> SEQUENCE: 841
gugagggcau gcaggccugg augggg                                         26

<210> SEQ ID NO 842
<211> LENGTH: 22
<212> TYPE: RNA
<213> ORGANISM: Homo sapiens

<400> SEQUENCE: 842
ucaccagccc uguguucccu ag                                             22

<210> SEQ ID NO 843
<211> LENGTH: 22
<212> TYPE: RNA
<213> ORGANISM: Homo sapiens

<400> SEQUENCE: 843
guggguacgg cccagugggg gg                                             22

<210> SEQ ID NO 844
<211> LENGTH: 22
<212> TYPE: RNA
<213> ORGANISM: Homo sapiens

<400> SEQUENCE: 844
ugagccccug ugccgccccc ag                                             22

<210> SEQ ID NO 845
<211> LENGTH: 19
<212> TYPE: RNA
<213> ORGANISM: Homo sapiens

<400> SEQUENCE: 845
gugaggacuc gggaggugg                                                 19

```
<210> SEQ ID NO 846
<211> LENGTH: 21
<212> TYPE: RNA
<213> ORGANISM: Homo sapiens

<400> SEQUENCE: 846
ccccaccucc ucucuccuca g                                              21

<210> SEQ ID NO 847
<211> LENGTH: 22
<212> TYPE: RNA
<213> ORGANISM: Homo sapiens

<400> SEQUENCE: 847
aacgccauua ucacacuaaa ua                                             22

<210> SEQ ID NO 848
<211> LENGTH: 22
<212> TYPE: RNA
<213> ORGANISM: Homo sapiens

<400> SEQUENCE: 848
uggaguguga caauguguu ug                                              22

<210> SEQ ID NO 849
<211> LENGTH: 20
<212> TYPE: RNA
<213> ORGANISM: Homo sapiens

<400> SEQUENCE: 849
ucacuguuca gacaggcgga                                                20

<210> SEQ ID NO 850
<211> LENGTH: 21
<212> TYPE: RNA
<213> ORGANISM: Homo sapiens

<400> SEQUENCE: 850
uggcagggag gcugggaggg g                                              21

<210> SEQ ID NO 851
<211> LENGTH: 18
<212> TYPE: RNA
<213> ORGANISM: Homo sapiens

<400> SEQUENCE: 851
ucagcuggcc cucauuuc                                                  18

<210> SEQ ID NO 852
<211> LENGTH: 21
<212> TYPE: RNA
<213> ORGANISM: Homo sapiens

<400> SEQUENCE: 852
uguucaugua gauguuuaag c                                              21

<210> SEQ ID NO 853
<211> LENGTH: 20
<212> TYPE: RNA
<213> ORGANISM: Homo sapiens

<400> SEQUENCE: 853
ucugcagggu uugcuuugag                                                20
```

```
<210> SEQ ID NO 854
<211> LENGTH: 21
<212> TYPE: RNA
<213> ORGANISM: Homo sapiens

<400> SEQUENCE: 854
ucguggccug gucuccauua u                                            21

<210> SEQ ID NO 855
<211> LENGTH: 21
<212> TYPE: RNA
<213> ORGANISM: Homo sapiens

<400> SEQUENCE: 855
cccggagcca ggaugcagcu c                                            21

<210> SEQ ID NO 856
<211> LENGTH: 21
<212> TYPE: RNA
<213> ORGANISM: Homo sapiens

<400> SEQUENCE: 856
gugccagcug cagugggga g                                             21

<210> SEQ ID NO 857
<211> LENGTH: 24
<212> TYPE: RNA
<213> ORGANISM: Homo sapiens

<400> SEQUENCE: 857
agccugauua aacacaugcu cuga                                         24

<210> SEQ ID NO 858
<211> LENGTH: 22
<212> TYPE: RNA
<213> ORGANISM: Homo sapiens

<400> SEQUENCE: 858
cuccugagcc auucugagcc uc                                           22

<210> SEQ ID NO 859
<211> LENGTH: 21
<212> TYPE: RNA
<213> ORGANISM: Homo sapiens

<400> SEQUENCE: 859
uaggacacau ggucuacuuc u                                            21

<210> SEQ ID NO 860
<211> LENGTH: 21
<212> TYPE: RNA
<213> ORGANISM: Homo sapiens

<400> SEQUENCE: 860
agaggauacc cuuuguaugu u                                            21

<210> SEQ ID NO 861
<211> LENGTH: 23
<212> TYPE: RNA
<213> ORGANISM: Homo sapiens

<400> SEQUENCE: 861
ccugcagcga cuugauggcu ucc                                          23
```

<210> SEQ ID NO 862
<211> LENGTH: 27
<212> TYPE: RNA
<213> ORGANISM: Homo sapiens

<400> SEQUENCE: 862
cacuguaggu gauggugaga gugggca                                        27

<210> SEQ ID NO 863
<211> LENGTH: 23
<212> TYPE: RNA
<213> ORGANISM: Homo sapiens

<400> SEQUENCE: 863
gagggucuug ggagggaugu gac                                            23

<210> SEQ ID NO 864
<211> LENGTH: 21
<212> TYPE: RNA
<213> ORGANISM: Homo sapiens

<400> SEQUENCE: 864
ccgucgccgc cacccgagcc g                                              21

<210> SEQ ID NO 865
<211> LENGTH: 22
<212> TYPE: RNA
<213> ORGANISM: Homo sapiens

<400> SEQUENCE: 865
uuuccggcuc gcguggugu gu                                              22

<210> SEQ ID NO 866
<211> LENGTH: 21
<212> TYPE: RNA
<213> ORGANISM: Homo sapiens

<400> SEQUENCE: 866
aagcauucuu ucauugguug g                                              21

<210> SEQ ID NO 867
<211> LENGTH: 21
<212> TYPE: RNA
<213> ORGANISM: Homo sapiens

<400> SEQUENCE: 867
uugcucacug uucuucccua g                                              21

<210> SEQ ID NO 868
<211> LENGTH: 22
<212> TYPE: RNA
<213> ORGANISM: Homo sapiens

<400> SEQUENCE: 868
acagauucga uucuagggga au                                             22

<210> SEQ ID NO 869
<211> LENGTH: 23
<212> TYPE: RNA
<213> ORGANISM: Homo sapiens

<400> SEQUENCE: 869

```
uacccuguag aaccgaauuu gug                                              23

<210> SEQ ID NO 870
<211> LENGTH: 22
<212> TYPE: RNA
<213> ORGANISM: Homo sapiens

<400> SEQUENCE: 870
caaauucgua ucuaggggaa ua                                               22

<210> SEQ ID NO 871
<211> LENGTH: 23
<212> TYPE: RNA
<213> ORGANISM: Homo sapiens

<400> SEQUENCE: 871
uacccuguag auccgaauuu gug                                              23

<210> SEQ ID NO 872
<211> LENGTH: 23
<212> TYPE: RNA
<213> ORGANISM: Homo sapiens

<400> SEQUENCE: 872
agcagcauug uacagggcua uca                                              23

<210> SEQ ID NO 873
<211> LENGTH: 22
<212> TYPE: RNA
<213> ORGANISM: Homo sapiens

<400> SEQUENCE: 873
ccgcacugug gguacuugcu gc                                               22

<210> SEQ ID NO 874
<211> LENGTH: 21
<212> TYPE: RNA
<213> ORGANISM: Homo sapiens

<400> SEQUENCE: 874
uaaagugcug acagugcaga u                                                21

<210> SEQ ID NO 875
<211> LENGTH: 22
<212> TYPE: RNA
<213> ORGANISM: Homo sapiens

<400> SEQUENCE: 875
cugcaaugua agcacuucuu ac                                               22

<210> SEQ ID NO 876
<211> LENGTH: 23
<212> TYPE: RNA
<213> ORGANISM: Homo sapiens

<400> SEQUENCE: 876
aaaagugcuu acagugcagg uag                                              23

<210> SEQ ID NO 877
<211> LENGTH: 22
<212> TYPE: RNA
<213> ORGANISM: Homo sapiens

<400> SEQUENCE: 877
```

| | |
|---|---|
| acggauguuu gagcaugugc ua | 22 |

<210> SEQ ID NO 878
<211> LENGTH: 23
<212> TYPE: RNA
<213> ORGANISM: Homo sapiens

<400> SEQUENCE: 878

| | |
|---|---|
| ucaaaugcuc agacccugu ggu | 23 |

<210> SEQ ID NO 879
<211> LENGTH: 23
<212> TYPE: RNA
<213> ORGANISM: Homo sapiens

<400> SEQUENCE: 879

| | |
|---|---|
| ucauagcccu guacaaugcu gcu | 23 |

<210> SEQ ID NO 880
<211> LENGTH: 23
<212> TYPE: RNA
<213> ORGANISM: Homo sapiens

<400> SEQUENCE: 880

| | |
|---|---|
| agcuucuuua cagugcugcc uug | 23 |

<210> SEQ ID NO 881
<211> LENGTH: 23
<212> TYPE: RNA
<213> ORGANISM: Homo sapiens

<400> SEQUENCE: 881

| | |
|---|---|
| agcagcauug uacagggcua uga | 23 |

<210> SEQ ID NO 882
<211> LENGTH: 22
<212> TYPE: RNA
<213> ORGANISM: Homo sapiens

<400> SEQUENCE: 882

| | |
|---|---|
| caguuaucac agugcugaug cu | 22 |

<210> SEQ ID NO 883
<211> LENGTH: 21
<212> TYPE: RNA
<213> ORGANISM: Homo sapiens

<400> SEQUENCE: 883

| | |
|---|---|
| uacaguacug ugauaacuga a | 21 |

<210> SEQ ID NO 884
<211> LENGTH: 22
<212> TYPE: RNA
<213> ORGANISM: Homo sapiens

<400> SEQUENCE: 884

| | |
|---|---|
| caagcuugua ucuauaggua ug | 22 |

<210> SEQ ID NO 885
<211> LENGTH: 22
<212> TYPE: RNA
<213> ORGANISM: Homo sapiens -continued

<400> SEQUENCE: 885
aacccguaga uccgaacuug ug                                    22

<210> SEQ ID NO 886
<211> LENGTH: 22
<212> TYPE: RNA
<213> ORGANISM: Homo sapiens

<400> SEQUENCE: 886
uggaauguaa agaaguaugu au                                    22

<210> SEQ ID NO 887
<211> LENGTH: 22
<212> TYPE: RNA
<213> ORGANISM: Homo sapiens

<400> SEQUENCE: 887
cugcgcaagc uacugccuug cu                                    22

<210> SEQ ID NO 888
<211> LENGTH: 22
<212> TYPE: RNA
<213> ORGANISM: Homo sapiens

<400> SEQUENCE: 888
ugagguagua guuugugcug uu                                    22

<210> SEQ ID NO 889
<211> LENGTH: 21
<212> TYPE: RNA
<213> ORGANISM: Homo sapiens

<400> SEQUENCE: 889
cuguacaggc cacugccuug c                                     21

<210> SEQ ID NO 890
<211> LENGTH: 22
<212> TYPE: RNA
<213> ORGANISM: Homo sapiens

<400> SEQUENCE: 890
ugagguagua guuuguacag uu                                    22

<210> SEQ ID NO 891
<211> LENGTH: 22
<212> TYPE: RNA
<213> ORGANISM: Homo sapiens

<400> SEQUENCE: 891
cuauacaguc uacugucuuu cc                                    22

<210> SEQ ID NO 892
<211> LENGTH: 22
<212> TYPE: RNA
<213> ORGANISM: Homo sapiens

<400> SEQUENCE: 892
cuauacaauc uauugccuuc cc                                    22

<210> SEQ ID NO 893
<211> LENGTH: 22
<212> TYPE: RNA
<213> ORGANISM: Homo sapiens

```
<400> SEQUENCE: 893
ugagguagua gauuguauag uu                                              22

<210> SEQ ID NO 894
<211> LENGTH: 22
<212> TYPE: RNA
<213> ORGANISM: Homo sapiens

<400> SEQUENCE: 894
cuauacggcc uccuagcuuu cc                                              22

<210> SEQ ID NO 895
<211> LENGTH: 22
<212> TYPE: RNA
<213> ORGANISM: Homo sapiens

<400> SEQUENCE: 895
ugagguagga gguuguauag uu                                              22

<210> SEQ ID NO 896
<211> LENGTH: 22
<212> TYPE: RNA
<213> ORGANISM: Homo sapiens

<400> SEQUENCE: 896
cuauacgacc ugcugccuuu cu                                              22

<210> SEQ ID NO 897
<211> LENGTH: 22
<212> TYPE: RNA
<213> ORGANISM: Homo sapiens

<400> SEQUENCE: 897
agagguagua gguugcauag uu                                              22

<210> SEQ ID NO 898
<211> LENGTH: 22
<212> TYPE: RNA
<213> ORGANISM: Homo sapiens

<400> SEQUENCE: 898
uagaguuaca cccugggagu ua                                              22

<210> SEQ ID NO 899
<211> LENGTH: 22
<212> TYPE: RNA
<213> ORGANISM: Homo sapiens

<400> SEQUENCE: 899
ugagguagua gguuguaugg uu                                              22

<210> SEQ ID NO 900
<211> LENGTH: 22
<212> TYPE: RNA
<213> ORGANISM: Homo sapiens

<400> SEQUENCE: 900
cuauacaacc uacugccuuc cc                                              22

<210> SEQ ID NO 901
<211> LENGTH: 22
<212> TYPE: RNA
```

```
<213> ORGANISM: Homo sapiens

<400> SEQUENCE: 901
ugagguagua gguugugugg uu                                              22

<210> SEQ ID NO 902
<211> LENGTH: 22
<212> TYPE: RNA
<213> ORGANISM: Homo sapiens

<400> SEQUENCE: 902
cuguacagcc uccuagcuuu cc                                              22

<210> SEQ ID NO 903
<211> LENGTH: 21
<212> TYPE: RNA
<213> ORGANISM: Homo sapiens

<400> SEQUENCE: 903
cuauacaauc uacugucuuu c                                               21

<210> SEQ ID NO 904
<211> LENGTH: 22
<212> TYPE: RNA
<213> ORGANISM: Homo sapiens

<400> SEQUENCE: 904
ugagguagua gguuguauag uu                                              22

<210> SEQ ID NO 905
<211> LENGTH: 22
<212> TYPE: RNA
<213> ORGANISM: Homo sapiens

<400> SEQUENCE: 905
uaauacugcc ugguaaugau ga                                              22

<210> SEQ ID NO 906
<211> LENGTH: 21
<212> TYPE: RNA
<213> ORGANISM: Homo sapiens

<400> SEQUENCE: 906
cucuccucuc cuaaccucgc u                                               21

<210> SEQ ID NO 907
<211> LENGTH: 23
<212> TYPE: RNA
<213> ORGANISM: Homo sapiens

<400> SEQUENCE: 907
agucgagagu gggagaagag cgg                                             23

<210> SEQ ID NO 908
<211> LENGTH: 19
<212> TYPE: RNA
<213> ORGANISM: Homo sapiens

<400> SEQUENCE: 908
aaaaccgucu aguuacagu                                                  19

<210> SEQ ID NO 909
<211> LENGTH: 23
```

```
<212> TYPE: RNA
<213> ORGANISM: Homo sapiens

<400> SEQUENCE: 909
cucagugaug aaaacuuugu cca                                              23

<210> SEQ ID NO 910
<211> LENGTH: 21
<212> TYPE: RNA
<213> ORGANISM: Homo sapiens

<400> SEQUENCE: 910
guugccuuuu uguucccaug c                                                21

<210> SEQ ID NO 911
<211> LENGTH: 21
<212> TYPE: RNA
<213> ORGANISM: Homo sapiens

<400> SEQUENCE: 911
uaggcaccaa aaagcaacaa c                                                21

<210> SEQ ID NO 912
<211> LENGTH: 21
<212> TYPE: RNA
<213> ORGANISM: Homo sapiens

<400> SEQUENCE: 912
gcugcaccgg agacugggua a                                                21

<210> SEQ ID NO 913
<211> LENGTH: 21
<212> TYPE: RNA
<213> ORGANISM: Homo sapiens

<400> SEQUENCE: 913
uacccagucu ccggugcagc c                                                21

<210> SEQ ID NO 914
<211> LENGTH: 24
<212> TYPE: RNA
<213> ORGANISM: Homo sapiens

<400> SEQUENCE: 914
uuccucugau gacuuccugu uagu                                             24

<210> SEQ ID NO 915
<211> LENGTH: 21
<212> TYPE: RNA
<213> ORGANISM: Homo sapiens

<400> SEQUENCE: 915
uggaacugag gaucugagga a                                                21

<210> SEQ ID NO 916
<211> LENGTH: 21
<212> TYPE: RNA
<213> ORGANISM: Homo sapiens

<400> SEQUENCE: 916
aguggcaaag ucuuuccaua u                                                21

<210> SEQ ID NO 917
```

```
<211> LENGTH: 22
<212> TYPE: RNA
<213> ORGANISM: Homo sapiens

<400> SEQUENCE: 917
uuagcucagc gguuacuucg ac                                            22

<210> SEQ ID NO 918
<211> LENGTH: 21
<212> TYPE: RNA
<213> ORGANISM: Homo sapiens

<400> SEQUENCE: 918
caagcaaccu gucugdgguug u                                            21

<210> SEQ ID NO 919
<211> LENGTH: 19
<212> TYPE: RNA
<213> ORGANISM: Homo sapiens

<400> SEQUENCE: 919
uaacgcauaa uauggacau                                                19

<210> SEQ ID NO 920
<211> LENGTH: 21
<212> TYPE: RNA
<213> ORGANISM: Homo sapiens

<400> SEQUENCE: 920
auguccauau uauggguuag u                                             21

<210> SEQ ID NO 921
<211> LENGTH: 21
<212> TYPE: RNA
<213> ORGANISM: Homo sapiens

<400> SEQUENCE: 921
caguugcuag uugcacuccu c                                             21

<210> SEQ ID NO 922
<211> LENGTH: 21
<212> TYPE: RNA
<213> ORGANISM: Homo sapiens

<400> SEQUENCE: 922
aggcagugua uugcuagcgg c                                             21

<210> SEQ ID NO 923
<211> LENGTH: 21
<212> TYPE: RNA
<213> ORGANISM: Homo sapiens

<400> SEQUENCE: 923
aguucuugcc ugguuucucu a                                             21

<210> SEQ ID NO 924
<211> LENGTH: 18
<212> TYPE: RNA
<213> ORGANISM: Homo sapiens

<400> SEQUENCE: 924
ucugcauugc cagggauu                                                 18
```

```
<210> SEQ ID NO 925
<211> LENGTH: 19
<212> TYPE: RNA
<213> ORGANISM: Homo sapiens

<400> SEQUENCE: 925
uagcuuuaga gacugagag                                                19

<210> SEQ ID NO 926
<211> LENGTH: 23
<212> TYPE: RNA
<213> ORGANISM: Homo sapiens

<400> SEQUENCE: 926
ugagacaggc uuaugcugcu auc                                           23

<210> SEQ ID NO 927
<211> LENGTH: 21
<212> TYPE: RNA
<213> ORGANISM: Homo sapiens

<400> SEQUENCE: 927
agcagcauga accugucuca c                                             21

<210> SEQ ID NO 928
<211> LENGTH: 21
<212> TYPE: RNA
<213> ORGANISM: Homo sapiens

<400> SEQUENCE: 928
ccggcggcag ggguggcacc g                                             21

<210> SEQ ID NO 929
<211> LENGTH: 20
<212> TYPE: RNA
<213> ORGANISM: Homo sapiens

<400> SEQUENCE: 929
gccuuaggag aaaguuucug                                               20

<210> SEQ ID NO 930
<211> LENGTH: 19
<212> TYPE: RNA
<213> ORGANISM: Homo sapiens

<400> SEQUENCE: 930
uccuaaggca gucccugga                                                19

<210> SEQ ID NO 931
<211> LENGTH: 21
<212> TYPE: RNA
<213> ORGANISM: Homo sapiens

<400> SEQUENCE: 931
aaggucgccc ucaaggugac c                                             21

<210> SEQ ID NO 932
<211> LENGTH: 21
<212> TYPE: RNA
<213> ORGANISM: Homo sapiens

<400> SEQUENCE: 932
augccuggga guugcgaucu g                                             21
```

```
<210> SEQ ID NO 933
<211> LENGTH: 21
<212> TYPE: RNA
<213> ORGANISM: Homo sapiens

<400> SEQUENCE: 933
uggaguuaaa gacuuuucu c                                              21

<210> SEQ ID NO 934
<211> LENGTH: 24
<212> TYPE: RNA
<213> ORGANISM: Homo sapiens

<400> SEQUENCE: 934
cagagaauag uuuaaauuag aauc                                          24

<210> SEQ ID NO 935
<211> LENGTH: 23
<212> TYPE: RNA
<213> ORGANISM: Homo sapiens

<400> SEQUENCE: 935
ugcaacuuac ugagggcuuu gaa                                           23

<210> SEQ ID NO 936
<211> LENGTH: 21
<212> TYPE: RNA
<213> ORGANISM: Homo sapiens

<400> SEQUENCE: 936
uggggguuug caguccuuag c                                             21

<210> SEQ ID NO 937
<211> LENGTH: 21
<212> TYPE: RNA
<213> ORGANISM: Homo sapiens

<400> SEQUENCE: 937
agacacuaua cgagucauau a                                             21

<210> SEQ ID NO 938
<211> LENGTH: 21
<212> TYPE: RNA
<213> ORGANISM: Homo sapiens

<400> SEQUENCE: 938
auaggacuca uauagugcca g                                             21

<210> SEQ ID NO 939
<211> LENGTH: 22
<212> TYPE: RNA
<213> ORGANISM: Homo sapiens

<400> SEQUENCE: 939
auccccagau acaauggaca au                                            22

<210> SEQ ID NO 940
<211> LENGTH: 23
<212> TYPE: RNA
<213> ORGANISM: Homo sapiens

<400> SEQUENCE: 940
uucaccuguu agccugucca gag                                           23
```

```
<210> SEQ ID NO 941
<211> LENGTH: 23
<212> TYPE: RNA
<213> ORGANISM: Homo sapiens

<400> SEQUENCE: 941
ugacagcgcc cugccuggcu cgg                                              23

<210> SEQ ID NO 942
<211> LENGTH: 23
<212> TYPE: RNA
<213> ORGANISM: Homo sapiens

<400> SEQUENCE: 942
agcgcgggcu gagcgcugcc agu                                              23

<210> SEQ ID NO 943
<211> LENGTH: 22
<212> TYPE: RNA
<213> ORGANISM: Homo sapiens

<400> SEQUENCE: 943
uauacuacau auaauauaug ua                                               22

<210> SEQ ID NO 944
<211> LENGTH: 22
<212> TYPE: RNA
<213> ORGANISM: Homo sapiens

<400> SEQUENCE: 944
uauacuacau auaauauaug ua                                               22

<210> SEQ ID NO 945
<211> LENGTH: 23
<212> TYPE: RNA
<213> ORGANISM: Homo sapiens

<400> SEQUENCE: 945
uagcaccauc ugaaaucggu uau                                              23

<210> SEQ ID NO 946
<211> LENGTH: 22
<212> TYPE: RNA
<213> ORGANISM: Homo sapiens

<400> SEQUENCE: 946
gugcaaaagu caucacgguu uu                                               22

<210> SEQ ID NO 947
<211> LENGTH: 21
<212> TYPE: RNA
<213> ORGANISM: Homo sapiens

<400> SEQUENCE: 947
accgcgauga cuuuugcauc a                                                21

<210> SEQ ID NO 948
<211> LENGTH: 23
<212> TYPE: RNA
<213> ORGANISM: Homo sapiens

<400> SEQUENCE: 948
```

```
ucaccgcggu cuuuccucc cac                                         23

<210> SEQ ID NO 949
<211> LENGTH: 21
<212> TYPE: RNA
<213> ORGANISM: Homo sapiens

<400> SEQUENCE: 949
uuggggaaac ggccgcugag u                                          21

<210> SEQ ID NO 950
<211> LENGTH: 21
<212> TYPE: RNA
<213> ORGANISM: Homo sapiens

<400> SEQUENCE: 950
uccucccaug ccaagaacuc c                                          21

<210> SEQ ID NO 951
<211> LENGTH: 21
<212> TYPE: RNA
<213> ORGANISM: Homo sapiens

<400> SEQUENCE: 951
gguucuuagc auaggagguc u                                          21

<210> SEQ ID NO 952
<211> LENGTH: 22
<212> TYPE: RNA
<213> ORGANISM: Homo sapiens

<400> SEQUENCE: 952
cugcgugucc cuaggugagg gg                                         22

<210> SEQ ID NO 953
<211> LENGTH: 22
<212> TYPE: RNA
<213> ORGANISM: Homo sapiens

<400> SEQUENCE: 953
ggcacagggc gaguggaaag aa                                         22

<210> SEQ ID NO 954
<211> LENGTH: 22
<212> TYPE: RNA
<213> ORGANISM: Homo sapiens

<400> SEQUENCE: 954
ucacuaccug acaauacagu au                                         22

<210> SEQ ID NO 955
<211> LENGTH: 22
<212> TYPE: RNA
<213> ORGANISM: Homo sapiens

<400> SEQUENCE: 955
ugcuguauug ucagguagug au                                         22

<210> SEQ ID NO 956
<211> LENGTH: 24
<212> TYPE: RNA
<213> ORGANISM: Homo sapiens

<400> SEQUENCE: 956
```

```
uggaggugau gaacugucug agcc                                              24

<210> SEQ ID NO 957
<211> LENGTH: 21
<212> TYPE: RNA
<213> ORGANISM: Homo sapiens

<400> SEQUENCE: 957
ugcguguccc gccuguuccc u                                                 21

<210> SEQ ID NO 958
<211> LENGTH: 24
<212> TYPE: RNA
<213> ORGANISM: Homo sapiens

<400> SEQUENCE: 958
ugugcugauu gucacguucu gauu                                              24

<210> SEQ ID NO 959
<211> LENGTH: 24
<212> TYPE: RNA
<213> ORGANISM: Homo sapiens

<400> SEQUENCE: 959
acagaugaug aacuuauuga cggg                                              24

<210> SEQ ID NO 960
<211> LENGTH: 23
<212> TYPE: RNA
<213> ORGANISM: Homo sapiens

<400> SEQUENCE: 960
accuuccucu ccauggucu uuc                                                23

<210> SEQ ID NO 961
<211> LENGTH: 22
<212> TYPE: RNA
<213> ORGANISM: Homo sapiens

<400> SEQUENCE: 961
agacccauug aggagaaggu uc                                                22

<210> SEQ ID NO 962
<211> LENGTH: 21
<212> TYPE: RNA
<213> ORGANISM: Homo sapiens

<400> SEQUENCE: 962
uucucaagag ggaggcaauc a                                                 21
```

MIRNA FINGERPRINT IN THE DIAGNOSIS OF PROSTATE CANCER

This application is a divisional of Ser. No. 13/520,014 filed Oct. 10, 2012, which is a 35 U.S.C. 371 National Phase Entry Application from PCT/EP2010/070924, filed Dec. 30, 2010, which claims the benefit of U.S. Provisional 61/291, 074 filed Dec. 30, 2009 and European Patent Application No. 09181024.2 filed on Dec. 30, 2009 the disclosures of which are incorporated herein in their entirety by reference.

BACKGROUND OF THE INVENTION

MicroRNAs (miRNA) are a recently discovered class of small non-coding RNAs (17-14 nucleotides). Due to their function as regulators of gene expression they play a critical role both in physiological and in pathological processes, such as cancer (Calin and Croce 2006; Esquela-Kerscher and Slack 2006; Zhang, Pan et al. 2007; Sassen, Miska et al. 2008).

There is increasing evidence that miRNAs are not only found in tissues but also in human blood both as free circulating nucleic acids and in mononuclear cells. A recent proof-of-principle study demonstrated miRNA expression pattern in pooled blood sera and pooled blood cells, both in healthy individuals and in cancer patients including patients with lung cancer (Chen, Ba et al. 2008). In addition, a remarkable stability of miRNAs in human sera was recently demonstrated (Chen, Ba et al. 2008; Gilad, Meiri et al. 2008). These findings make miRNA a potential tool for diagnostics for various types of diseases based on blood analysis.

Thus, although various markers have been proposed to indicate specific types of disorders such as prostate cancer, Wilms' tumour or COPD (Chronic obstructive pulmonary disease) there is still a need for more efficient and effective methods and compositions for the diagnosis of diseases.

SUMMARY OF THE INVENTION

The present invention provides novel methods for diagnosing diseases based on the determination of specific miRNAs that have altered expression levels in disease states compared to healthy controls or altered expression levels in a condition 1 (biological state or health state 1) compared to a condition 2 (biological state or health state 2). The disease is particularly selected from prostate cancer.
Definitions
miRNA
microRNAs (miRNA or pRNA) are single-stranded RNA molecules of ~21-23 nucleotides in length, which regulate gene expression. miRNAs are encoded by genes from whose DNA they are transcribed but miRNAs are not translated into protein (i.e. they are non-coding RNAs). The genes encoding miRNAs are much longer than the processed mature miRNA molecule; miRNAs are first transcribed as primary transcripts or pri-miRNA with a cap and poly-A tail and processed to short, 70-nucleotide stem-loop structures known as pre-miRNA in the cell nucleus. This processing is performed in animals by a protein complex known as the Microprocessor complex, consisting of the nuclease Drosha and the double-stranded RNA binding protein Pasha. These pre-miRNAs are then processed to mature miRNAs in the cytoplasm by interaction with the endonuclease Dicer, which also initiates the formation of the RNA-induced silencing complex (RISC). When Dicer cleaves the pre-miRNA stem-loop, two complementary short RNA molecules are formed, but only one is integrated into the RISC. This strand is known as the guide strand and is selected by the argonaute protein, the catalytically active RNase in the RISC, on the basis of the stability of the 5' end. The remaining strand, known as the miRNA*, anti-guide or passenger strand, is degraded as a RISC substrate. Therefore the miRNA*s are derived from the same hairpin structure like the "normal" miRNAs. So if the "normal" miRNA is then later called the "mature miRNA" or "guided strand", the miRNA* is the passenger strand.
miRNA* (See Also Above "miRNA")

The miRNA*s, also known as the anti-guide or passenger strand, are mostly complementary to the guide strand, but there are usually single-stranded overhangs on each end, there is usually one or a few mispairs and there are sometimes extra or missing bases causing single-stranded "bubbles. The miRNA*s are likely to act in a regulatory fashion as the miRNAs.

It is understood that according to the present invention the term "miRNA" also includes the term "miRNA*".
miRBase A well established repository of validated miRNAs is the miRBase. The miRBase (www.mirbase.org) is a searchable database of published miRNA sequences and annotation. Each entry in the miRBase Sequence database represents a predicted hairpin portion of a miRNA transcript (termed mir in the database), with information on the location and sequence of the mature miRNA sequence (termed miR). Both hairpin and mature sequences are available for searching and browsing, and entries can also be retrieved by name, keyword, references and annotation. All sequence and annotation data are also available for download.
miRNA-(Expression) Profile or m iRNA Fingerprint A miRNA-Profile represents the collection of expression levels of a plurality of miRNAs, therefore it is a quantitative measure of individual miRNA expression levels. Hereby, each miRNA is represented by a numerical value. The higher the value of an individual miRNA the higher is the expression level of this miRNA. A miRNA-profile is obtained from the RNA of a biological sample. The are various technologies to determine a miRNA-Profile, e.g. microarrays, RT-PCR, Next Generation Sequencing. As a starting material for analysis, RNA or total-RNA or any fraction thereof can be used. The plurality of miRNAs that are determined by a miRNA-profile can range from a selection of one up to all known miRNAs.
Pre-determined Set of miRNAs or miRNA Signature The pre-determined set of miRNAs or miRNA signature is understood in the present invention as a fixed defined set of miRNAs which is able to differentiate between a condition 1 and another condition 2. e.g. when condition 1 is lung cancer and condition 2 is normal control, the corresponding pre-determined set of miRNAs is able to differentiate between a samples derived from a lung cancer patient or a normal control patient. Alternatively, condition 1 is lung cancer and condition 2 is multiple sclerosis, the corresponding pre-determined set of miRNAs is able to differentiate between a lung cancer patient and a multiple sclerosis patient. In order to be able to perform the sample analysis it is required that, e.g. on the matrix that will be used to determine a miRNA profile, these fixed defined set of miRNAs have to be represented by capture probes that are defined by the pre-determined set of miRNAs. For example, when the predetermined set of miRNAs for diagnosing lung cancer from healthy controls consists of 25 miRNAs, probes capable for detecting these 25 miRNAs have to be implemented for performing the diagnostic analysis.

Common miRNA Signature Profile

A common miRNA signature profile is understood in the present invention as a non-fixed defined set of miRNAs or non-coding RNAs which is able to differentiate between a condition 1 and another condition 2. The common miRNA or non-coding RNA signature profile is calculated "on-the-fly" from a plurality of miRNA-profiles that are stored, e.g. in database. The common miRNA signature profile which is able to differentiate between a condition 1 and another condition 2 is changing as soon as an new profile is added to the database which is relevant to either to state of health 1 or another condition 2. In this respect it is different from a predetermined set of miRNAs (see above). Furthermore, the basis for generating the common miRNA signature profile—hence the miRNA profiles stored in the database—is generated from capture probes, e.g. on a matrix that is representing as much as possible different capture probes for detecting as much as possible, ideally all known, miRNAs.

Non-coding RNA

A non-coding RNA (ncRNA) is a functional RNA molecule that is not translated into a protein. Less-frequently used synonyms are non-protein-coding RNA (npcRNA), non-messenger RNA (nmRNA), small non-messenger RNA (snmRNA), functional RNA (fRNA). The term small RNA (sRNA) is often used for bacterial ncRNAs. The DNA sequence from which a non-coding RNA is transcribed as the end product is often called an RNA gene or non-coding RNA gene.

Non-coding RNA genes include highly abundant and functionally important RNAs such as transfer RNA (tRNA) and ribosomal RNA (rRNA), as well as RNAs such as snoRNAs, microRNAs, siRNAs and piRNAs and the long ncRNAs that include examples such as Xist and HOTAIR (see here for a more complete list of ncRNAs). The number of ncRNAs encoded within the human genome is unknown, however recent transcriptomic and bioinformatic studies suggest the existence of thousands of ncRNAs. Since most of the newly identified ncRNAs have not been validated for their function, it is possible that many are non-functional.

Condition

A condition (biological state or health state or state of health) is understood in the present invention as status of a subject that can be described by physical, mental or social criteria. It includes as well so-called "healthy" and "diseased" conditions, therefore it is not limited to the WHO definition of health as "a state of complete physical, mental, and social well-being and not merely the absence of disease or infirmity." but includes disease and infirmity. For the definition of diseases comprised, e.g. by the conditions of the present invention, it is referred to the international classification of diseases (ICD) of the WHO website (.who.int/classifications/icd/en/index.html). When 2 or more conditions are compared according to the present invention, it is understood that this is possible for all conditions that can be defined and is not limited to a comparison of a disease versus healthy and extends to multi-way comparisons. Examples for comparison are, but not limited to:

pairwise comparisons:
lung cancer vs. healthy control, pancreatic cancer vs. healthy control
lung cancer vs. pancreatic cancer, lung cancer vs. multiple sclerosis
lung cancer WHO grade 1 vs. lung cancer WHO grade 2
lung cancer WHO grade 1 metastasing vs. lung cancer WHO grade 1 non-metastasing
Morbus Crohn vs. collitis
Pancreatic cancer vs. pancreatitis multi-way comparisons:
Lung cancer vs. pancreatic cancer vs. multiple sclerosis
Pancreas cancer vs. pancreatitis vs. lung cancer WHO grade 1 non-metastasing Prostate Cancer Prostate cancer is a form of cancer that develops in the prostate, a gland in the male reproductive system. The cancer cells may metastasize (spread) from the prostate to other parts of the body, particularly the bones and lymph nodes. Prostate cancer may cause pain, difficulty in urinating, problems during sexual intercourse, or erectile dysfunction. Other symptoms can potentially develop during later stages of the disease.

Rates of detection of prostate cancers vary widely across the world, with South and East Asia detecting less frequently than in Europe, and especially the United States.Prostate cancer tends to develop in men over the age of fifty and although it is one of the most prevalent types of cancer in men, many never have symptoms, undergo no therapy, and eventually die of other causes. This is because cancer of the prostate is, in most cases, slow-growing, symptom free and men with the condition often die of causes unrelated to the prostate cancer, such as heart/circulatory disease, pneumonia, other unconnected cancers, or old age. Many factors, including genetics and diet, have been implicated in the development of prostate cancer. The presence of prostate cancer may be indicated by symptoms, physical examination, prostate specific antigen (PSA), or biopsy. There is controversy about the accuracy of the PSA test and the value of screening. Suspected prostate cancer is typically confirmed by taking a biopsy of the prostate and examining it under a microscope. Further tests, such as CT scans and bone scans, may be performed to determine whether prostate cancer has spread.

Treatment options for prostate cancer with intent to cure are primarily surgery, radiation therapy, and proton therapy. Other treatments, such as hormonal therapy, chemotherapy, cryosurgery, and high intensity focused ultrasound (HIFU) also exist, depending on the clinical scenario and desired outcome.

The age and underlying health of the man, the extent of metastasis, appearance under the microscope, and response of the cancer to initial treatment are important in determining the outcome of the disease. The decision whether or not to treat localized prostate cancer (a tumour that is contained within the prostate) with curative intent is a patient trade-off between the expected beneficial and harmful effects in terms of patient survival and quality of life.

A "biological sample" in terms of the invention means a sample of biological tissue or fluid. Examples of biological samples are sections of tissues, blood, blood fractions, plasma, serum, urine or samples from other peripheral sources. or cell cultures, cell colonies of even single cells, or a collection of single cells. Furthermore, also pools or mixture of the above mentioned samples may be employed. A biological sample may be provided by removing a sample of cells from a subject, but can also be provided by using a previously isolated sample. For example, a tissue sample can be removed from a subject suspected of having a disease by conventional biopsy techniques. In a preferred embodiment, a blood sample is taken from the subject. In one embodiment, the blood or tissue sample is obtained from the subject prior to initiation of radiotherapy, chemotherapy or other therapeutic treatment. According to the invention, the biological sample preferably is a blood or a serum sample. Further, it is also preferred to use blood cells, e.g. erythrocytes, leukocytes or thrombocytes.

A biological sample from a patient means a sample from a subject suspected to be affected by a disease. As used herein, the term "subject" refers to any mammal, including both human and other mammals. Preferably, the methods of the present invention are applied to human subjects.

Subject-matter of the invention is a method for diagnosing a disease, comprising the steps (a) determining an expression profile of a predetermined set of miRNAs in a biological sample from a patient (or subject); and (b) comparing said expression profile to a reference expression profile, wherein the comparison of said determined expression profile to said reference expression profile allows for the diagnosis of the disease.

In step (a) of the above method of the invention, an expression profile of a predetermined set of miRNAs is determined. The determination may be carried out by any convenient means for determining nucleic acids. For expression profiling, qualitative, semi-quantitative and preferably quantitative detection methods can be used. A variety of techniques are well known to those of skill in the art. In particular, the determination may comprise nucleic acid hybridization and/or nucleic acid amplification steps.

Nucleic acid hybridization may for example be performed using a solid phase nucleic acid biochip array, in particular a microarray, or in situ hybridization. The miRNA microarray technology affords the analysis of a complex biological sample for all expressed miRNAs. Nucleotides with complementarity to the corresponding miRNAs are spotted on coated carriers or are fabricated by in-situ synthesis methods on a carrier. Preferably, miRNAs isolated from the sample of interest are not labelled, e.g. before hybridization of the miRNAs to the complementary sequences on the carrier and the resulting signal indicating the occurrence of a distinct miRNA is generated by incorporation of a detectable label (e.g. biotin, fluorescent dye) by means of an enzyme reaction.

According to another embodiment of the invention, miRNAs isolated from the sample of interest are labelled, e.g. fluorescently labelled, so that upon hybridization of the miRNAs to the complementary sequences on the carrier the resulting signal indicates the occurrence of a distinct miRNA. On one miRNA microarray, preferably at least the whole predetermined set of miRNAs can be analyzed.

Further, quantitative real-time polymerase chain reaction (RT-PCR) can be used to detect miRNAs even at very low abundance.

Alternative methods for obtaining expression profiles may also contain sequencing, next generation sequencing or mass spectroscopy.

The predetermined set of miRNAs in step (a) of the above method of the invention depends on the disease to be diagnosed. The inventors found out that single miRNA biomarkers lack sufficient accuracy, specificity and sensitivity, and therefore it is preferred to analyze more complex miRNA expression patterns, so-called miRNA signatures. The predetermined set of miRNAs comprises one or more, preferably a larger number of miRNAs (miRNA signatures) that are differentially regulated in samples of a patient affected by a particular disease compared to healthy controls. Alternatively, the disease can also be compared to any other defined condition (e.g. another disease).

The expression profile determined in the above step (a) is subsequently compared to a reference expression profile or to a plurality of reference profiles in the above step (b). The reference expression profile is the expression profile of the same set of miRNAs in a biological sample originating from the same source as the biological sample from a patient but obtained from a healthy subject. Preferably, both the reference expression profile and the expression profile of the above step (a) are determined in a blood or serum sample or in a sample of erythrocytes, leukocytes and/or thrombocytes. It is understood that the reference expression profile is not necessarily obtained from a single healthy subject but may be an average expression profile of a plurality of healthy subjects. It is preferred to use a reference expression profile obtained from a person of the same gender, and a similar age as the patient.

The above method of the invention is suitable for diagnosing any diseases for which a differential expression of miRNAs compared to healthy controls or other diseases exists. In particular, the method may be used for diagnosing cancer including bladder cancer, brain cancer, breast cancer, colon cancer, endometrium cancer, gastrointestinal stromal cancer, glioma, head- and neck cancer, kidney cancer, leukemia, liver cancer, lung cancer, lymph node cancer, melanoma, meninges cancer, ovarian cancer, pancreas cancer, prostate cancer, sarcoma, stomach cancer, testicular cancer, thyroid cancer, thymus cancer and Wilms' tumour or COPD. The diagnosis may comprise determining type, rate and/or stage of cancer. The course of the disease and the success of therapy such as chemotherapy may be monitored. The method of the invention provides a prognosis on the survivor rate and enables to determine a patient's response to drugs.

In addition to cancer, also different types of diseases may be diagnosed by means of the above method of the invention, if the disease state is correlated with a differential expression of miRNAs compared to a healthy control. For example the disease may be Alzheimer's disease, multiple sclerosis, melanoma, Morbus Crohn and cardiovascular diseases. The inventors found out that also these diseases are correlated with a specific expression profile of miRNAs.

The inventors succeeded in developing a generally applicable approach to arrive at miRNA signatures that are correlated with a particular disease. In more detail, the following steps are accomplished:

1. miRNAs are extracted from a biological sample of a patient, preferably a blood or serum or urine sample or a sample comprising erythrocytes, leukocytes or thrombocytes, using suitable kits/purification methods. From these samples preferably the RNA-fraction is used for analysis.

2. The respective samples are measured using experimental techniques. These techniques include but are not restricted to:

Array based approaches
   Real time quantitative polymerase chain reaction
   Sequencing
   Next Generation Sequencing
   Mass Spectroscopy 3. Mathematical approaches are applied to gather information on the value and the redundancy of single biomarkers. These methods include, but are not restricted to:

basic mathematic approaches (e.g. Fold Quotients, Signal to Noise ratios, Correlation)
   statistical methods as hypothesis tests (e.g. t-test, Wilcoxon-Mann-Whitney test), the Area under the Receiver operator Characteristics Curve
   Information Theory approaches, (e.g. the Mutual Information, Cross-entropy)
   Probability theory (e.g. joint and conditional probabilities)
   Combinations and modifications of the previously mentioned examples 4. The information collected in 3) are used to estimate for each biomarker the diagnostic content or value. Usually, however, this diagnostic value of only one biomarker is too small to get a highly accurate diagnosis with accuracy rates, specificities and sensitivities beyond the 90% barrier. Please note that the diagnostic content for our miRNAs can be found in the tables in FIGS. 2 and 5. These tables includes the miRNAs with the sequences, and the significance value as computed by a t-test and further statistical measures.

5. Thus statistical learning/machine learning/bioinformatics/computational approaches are applied to define subsets of biomarkers that are tailored for the detection of diseases. These techniques includes but are not restricted to
   Wrapper subset selection techniques (e.g. forward step-wise, backward step-wise, combinatorial approaches, optimization approaches)
   Filter subset selection methods (e.g. the methods mentioned in 3)
   Principal Component Analysis
   Combinations and modifications of such methods (e.g. hybrid approaches)

6. The diagnostic content of each detected set can be estimated by mathematical and/or computational techniques to define the diagnostic information content of subsets.

7. The subsets, detected in step 5, which may range from only a small number (at least two) to all measured biomarkers is then used to carry out a diagnosis. To this end, statistical learning/machine learning/bioinformatics/computational approaches are applied that include but are not restricted to any type of supervised or unsupervised analysis:
   Classification techniques (e.g. naïve Bayes, Linear Discriminant Analysis, Quadratic Discriminant Analysis Neural Nets, Tree based approaches, Support Vector Machines, Nearest Neighbour Approaches)
   Regression techniques (e.g. linear Regression, Multiple Regression, logistic regression, probit regression, ordinal logistic regression ordinal Probit-Regression, Poisson Regression, negative binomial Regression, multinomial logistic Regression, truncated regression)
   Clustering techniques (e.g. -means clustering, hierarchical clustering, PCA)
   Adaptations, extensions, and combinations of the previously mentioned approaches The inventors surprisingly found out that the described approach yields in miRNA signatures that provide high diagnostic accuracy, specificity and sensitivity in the determination of diseases.

According to a preferred embodiment of the invention, the disease to be determined is prostate cancer.

The inventors succeeded in determining miRNAs that are differentially regulated in samples from prostate cancer patients as compared to healthy controls. A complete overview of all miRNAs that are found to be differentially regulated in blood samples of prostate cancer patients is provided in the tables shown in FIGS. 2 and 5.

In the tables shown in FIGS. 2 and 5, the miRNAs that are found to be differentially regulated are sorted in the order of their t-test significance. Another method for assessing the significance is to compute the Mutual information (MI) (Shannon, 1984) which is an adequate measure to estimate the overall diagnostic information content of single biomarkers (Keller, Ludwig et al., 2006). According to the invention mutual information is considered as the reduction in uncertainty about the class labels "0" for controls and "1" for tumour samples due to the knowledge of the miRNA expression. The higher the value of the MI of a miRNA, the higher is the diagnostic content of the respective miRNA.

Diagnosis of Prostate Cancer

According to a preferred embodiment of the invention, the disease to be determined is prostate cancer. Surprisingly, the inventors found out that miRNAs are differentially regulated in samples from prostate cancer patients as compared to healthy controls. A complete overview of all miRNAs that are found to be differentially regulated in blood samples of prostate cancer patients is provided in the table shown in FIG. 2 and FIG. 5. In FIG. 2 in total, 241 miRNAs were found to be significantly deregulated (t-test significance <0.05) in blood cells of prostate cancer patients as compared to the healthy controls.

Preferably, the predetermined set of miRNAs for the diagnosis of prostate cancer comprises one or more nucleic acids selected from the deregulated miRNAs presented in the tables in FIG. 2 or FIG. 5.

The predetermined set of miRNAs should preferably comprise at least 1, preferably at least 7, 10, 15, 20, 25, 30, 35, 40, 50, 75 or 100 of the indicated nucleic acids. It is particularly preferred to include the 100, 75, 50, 40, 35, 30, 25, 20, 15, 10 or at least 7 of the first mentioned miRNAs according to their order in the tables in FIG. 2 or FIG. 5.

Thus, preferably the predetermined set of miRNAs for the diagnosis of prostate cancer comprises one or more nucleic acids selected from the 241 most deregulated miRNAs.

Preferably, the predetermined set of miRNAs comprises at least 7, preferably at least 10, 15, 20, 25, 30, 35, 40, 50, 75, 100 or all of the above-indicated nucleic acids.

In a further embodiment the predetermined set of miRNAs for the diagnosis of prostate cancer comprises one or more miRNAs selected from the group consisting of hsa-miR-144*, hsa-miR-148a, hsa-miR-519b-5p, hsa-miR-1324, hsa-miR-137, hsa-miR-556-5p, hsa-miR-330-3p.

In a further embodiment the predetermined set of miRNAs for the diagnosis of prostate cancer comprises one or more miRNAs selected from the group consisting of hsa-miR-144*, hsa-miR-148a, hsa-miR-519b-5p, hsa-miR-1324, hsa-miR-137, hsa-miR-556-5p, hsa-miR-330-3p, hsa-miR-361-5p, hsa-miR-891 b, hsa-miR-767-5p.

In a further embodiment the predetermined set of miRNAs for the diagnosis of prostate cancer comprises one or more miRNAs selected from the group consisting of hsa-miR-144*, hsa-miR-148a, hsa-miR-519b-5p, hsa-miR-1324, hsa-miR-137, hsa-miR-556-5p, hsa-miR-330-3p, hsa-miR-361-5p, hsa-miR-891 b, hsa-miR-767-5p, hsa-miR-744*, hsa-miR-208b, hsa-miR-548p, hsa-miR-20a*, hsa-miR-195.

In a further embodiment the predetermined set of miRNAs for the diagnosis of prostate cancer comprises one or more miRNAs selected from the group consisting of hsa-miR-144*, hsa-miR-148a, hsa-miR-519b-5p, hsa-miR-1324, hsa-miR-137, hsa-miR-556-5p, hsa-miR-330-3p, hsa-miR-361-5p, hsa-miR-891 b, hsa-miR-767-5p, hsa-miR-744*, hsa-miR-208b, hsa-miR-548p, hsa-miR-20a*, hsa-miR-195, hsa-miR-33b, hsa-miR-1283, hsa-miR-519c-5p, hsa-miR-497, hsa-miR-9*.

In a further embodiment the predetermined set of miRNAs for the diagnosis of prostate cancer comprises one or more miRNAs selected from the group consisting of hsa-miR-144*, hsa-miR-148a, hsa-miR-519b-5p, hsa-miR-1324, hsa-miR-137, hsa-miR-556-5p, hsa-miR-330-3p, hsa-miR-361-5p, hsa-miR-891 b, hsa-miR-767-5p, hsa-miR-744*, hsa-miR-208b, hsa-miR-548p, hsa-miR-20a*, hsa-miR-195, hsa-miR-33b, hsa-miR-1283, hsa-miR-519c-5p, hsa-miR-497, hsa-miR-9*, hsa-miR-200a, hsa-miR-338-3p, hsa-miR-515-5p, hsa-miR-31*, hsa-miR-551 b*.

In a further embodiment the predetermined set of miR-NAs for the diagnosis of prostate cancer comprises one or more miRNAs selected from the group consisting of hsa-miR-144*, hsa-miR-148a, hsa-miR-519b-5p, hsa-miR-1324, hsa-miR-137, hsa-miR-556-5p, hsa-miR-330-3p, hsa-miR-361-5p, hsa-miR-891 b, hsa-miR-767-5p, hsa-miR-744*, hsa-miR-208b, hsa-miR-548p, hsa-miR-20a*, hsa-miR-195, hsa-miR-33b, hsa-miR-1283, hsa-miR-519c-5p, hsa-miR-497, hsa-miR-9*, hsa-miR-200a, hsa-miR-338-3p, hsa-miR-515-5p, hsa-miR-31*, hsa-miR-551b*, hsa-miR-518e*, hsa-miR-127-5p, hsa-miR-21*, hsa-miR-216a, hsa-miR-452*.

In a further embodiment the predetermined set of miR-NAs for the diagnosis of prostate cancer comprises one or more miRNAs selected from the group consisting of hsa-miR-144*, hsa-miR-148a, hsa-miR-519b-5p, hsa-miR-1324, hsa-miR-137, hsa-miR-556-5p, hsa-miR-330-3p, hsa-miR-361-5p, hsa-miR-891 b, hsa-miR-767-5p, hsa-miR-744*, hsa-miR-208b, hsa-miR-548p, hsa-miR-20a*, hsa-miR-195, hsa-miR-33b, hsa-miR-1283, hsa-miR-519c-5p, hsa-miR-497, hsa-miR-9*, hsa-miR-200a, hsa-miR-338-3p, hsa-miR-515-5p, hsa-miR-31*, hsa-miR-551b*, hsa-miR-518e*, hsa-nniR-127-5p, hsa-miR-21*, hsa-miR-216a, hsa-miR-452*, hsa-miR-183*, hsa-miR-500, hsa-miR-1826, hsa-miR-625*, hsa-miR-513b.

In a further embodiment the predetermined set of miR-NAs for the diagnosis of prostate cancer comprises one or more miRNAs selected from the group consisting of hsa-miR-144*, hsa-miR-148a, hsa-miR-519b-5p, hsa-miR-1324, hsa-miR-137, hsa-miR-556-5p, hsa-miR-330-3p, hsa-miR-361-5p, hsa-miR-891 b, hsa-miR-767-5p, hsa-miR-744*, hsa-miR-208b, hsa-miR-548p, hsa-miR-20a*, hsa-miR-195, hsa-miR-33b, hsa-miR-1283, hsa-miR-519c-5p, hsa-miR-497, hsa-miR-9*, hsa-miR-200a, hsa-miR-338-3p, hsa-miR-515-5p, hsa-miR-31*, hsa-miR-551b*, hsa-miR-518e*, hsa-miR-127-5p, hsa-miR-21*, hsa-miR-216a, hsa-miR-452*, hsa-miR-183*, hsa-miR-500, hsa-miR-1826, hsa-miR-625*, hsa-miR-513b, hsa-miR-526a, hsa-miR-33a, hsa-miR-1243, hsa-miR-517*, hsa-miR-541.

In a further embodiment the predetermined set of miR-NAs for the diagnosis of prostate cancer comprises one or more miRNAs selected from the group consisting of hsa-miR-144*, hsa-miR-148a, hsa-miR-519b-5p, hsa-miR-1324, hsa-miR-137, hsa-miR-556-5p, hsa-miR-330-3p, hsa-miR-361-5p, hsa-miR-891b, hsa-miR-767-5p, hsa-miR-744*, hsa-miR-208b, hsa-miR-548p, hsa-miR-20a*, hsa-miR-195, hsa-miR-33b, hsa-miR-1283, hsa-miR-519c-5p, hsa-miR-497, hsa-miR-9*, hsa-miR-200a, hsa-miR-338-3p, hsa-miR-515-5p, hsa-miR-31*, hsa-miR-551b*, hsa-miR-518e*, hsa-miR-127-5p, hsa-miR-21*, hsa-miR-216a, hsa-miR-452*, hsa-miR-183*, hsa-miR-500, hsa-miR-1826, hsa-miR-625*, hsa-miR-513b, hsa-miR-526a, hsa-miR-33a, hsa-miR-1243, hsa-miR-517*, hsa-miR-541, hsa-miR-217, hsa-miR-621, hsa-miR-518d-5p, hsa-miR-873, hsa-miR-103-as, hsa-miR-450b-5p, hsa-miR-545, hsa-miR-1251, hsa-miR-885-5p, hsa-miR-922.

In a further embodiment the predetermined set of miR-NAs for the diagnosis of prostate cancer comprises one or more miRNAs selected from the group consisting of hsa-miR-144*, hsa-miR-148a, hsa-miR-519b-5p, hsa-miR-1324, hsa-miR-137, hsa-miR-556-5p, hsa-miR-330-3p, hsa-miR-361-5p, hsa-miR-891b, hsa-miR-767-5p, hsa-miR-744*, hsa-miR-208b, hsa-miR-548p, hsa-miR-20a*, hsa-miR-195, hsa-miR-33b, hsa-miR-1283, hsa-miR-519c-5p, hsa-miR-497, hsa-miR-9*, hsa-miR-200a, hsa-miR-338-3p, hsa-miR-515-5p, hsa-miR-31*, hsa-miR-551b*, hsa-miR-518e*, hsa-miR-127-5p, hsa-miR-21*, hsa-miR-216a, hsa-miR-452*, hsa-miR-183*, hsa-miR-500, hsa-miR-1826, hsa-miR-625*, hsa-miR-513b, hsa-miR-526a, hsa-miR-33a, hsa-miR-1243, hsa-miR-517*, hsa-miR-541, hsa-miR-217, hsa-miR-621, hsa-miR-518d-5p, hsa-miR-873, hsa-miR-103-as, hsa-miR-450b-5p, hsa-miR-545, hsa-miR-1251, hsa-miR-885-5p, hsa-miR-922, hsa-miR-628-5p, hsa-miR-548f, hsa-miR-802, hsa-miR-25, hsa-miR-423-3p, hsa-miR-522*, hsa-miR-519a*, hsa-miR-455-3p, hsa-miR-1245, hsa-miR-362-5p, hsa-miR-1184, hsa-miR-191, hsa-miR-487a, hsa-miR-216b, hsa-miR-525-5p, hsa-miR-509-3-5p, hsa-miR-27a*, hsa-miR-488*, hsa-miR-1226, hsa-miR-646, hsa-miR-527, hsa-miR-635, hsa-miR-1825, hsa-let-7i*.

Most preferably, the predetermined set of miRNAs comprises those miRNAs that were most significantly deregulated.

Figure 4:
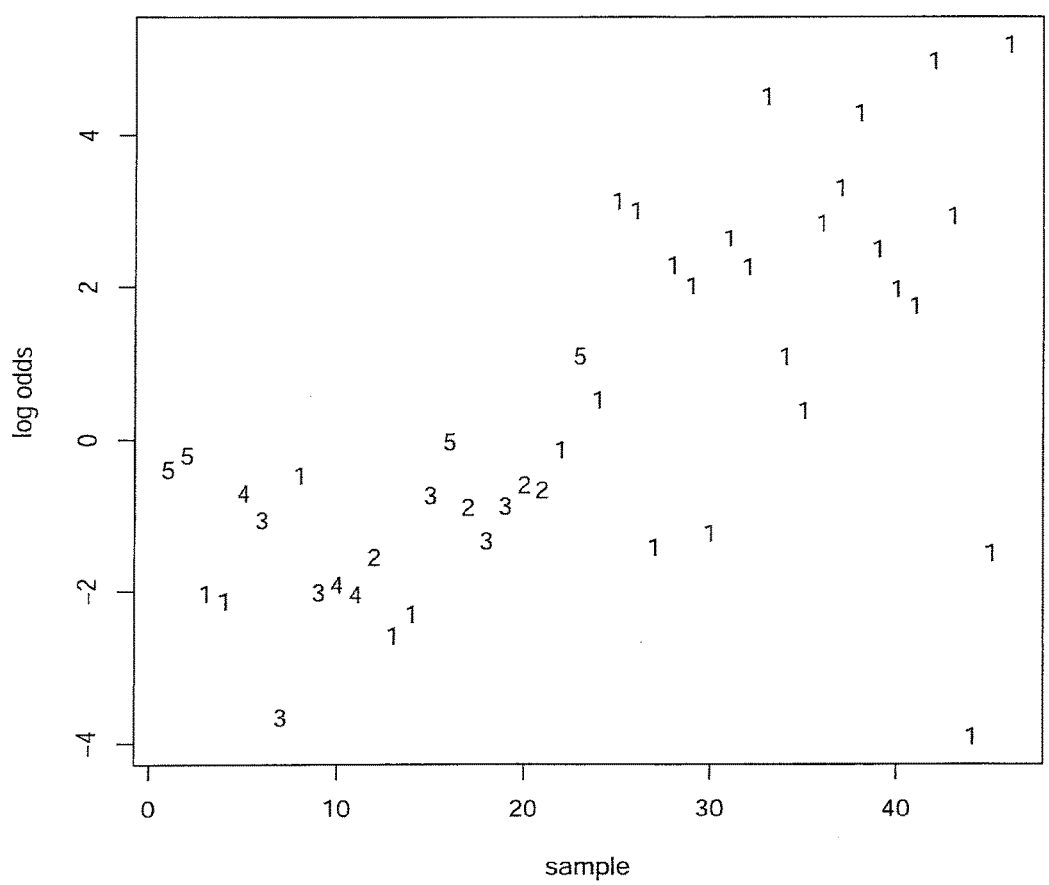

In a further embodiment, the measured miRNA profiles were classified using statistical learning approaches in order to compute accuracy, specificity, and sensitivity for the diagnosis of prostate cancer (see FIG. 4). The miRNAs that performed best for the diagnosis of prostate cancer according to their accuracy, specificity, and sensitivity are the 270 miRNAs shown in Table in FIG. 2 (entries No. 1-270) leading to an accuracy 82.8%, a specificity of 87.5% and a sensitivity of 71.9%.

The predetermined set of miRNAs for the diagnosis of prostate cancer should preferably comprise at least 7, preferably at least 10, 15, 20, 25, 30, 35, 40, 50, 75, 100, preferably all of the known miRNAs, preferably all of the 863 (see FIG. 1, representing the current status of all known miRNAs in the version 12, 13, and 14 of the miRBase repository (www.mirbase.org).

Another embodiment of the present invention is a kit for diagnosing a disease, comprising means for determining an expression profile of a predetermined set of miRNAs in a biological sample, in particular in a blood and/or serum sample. Preferably, one or more reference expression profiles are also provided which show the expression profile of the same set of miRNAs in the same type of biological sample, in particular in a blood and/or serum sample, obtained from one or more healthy subjects. A comparison to said reference expression profile(s) allows for the diagnosis of the disease.

Another preferred embodiment of the present invention is a kit for diagnosing prostate cancer, comprising means for determining the expression profile of one or more miRNAs presented in the table in FIG. 2, preferably one or more miRNAs selected from the group consisting of hsa-miR-144*, hsa-miR-148a, hsa-miR-519b-5p, hsa-miR-1324, hsa-miR-137, hsa-miR-556-5p, hsa-miR-330-3p, hsa-miR-361-5p, hsa-miR-891 b, hsa-miR-767-5p, hsa-miR-744*, hsa-miR-208b, hsa-miR-548p, hsa-miR-20a*, hsa-miR-195, hsa-miR-33b, hsa-miR-1283, hsa-miR-519c-5p, hsa-miR-497, hsa-miR-9*, hsa-miR-200a, hsa-miR-338-3p, hsa-miR-515-5p, hsa-miR-31*, hsa-miR-551 b*, hsa-miR-518e*, hsa-miR-127-5p, hsa-miR-21*, hsa-miR-216a, hsa-miR-452*, hsa-miR-183*, hsa-miR-500, hsa-miR-1826, hsa-miR-625*, hsa-miR-513b, hsa-miR-526a, hsa-miR-33a, hsa-miR-1243, hsa-miR-517*, hsa-miR-541, hsa-miR-217, hsa-miR-621, hsa-miR-518d-5p, hsa-miR-873, hsa-miR-103-as, hsa-miR-450b-5p, hsa-miR-545, hsa-miR-1251, hsa-miR-885-5p, hsa-miR-922.

In a preferred embodiment the kit comprises means for determining at least 7, preferably at least 10, 15, 20, 25, 30, 35, 40, 50, 75, 100 or all of the indicated miRNAs. It is particularly preferred to include means for determining the 100, 75, 50, 45, 40, 35, 30, 25, 20, 15, 10 or at least 7 first mentioned miRNAs in the order of their diagnostic significance as represented by their order in the table in FIG. 2. The kit for diagnosing prostate cancer is particularly suitable for diagnosing prostate cancer in a blood and/or serum sample or in a sample comprising erythrocytes, leukocytes and/or thrombocytes.

The means for determining a predetermined set of miRNAs may for example comprise a microarray comprising miRNA-specific oligonucleotide probes. In a preferred embodiment, the microarray comprises miRNA-specific oligonucleotide probes for the detection of miRNAs. Depending on the intended use of the microarray in the diagnosis or prognosis of a particular disease, probes for detecting different miRNAs may be included.

A microarray intended for use in the diagnosis of prostate cancer preferably comprises miRNA specific oligonucleotide probes for one or more miRNAs presented in the table in FIG. 2, preferably for one or more miRNAs selected from the group consisting of hsa-miR-144*, hsa-miR-148a, hsa-miR-519b-5p, hsa-miR-1324, hsa-miR-137, hsa-miR-556-5p, hsa-miR-330-3p, hsa-miR-361-5p, hsa-miR-891 b, hsa-miR-767-5p, hsa-miR-744*, hsa-miR-208b, hsa-miR-548p, hsa-miR-20a*, hsa-miR-195, hsa-miR-33b, hsa-miR-1283, hsa-miR-519c-5p, hsa-miR-497, hsa-miR-9*, hsa-miR-200a, hsa-miR-338-3p, hsa-miR-515-5p, hsa-miR-31*, hsa-miR-551 b*, hsa-miR-518e*, hsa-miR-127-5p, hsa-miR-21*, hsa-miR-216a, hsa-miR-452*, hsa-miR-183*, hsa-miR-500, hsa-miR-1826, hsa-miR-625*, hsa-miR-513b, hsa-miR-526a, hsa-miR-33a, hsa-miR-1243, hsa-miR-517*, hsa-miR-541, hsa-miR-217, hsa-miR-621, hsa-miR-518d-5p, hsa-miR-873, hsa-miR-103-as, hsa-miR-450b-5p, hsa-miR-545, hsa-miR-1251, hsa-miR-885-5p, hsa-miR-922.

In a preferred embodiment the microarray comprises oligonucleotide probes for determining at least 7, preferably at least 10, 15, 20, 25, 30, 35, 40, 50, 75, 100 or all of the indicated miRNAs. It is particularly preferred to include oligonucleotide probes for determining the most significant miRNAs, which is represented by their order in the table depicted in FIG. 2.

The microarray can comprise oligonucleotide probes obtained from known or predicted miRNA sequences. The array may contain different oligonucleotide probes for each miRNA, for example one containing the active mature sequence and another being specific for the precursor of the miRNA. The array may also contain controls such as one or more sequences differing from the human orthologs by only a few bases, which can serve as controls for hybridization stringency conditions. It is also possible to include viral miRNAs or putative miRNAs as predicted from bioinformatic tools. Further, it is possible to include appropriate controls for non-specific hybridization on the microarray.

In summary the present invention is composed of the following items:
1. A method of diagnosing a disease, comprising the steps
   (a) determining an expression profile of a predetermined set of non-coding RNAs, including miRNAs, in a biological sample from a patient; and
   (b) comparing said expression profile to a reference expression profile,
   wherein the comparison of said determined expression profile to said reference expression profile allows for the diagnosis of the disease, wherein the disease is prostate cancer.
2. The method according to any one of item 1, wherein the expression profile is determined of non-coding RNAs, including miRNAs selected from the group consisting of hsa-miR-99b*, hsa-miR-99b, hsa-miR-99a*, hsa-miR-99a, hsa-miR-98, hsa-miR-96*, hsa-miR-96, hsa-miR-95, hsa-miR-944, hsa-miR-943, hsa-miR-942, hsa-miR-941, hsa-miR-940; hsa-miR-939, hsa-miR-938, hsa-miR-937, hsa-miR-936, hsa-miR-935, hsa-miR-934, hsa-miR-933, hsa-miR-93*, hsa-miR-93, hsa-miR-92b*, hsa-miR-92b, hsa-miR-92a-2*, hsa-miR-92a-1*, hsa-miR-92a, hsa-miR-924, hsa-miR-922, hsa-miR-921, hsa-miR-920, hsa-miR-9*, hsa-miR-9, hsa-miR-892b, hsa-miR-892a, hsa-miR-891 b, hsa-miR-891a, hsa-miR-890, hsa-miR-889, hsa-miR-888*, hsa-miR-888, hsa-miR-887, hsa-miR-886-5p, hsa-miR-886-3p, hsa-miR-885-5p, hsa-miR-885-3p, hsa-miR-877*, hsa-miR-877, hsa-miR-876-5p, hsa-miR-876-3p, hsa-miR-875-5p, hsa-miR-875-3p, hsa-miR-874, hsa-miR-873, hsa-miR-802, hsa-miR-770-5p, hsa-miR-769-5p, hsa-miR-769-3p, hsa-miR-767-5p, hsa-miR-767-3p, hsa-miR-766, hsa-miR-765, hsa-miR-764, hsa-miR-762, hsa-miR-761, hsa-miR-760, hsa-miR-759, hsa-miR-758, hsa-miR-744*, hsa-miR-744, hsa-miR-720, hsa-miR-7-2*, hsa-miR-718, hsa-miR-711, hsa-miR-7-1*, hsa-miR-708*, hsa-miR-708, hsa-miR-7, hsa-miR-675*, hsa-miR-675, hsa-miR-671-5p, hsa-miR-671-3p, hsa-miR-670, hsa-miR-668, hsa-miR-665, hsa-miR-664*, hsa-miR-664, hsa-miR-663b, hsa-miR-663, hsa-miR-662, hsa-miR-661, hsa-miR-660, hsa-miR-659, hsa-miR-658, hsa-miR-657, hsa-miR-656, hsa-miR-655, hsa-miR-654-5p, hsa-miR-654-3p, hsa-miR-653, hsa-miR-652, hsa-miR-651, hsa-miR-650, hsa-miR-649, hsa-miR-648, hsa-miR-647, hsa-miR-646, hsa-miR-645, hsa-miR-644, hsa-miR-643, hsa-miR-642, hsa-miR-641, hsa-miR-640, hsa-miR-639, hsa-miR-638, hsa-miR-637, hsa-miR-636, hsa-miR-635, hsa-miR-634, hsa-miR-633, hsa-miR-632, hsa-miR-63.1, hsa-miR-630, hsa-miR-629*, hsa-miR-629, hsa-miR-628-5p, hsa-miR-628-3p, hsa-miR-627, hsa-miR-626, hsa-miR-625*, hsa-miR-625, hsa-miR-624*, hsa-miR-624, hsa-miR-623, hsa-miR-622, hsa-miR-621, hsa-miR-620, hsa-miR-619, hsa-miR-618, hsa-miR-617, hsa-miR-616*, hsa-miR-616, hsa-miR-615-5p, hsa-miR-615-3p, hsa-miR-614, hsa-miR-613, hsa-miR-612, hsa-miR-611, hsa-miR-610, hsa-miR-609, hsa-miR-608, hsa-miR-607, hsa-miR-606, hsa-miR-605, hsa-miR-604, hsa-miR-603, hsa-miR-602, hsa-miR-601, hsa-miR-600, hsa-miR-599, hsa-miR-598, hsa-miR-597, hsa-miR-596, hsa-miR-595, hsa-miR-593*, hsa-miR-593, hsa-miR-592, hsa-miR-591, hsa-miR-590-5p, hsa-miR-590-3p, hsa-miR-589*, hsa-miR-589, hsa-miR-588, hsa-miR-587, hsa-miR-586, hsa-miR-585, hsa-miR-584, hsa-miR-583, hsa-miR-582-5p, hsa-miR-582-3p, hsa-miR-581, hsa-miR-580, hsa-miR-579, hsa-miR-578, hsa-miR-577, hsa-miR-576-5p, hsa-miR-576-3p, hsa-miR-575, hsa-miR-574-5p, hsa-miR-574-3p, hsa-miR-573, hsa-miR-572, hsa-miR-571, hsa-miR-570, hsa-miR-569, hsa-miR-568, hsa-miR-567, hsa-miR-566, hsa-miR-564, hsa-miR-563, hsa-miR-562, hsa-miR-561, hsa-miR-559, hsa-miR-558, hsa-miR-557, hsa-miR-556-5p, hsa-miR-556-3p, hsa-miR-555, hsa-miR-554, hsa-miR-553, hsa-miR-552, hsa-miR-551b*, hsa-miR-551 b, hsa-miR-551a, hsa-miR-550*, hsa-miR-550, hsa-miR-549, hsa-miR-548q, hsa-miR-548p, hsa-miR-548o, hsa-miR-548n, hsa-miR-548m, hsa-miR-548l, hsa-miR-548k, hsa-miR-548j, hsa-miR-548i, hsa-miR-548h, hsa-miR-548g, hsa-miR-548f, hsa-miR-548e, hsa-miR-548d-5p, hsa-miR-548d-3p, hsa-miR-548c-5p, hsa-miR-548c-3p, hsa-miR-548b-5p, hsa-miR-548b-3p, hsa-miR-548a-5p, hsa-miR-548a-3p, hsa-miR-545*, hsa-miR-545, hsa-miR-544, hsa-miR-543, hsa-miR-542-5p, hsa-miR-542-3p, hsa-miR-541*, hsa-miR-541, hsa-miR-539, hsa-miR-532-5p, hsa-miR-532-

3p, hsa-miR-527, hsa-miR-526b*, hsa-miR-526b, hsa-miR-526a, hsa-miR-525-5p, hsa-miR-525-3p, hsa-miR-524-5p, hsa-miR-524-3p, hsa-miR-523*, hsa-miR-523, hsa-miR-522*, hsa-miR-522, hsa-miR-521, hsa-miR-520h, hsa-miR-520g, hsa-miR-520f, hsa-miR-520e, hsa-miR-520d-5p, hsa-miR-520d-3p, hsa-miR-520c-5p, hsa-miR-520c-3p, hsa-miR-520b, hsa-miR-520a-5p, hsa-miR-520a-3p, hsa-miR-519e*, hsa-miR-519e, hsa-miR-519d, hsa-miR-519c-5p, hsa-miR-519c-3p, hsa-miR-519b-5p, hsa-miR-519b-3p, hsa-miR-519a*, hsa-miR-519a, hsa-miR-518f*, hsa-miR-518f, hsa-miR-518e*, hsa-miR-518e, hsa-miR-518d-5p, hsa-miR-518d-3p, hsa-miR-518c*, hsa-miR-518c, hsa-miR-518b, hsa-miR-518a-5p, hsa-miR-518a-3p, hsa-miR-517c, hsa-miR-517b, hsa-miR-517a, hsa-miR-517*, hsa-miR-516b*, hsa-miR-516b, hsa-miR-516a-5p, hsa-miR-516a-3p, hsa-miR-515-5p, hsa-miR-515-3p, hsa-miR-514, hsa-miR-513c, hsa-miR-513b, hsa-miR-513a-5p, hsa-miR-513a-3p, hsa-miR-512-5p, hsa-miR-512-3p, hsa-miR-511, hsa-miR-510, hsa-miR-509-5p, hsa-miR-509-3p, hsa-miR-509-3-5p, hsa-miR-508-5p, hsa-nniR-508-3p, hsa-miR-507, hsa-miR-506, hsa-miR-505*, hsa-miR-505, hsa-miR-504, hsa-miR-503, hsa-miR-502-5p, hsa-miR-502-3p, hsa-miR-501-5p, hsa-miR-501-3p, hsa-miR-500*, hsa-miR-500, hsa-miR-499-5p, hsa-miR-499-3p, hsa-miR-498, hsa-miR-497*, hsa-miR-497, hsa-miR-496, hsa-miR-495, hsa-miR-494, hsa-miR-493*, hsa-miR-493, hsa-miR-492, hsa-miR-491-5p, hsa-miR-491-3p, hsa-miR-490-5p, hsa-miR-490-3p, hsa-miR-489, hsa-miR-488*, hsa-miR-488, hsa-miR-487b, hsa-miR-487a, hsa-miR-486-5p, hsa-miR-486-3p, hsa-miR-485-5p, hsa-miR-485-3p, hsa-miR-484, hsa-miR-483-5p, hsa-miR-483-3p, hsa-miR-455-5p, hsa-miR-455-3p, hsa-miR-454*, hsa-miR-454, hsa-miR-453, hsa-miR-452*, hsa-miR-452, hsa-miR-451, hsa-miR-450b-5p, hsa-miR-450b-3p, hsa-miR-450a, hsa-miR-449c*, hsa-miR-449c, hsa-miR-449b*, hsa-miR-449b, hsa-miR-449a, hsa-miR-448, hsa-miR-433, hsa-miR-432*, hsa-miR-432, hsa-miR-431*, hsa-miR-431, hsa-miR-429, hsa-miR-425*, hsa-miR-425, hsa-miR-424*, hsa-miR-424, hsa-miR-423-5p, hsa-miR-423-3p, hsa-miR-422a, hsa-miR-421, hsa-miR-412, hsa-miR-411*, hsa-miR-411, hsa-miR-410, hsa-miR-409-5p, hsa-miR-409-3p, hsa-miR-384, hsa-miR-383, hsa-miR-382, hsa-miR-381, hsa-miR-380*, hsa-miR-380, hsa-miR-379*, hsa-miR-379, hsa-miR-378*, hsa-miR-378, hsa-miR-377*, hsa-miR-377, hsa-miR-376c, hsa-miR-376b, hsa-miR-376a*, hsa-miR-376a, hsa-miR-375, hsa-miR-374b*, hsa-miR-374b, hsa-miR-374a*, hsa-miR-374a, hsa-miR-373*, hsa-miR-373, hsa-miR-372, hsa-nniR-371-5p, hsa-miR-371-3p, hsa-miR-370, hsa-miR-369-5p, hsa-miR-369-3p, hsa-miR-367*, hsa-miR-367, hsa-miR-365*, hsa-miR-365, hsa-miR-363*, hsa-miR-363, hsa-miR-362-5p, hsa-miR-362-3p, hsa-miR-361-5p, hsa-miR-361-3p, hsa-miR-34c-5p, hsa-miR-34c-3p, hsa-miR-34b*, hsa-miR-34b, hsa-miR-34a*, hsa-miR-34a, hsa-miR-346, hsa-miR-345, hsa-miR-342-5p, hsa-miR-342-3p, hsa-miR-340*, hsa-miR-340, hsa-miR-33b*, hsa-miR-33b, hsa-miR-33a*, hsa-miR-33a, hsa-miR-339-5p, hsa-miR-339-3p, hsa-miR-338-5p, hsa-miR-338-3p, hsa-miR-337-5p, hsa-miR-337-3p, hsa-miR-335*, hsa-miR-335, hsa-miR-331-5p, hsa-miR-331-3p, hsa-miR-330-5p, hsa-miR-330-3p, hsa-miR-329, hsa-miR-328, hsa-miR-326, hsa-miR-325, hsa-miR-324-5p, hsa-miR-324-3p, hsa-miR-323-5p, hsa-miR-323-3p, hsa-miR-320d, hsa-miR-320c, hsa-miR-320b, hsa-miR-320a, hsa-miR-32*, hsa-miR-32, hsa-miR-31*, hsa-miR-31, hsa-miR-30e*, hsa-miR-30e, hsa-miR-30d*, hsa-miR-30d, hsa-miR-30c-2*, hsa-miR-30c-1*, hsa-miR-30c, hsa-miR-30b*, hsa-miR-30b, hsa-miR-30a*, hsa-miR-30a, hsa-miR-302f, hsa-miR-302e, hsa-miR-302d*, hsa-miR-302d, hsa-miR-302c*, hsa-miR-302c, hsa-miR-302b*, hsa-miR-302b, hsa-miR-302a*, hsa-miR-302a, hsa-miR-301 b, hsa-miR-301a, hsa-miR-300, hsa-miR-29c*, hsa-miR-29c, hsa-miR-29b-2*, hsa-miR-29b-1*, hsa-miR-29b, hsa-miR-29a*, hsa-miR-29a, hsa-miR-299-5p, hsa-miR-299-3p, hsa-miR-298, hsa-miR-297, hsa-miR-296-5p, hsa-miR-296-3p, hsa-miR-28-5p, hsa-miR-28-3p, hsa-miR-27b*, hsa-miR-27b, hsa-miR-27a*, hsa-miR-27a, hsa-miR-26b*, hsa-miR-26b, hsa-miR-26a-2*, hsa-miR-26a-1*, hsa-miR-26a, hsa-miR-25*, hsa-miR-25, hsa-miR-24-2*, hsa-miR-24-1*, hsa-miR-24, hsa-miR-23b*, hsa-miR-23b, hsa-miR-23a*, hsa-miR-23a, hsa-miR-2278, hsa-miR-2277, hsa-miR-2276, hsa-miR-224*, hsa-miR-224, hsa-miR-223*, hsa-miR-223, hsa-miR-222*, hsa-miR-222, hsa-miR-221*, hsa-miR-221, hsa-miR-220c, hsa-miR-220b, hsa-miR-220a, hsa-miR-22*, hsa-miR-22, hsa-miR-219-5p, hsa-miR-219-2-3p, hsa-miR-219-1-3p, hsa-miR-218-2*, hsa-miR-218-1*, hsa-miR-218, hsa-miR-217, hsa-miR-216b, hsa-miR-216a, hsa-miR-215, hsa-miR-214*, hsa-miR-214, hsa-miR-212, hsa-miR-2117, hsa-miR-2116*, hsa-miR-2116, hsa-nniR-2115*, hsa-miR-2115, hsa-miR-2114*, hsa-miR-2114, hsa-miR-2113, hsa-miR-2110, hsa-miR-211, hsa-miR-210, hsa-miR-21*, hsa-miR-21, hsa-miR-20b*, hsa-miR-20b, hsa-miR-20a*, hsa-miR-20a, hsa-miR-208b, hsa-miR-208a, hsa-miR-206, hsa-miR-2054, hsa-miR-2053, hsa-miR-2052, hsa-miR-205*, hsa-miR-205, hsa-miR-204, hsa-miR-203, hsa-miR-202*, hsa-miR-202, hsa-miR-200c*, hsa-miR-200c, hsa-miR-200b*, hsa-miR-200b, hsa-miR-200a*, hsa-miR-200a, hsa-miR-19b-2*, hsa-miR-19b-1*, hsa-miR-19b, hsa-miR-19a*, hsa-miR-19a, hsa-miR-199b-5p, hsa-miR-199b-3p, hsa-miR-199a-5p, hsa-miR-199a-3p, hsa-miR-198, hsa-miR-1979, hsa-miR-1978, hsa-miR-1977, hsa-miR-1976, hsa-miR-1975, hsa-miR-1974, hsa-miR-1973, hsa-miR-1972, hsa-miR-197, hsa-miR-196b*, hsa-miR-196b, hsa-miR-196a*, hsa-miR-196a, hsa-miR-195*, hsa-miR-195, hsa-miR-194*, hsa-miR-194, hsa-miR-193b*, hsa-miR-193b, hsa-miR-193a-5p, hsa-miR-193a-3p, hsa-miR-192*, hsa-miR-192, hsa-miR-1915*, hsa-miR-1915, hsa-miR-1914*, hsa-miR-1914, hsa-miR-1913, hsa-miR-1912, hsa-miR-1911*, hsa-miR-1911, hsa-miR-1910, hsa-miR-191*, hsa-miR-191, hsa-miR-190b, hsa-miR-1909*, hsa-miR-1909, hsa-miR-1908, hsa-miR-190, hsa-miR-18b*, hsa-miR-18b, hsa-miR-18a*, hsa-miR-18a, hsa-miR-188-5p, hsa-miR-188-3p, hsa-miR-187*, hsa-miR-187, hsa-miR-186*, hsa-miR-186, hsa-miR-185*, hsa-miR-185, hsa-miR-184, hsa-miR-183*, hsa-miR-183, hsa-miR-1827, hsa-miR-1826, hsa-miR-1825, hsa-miR-182*, hsa-miR-182, hsa-miR-181d, hsa-miR-181e, hsa-miR-181c, hsa-miR-181b, hsa-miR-181a-2*, hsa-miR-181a*, hsa-nniR-181a, hsa-miR-17*, hsa-miR-17, hsa-miR-16-2*, hsa-miR-16-1*, hsa-miR-16, hsa-miR-15b*, hsa-miR-15b, hsa-miR-15a*, hsa-miR-15a, hsa-miR-155*, hsa-miR-155, hsa-miR-154*, hsa-miR-154, hsa-miR-1539, hsa-miR-1538, hsa-miR-1537, hsa-miR-153, hsa-miR-152, hsa-miR-151-5p, hsa-miR-151-3p, hsa-miR-150*, hsa-miR-150, hsa-miR-149*, hsa-nniR-149, hsa-miR-148b*, hsa-miR-148b, hsa-miR-148a*, hsa-miR-148a, hsa-miR-147b, hsa-miR-1471, hsa-miR-1470, hsa-miR-147, hsa-miR-146b-5p, hsa-miR-146b-3p, hsa-miR-146*, hsa-miR-146a, hsa-miR-1469, hsa-miR-1468, hsa-miR-145*, hsa-miR-145, hsa-miR-144*, hsa-miR-144, hsa-miR-143*, hsa-miR- 143, hsa-miR-142-5p, hsa-miR-142-3p, hsa-miR-141*, hsa-miR-141, hsa-miR-140-5p, hsa-miR-140-3p, hsa-miR-139-5p, hsa-miR-139-3p, hsa-miR-138-2*, hsa-miR-138-1*, hsa-miR-138, hsa-miR-137, hsa-miR-136*, hsa-miR-136, hsa-miR-135b*, hsa-miR-135b, hsa-miR-135a*, hsa-miR-135a, hsa-miR-134, hsa-miR-133b, hsa-miR-133a, hsa-miR-1324, hsa-miR-1323, hsa-miR-1322, hsa-miR-1321, hsa-miR-132*, hsa-miR-132, hsa-miR-130b*, hsa-miR-130b, hsa-miR-130a*, hsa-miR-130a, hsa-miR-1308, hsa-miR-1307, hsa-miR-1306, hsa-miR-1305, hsa-miR-1304, hsa-miR-1303, hsa-miR-1302, hsa-miR-1301, hsa-miR-1299, hsa-miR-1298, hsa-miR-1297, hsa-miR-1296, hsa-miR-129-5p, hsa-miR-1295, hsa-miR-1294, hsa-miR-129-3p, hsa-miR-1293, hsa-miR-1292, hsa-miR-1291, hsa-miR-1290, hsa-miR-129*, hsa-miR-1289, hsa-miR-1288, hsa-miR-1287, hsa-miR-1286, hsa-miR-1285, hsa-miR-1284, hsa-miR-1283, hsa-miR-1282, hsa-miR-1281, hsa-miR-1280, hsa-miR-128, hsa-miR-1279, hsa-miR-1278, hsa-miR-1277, hsa-miR-1276, hsa-miR-127-5p, hsa-miR-1275, hsa-miR-1274b, hsa-miR-1274a, hsa-miR-127-3p, hsa-miR-1273, hsa-miR-1272, hsa-miR-1271, hsa-miR-1270, hsa-miR-1269, hsa-miR-1268, hsa-miR-1267, hsa-miR-1266, hsa-miR-1265, hsa-miR-1264, hsa-miR-1263, hsa-miR-1262, hsa-miR-1261, hsa-miR-1260, hsa-miR-126*, hsa-miR-126, hsa-miR-125b-2*, hsa-miR-125b-1*, hsa-miR-125b, hsa-miR-125a-5p, hsa-miR-125a-3p, hsa-miR-1259, hsa-miR-1258, hsa-miR-1257, hsa-miR-1256, hsa-miR-1255b, hsa-miR-1255a, hsa-miR-1254, hsa-miR-1253, hsa-miR-1252, hsa-miR-1251, hsa-miR-1250, hsa-miR-1249, hsa-miR-1248, hsa-miR-1247, hsa-miR-1246, hsa-miR-1245, hsa-miR-1244, hsa-miR-1243, hsa-miR-124*, hsa-miR-124, hsa-miR-1238, hsa-miR-1237, hsa-miR-1236, hsa-miR-1234, hsa-miR-1233, hsa-miR-1231, hsa-miR-1229, hsa-miR-1228*, hsa-miR-1228, hsa-miR-1227, hsa-miR-1226*, hsa-miR-1226, hsa-miR-1225-5p, hsa-miR-1225-3p, hsa-miR-1224-5p, hsa-miR-1224-3p, hsa-miR-122*, hsa-miR-122, hsa-miR-1208, hsa-miR-1207-5p, hsa-miR-1207-3p, hsa-miR-1206, hsa-miR-1205, hsa-miR-1204, hsa-miR-1203, hsa-miR-1202, hsa-miR-1201, hsa-miR-1200, hsa-miR-1197, hsa-miR-1185, hsa-miR-1184, hsa-miR-1183, hsa-miR-1182, hsa-miR-1181, hsa-miR-1180, hsa-miR-1179, hsa-miR-1178, hsa-miR-10b*, hsa-miR-10b, hsa-miR-10a*, hsa-miR-a, hsa-miR-107, hsa-miR-106b*, hsa-miR-106b, hsa-miR-106a*, hsa-miR-106a, hsa-miR-105*, hsa-miR-105, hsa-miR-103-as, hsa-miR-103-2*, hsa-miR-103, hsa-miR-101*, hsa-miR-101, hsa-miR-100*, hsa-miR-100, hsa-miR-1, hsa-let-7i*, hsa-let-7i, hsa-let-7g*, hsa-let-7g, hsa-let-7f-2*, hsa-let-7f-1*, hsa-let-7f, hsa-let-7e*, hsa-let-7e, hsa-let-7d*, hsa-let-7d, hsa-let-7c*, hsa-let-7c, hsa-let-7b*, hsa-let-7b, hsa-let-7a-2*, hsa-let-7a*, hsa-let-7a, hsa-life-1, hsa-life-2, hsa-life-2-AS, hsa-life-3, hsa-life-4, hsa-life-6-5p, hsa-life-6-3p, hsa-life-7-AS, hsa-life-7, hsa-life-9, hsa-life-9-AS, hsa-life-11, hsa-life-12-5p, hsa-life-12-3p, hsa-life-13-3p, hsa-life-13-5p, hsa-life-14-3p, hsa-life-14-5p, hsa-life-17, hsa-life-21, hsa-life-22, hsa-life-26-3p, hsa-life-26-5p, hsa-life-27, hsa-life-31-5p, hsa-life-31-3p, hsa-life-33-AS, hsa-life-33, hsa-life-36-3p, hsa-life-36-5p, hsa-life-37-3p, hsa-life-37-5p, hsa-life-5-5p, hsa-life-5-3p, hsa-life-8, hsa-life-10, hsa-life-15-3p, hsa-life-15-5p, hsa-life-16-5p, hsa-life-16-3p, hsa-life-18, hsa-life-19-5p, hsa-life-19-3p, hsa-life-20-3p, hsa-life-20-5p, hsa-life-23-3p, hsa-life-23-5p, hsa-life-24, hsa-life-25, hsa-life-28-3p, hsa-life-28-5p, hsa-life-29, hsa-life-30, hsa-life-32-AS, hsa-life-32, hsa-life-34-3p, hsa-life-34-5p, hsa-life-35.

3. The method according to item 1 or 2, wherein the predetermined set of non-coding RNAs, including miRNAs representative for diagnosis of prostate cancer comprises at least 1, 7, 10, 15, 20, 25, 30, 35, 40, 50, 75, 100 of non-coding RNAs including miRNAs.

4. The method according to item 1, 2 or 3, wherein the predetermined set of miRNAs representative for diagnosis of prostate cancer comprises at least 1, 7, 10, 15, 20, 25, 30, 35, 40, 50, 75, 100 of the miRNAs selected from the group consisting of hsa-miR-144*, hsa-miR-148a, hsa-miR-519b-5p, hsa-miR-1324, hsa-miR-137, hsa-miR-556-5p, hsa-miR-330-3p, hsa-miR-361-5p, hsa-miR-891 b, hsa-miR-767-5p, hsa-miR-744*, hsa-miR-208b, hsa-miR-548p, hsa-miR-20a*, hsa-miR-195, hsa-miR-33b, hsa-miR-1283, hsa-miR-519c-5p, hsa-miR-497, hsa-miR-9*, hsa-miR-200a, hsa-miR-338-3p, hsa-miR-515-5p, hsa-miR-31*, hsa-miR-551b*, hsa-miR-518e*, hsa-miR-127-5p, hsa-miR-21*, hsa-miR-216a, hsa-miR-452*, hsa-miR-183*, hsa-miR-500, hsa-miR-1826, hsa-miR-625*, hsa-miR-513b, hsa-miR-526a, hsa-miR-33a, hsa-miR-1243, hsa-miR-517*, hsa-miR-541, hsa-miR-217, hsa-miR-621, hsa-miR-518d-5p, hsa-miR-873, hsa-miR-103-as, hsa-miR-450b-5p, hsa-miR-545, hsa-miR-1251, hsa-miR-885-5p, hsa-miR-922, hsa-miR-628-5p, hsa-miR-548f, hsa-miR-802, hsa-miR-25, hsa-miR-423-3p, hsa-miR-522*, hsa-miR-519e, hsa-miR-455-3p, hsa-miR-1245, hsa-miR-362-5p, hsa-miR-1184, hsa-miR-191, hsa-miR-487a, hsa-miR-216b, hsa-miR-525-5p, hsa-miR-509-3-5p, hsa-miR-27a*, hsa-miR-488*, hsa-miR-1226, hsa-miR-646, hsa-miR-527, hsa-miR-635, hsa-miR-1825, hsa-let-7i*.

5. The method according to any one of items 1-4 wherein said biological sample is selected from blood and/or serum or urine samples.

6. The method according to any one of items 1-5 wherein miRNA the expression profile is determined by nucleic acid hybridization, nucleic acid amplification, polymerase extension, sequencing, mass spectroscopy or any combinations thereof.

7. The method according to any one of items 1-6, wherein the miRNA expression profile of said subject and the reference expression profiles and optionally the predetermined set of miRNAs are stored in a database.

8. The method according to any one of items 1-7, wherein the biological sample is not labeled prior to determination of the expression profile.

9. The method according to any one of items 1-8 wherein the diagnosis comprises determining survival rate, responsiveness to drugs, and/or monitoring the course of the disease or the therapy, e.g. chemotherapy.

10. The method of item 6 wherein the nucleic acid hybridisation is performed using a solid-phase nucleic acid biochip array, in particular a microarray or in situ hybridisation, and/or wherein the nucleic acid amplification is performed via a real-time PCR (RT-PCR).

11. A kit for diagnosing and/or predicting prostate cancer of a subject, comprising:
    (a) means for determining the miRNA expression profile of a RNA sample of a subject, and
    (b) at least one reference set of miRNA profile characteristic for a particular condition.

So far, miRNAs have been extensively studied in tissue material. It has been found that miRNAs are expressed in a highly tissue-specific manner. Disease-specific expression of miRNAs have been reported in many human cancers employing primarily tissue material as the miRNA source. In this context miRNAs expression profiles were found to be useful in identifying the tissue of origin for cancers of unknown primary origin. Since recently it is known that miRNAs are not only present in tissues but also in other body fluid samples, including human blood. Nevertheless, the mechanism why miRNAs are found in body fluids, especially in blood, or their function in these body fluids is not understood yet.

Various miRNA biomarkers found in tissue material have been proposed to be correlated with certain diseases, e.g. cancer. However, there is still a need for novel miRNAs as biomarkers for the detection and/or prediction of these and other types of diseases. Especially desirable are non-invasive biomarkers, that allow for quick, easy and cost-effective diagnosis/prognosis which cause only minimal stress for the patient eliminating the need for surgical intervention.

Particularly, the potential role of miRNAs as non-invasive biomarkers for the diagnosis and/or prognosis of prostate cancer has not been systematically evaluated yet. In addition, many of the miRNA biomarkers presently available for diagnosing and/or prognosing of diseases have shortcomings such as reduced sensitivity, not sufficient specificity or do not allow timely diagnosis or represent invasive biomarkers. Accordingly, there is still a need for novel and efficient miRNAs or sets of miRNAs as markers, effective methods and kits for the non-invasive diagnosis and/or prognosis of diseases such as prostate cancer.

The inventors of the present invention assessed for the first time the expression of miRNAs on a whole-genome level in subjects with prostate cancer as non-invasive biomarkers from body fluids, preferably in blood. They surprisingly found that miRNAs are significantly dysregulated in blood of prostate cancer subjects in comparison to healthy controls and thus, miRNAs are appropriated non-invasive biomarkers for diagnosing and/or prognosing of prostate cancer. This finding is surprising, since there is nearly no overlap of the miRNA biomarkers found in blood and the miRNA biomarkers found in tissue material representing the origin of the disease. The inventors of the present invention surprisingly found miRNA biomarkers in body fluids, especially in blood, that have not been found to be correlated to prostate cancer when tissues material was used for this kind of analysis. Therefore, the inventors of the invention identified for the first time miRNAs as non-invasive surrogate biomarkers for diagnosis and/or prognosis of prostate cancer. The inventors of the present invention identified single miRNAs which predict prostate cancer with high specificity, sensitivity and accuracy. The inventors of the present invention also pursued a multiple biomarker strategy, thus implementing sets of miRNA biomarkers for diagnosing and/or prognosing of prostate cancer leading to added specificity, sensitivity, accuracy and predictive power, thereby circumventing the limitations of single biomarker. In detail, by using a machine learning algorithms, they identified unique sets of miRNAs (miRNA signatures) that allow for non-invasive diagnosis of prostate cancer with even higher power, indicating that sets of miRNAs (miRNA signatures) derived from a body fluid sample, such as blood from a subject (e.g. human) can be used as novel non-invasive biomarkers.

The inventors of the present invention surprisingly found that miRNAs are significantly dysregulated in body fluid samples such as blood of prostate cancer subjects in comparison to a cohort of controls (healthy subjects) and thus, miRNAs are appropriated biomarkers for diagnosing and/or prognosing of prostate cancer in a non-invasive fashion. Furthermore, the predetermined sets of miRNAs of the present invention lead to high performance in diagnosing and/or prognosing of prostate cancer, thus expose very high specificity, sensitivity and accuracy. They succeeded in determining the miRNAs that are differentially regulated in body fluid samples from patients having prostate cancer compared to a cohort of controls (healthy subjects) (see experimental section for experimental details). Additionally, the inventors of the present invention performed hypothesis tests (e.g. t-test, limma-test) or other measurements (e.g. AUC, mutual information) on the expression level of the found miRNAs, in all controls (healthy subjects) and subjects suffering from prostate cancer.

These tests resulted in a significance value (p-value) for each miRNA. This p-value is a measure for the diagnostic power of each of these single miRNAs to discriminate, for example, between the two clinical conditions: controls (healthy subjects), i.e. not suffering from prostate cancer, or diseased, i.e. suffering from prostate cancer. Since a manifold of tests are carried out, one for each miRNA, the p-values may be too optimistic and, thus, over-estimate the actual discriminatory power. Hence, the p-values are corrected for multiple testing by the Benjamini Hochberg approach.

The term "body fluid sample", as used in the context of the present invention, refers to liquids originating from the body of a subject. Said body fluid samples include, but are not limited to, blood, urine, sputum, breast milk, cerebrospinal fluid, cerumen (earwax), endolymph, perilymph, gastric juice, mucus, peritoneal fluid, pleural fluid, saliva, sebum (skin oil), semen, sweat, tears, vaginal secretion, vomit including components or fractions thereof. Said body fluid samples may be mixed or pooled, e.g. a body fluid sample may be a mixture of blood and urine samples or blood and tissue material. A "body fluid sample" may be provided by removing a body liquid from a subject, but may also be provided by using previously isolated sample material. Preferably, the body fluid sample from a subject (e.g. human or animal) has a volume of between 0.1 and 20 ml, more preferably of between 0.5 and 10 ml, more preferably between 1 and 8 ml and most preferably between 2 and 5 ml, i.e. 0.1, 0.2, 0.3, 0.4, 0.5, 0.6, 0.7, 0.8, 0.9, 1, 2, 2.5, 3, 4, 5, 6, 7, 8, 9, 10, 11, 12, 13, 14, 15, 16, 17, 18, 19, or 20 ml. In the context of the present invention said "body fluid sample" allows for a non-invasive diagnosis/and or prognosis of a subject.

The term "blood sample", as used in the context of the present invention, refers to a blood sample originating from a subject. The "blood sample" may be derived by removing blood from a subject by conventional blood collecting techniques, but may also be provided by using previously isolated and/or stored blood samples. For example a blood sample may be whole blood, plasma, serum, PBMC (peripheral blood mononuclear cells), blood cellular fractions including red blood cells (erythrocytes), white blood cells (leukocytes), platelets (thrombocytes), or blood collected in blood collection tubes (e.g. EDTA-, heparin-, citrate-, PAXgene-, Tempus-tubes) including components or fractions thereof. For example, a blood sample may be taken from a subject suspected to be affected or to be suspected to be affected by prostate cancer, prior to initiation of a therapeutic treatment, during the therapeutic treatment and/or after the therapeutic treatment. Preferably, the blood sample from a subject (e.g. human or animal) has a volume of between 0.1 and 20 ml, more preferably of between 0.5 and 10 ml, more preferably between 1 and 8 ml and most preferably between 2 and 5 ml, i.e. 0.1, 0.2, 0.3, 0.4, 0.5, 0.6, 0.7, 0.8, 0.9, 1, 2, 2.5, 3, 4, 5, 6, 7, 8, 9, 10, 11, 12, 13, 14, 15, 16, 17, 18, 19, or 20 ml. In the context of the present invention said "body fluid sample" allows for a non-invasive diagnosis/and or prognosis of a subject.

Preferably, when the blood sample is collected from the subject the RNA-fraction, especially the the miRNA fraction, is guarded against degradation. For this purpose special collection tubes (e.g. PAXgene RNA tubes from Preanalytix, Tempus Blood RNA tubes from Applied Biosystems) or additives (e.g. RNAlater from Ambion, RNAsin from Promega) that stabilize the RNA fraction and/or the miRNA fraction are employed.

The biological sample, preferably the body fluid sample may be from a subject (e.g. human or mammal) that has been therapeutically treated or that has not been therapeutically treated. In one embodiment, the therapeutical treatment is monitored on the basis of the detection of the miRNA or set of miRNAs by the polynucleotide or set of polynucleotides of the invention. It is also preferred that total RNA or a subfraction thereof, isolated (e.g. extracted) from a biological sample of a subject (e.g. human or animal), is used for detecting the miRNA or set of miRNAs by the polynucleotide or set of polynucleotides or primer pairs of the invention.

The term "non-invasive", as used in the context of the present invention, refers to methods for obtaining a biological sample, particularly a body fluid sample, without the need for an invasive surgical intervention or invasive medical procedure. In the context of the present invention, a blood drawn represents a non-invasive procedure, therefore a blood-based test (utilizing blood or fractions thereof) is a non-invasive test. Other body fluid samples for non-invasive tests are e.g. urine, sputum, tears, mothers mild, cerumen, sweat, saliva, vaginal secretion, vomit, etc.

The term "diagnosis" as used in the context of the present invention refers to the process of determining a possible disease or disorder and therefore is a process attempting to define the (clinical) condition of a subject. The determination of the expression level of a set of miRNAs according to the present invention correlates with the (clinical) condition of a subject. Preferably, the diagnosis comprises (i) determining the occurrence/presence of prostate cancer, (ii) monitoring the course of prostate cancer, (iii) staging of prostate cancer, (iv) measuring the response of a patient with prostate cancer to therapeutic intervention, and/or (v) segmentation of a subject suffering from prostate cancer.

The term "prognosis" as used in the context of the present invention refers to describing the likelihood of the outcome or course of a disease or a disorder. Preferably, the prognosis comprises (i) identifying of a subject who has a risk to develop prostate cancer, (ii) predicting/estimating the occurrence, preferably the severity of occurrence of prostate cancer, and/or (iii) predicting the response of a subject with prostate cancer to therapeutic intervention.

The term "suffering or suspected to be suffering from prostate cancer" as used in the context of the present invention comprises the diagnosis and/or prognosis of prostate cancer in a suspect as defined above.

In a first aspect, the present invention relates to a method for diagnosing and/or prognosing of prostate cancer comprising the steps of:
(i) determining an expression profile of a predetermined set comprising at least two miRNAs representative for prostate cancer in a body fluid sample from a subject, and
(ii) comparing said expression profile to a reference expression profile, wherein the comparison of said expression profile to said reference expression profile allows for the diagnosis and/or prognosis of prostate cancer.

It is preferred that the body fluid sample is a blood sample, particularly preferred it is a whole blood, PBMC, serum or plasma sample, more particularly preferred it is a whole blood sample.

It is preferred that the subject is a mammal including both a human and another mammal, e.g. an animal such as a mouse, a rat, a rabbit, or a monkey. It is particularly preferred that the subject is a human.

Preferably, the predetermined set comprising at least two miRNAs is selected from the set of miRNAs listed in FIG. 2 or 5.

It is preferred that the predetermined set comprising at least two miRNAs is selected from the sets of miRNAs listed in FIG. 6 (SNP-1 to SNP-911). It is also preferred that the predetermined set comprising at least two miRNAs comprises at least one set of miRNAs listed in FIG. 6.

Further, in a preferred embodiment of the method of the present invention, for determining an expression profile of the predetermined set comprising at least two miRNAs representative for prostate cancer in a body fluid sample from a subject comprises the miRNAs from one set or a plurality of sets of miRNAs listed in FIG. 6.

For example, a set comprising 30 miRNAs representative for prostate cancer in a body fluid sample from a subject comprises at least the miRNAs from one predetermined set or several sets of miRNAs listed in FIG. 6. Alternatively, a set comprising 29, 28, 27, 26, 25, 24, 23, 22, 21, 20, 19, 18, 17, 16, 15, 14, 13, 12, 11, 10, 9, 8, 7, 6, 5, 4 or 3 miRNAs representative for prostate cancer comprises at least the miRNAs from one set or several sets of miRNAs listed in FIG. 6.

Further, in another preferred embodiment of the method of the present invention, for determining an expression profile of the predetermined set comprising at least two miRNAs representative for prostate cancer in a body fluid sample from a subject comprises combinations of sets of miRNAs listed in FIG. 6.

For example, said predetermined set comprising 30 miRNAs representative for prostate cancer in a body fluid sample from a subject comprises at least 2, e.g. 2, 3, 4, 5 or 6, sets of miRNAs listed in FIG. 6. Alternatively, said set comprising 29, 28, 27, 26, 25, 24, 23, 22, 21, 20, 19, 18, 17, 16, 15, 14, 13, 12, 11, 10, 9, 8, 7, 6, 5 or 4 miRNAs comprises a least 2, e.g. 2, 3, 4, 5 or 6, sets of miRNAs listed in FIG. 6.

The reference expression profile may be obtained from at least two subjects (e.g. human or animal). Preferably the reference expression profile is an average expression profile (data) of at least 2 to 400 subjects, more preferably at least 20 to 200 subjects, and most preferably at least 40 to 150 subjects, with one known clinical condition which is prostate cancer or a specific form of prostate cancer.

It is particularly preferred that the reference expression profile is an algorithm or mathematical function. Preferably the algorithm or mathematical function is obtained from a reference expression profile (data) of at least two subjects, preferably the algorithm or mathematical function is obtained from an average reference expression profile (data) of at least 2 to 400 subjects, more preferably of at least 20 to 200 subjects, and most preferably of at least 40 to 150 subjects.

It is preferred that the algorithm or mathematical function is obtained using a machine learning approach.

Preferably, the algorithm or mathematical function is saved on a data carrier comprised in the kit (according to the seventh aspect of the invention) or the computer program, wherein the algorithm or mathematical function is comprised, is saved on a data carrier comprised in the kit.

It is preferred that the miRNA expression profile may be generated by any convenient means, e.g. nucleic acid hybridization (e.g. to a microarray), nucleic acid amplification (PCR, RT-PCR, qRT-PCR, high-throughput RT-PCR), ELISA for quantitation, next generation sequencing (e.g. ABI SOLID, Illumina Genome Analyzer, Roche/454 GS FLX), flow cytometry (e.g. LUMINEX) and the like, that allow the analysis of differential miRNA expression levels between samples of a subject (e.g. diseased) and a control subject (e.g. healthy, reference sample).

Nucleic acid hybridization may be performed using a microarray/biochip or in situ hybridization. In situ hybridization is preferred for the analysis of a single miRNA or a set comprising a low number of miRNAs (e.g. a set of at least 2 to 50 miRNAs such as a set of 2, 5, 10, 20, 30, or 40 miRNAs). The microarray/biochip, however, allows the analysis of a single miRNA as well as a complex set of miRNAs (e.g. a all known miRNAs or subsets thereof).

Nucleic acid amplification may be performed using real time polymerase chain reaction (RT-PCR) such as real time quantitative polymerase chain reaction (RT qPCR). The standard real time polymerase chain reaction (RT-PCR) is preferred for the analysis of a single miRNA or a set comprising a low number of miRNAs (e.g. a set of at least 2 to 50 miRNAs such as a set of 2, 5, 10, 20, 30, or 40 miRNAs), whereas high-throughput RT-PCR technologies (e.g. OpenArray from Applied Biosystems, SmartPCR from Wafergen, Biomark System from Fluidigm) are also able to measure large sets of miRNAS (e.g a set of 10, 20, 30, 50, 80, 100, 200 or more) or all known miRNAs in a high parallel fashion. RT-PCR is particularly suitable for detecting low abandoned miRNAs.

In a second aspect, the invention relates to a set comprising polynucleotides for detecting a predetermined set comprising at least two miRNAs for diagnosing and/or prognosing of prostate cancer in a body fluid sample from a subject.

It is preferred that the body fluid sample is a blood sample, particularly preferred it is a whole blood, PBMC, serum or plasma sample, more particularly preferred it is a whole blood sample.

It is preferred that the subject is a mammal including both a human and another mammal, e.g. an animal such as a mouse, a rat, a rabbit, or a monkey. It is particularly preferred that the subject is a human.

Preferably, the predetermined set comprising at least two miRNAs is selected from the set of miRNAs listed in FIG. 2 or 5.

It is preferred that the predetermined set comprising at least two miRNAs is selected from the set of miRNAs listed in FIG. 6. It is preferred that the predetermined set comprising at least two miRNAs comprises at least one set of miRNAs listed in FIG. 6.

It is preferred that the polynucleotides comprised in the set of the present invention are complementary to the miRNAs comprised in the predetermined set, wherein the nucleotide sequences of said miRNAs are preferably selected from the group consisting of miRNAs listed in FIG. 2 or 5 or set of miRNAs listed in FIG. 6, a fragment thereof, and a sequence having at least 80%, 85%, 90% or 95% sequence identity thereto.

For example, the polynucleotides of the present invention are for detecting a predetermined set of 40 or 39 or 38 or 37 or 36 or 35 or 34 or 33 or 32 or 31 or 30 or 29 or 28 or 27 or 26 or 25 or 24 or 23 or 22 or 21 or 20 or 19 or 18 or 17 or 16 or 15 or 14 or 13 or 12 or 11 or 10 or 9 or 8 or 7 or 6 or 5 or 4 or 3 miRNAs wherein the set of miRNAs comprises at least one, e.g. 1, 2, 3, 4, 5 or 6, of the set of miRNAs listed in FIG. 6.

In a third aspect, the invention relates to the use of set of polynucleotides according to the second aspect of the invention for diagnosing and/or prognosing prostate cancer in a subject.

In a fourth aspect, the invention relates to a set of at least two primer pairs for determining the expression level of a predetermined set of miRNAs in a body fluid sample of a subject suffering or suspected of suffering from prostate cancer.

It is preferred that the body fluid sample is a blood sample, particularly preferred it is a whole blood, PBMC, serum or plasma sample, more particularly preferred it is a whole blood sample.

It is preferred that the subject is a mammal including both a human and another mammal, e.g. an animal such as a mouse, a rat, a rabbit, or a monkey. It is particularly preferred that the subject is a human.

Preferably, the predetermined set comprising at least two miRNAs is selected from the set of miRNAs listed in FIG. 2 or 5.

It is preferred that the predetermined set comprising at least two miRNAs is selected from the sets of miRNAs listed in FIG. 6. It is preferred that the predetermined set comprising at least two miRNAs comprises at least one set of miRNAs listed in FIG. 6.

It is preferred that the set of at least two primer pairs for determining the expression level of a predetermined set of miRNAs in a body fluid sample of a subject suffering or suspected of suffering from prostate cancer are primer pairs that are specific for at least one miRNA listed in FIG. 2 or 5.

It is preferred that the set of at least two primer pairs for determining the expression level of a predetermined set of miRNAs in a body fluid sample of a subject suffering or suspected of suffering from prostate cancer are primer pairs that are specific for at least one set of miRNAs listed in FIG. 6.

It is preferred that the set of at least two primer pairs of the present invention are for detecting a set comprising, essentially consisting of, or consisting of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40 or more miRNAs, and wherein the set of miRNAs comprises at least one of the sets listed in FIG. 6.

For example, the set of at least two primer pairs of the present invention are for detecting a predetermined set of 40 or 39 or 38 or 37 or 36 or 35 or 34 or 33 or 32 or 31 or 30 or 29 or 28 or 27 or 26 or 25 or 24 or 23 or 22 or 21 or 20 or 19 or 18 or 17 or 16 or 15 or 14 or 13 or 12 or 11 or 10 or 9 or 8 or 7 or 6 or 5 or 4 or 3 or 2 miRNAs wherein the predetermined set of miRNAs comprises at least one of the set of miRNAs listed in FIG. 6.

Preferably, the said primer pairs may be used for amplifying cDNA transcripts of the predetermined set of miRNAs selected from the miRNAs listed in FIG. 2 or FIG. 5. Furthermore, the said primer pairs may be used for amplifying cDNA transcripts of the set of miRNAs listed in FIG. 6.

It is understood that the primer pairs for detecting a predetermined set of miRNAs may consist of specific and or non-specific primers. Additionally, the set of primer pairs may be complemented by other substances or reagents (e.g. buffers, enzymes, dye, labelled probes) known to the skilled in the art for conducting real time polymerase chain reaction (RT-PCR).

In a fifth aspect, the invention relates to the use of a set of primer pairs according to the fourth aspect of the invention for diagnosing and/or prognosing prostate cancer in a subject.

In a sixth aspect, the invention relates to means for diagnosing and/or prognosing of prostate cancer in a body fluid sample of a subject.

Preferably, the invention relates to means for diagnosing and/or prognosing of prostate cancer in a body fluid sample of a subject comprising
(i) a set of at least two polynucleotides according to the second aspect of the invention or
(ii) a set of at least two primer pairs according the fourth aspect of the invention.

It is preferred that the body fluid sample is a blood sample, particularly preferred it is a whole blood, PBMC, serum or plasma sample, more particularly preferred it is a whole blood sample.

It is preferred that the subject is a mammal including both a human and another mammal, e.g. an animal such as a mouse, a rat, a rabbit, or a monkey. It is particularly preferred that the subject is a human.

Preferably, that the set of at least two polynucleotides or the set of at least 2 primer pairs are for detecting a predetermined set comprising at least two miRNAs for diagnosing and/or prognosing of prostate cancer in a body fluid sample, e.g. blood sample, from a subject, e.g. patient, human or animal, wherein the set of miRNAs is selected from the miRNAs listed in FIG. 2 or FIG. 5.

It is preferred that the set of at least two polynucleotides or the set of at least 2 primer pairs are for detecting a predetermined set comprising at least two miRNAs for diagnosing and/or prognosing of prostate cancer in a body fluid sample, e.g. blood sample, from a subject, e.g. patient, human or animal, wherein the set of miRNAs is selected from the sets of miRNAs listed in FIG. 6.

It is preferred that the set of at least two primer pairs for determining the expression level of a predetermined set of miRNAs in a body fluid sample of a subject suffering or suspected of suffering from prostate cancer are primer pairs that are specific for at least two miRNAs selected from the miRNAs listed in FIG. 2 or FIG. 5.

It is preferred that the set of at least two primer pairs for determining the expression level of a set of miRNAs in a body fluid sample of a subject suffering or suspected of suffering from prostate cancer are primer pairs that are specific for at least one set of miRNAs listed in FIG. 6.

It is also preferred that said means for diagnosing and/or prognosing of prostate cancer comprise, of a set of beads comprising a at least two polynucleotides according to the second aspect of the present invention. It is especially preferred that the beads are employed within a flow cytometer setup for diagnosing and/or prognosing of prostate cancer, e.g. in a LUMINEX system (www.luminexcorp.com).

In a seventh aspect, the invention relates to a kit for diagnosing and/or prognosing of prostate cancer in a subject.

Preferably, the invention relates to a kit for diagnosing and/or prognosing of prostate cancer comprising
(i) means for determining an expression profile of a predetermined set comprising at least two miRNAs representative for prostate cancer in a body fluid sample from a subject, and
(ii) at least one reference.

It is preferred that the body fluid sample is a blood sample, particularly preferred it is a whole blood, PBMC, serum or plasma sample, more particularly preferred it is a whole blood sample.

It is preferred that the subject is a mammal including both a human and another mammal, e.g. an animal such as a mouse, a rat, a rabbit, or a monkey. It is particularly preferred that the subject is a human.

Said means may comprise of at least two polynucleotides according to the second aspect of the present invention, a set of at least 2 primer pairs according to the fourth aspect of the invention; means according to the sixth aspect of the present invention; primers suitable to perform reverse transcriptase reaction and/or real time polymerase chain reaction such as quantitative polymerase chain reaction; and/or means for conducting next generation sequencing.

In an eighth aspect, the invention relates to a predetermined set of miRNAs in a body fluid sample isolated from a subject for diagnosing and/or prog nosing of prostate cancer.

It is preferred that the body fluid sample is a blood sample, particularly preferred it is a whole blood, PBMC, serum or plasma sample, more particularly preferred it is a whole blood sample.

It is preferred that the subject is a mammal including both a human and another mammal, e.g. an animal such as a mouse, a rat, a rabbit, or a monkey. It is particularly preferred that the subject is a human.

Preferably, the predetermined set comprising at least two miRNAs is selected from the set of miRNAs listed in FIG. 2 or 5.

It is preferred that the predetermined set comprising at least two miRNAs is selected from the set of miRNAs listed in FIG. 6. It is preferred that the predetermined set comprising at least two miRNAs comprises at least one set of miRNAs listed in FIG. 6.

In a ninth aspect, the invention relates to the use of a set of miRNAs according to the eighth aspect of the invention for diagnosing and/or prognosing of prostate cancer in a subject.

The invention will now be illustrated by the following figures and the non-limiting experimental examples.

FIGURES

FIG. 1: Overview of miRNA sequences published in the miRNA database 14.0 plus additional miRNA sequences.

FIG. 2: Overview of all miRNAs that are found to be differentially regulated in blood samples of prostate cancer patients, grouped accordingly to their results in t-tests.

FIG. 3: General overview of the method of diagnosing and/or predicting the state of health employing predetermined sets of miRNAs.

FIG. 4: Prostate cancer patients against healthy controls—classification of: according to t-test with the 270 miRNAs with the lowest p-values (see FIG. 2) lead to an accuracy 82.8% a specificity of 87.5% and a sensitivity of 71.9%
red=prostate cancer patients (1=derived from 1 independent sample collection); blue=healthy controls (1, 2, 3, 4, 5=derived from 5 independent sample collections)

FIG. 5: Overview of miRNAs that are found to be differentially regulated between healthy control and subjects suffering from prostate cancer. Experimental details: SEQ ID NO: sequence identification number, miRNA: identifier of the miRNA according to miRBase, median g1: median intensity obtained from microarray analysis for healthy controls, median g2: median intensity obtained from microarray analysis for individuals with prostate cancer, qnnedian: ratio of median g1/median g2, logqmedian: log of qmedian, ttest_rawp: p-value obtained when applying t-test, ttest_adjp: adjusted p-value in order to reduce false discovery rate by Benjamini-Hochberg adjustment, AUC: Area under the curve, limma_rawp: p-value obtained when applying limma-test, limma_adjp: adjusted p-value in order to reduce false discovery rate by Benjamini-Hochberg adjustment.

FIG. 6: Predetermined sets of miRNAs (miRNA signatures SNP-1 to 911) that allow for effective diagnosis and/or prognosis of subjects suffering or subjects suspected to suffering from prostate cancer. Experimental details: SEQ ID NO: sequence identification number, miRNA: identifier of the miRNA according to miRBase, Acc=accuracy, Spec=specificity, Sens=sensitivity.

REFERENCES

Alvarez-Garcia, I. and E. A. Miska (2005). "MicroRNA functions in animal development and human disease." *Development* 132(21): 4653-62.

Benjamini, Y. and Y. Hochberg (1995). "Controlling the false discovery rate: A practical and powerful approach to multiple testing." *J R Statist Soc B* 57: 289-300.

Bolstad, B. M., R. A. Irizarry, et al. (2003). "A comparison of normalization methods for high density oligonucleotide array data based on variance and bias." *Bioinformatics* 19(2): 185-93.

Calin, G. A. and C. M. Croce (2006). "MicroRNA-cancer connection: the beginning of a new tale." *Cancer Res* 66(15): 7390-4.

Calin, G. A. and C. M. Croce (2006). "MicroRNA signatures in human cancers." *Nat Rev Cancer* 6(11): 857-66.

Chen, X., Y. Ba, et al. (2008). "Characterization of microRNAs in serum: a novel class of biomarkers for diagnosis of cancer and other diseases." *Cell Res* 18(10): 997-1006.

Crawford, M., E. Brawner, et al. (2008). "MicroRNA-126 inhibits invasion in non-small cell lung carcinoma cell lines." *Biochem Biophys Res Commun* 373(4): 607-12.

Esquela-Kerscher, A. and F. J. Slack (2006). "Oncomirs-microRNAs with a role in cancer." *Nat Rev Cancer* 6(4): 259-69.

Feitelson, M. A. and J. Lee (2007). "Hepatitis B virus integration, fragile sites, and hepatocarcinogenesis." *Cancer Lett* 252(2): 157-70.

Gilad, S., E. Meiri, et al. (2008). "Serum microRNAs are promising novel biomarkers." *PLoS ONE* 3(9): e3148.

Griffiths-Jones, S., R. J. Grocock, et al. (2006). "miRBase: microRNA sequences, targets and gene nomenclature." *Nucleic Acids Res* 34(Database issue): D140-4.

Griffiths-Jones, S., S. Moxon, et al. (2005). "Rfam: annotating non-coding RNAs in complete genomes." *Nucleic Acids Res* 33(Database issue): D121-4.

Griffiths-Jones, S., H. K. Saini, et al. (2008). "miRBase: tools for microRNA genomics." *Nucleic Acids Res* 36(Database issue): D154-8.

Guo, L., Z. X. Huang, et al. (2008). "Differential Expression Profiles of microRNAs in NIH3T3 Cells in Response to UVB Irradiation." *Photochem Photobiol*.

Harris, T. A., M. Yamakuchi, et al. (2008). "MicroRNA-126 regulates endothelial expression of vascular cell adhesion molecule 1." *Proc Natl Acad Sci USA* 105(5): 1516-21.

Hayashita, Y., H. Osada, et al. (2005). "A polycistronic microRNA cluster, miR-17-92, is overexpressed in human lung cancers and enhances cell proliferation." *Cancer Res* 65(21): 9628-32.

He, L, J. M. Thomson, et al. (2005). "A microRNA polycistron as a potential human oncogene." *Nature* 435 (7043): 828-33.

Henschke, C. I. and D. F. Yankelevitz (2008). "CT screening for lung cancer: update 2007." *Oncologist* 13(1): 65-78.

Hochberg, Y. (1988). "A sharper bonferroni procedure for multiple tests of significance." *Biometrica* 75: 185-193.

Ichimi, T., H. Enokida, et al. (2009). "Identification of novel microRNA targets based on microRNA signatures in bladder cancer." *Int J Cancer*.

Jemal, A., R. Siegel, et al. (2008). "Cancer statistics, 2008." *CA Cancer J Clin* 58(2): 71-96.

Johnson, S. M., H. Grosshans, et al. (2005). "RAS is regulated by the let-7 microRNA family." *Cell* 120(5): 635-47.

Keller, A., N. Ludwig, et al. (2006). "A minimally invasive multiple marker approach allows highly efficient detection of meningioma tumours." *BMC Bioinformatics* 7: 539.

Lee, R. C., R. L. Feinbaum, et al. (1993). "The *C. elegans* heterochronic gene lin-4 encodes small RNAs with antisense complementarity to lin-14." *Cell* 75(5): 843-54.

Lu, J., G. Getz, et al. (2005). "MicroRNA expression profiles classify human cancers." *Nature* 435(7043): 834-8.

Mann, H. and F. Wilcoxon (1947). "On a test whether one of two random variables is stochastically larger than the other." *Ann Mat Stat* 18: 50-60.

Sassen, S., E. A. Miska, et al. (2008). "MicroRNA: implications for cancer." *Virchows Arch* 452(1): 1-10.

Scott, W. J., J. Howington, et al. (2007). "Treatment of non-small cell lung cancer stage I and stage II: ACCP evidence-based clinical practice guidelines (2nd edition)." *Chest* 132(3 Suppl): 234S-242S.

Shannon, C. (1984). "A mathematical theory of communication." *The Bell System Technical Journal* 27: 623-656.

Stahlhut Espinosa, C. E. and F. J. Slack (2006). "The role of microRNAs in cancer." *Yale J Biol Med* 79(3-4): 131-40.

Takamizawa, J., H. Konishi, et al. (2004). "Reduced expression of the let-7 microRNAs in human lung cancers in association with shortened postoperative survival." *Cancer Res* 64(11): 3753-6.

Team, R. D. C. (2008). *R: A Language and Environment for Statistical Computing*. Vienna, Austria, R Foundation for Statistical Computing.

Tong, A. W. (2006). "Small RNAs and non-small cell lung cancer." *Curr Mol Med* 6(3): 339-49.

Vapnik, V. (2000). *The Nature of Statistical Learning Theory*., Springer.

Volinia, S., G. A. Calin, et al. (2006). "A microRNA expression signature of human solid tumours defines cancer gene targets." *Proc Natl Acad Sci USA* 103(7): 2257-61.

Vorwerk, S., K. Ganter, et al. (2008). "Microfluidic-based enzymatic on-chip labeling of miRNAs." *N Biotechnol* 25(2-3): 142-9.

Wilcoxon, F. (1945). "Individual comparisons by ranking methods." *Biometric Bull* 1: 80-83.

Williams, A. E. (2008). "Functional aspects of animal microRNAs." *Cell Mol Life Sci* 65(4): 545-62.

Yanaihara, N., N. Caplen, et al. (2006). "Unique microRNA molecular profiles in lung cancer diagnosis and prognosis." *Cancer Cell* 9(3): 189-98.

Zhang, B., X. Pan, et al. (2007). "microRNAs as oncogenes and tumour suppressors." *Dev Biol* 302(1): 1-12.

Zhang, B., Q. Wang, et al. (2007). "MicroRNAs and their regulatory roles in animals and plants." *J Cell Physiol* 210(2): 279-89.

The invention claimed is:

1. A method for diagnosing prostate cancer, comprising:
   (a) determining an expression profile of hsa-miR-144* (SEQ ID NO:714) and hsa-miR-148a (SEQ ID NO:701) in blood cells obtained from a blood sample from a subject suspected to be affected by prostate cancer, wherein said blood cells consist of erythrocytes, leukocytes and thrombocytes and are obtained by removing the acellular fraction from the blood sample, and wherein determining said expression profile comprises nucleic acid amplification performed using real-time polymerase chain reaction (RT-PCR),
   (b) comparing said expression profile to a reference expression profile of healthy subjects,
   (c) diagnosing the presence of prostate cancer in the subject suspected to be affected by prostate cancer when down-regulation of each of hsa-miR-144* and hsa-miR-148a is detected in comparison to the reference expression profile, and
   (d) subjecting the subject diagnosed to be affected by prostate cancer to therapy for prostate cancer selected from the group consisting of surgery, radiation therapy, hormonal therapy, chemotherapy, cryosurgery, and high intensity focused ultrasound.

2. The method according to claim 1, wherein determining the expression profile in step (a) comprises:
   (i) extracting any RNA-fraction from said blood cells,
   (ii) performing a reverse transcriptase reaction using miRNA specific primers to produce non naturally occurring cDNA-transcripts of the predetermined set of miRNAs,
   (iii) amplifying the cDNA-transcripts using a set of primer pairs, and
   (iv) quantifying the cDNA-transcripts to produce an expression profile.

3. The method according to claim 1, wherein the reference expression profile is an averaged expression profile determined using blood cells from a plurality of healthy subjects.

4. The method according to claim 3, wherein said plurality of healthy subjects are the same gender and of similar age as the subject to be diagnosed.

5. The method according to claim 1, wherein the miRNA from blood cells is protected against degradation by collection tubes or by additives that stabilize the miRNA.

6. The method according to claim 1, wherein the predetermined set of miRNAs from blood cells is protected against degradation by collection tubes.

7. The method of claim 1, wherein the diagnosis comprises determining survival rate, responsiveness to drugs, or monitoring the course of the prostate cancer or the therapy, staging the prostate cancer, measuring the response of a patient to therapeutic intervention, segmentation of patients suffering from the prostate cancer estimating the severity of the prostate cancer, or predicting the response of a patient with the prostate cancer to therapeutic intervention.

8. The method of claim 7, wherein said therapeutic intervention is chemotherapy.

9. The method according to claim 1, wherein the reference expression profile is a mathematical average expression profile of the predetermined set of miRNAs.

10. The method according to claim 1, wherein the expression profile of said subject and the reference expression profile and optionally the predetermined set of miRNAs are stored in a database.

11. The method according to claim 1, further comprising determining the expression profile of at least 2, 7, 10, 15, 20, 25, 30, 35, 40, 50, 75, or 100 additional miRNAs.

12. The method according to claim 11, further comprising determining the expression profile of hsa-miR-519b-5p, hsa-miR-1324, hsa-miR-137, hsa-miR-556-5p, and hsa-miR-330-3p.

\* \* \* \* \*